(12) United States Patent
Pourille

(10) Patent No.: US 9,345,652 B2
(45) Date of Patent: *May 24, 2016

(54) COMPOSITION FOR DYEING KERATIN FIBRES COMPRISING A DIRECT DYE BEARING A DISULPHIDE/THIOL FUNCTION, A SPARINGLY OR NON-ETHOXYLATED FATTY ALCOHOL, A CATIONIC SURFACTANT, AN ALKALINE AGENT AND A REDUCING AGENT

(75) Inventor: Chrystel Pourille, Sannois (FR)

(73) Assignee: L'OREAL, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 14/001,318

(22) PCT Filed: Feb. 17, 2012

(86) PCT No.: PCT/EP2012/052752
§ 371 (c)(1),
(2), (4) Date: Aug. 23, 2013

(87) PCT Pub. No.: WO2012/113724
PCT Pub. Date: Aug. 30, 2012

(65) Prior Publication Data
US 2013/0326826 A1  Dec. 12, 2013

Related U.S. Application Data

(60) Provisional application No. 61/450,357, filed on Mar. 8, 2011.

(30) Foreign Application Priority Data

Feb. 25, 2011 (FR) ...................................... 11 51558

(51) Int. Cl.
*A61Q 5/10* (2006.01)
*A61K 8/49* (2006.01)
*A61K 8/34* (2006.01)
*A61K 8/41* (2006.01)
*A61Q 5/06* (2006.01)

(52) U.S. Cl.
CPC ............... *A61K 8/4933* (2013.01); *A61K 8/342* (2013.01); *A61K 8/416* (2013.01); *A61Q 5/065* (2013.01); *A61Q 5/10* (2013.01); *A61K 2800/4322* (2013.01)

(58) Field of Classification Search
CPC ....... A61Q 5/056; A61Q 5/10; A61K 8/4926; A61K 8/4933; A61K 2800/4322
USPC ............... 8/405, 407, 437, 465, 648
See application file for complete search history.

(56) References Cited

U.S. PATENT DOCUMENTS

| 2,798,053 A | 7/1957 | Brown |
| 2,923,692 A | 2/1960 | Ackerman et al. |
| 3,100,739 A | 8/1963 | Kaiser et al. |
| 3,148,125 A | 9/1964 | Strianse et al. |
| 3,524,842 A | 8/1970 | Grossmann et al. |
| 3,578,386 A | 5/1971 | Kalopissis et al. |
| 3,617,163 A | 11/1971 | Kalopissis et al. |
| 3,645,705 A | 2/1972 | Miller et al. |
| 3,665,036 A | 5/1972 | Kalopissis et al. |
| 3,817,698 A | 6/1974 | Kalopissis et al. |
| 3,867,456 A | 2/1975 | Kalopissis et al. |
| 3,869,454 A | 3/1975 | Lang et al. |
| 3,915,921 A | 10/1975 | Schlatzer, Jr. |
| 3,955,918 A | 5/1976 | Lang |
| 3,969,087 A | 7/1976 | Saito et al. |
| 3,985,499 A | 10/1976 | Lang et al. |
| 4,025,301 A | 5/1977 | Lang |
| 4,131,576 A | 12/1978 | Iovine et al. |
| 4,137,180 A | 1/1979 | Naik et al. |
| 4,151,162 A | 4/1979 | Lang et al. |
| 4,226,784 A | 10/1980 | Kalopissis et al. |
| 4,237,243 A | 12/1980 | Quack et al. |
| 4,509,949 A | 4/1985 | Huang et al. |
| 4,823,985 A | 4/1989 | Grollier et al. |
| 4,874,554 A | 10/1989 | Lange et al. |

(Continued)

FOREIGN PATENT DOCUMENTS

| DE | 2527638 A1 | 5/1976 |
| DE | 2538363 A1 | 5/1976 |

(Continued)

OTHER PUBLICATIONS

STIC Search Report dated dated Aug. 20, 2014.*

(Continued)

*Primary Examiner* — Eisa Elhilo
(74) *Attorney, Agent, or Firm* — The Marbury Law Group, PLLC

(57) ABSTRACT

The invention relates to a process for dyeing and/or lightening keratin fibers such as the hair, using i) at least one direct dye bearing a disulfide, thiol or protected-thiol function and ii) at least one sparingly or non-ethoxylated fatty alcohol, iii) at least one cationic surfactant, iv) at least one alkaline agent, and v) at least one reducing agent. The invention also relates to a composition comprising the ingredients i) to v), to the use of the combination of i), ii), iii), iv) and v) for the dyeing and/or lightening of keratin fibers, and to a multi-compartment kit comprising the ingredients i) to v). The dyeing process and the composition according to the invention especially afford a long-lasting coloration on keratin fibers, which is strong, chromatic and/or homogeneous, with or without the use of an oxidizing agent.

27 Claims, No Drawings

(56) References Cited

U.S. PATENT DOCUMENTS

| | | |
|---|---|---|
| 4,886,517 A | 12/1989 | Bugaut et al. |
| 4,956,175 A | 9/1990 | Maignan et al. |
| 5,015,767 A | 5/1991 | Maignan et al. |
| 5,085,860 A | 2/1992 | Junino et al. |
| 5,089,578 A | 2/1992 | Valint et al. |
| 5,106,612 A | 4/1992 | Maignan et al. |
| 5,154,918 A | 10/1992 | Maignan et al. |
| 5,156,911 A | 10/1992 | Stewart |
| 5,334,377 A | 8/1994 | Junino et al. |
| 5,449,805 A | 9/1995 | Junino et al. |
| 5,466,878 A | 11/1995 | Junino et al. |
| 5,468,477 A | 11/1995 | Kumar et al. |
| 5,500,209 A | 3/1996 | Mendolia et al. |
| 5,519,063 A | 5/1996 | Mondet et al. |
| 5,583,257 A | 12/1996 | Junino et al. |
| 5,700,454 A | 12/1997 | Malle |
| 5,708,151 A | 1/1998 | Möckli |
| 5,725,882 A | 3/1998 | Kumar et al. |
| 5,736,125 A | 4/1998 | Morawsky et al. |
| 5,783,657 A | 7/1998 | Pavlin et al. |
| 5,843,416 A | 12/1998 | Malle |
| 5,879,413 A | 3/1999 | Pengilly et al. |
| 5,888,252 A | 3/1999 | Möckli |
| 5,919,273 A | 7/1999 | Rondeau et al. |
| 5,935,558 A | 8/1999 | Malle |
| 5,985,257 A | 11/1999 | Malle |
| 5,993,490 A | 11/1999 | Rondeau et al. |
| 6,045,591 A | 4/2000 | Deneulenaere |
| 6,136,042 A | 10/2000 | Maubru |
| 6,174,968 B1 | 1/2001 | Hoxmeier |
| 6,179,881 B1 | 1/2001 | Henrion et al. |
| 6,225,390 B1 | 5/2001 | Hoxmeier |
| 6,458,167 B1 | 10/2002 | Genet et al. |
| 6,492,502 B2 | 12/2002 | Henrion et al. |
| 6,797,013 B1 | 9/2004 | Lang et al. |
| 6,822,039 B1 | 11/2004 | Monfreux-Gaillard et al. |
| 6,863,883 B1 | 3/2005 | Tsujino et al. |
| 7,717,964 B2 * | 5/2010 | Daubresse et al. ............... 8/405 |
| 7,744,657 B2 | 6/2010 | Greaves et al. |
| 7,780,743 B2 | 8/2010 | Greaves et al. |
| 8,038,731 B2 | 10/2011 | Daubresse et al. |
| 8,328,880 B2 | 12/2012 | Daubresse et al. |
| 2001/0001332 A1 | 5/2001 | Henrion et al. |
| 2002/0165368 A1 | 11/2002 | Henrion et al. |
| 2006/0080791 A1 | 4/2006 | Daubresse et al. |
| 2006/0195990 A1 | 9/2006 | Lagrange |
| 2006/0248662 A1* | 11/2006 | Legrand ........................... 8/405 |
| 2009/0126125 A1 | 5/2009 | Greaves et al. |
| 2009/0172897 A1 | 7/2009 | Daubresse et al. |
| 2009/0313769 A1 | 12/2009 | Daubresse et al. |
| 2009/0320216 A1 | 12/2009 | Greaves et al. |
| 2010/0287714 A1 | 11/2010 | Greaves et al. |
| 2011/0011417 A1 | 1/2011 | Greaves et al. |
| 2012/0177587 A1 | 7/2012 | Daubresse et al. |
| 2013/0074276 A1 | 3/2013 | Daubresse et al. |
| 2014/0082855 A1* | 3/2014 | Rapold et al. ..................... 8/406 |

FOREIGN PATENT DOCUMENTS

| | | |
|---|---|---|
| DE | 4137005 A1 | 5/1993 |
| DE | 4220388 A1 | 12/1993 |
| EP | 0173109 A2 | 3/1986 |
| EP | 0354835 A1 | 2/1990 |
| EP | 0368763 A1 | 5/1990 |
| EP | 0432000 A1 | 6/1991 |
| EP | 0465342 A1 | 1/1992 |
| EP | 0503853 A2 | 9/1992 |
| EP | 0514282 A1 | 11/1992 |
| EP | 0497144 A1 | 8/1993 |
| EP | 0577473 A1 | 1/1994 |
| EP | 0653202 A1 | 5/1995 |
| EP | 0714954 A2 | 6/1996 |
| EP | 0750899 A2 | 1/1997 |
| EP | 0850636 A1 | 7/1998 |
| EP | 0850637 A1 | 7/1998 |
| EP | 0918053 A1 | 5/1999 |
| EP | 0920856 A1 | 6/1999 |
| EP | 1062940 A1 | 12/2000 |
| EP | 1133975 A2 | 9/2001 |
| EP | 1133976 A2 | 9/2001 |
| EP | 1647580 A1 | 4/2006 |
| EP | 1652554 A1 | 5/2006 |
| EP | 2070988 A2 | 6/2009 |
| EP | 2075289 A1 | 7/2009 |
| FR | 1221122 A | 5/1960 |
| FR | 1516943 A2 | 2/1968 |
| FR | 1540423 A | 8/1968 |
| FR | 1560664 A | 3/1969 |
| FR | 1567219 A | 5/1969 |
| FR | 2189006 A1 | 1/1974 |
| FR | 2275462 A1 | 1/1976 |
| FR | 2281162 A1 | 3/1976 |
| FR | 2285851 A1 | 4/1976 |
| FR | 2416723 A1 | 9/1979 |
| FR | 2570946 A1 | 4/1986 |
| FR | 2586913 A1 | 3/1987 |
| FR | 2679448 A1 | 1/1993 |
| FR | 2692481 A1 | 12/1993 |
| FR | 2757385 A1 | 6/1998 |
| FR | 2788433 A1 | 7/2000 |
| FR | 2910278 A1 | 6/2008 |
| FR | 2921256 A1 | 3/2009 |
| FR | 2921380 A1 | 3/2009 |
| FR | 2933297 A1 | 1/2010 |
| GB | 738585 A | 10/1955 |
| GB | 1163385 A | 9/1969 |
| GB | 1195386 A | 6/1970 |
| GB | 1514466 A | 6/1978 |
| WO | 9301797 A1 | 2/1993 |
| WO | 9501772 A1 | 1/1995 |
| WO | 9515144 A1 | 6/1995 |
| WO | 9744004 A1 | 11/1997 |
| WO | 9842298 A1 | 10/1998 |
| WO | 9844012 A1 | 10/1998 |
| WO | 9948465 A1 | 9/1999 |
| WO | 0031154 A1 | 6/2000 |
| WO | 0068282 A1 | 11/2000 |
| WO | 0119333 A1 | 3/2001 |
| WO | 0166646 A1 | 9/2001 |
| WO | 03029359 A1 | 4/2003 |
| WO | 2005097051 A2 | 10/2005 |
| WO | 2007110531 A2 | 10/2007 |
| WO | 2007110532 A2 | 10/2007 |
| WO | 2007110533 A2 | 10/2007 |
| WO | 2007110534 A2 | 10/2007 |
| WO | 2007110535 A2 | 10/2007 |
| WO | 2007110536 A2 | 10/2007 |
| WO | 2007110537 A2 | 10/2007 |
| WO | 2007110538 A2 | 10/2007 |
| WO | 2007110539 A2 | 10/2007 |
| WO | 2007110540 A2 | 10/2007 |
| WO | 2007110541 A2 | 10/2007 |
| WO | 2007110542 A2 | 10/2007 |
| WO | 2009034059 A2 | 3/2009 |
| WO | 2009040354 A1 | 4/2009 |
| WO | 2009109457 A2 | 9/2009 |
| WO | WO 2009/109457 A2 * | 9/2009 ............... A61Q 5/10 |
| WO | 2012113720 A2 | 8/2012 |
| WO | 2012113722 A2 | 8/2012 |
| WO | 2012113723 A2 | 8/2012 |

OTHER PUBLICATIONS

Antioxidant (Wikipedia, the free encyclopedia (No date).*
International Search Report and Written Opinion for PCT/EP2012/052746.
Co-pending U.S. Appl. No. 14/001,321; National Stage of International Application No. PCT/EP2012/052746; Frédéric Guerin et al., "Composition for Dyeing Keratinous Fibers Comprising a Direct Dye Having a Disulphide/Thiol Functional Group, a Thickening Polymer, an Ethoxylated Fatty Alcohol and/or a Nonionic Surfactant, an Alkaline Agent and a Reducing Agent" filed Aug. 23, 2013.

(56) References Cited

OTHER PUBLICATIONS

International Search Report and Written Opinion for PCT/EP2012/052748.
Co-pending U.S. Appl. No. 14/001,324; National Stage of International Application No. PCT/EP2012/052748; Frédéric Guerin et al., "Composition for Dyeing Keratin Fibres Comprising a Direct Dye Bearing a Disulfide/Thiol Function, a Nonionic Surfactant, an Amphoteric Surfactant, an Ethoxylated Fatty Alcohol, an Alkaline Agent and a Reducing Agent," filed Aug. 23, 2013.
International Search Report and Written Opinion for related application PCT/EP2012/052751.
Co-pending U.S. Appl. No. 14/001,326; National Stage of International Application No. PCT/EP2012/052751; Frédéric Guerin et al., "Composition for Dyeing Keratin Fibres Comprising a Direct Dye Bearing a Disulfide/Thiol Function, a Non-Cellulose-Based Thickening Polymer, an Alkaline Agent and a Reducing Agent," filed Aug. 23, 2013.
English language abstract for FR 2910278 (Jun. 27, 2008).
English language abstract for FR 2921380 (Mar. 27, 2009).
English language abstract for FR 2933297 (Jan. 8, 2010).
International Search Report and Written Opinion for PCT/EP2012/052752.
Morishima, Yotaro, "Self-Assembling Amphiphilic Polyelectrolytes and their Nanostructures," Chinese Journal of Polymer Science, vol. 18, No. 40, 2000, pp. 323-336.
Morishima, Yotaro, "Micelle Formation of Random Copolymers of Sodium 2-(acrylamido)-2-methylpropanesulfonate and a Nonionic Surfactant Macromonomer in Water as Studied by Fluorescence and Dynamic Light Scattering," Macromolecules, vol. 33, No. 10, 2000, pp. 3694-3704.
Morishima, Yotaro, "Solution Properties of Micelle Networks Formed by Nonionic Moieties Covalently Bound to a Polyelectrolyte: Salt Effects on Rheological Behavior," Langmuir, vol. 16, No. 12, 2000, pp. 5324-5332.
Morishima, Yotaro, "Stimuli Responsive Amphiphilic Copolymers of Sodium 2-(acrylamido)-2-methylpropanesulfonate and Associative Macromonomers," Polym. Preprint, Div. Polym. Chem., 40(2), 1999, pp. 220-221.
English language abstract for DE 4137005 (May 13, 1993).
English language abstract for DE 4220388 (Dec. 23, 1993).
English language abstract for EP 0368763 (May 16, 1990).
English language abstract for EP 0577473 (Jan. 5, 1994).
English language abstract for FR 2679448 (Jan. 29, 1993).
English language abstract for FR 2692481 (Dec. 24, 1993).
English language abstract for FR 2921256 (Mar. 27, 2009).
Griffin, William C., "Calculation of HLB Values of Non-Ionic Surfactants," Journal of the Society of Cosmetic Chemists, May 1954, pp. 249-256.
Hamley, I.W., "Crystallization in Block Copolymers," Advances in Polymer Science, vol. 148, (1999), pp. 113-137.
Hunger, Klaus et al., "Pigments, Organic," Ullmann's Encyclopedia of Industrial Chemistry, vol. 27, (2012), pp. 380-423.
"Microbial Polysaccharides," Kirk-Othmer Encyclopedia of Chemical Technology, Third Edition, vol. 15, pp. 439-458.
McGregor, E.A., et al., "Polymers in Nature," published by John Wiley & Sons, Chapter 6, (1980), pp. 240-328.
Nojima, Shuichi et al., Melting Behavior of Poly(•-caprolactoney)-block-Polybutadiene Copolymers, American Chemical Society, Macromolecules 1999, 32, pp. 3727-3734.
Rangarajan, Pratima et al., Morphology of Semicrystalline Block Copolymere of Ethylene-(Ethylene-alt-propylene), American Chemical Society, Macromolecules 1993, 26, pp. 4640-4645.
Richter, D., et al., "Polymer Aggregates with Crystalline Cores: The System Polyethylene-Poly (ethylenepropylene)," American Chemical Society, Macromolecules 1997, 30, pp. 1053-1068.
Viscardi, Guido et al., "Disperse and Cationic Azo Dyes from Heterocyclic Intermediates," Dyes and Pigments, 19 (1992), pp. 69-79.
Volz, Hans G., "Pigments, Inorganic, 1. General," Ullmann's Encyclopedia of Industrial Chemistry, vol. 27, pp. 225-256.
Non-Final Office Action for co-pending U.S. Appl. No. 14/001,321 (Sep. 4, 2014).
Final Office Action for co-pending U.S. Appl. No. 14/001,321 (Dec. 18, 2014).
Non-Final Office Action for co-pending U.S. Appl. No. 14/001,326 (Sep. 4, 2014).
Final Office Action for co-pending U.S. Appl. No. 14/001,326 (Dec. 18, 2014).
Non-Final Office Action for co-pending U.S. Appl. No. 14/001,324 (Sep. 5, 2014).
Final Office Action for co-pending U.S. Appl. No. 14/001,324 (Dec. 29, 2014).
Non-Final Office Action for co-pending U.S. Appl. No. 14/001,326 (Jun. 1, 2015).

* cited by examiner

COMPOSITION FOR DYEING KERATIN FIBRES COMPRISING A DIRECT DYE BEARING A DISULPHIDE/THIOL FUNCTION, A SPARINGLY OR NON-ETHOXYLATED FATTY ALCOHOL, A CATIONIC SURFACTANT, AN ALKALINE AGENT AND A REDUCING AGENT

CROSS REFERENCE TO RELATED APPLICATIONS

This is a national stage application of PCT/EP2012/052752, filed internationally on Feb. 17, 2012, which claims priority to U.S. Provisional Application No. 61/450,357, filed on Mar. 8, 2011, as well as French Application No. FR 1151558, filed on Feb. 25, 2011, all of which are incorporated herein by reference in their entireties.

The invention relates to a process for dyeing and/or lightening keratin fibres using direct dyes.

It is known practice to dye keratin fibres by direct dyeing or semi-permanent dyeing. Direct dyeing or semi-permanent dyeing consists in introducing colour via a coloured molecule that becomes adsorbed onto the surface of the hair or that penetrates into the hair. Thus, the process conventionally used in direct dyeing consists in applying to keratin fibres direct dyes, which are coloured and colouring molecules that have affinity for the fibres, leaving the fibres in contact with the colouring molecules and then optionally rinsing the fibres. Generally, this technique leads to chromatic colorations.

Scientific research has been conducted for several years to modify the colour of keratin materials, especially keratin fibres, and in particular to mask white fibres, to modify the colour of the fibres permanently or temporarily, and to satisfy new desires and needs in terms of colours and durability.

Patent applications EP 1 647 580, WO 2005/097 051, EP 2 004 759, EP 2 075 289, WO 2007/110 541, WO 2007/110 540, WO 2007/110 539, WO 2007/110 538, WO 2007/110 537, WO 2007/110 536, WO 2007/110 535, WO 2007/110 534, WO 2007/110 533, WO 2007/110 532, WO 2007/110 531, EP 2 070 988, WO 2009/040 354 and WO 2009/034 059 disclose direct dyes bearing a disulfide, thiol or protected-thiol function, for dyeing the hair. The colours obtained are not sufficiently satisfactory, especially in terms of coloration intensity, colour selectivity between the root and the end, and chromaticity of the colour.

The aim of the present invention is to provide novel systems for dyeing the hair, even without the use of a chemical oxidizing agent, which make it possible to obtain improved colorations, especially in terms of fastness with respect to external agents, homogeneity of the coloration (little selectivity between the root and the end of the keratin fibres), and intensity, and/or which do not impair the cosmetic properties of the keratin fibres.

This aim is achieved with the present invention, a first subject of which is a cosmetic composition comprising:
i) at least one direct dye bearing a disulfide function, a thiol function or a protected-thiol function, especially of formula (I):

$$A\text{-}(X)_p\text{—}C_{sat}\text{—}S\text{—}U \qquad (I)$$

salts thereof with an organic or mineral acid, optical or geometric isomers thereof, tautomers thereof, and solvates thereof such as the hydrates,
in which formula (I):
U represents a radical chosen from:
a) —S—C'$_{sat}$—(X')$_{p'}$-A'; and
b) —Y;

A and A', which may be identical or different, represent a radical containing at least one quaternized cationic chromophore or at least one chromophore bearing a quaternized or quaternizable cationic group;
Y represents i) a hydrogen atom; or ii) a thiol-function protecting group;
X and X', which may be identical or different, represent a linear or branched, saturated or unsaturated divalent $C_1$-$C_{30}$ hydrocarbon-based chain, optionally interrupted and/or optionally terminated at one or both of its ends with one or more divalent groups or combinations thereof chosen from:
—N(R)—, —N$^+$(R)(R)—, —O—, —S—, —CO—, —SO$_2$— with R, which may be identical or different, chosen from a hydrogen and a $C_1$-$C_4$ alkyl, hydroxyalkyl or aminoalkyl radical;
an aromatic or non-aromatic, saturated or unsaturated, fused or non-fused (hetero)cyclic radical optionally comprising one or more identical or different, optionally substituted heteroatoms;
p and p', which may be identical or different, are equal to 0 or 1;
$C_{sat}$ and $C'_{sat}$, which may be identical or different, represent an optionally substituted linear or branched, or cyclic, $C_1$-$C_{18}$ alkylene chain;
ii) at least one sparingly ethoxylated or non-ethoxylated fatty alcohol;
iii) at least one cationic surfactant;
iv) at least one alkaline agent; and
v) at least one reducing agent.

Another subject of the invention is a process for dyeing and/or lightening keratin fibres, especially dark keratin fibres, by applying to the said fibres the ingredients i) to v) as defined previously, the said ingredients being applied together or separately.

Another subject of the invention is the use of the composition comprising i), ii), iii), iv) and v) as defined previously, for the dyeing and/or lightening of keratin fibres.

Another subject of the invention is a multi-compartment kit comprising i), ii), iii), iv) and v) as defined previously.

The colorations obtained are attractive, aesthetic, intense, strong, chromatic and very fast or persistent with respect to common attacking factors or everyday assaults such as sun, sebum and especially with respect to perspiration, and other hair treatments such as successive shampooing, while at the same time respecting the keratin fibres. The intensity obtained is particularly noteworthy. The same is true for the colour homogeneity or selectivity of the colour.

For the purposes of the present invention, and unless otherwise indicated:
a "direct dye bearing a disulfide function" is a direct dye comprising one or more cationic chromophores that absorb light in the visible spectrum, and comprising a disulfide bond: —S—S— between two carbon atoms and is preferably indirectly bonded to the chromophore(s) of the dye, i.e. between the chromophores and the —S—S— function there is at least one methylene group;
a "direct dye bearing a protected-thiol function" is a direct dye comprising a chromophore, comprising a protected-thiol function —SY in which Y is a protecting group known to those skilled in the art, for instance those described in the publications *Protective Groups in Organic Synthesis*, T. W. Greene, John Wiley & Sons ed., NY, 1981, pp. 193-217; *Protecting Groups*, P. Kocienski, Thieme, 3$^{rd}$ ed., 2005, chap. 5; and Ullmann's Encyclopedia, *Peptide Synthesis*, pp. 4-5, 2005

Wiley-VCH Verlag GmbH & Co. KGaA, Weinheim 10.1002/14356007.a19 157; it being understood that the said protected-thiol function is preferably indirectly bonded to the chromophore of the dye, i.e. between the chromophore and the function —SY there is at least one methylene group;

a "direct dye bearing a thiol function" is a direct dye comprising a chromophore, and comprising a thiol function —SY' in which Y' is i) a hydrogen atom; ii) an alkali metal; iii) an alkaline-earth metal; iv) an ammonium group: $N^+R\,R\,R\,R$ or a phosphonium group: $P^+R\,R\,R\,R$ with R, R, R and R, which may be identical or different, representing a hydrogen atom or a group $(C_1-C_4)$alkyl, preferentially comprising a thiol function —SH, it being understood that the said thiol function is preferably indirectly bonded to the chromophore of the dye, i.e. between the chromophore and the function —SY' there is at least one methylene group;

a "chromophore" is a radical derived from a dye, i.e. a radical derived from the molecule that absorbs light in the visible radiation range that is visually perceptible by man, i.e. an absorption wavelength $\lambda_{abs}$ inclusively between 400 and 800 nm; the chromophore may be fluorescent, i.e. it is capable of absorbing in the UV and visible radiation range at a wavelength $\lambda_{abs}$ inclusively between 250 and 800 nm and capable of re-emitting in the visible range at an emission wavelength $\lambda_{em}$ inclusively between 400 and 800 nm;

a "chromophore" is said to be "quaternized cationic" or "bearing a quaternized cationic group" if it comprises in its structure at least one permanent cationic charge formed from at least one quaternized nitrogen atom (ammonium) or quaternized phosphorus atom (phosphonium), preferably nitrogen;

a group is said to be "bearing a quaternizable cationic group" when it comprises in its structure at least one tertiary amine or tertiary phosphine at the end of a hydrocarbon-based chain, preferably $C_1-C_{10}$ alkyl, such as —$(CR'R'')_p$—$N(R_a)$—$R_b$ with R' and R", which may be identical or different, representing a hydrogen atom or a $(C_1-C_6)$ alkyl group; $R_a$ and $R_b$, which may be identical or different, representing a $(C_1-C_6)$alkyl group, a monohydroxy$(C_1-C_6)$alkyl group, a (poly)(hydroxy)$(C_1-C_6)$ alkyl group or $R_a$ and $R_b$ form, together with the nitrogen atom that bears them, a heterocycloalkyl group such as morpholino, which, once quaternized, will become morpholinium, piperidino, which, once quaternized, will become piperidinium, or piperazino, which, once quaternized, will become piperazinium; and p representing an integer between 1 and 10 inclusive; preferably, R' and R" represent a hydrogen atom, $R_a$ and $R_b$ represent a $(C_1-C_4)$alkyl group and p is between 2 and 5;

the dyes according to the invention contain one or more chromophores, and these dyes are capable of absorbing light at a wavelength $\lambda_{abs}$ particularly of between 400 and 700 nm inclusive;

the "fluorescent" dyes according to the invention are dyes containing at least one fluorescent chromophore, and these dyes are capable of absorbing in the visible range at a wavelength $\lambda_{abs}$ particularly inclusively between 400 and 800 nm and of re-emitting in the visible range at a longer wavelength $\lambda_{em}$ than that absorbed, inclusively between 400 and 800 nm. The difference between the absorption and emission wavelengths, also known as the Stoke's shift, is inclusively between 1 nm and 100 nm. More preferentially, fluorescent dyes are dyes that are capable of absorbing at a wavelength $\lambda_{abs}$ inclusively between 420 and 550 nm and of re-emitting in the visible range at a wavelength $\lambda_{em}$ inclusively between 470 and 600 nm;

chromophores are said to be "different" when they differ in their chemical structure and may be chromophores derived from different families or from the same family on condition that they have different chemical structures: for example, the chromophores may be chosen from the family of azo dyes but differ in the chemical structure of the radicals constituting them or in the respective position of these radicals;

an "alkylene chain" represents a divalent acyclic $C_1-C_{20}$ hydrocarbon-based chain; particularly $C_1-C_6$ and more particularly $C_1-C_2$ when the chain is linear; optionally substituted with one or more groups, which may be identical or different, chosen from i) hydroxyl, ii) $(C_1-C_2)$alkoxy, iii) (poly)hydroxy$(C_2-C_4)$alkoxy(di)$(C_1-C_2)$ (alkyl)amino, iv) $R^a$—$Z^a$—$C(Z^b)$—$Z^c$—, and v) $R^a$—$Z^a$—$S(O)_t$—$Z^c$— with $Z^a$ and $Z^b$, which may be identical or different, representing an oxygen or sulfur atom, or a group $NR^{a'}$, $Z^c$, representing a bond, an oxygen or sulfur atom, or a group $NR^a$; $R^a$, representing an alkali metal, a hydrogen atom, an alkyl group, or alternatively is absent if another part of the cationic molecule and $R^{a'}$ representing a hydrogen atom or an alkyl group and t is equal to 1 or 2; more particularly, the groups iv) are chosen from carboxylate —C(O)O⁻ or —C(O)OMetal (metal=alkali metal), carboxyl —O(O)—OH, guanidino $H_2H$—$C(NH_2)$—NH—, amidino $H_2H$—C$(NH_2)$—, (thio)ureo $H_2N$—C(O)—NH— and $H_2N$—C(S)—NH—, aminocarbonyl —O(O)—$NRa'_2$ or aminothiocarbonyl —C(S)—$NRa'_2$; carbamoyl Ra'—C(O)—NRa' or thiocarbamoyl Ra'—C(S)—NRa'— with Ra', which may be identical or different, representing a hydrogen atom or a $(C_1-C_4)$alkyl group;

an "optionally substituted, saturated or unsaturated $C_1-C_{30}$ divalent hydrocarbon-based chain" represents a hydrocarbon-based chain, particularly of $C_1-C_8$, optionally comprising one or more conjugated or unconjugated double bonds, and in particular the hydrocarbon-based chain is saturated; the said chain is optionally substituted with one or more groups, which may be identical or different, chosen from i) hydroxyl, ii) $(C_1-C_2)$alkoxy, iii) (poly)hydroxy$(C_2-C_4)$alkoxy(di)$(C_1-C_2)$(alkyl)amino, iv) $R^a$—$Z^a$—$C(Z^b)$—$Z^c$—, and v) $R^a$—$Z^a$—$S(O)_t$—$Z^c$—with $Z^a$ and $Z^b$, which may be identical or different, representing an oxygen or sulfur atom, or a group $NR^{a'}$, $Z^c$, representing a bond, an oxygen or sulfur atom, or a group $NR^a$; $R^a$, representing an alkali metal, a hydrogen atom, an alkyl group, or alternatively is absent if another part of the cationic molecule and $R^{a'}$ representing a hydrogen atom or an alkyl group and t is equal to 1 or 2; more particularly, the groups iv) are chosen from carboxylate —O(O)O⁻ or —O(O)OMetal (metal=alkali metal), carboxyl —O(O)—OH, guanidino $H_2H$—C$(NH_2)$—NH—, amidino $H_2H$—C$(NH_2)$—, (thio)ureo $H_2N$—C(O)—NH— and $H_2N$—C(S)—NH—, aminocarbonyl —O(O)—$NRa'_2$ or aminothiocarbonyl —C(S)—$NRa'_2$; carbamoyl Ra'—C(O)—NRa'— or thiocarbamoyl Ra'—C(S)—NRa'— with Ra', which may be identical or different, representing a hydrogen atom or a $(C_1-C_4)$alkyl group;

an "optionally substituted, saturated or unsaturated $C_1-C_{30}$ divalent hydrocarbon-based chain" represents a hydrocarbon-based chain, particularly of $C_1-C_8$, optionally comprising one or more conjugated or unconjugated double bonds, and in particular the hydrocarbon-based chain is saturated; the said chain is optionally substituted with one or more groups, which may be identical or different, chosen from i) hydroxyl, ii) ($C_1$-$C_2$)alkoxy, iii) (poly)hydroxy($C_2$-$C_4$)alkoxy(di)($C_1$-$C_2$)(alkyl)amino, iv) $R^a$—$Z^a$—$C(Z^b)$—$Z^c$—, and v) $R^a$—$Z^a$—$S(O)_t$—$Z^c$— with $Z^a$ and $Z^b$, which may be identical or different, representing an oxygen or sulfur atom, or a group $NR^a$, $Z^c$, representing a bond, an oxygen or sulfur atom, or a group $NR^a$; $R^a$, representing an alkali metal, a hydrogen atom, an alkyl group, or alternatively is absent if another part of the cationic molecule and $R^a$ representing a hydrogen atom or an alkyl group and t is equal to 1 or 2; more particularly, the groups iv) are chosen from carboxylate —C(O)O⁻ or —C(O)OMetal (metal=alkali metal), carboxyl —O(O)—OH, guanidino $H_2H$—C($NH_2$)—NH—, amidino $H_2H$—C($NH_2$)—, (thio)ureo $H_2N$—C(O)—NH— and $H_2N$—C(S)—NH—, aminocarbonyl —C(O)—NRa'$_2$ or aminothiocarbonyl —C(S)—NRa'$_2$; carbamoyl Ra'—C(O)—NRa'— or thiocarbamoyl Ra'—C(S)—NRa'— with Ra', which may be identical or different, representing a hydrogen atom or a ($C_1$-$C_4$)alkyl group;

the "aryl" or "heteroaryl" radicals or the aryl or heteroaryl part of a radical may be substituted with at least one substituent borne by a carbon atom, chosen from:
 a $C_1$-$C_{16}$ and preferably $C_1$-$C_8$ alkyl radical optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another heteroatom identical to or different from nitrogen;
 a halogen atom;
 a hydroxyl group;
 a $C_1$-$C_2$ alkoxy radical;
 a $C_2$-$C_4$ (poly)hydroxyalkoxy radical;
 an amino radical;
 a 5- or 6-membered heterocycloalkyl radical;
 an optionally cationic 5- or 6-membered heteroaryl radical, preferentially imidazolium, optionally substituted with a ($C_1$-$C_4$)alkyl radical, preferentially methyl;
 an amino radical substituted with one or two identical or different $C_1$-$C_6$ alkyl radicals, optionally bearing at least:
  i) a hydroxyl group,
  ii) an amino group optionally substituted with one or two optionally substituted $C_1$-$C_3$ alkyl radicals, the said alkyl radicals possibly forming with the nitrogen atom to which they are attached a saturated or unsaturated, optionally substituted 5- to 7-membered heterocycle, optionally comprising at least one other heteroatom identical to or different from nitrogen,
  iii) a quaternary ammonium group —N⁺R'R''R''', M⁻ for which R', R'' and R''', which may be identical or different, represent a hydrogen atom or a $C_1$-$C_4$ alkyl group; and M⁻ represents the counterion of the organic or mineral acid or of the corresponding halide;
  iv) an optionally cationic 5- or 6-membered heteroaryl radical, preferentially imidazolium, optionally substituted with a ($C_1$-$C_4$)alkyl radical, preferentially methyl;
 an acylamino radical (—NR—C(O)—R') in which the radical R is a hydrogen atom or a $C_1$-$C_4$ alkyl radical optionally bearing at least one hydroxyl group and the radical R' is a $C_1$-$C_2$ alkyl radical;
 a carbamoyl radical (($R)_2$N—C(O)—) in which the radicals R, which may be identical or different, represent a hydrogen atom or a $C_1$-$C_4$ alkyl radical optionally bearing at least one hydroxyl group;
 an alkylsulfonylamino radical (R'—$S(O)_2$—N(R)—) in which the radical R represents a hydrogen atom or a $C_1$-$C_4$ alkyl radical optionally bearing at least one hydroxyl group and the radical R' represents a $C_1$-$C_4$ alkyl radical, or a phenyl radical;
 an aminosulfonyl radical (($R)_2$N—$S(O)_2$—) in which the radicals R, which may be identical or different, represent a hydrogen atom or a $C_1$-$C_4$ alkyl radical optionally bearing at least one hydroxyl group;
 a carboxylic radical in acid or salified form (preferably with an alkali metal or a substituted or unsubstituted ammonium);
 a cyano group;
 a nitro or nitroso group;
 a polyhaloalkyl group, preferentially trifluoromethyl;
the cyclic or heterocyclic part of a non-aromatic radical may be substituted with at least one substituent chosen from the following groups:
 hydroxyl;
 $C_1$-$C_4$ alkoxy, $C_2$-$C_4$ (poly)hydroxyalkoxy,
 ($C_1$-$C_4$)alkyl;
 alkylcarbonylamino (R—C(O)—N(R')—) in which the radical R' is a hydrogen atom or a $C_1$-$C_4$ alkyl radical optionally bearing at least one hydroxyl group, and the radical R is a $C_1$-$C_2$ alkyl radical or an amino radical optionally substituted with one or two $C_1$-$C_4$ alkyl groups, which may be identical or different, themselves optionally bearing at least one hydroxyl group, the said alkyl radicals possibly forming, with the nitrogen atom to which they are attached, a saturated or unsaturated, optionally substituted 5- to 7-membered heterocycle optionally comprising at least one other nitrogen or non-nitrogen heteroatom;
 alkylcarbonyloxy (R—C(O)—O—) in which the radical R is a $C_1$-$C_4$ alkyl radical or an amino radical substituted with one or two identical or different $C_1$-$C_4$ alkyl groups, themselves optionally bearing at least one hydroxyl group, the said alkyl radicals possibly forming with the nitrogen atom to which they are attached a saturated or unsaturated, optionally substituted 5- to 7-membered heterocycle, optionally comprising at least one other nitrogen or non-nitrogen heteroatom;
 alkoxycarbonyl (R-G-C(O)—) in which the radical R is a $C_1$-$C_4$ alkoxy radical, G is an oxygen atom or an amino group optionally substituted with a $C_1$-$C_4$ alkyl group optionally bearing at least one hydroxyl group, the said alkyl radical possibly forming, with the nitrogen atom to which they are attached, a saturated or unsaturated, optionally substituted 5- to 7-membered heterocycle, optionally comprising at least one other nitrogen or non-nitrogen heteroatom;
a cyclic or heterocyclic radical, or a non-aromatic portion of an aryl or heteroaryl radical, may also be substituted with one or more oxo groups;

a hydrocarbon-based chain is unsaturated when it comprises one or more double bonds and/or one or more triple bonds;

an "aryl" radical represents a fused or non-fused monocyclic or polycyclic carbon-based group containing from 6 to 22 carbon atoms, and in which at least one ring is aromatic; preferentially, the aryl radical is a phenyl, biphenyl, naphthyl, indenyl, anthracenyl or tetrahydronaphthyl;

a "heteroaryl radical" represents a fused or non-fused, optionally cationic, 5- to 22-membered monocyclic or polycyclic group, comprising from 1 to 6 heteroatoms chosen from nitrogen, oxygen, sulfur and selenium, and at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, dihydrothiazolyl, imidazopyridyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazinyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl, xanthyl and the ammonium salt thereof;

a "heterocyclic radical" or "heterocycle" is a fused or non-fused, 5- to 22-membered monocyclic or polycyclic non-aromatic radical, comprising from 1 to 6 heteroatoms chosen from nitrogen, oxygen, sulfur and selenium;

a "heterocycloalkyl radical" is a heterocyclic radical comprising at least one saturated ring;

a "cationic heteroaryl radical" is a heteroaryl group as defined previously, which comprises a quaternized endocyclic or exocyclic cationic group,
when the cationic charge is endocyclic, it is included in the electron delocalization via the mesomeric effect, for example it is a pyridinium, imidazolium or indolinium group;

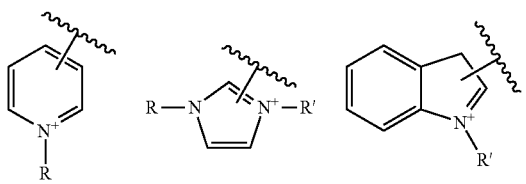

with R and R' being a heteroaryl substituent as defined previously and particularly a (hydroxy)(C$_1$-C$_8$)alkyl group such as methyl;
when the cationic charge is exocyclic, for example, it is an ammonium or phosphonium substituent R$^+$ such as trimethylammonium, which is outside the heteroaryl such as pyridyl, indolyl, imidazolyl or naphthalimidyl in question;

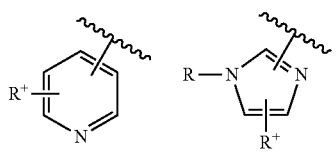

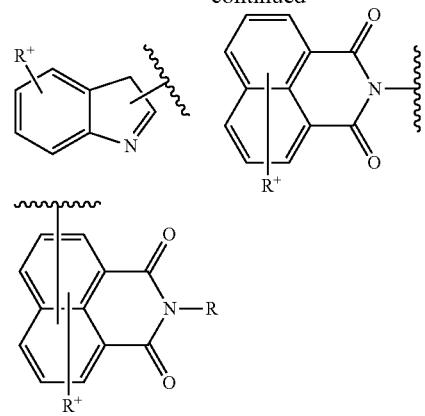

with R being a heteroaryl substituent as defined previously and R' an ammonium R$_a$R$_b$R$_c$N$^+$—, phosphonium R$_a$R$_b$R$_c$P$^+$— or ammonium R$_a$R$_b$R$_c$N$^+$—(C$_1$-C$_6$)alkylamino group with R$_a$, R$_b$ and R$_c$, which may be identical or different, representing a hydrogen atom or a (C$_1$-C$_8$) alkyl group such as methyl;

the term "cationic aryl bearing an exocyclic charge" means an aryl ring whose quaternized cationic group is outside the said ring: it is especially an ammonium or phosphonium substituent R$^+$ such as trimethylammonium, outside the aryl such as phenyl or naphthyl:

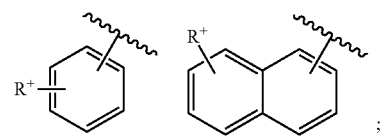

an "alkyl radical" is a linear or branched C$_1$-C$_{20}$ and preferably C$_1$-C$_8$ hydrocarbon-based radical;

an "alkenylene radical" is an unsaturated hydrocarbon-based divalent radical as defined previously, which may contain from 1 to 4 conjugated or unconjugated double bonds —C=C—; the alkenylene group particularly contains 1 or 2 unsaturations;

the term "optionally substituted" attributed to the alkyl radical means that the said alkyl radical may be substituted with one or more radicals chosen from the following radicals: i) hydroxyl, ii) C$_1$-C$_4$ alkoxy, iii) acylamino, iv) amino optionally substituted with one or two identical or different C$_1$-C$_4$ alkyl radicals, the said alkyl radicals possibly forming with the nitrogen atom that bears them a 5- to 7-membered heterocycle, optionally comprising another heteroatom identical to or different from nitrogen; v) or a quaternary ammonium group —N$^+$R'R"R''', M$^-$ for which R', R" and which may be identical or different, represent a hydrogen atom or a C$_1$-C$_4$ alkyl group, or else —N$^+$R'R"R''', forms a heteroaryl such as imidazolium optionally substituted with a C$_1$-C$_4$ alkyl group, and M$^-$ represents the counterion of the organic or mineral acid or of the corresponding halide;

an "alkoxy" radical is an alkyl-oxy radical for which the alkyl radical is a linear or branched C$_1$-C$_{16}$ and preferentially C$_1$-C$_8$ hydrocarbon-based radical;

when the alkoxy group is optionally substituted, this implies that the alkyl group is optionally substituted as defined hereinabove;

the "tone depth" is the unit known to hairstyling professionals, published in the book *Sciences des traitements capillaires* [Hair treatment sciences] by Charles Zviak, 1988, published by Masson, pp. 215 and 278; the tone depths range from 1 (black) to 10 (very light blond), one unit corresponding to one tone; the higher the figure, the lighter the shade;

a "dark" keratin fibre is a keratin fibre whose lightness L* measured in the CIEL L*a*b* system is less than or equal to 45 and preferably less than or equal to 40, given that L*=0 is equivalent to black and L*=100 is equivalent to white;

"naturally or artificially dark hair" means hair whose tone depth is less than or equal to 6 (dark blond) and preferably less than or equal to 4 (chestnut-brown). Artificially dyed hair is hair whose colour has been modified by a coloration treatment, for example a coloration with direct dyes or oxidation dyes;

the term "thickening polymer" means a polymer which, when introduced at 1% by weight in an aqueous solution or an aqueous-alcoholic solution containing 30% ethanol, and at pH 7, or in an oil chosen from liquid petroleum jelly, isopropyl myristate or cyclopentadimethylsiloxane, makes it possible to achieve a viscosity of at least 100 cps and preferably of at least 500 cps, at 25° C. and at a shear rate of 1 $s^{-1}$. This viscosity may be measured using a cone/plate viscometer (Haake R600 rheometer or the like). The thickening polymers may thicken the aqueous phase and/or the fatty phase, preferentially the aqueous phase.

The term "fatty alcohols" means saturated or unsaturated, linear or branched fatty alcohols comprising between 8 and 200 carbon atoms, preferably $C_8$-$C_{40}$.

The term "sparingly ethoxylated" fatty alcohol means a fatty alcohol comprising from 1 to 6 ethylene oxide units and preferably from 1 to 3 ethylene oxide units per molecule;

an "organic or mineral acid salt" is more particularly chosen from salts chosen from a salt derived from i) hydrochloric acid HCl, ii) hydrobromic acid HBr, iii) sulfuric acid $H_2SO_4$, iv) alkylsulfonic acids: Alk-S(O)$_2$OH such as methanesulfonic acid and ethanesulfonic acid; v) arylsulfonic acids: Ar—S(O)$_2$OH such as benzenesulfonic acid and toluenesulfonic acid; vi) citric acid; vii) succinic acid; viii) tartaric acid; ix) lactic acid; x) alkoxysulfinic acids: Alk-O—S(O)OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii) acetic acid $CH_3C(O)OH$; xiv) triflic acid $CF_3SO_3H$; and xv) tetrafluoroboric acid $HBF_4$;

an "anionic counterion" means an anion or an anionic group derived from an organic or mineral acid salt which counterbalances the cationic charge of the dye; more particularly, the anionic counterion is chosen from: i) halides such as chloride or bromide; ii) nitrates; iii) sulfonates, including $C_1$-$C_6$ alkylsulfonates: Alk-S(O)$_2$O$^-$ such as methanesulfonate or mesylate and ethanesulfonate; iv) arylsulfonates: Ar—S(O)$_2$O$^-$ such as benzenesulfonate and toluenesulfonate or tosylate; v) citrate; vi) succinate; vii) tartrate; viii) lactate; ix) alkyl sulfates: Alk-O—S(O)O$^-$ such as methyl sulfate and ethyl sulfate; x) aryl sulfates: Ar—O—S(O)O$^-$ such as benzene sulfate and toluene sulfate; xi) alkoxy sulfates: Alk-O—S(O)$_2$O$^-$ such as methoxy sulfate and ethoxy sulfate; xii) aryloxy sulfates: Ar—O—S(O)$_2$O$^-$, xiii) phosphates O=P(OH)$_2$—O$^-$, O=P(O$^-$)$_2$—OH O=P(O$^-$)$_3$, HO—[P(O)(O$^-$)]$_w$—P(O)(O$^-$)$_2$ with w being an integer; xiv) acetate; xv) triflate; and xvi) borates such as tetrafluoroborate, xvii) disulfate (O=)$_2$S(O$^-$)$_2$ or $SO_4^{2-}$ and monosulfate $HSO_4^-$;

the anionic counterion, derived from the organic or mineral acid salt, ensures the electrical neutrality of the molecule; thus, it is understood that when the anion comprises several anionic charges, then the same anion may serve for the electrical neutrality of several cationic groups in the same molecule or else may serve for the electrical neutrality of several molecules; for example, a disulfide dye of formula (I) which contains two cationic chromophores may contain either two "singly charged" anionic counterion or a "doubly charged" anionic counterion such as (O=)$_2$S(O$^-$)$_2$ or O=P(O$^-$)$_2$—OH;

moreover, the addition salts that may be used in the context of the invention are especially chosen from addition salts with a cosmetically acceptable base such as basifying agents as defined below, for instance alkali metal hydroxides such as sodium hydroxide, potassium hydroxide, aqueous ammonia, amines or alkanolamines;

the term "at least one" is equivalent to the term "one or more"; and the term "inclusive" for a range of concentrations means that the limits of that range are included in the defined range.

1). THE COMPOSITION OF THE INVENTION

The composition according to the invention is cosmetic, i.e. it is in a cosmetic medium and comprises:
i) at least one cationic direct dye bearing a disulfide function, a thiol function or a protected-thiol function;
ii) at least one sparingly ethoxylated or non-ethoxylated fatty alcohol;
iii) at least one cationic surfactant;
iv) at least one alkaline agent; and
v) at least one reducing agent;

The Cosmetic Medium:

The term "cosmetic medium" means a medium that is suitable for dyeing keratin fibres, also known as a dye support, which is a cosmetic medium generally formed from water or a mixture of water and one or more organic solvents or a mixture of organic solvents. Preferably, the composition comprises water in a content especially inclusively between 5% and 95% relative to the total weight of the composition.

The term "organic solvent" means an organic substance that is capable of dissolving another substance without chemically modifying it.

Organic Solvents:

Examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

The organic solvents are preferably present in proportions preferably inclusively between 0.1% and 40% by weight approximately relative to the total weight of the dye composition, more preferentially between 1% and 30% by weight approximately and even more particularly inclusively between 5% and 25% by weight relative to the total weight of the composition.

i) Direct Dyes Bearing a Disulfide or Thiol Function of the Invention:

The direct dye(s) bearing a disulfide, thiol or protected-thiol function used in the invention are of formula (I) as defined previously.

According to one particular mode of the invention, the dyes (I) are disulfide dyes, i.e. for which U represents the following radical a) —S—C'$_{sat}$—(X')$_{p'}$-A', and more particularly the dyes of formula (I) are symmetrical, i.e. they are such that A=A', C$_{sat}$=C'$_{sat}$, X=X' and p=p'.

According to another particular mode of the invention, the dyes of formula (I) bearing a thiol function are as defined previously, i.e. U representing the radical b) Y.

Another particular embodiment of the invention relates to fluorescent dyes bearing a disulfide, thiol or protected-thiol function.

i). 1) Y:

According to one particular embodiment of the invention, the direct dye of formula (I) is a thiol dye, i.e. Y represents i) a hydrogen atom.

In accordance with another particular embodiment of the invention, in the abovementioned formula (I), Y is a protecting group known to those skilled in the art, for instance those described in the publications "*Protective Groups in Organic Synthesis*", T. W. Greene, published by John Wiley & Sons, NY, 1981, pp. 193-217; "Protecting Groups", P. Kocienski, Thieme, 3rd edition, 2005, chapter 5, and Ullmann's Encyclopedia, "*Peptide Synthesis*", pp. 4-5, 2005 Wiley-VCH Verlag GmbH & Co. KGaA, Weinheim 10.1002/14356007.a19 157;

In particular, Y represents a thiol-function protecting group chosen from the following radicals:
- (C$_1$-C$_4$)alkylcarbonyl;
- (C$_1$-C$_4$)alkylthiocarbonyl;
- (C$_1$-C$_4$)alkoxycarbonyl;
- (C$_1$-C$_4$)alkoxythiocarbonyl;
- (C$_1$-C$_4$)alkylthio-thiocarbonyl;
- (di)(C$_1$-C$_4$)(alkyl)aminocarbonyl;
- (di)(C$_1$-C$_4$)(alkyl)aminothiocarbonyl;
- arylcarbonyl, for instance phenylcarbonyl;
- aryloxycarbonyl;
- aryl(C$_1$-C$_4$)alkoxycarbonyl;
- (di)(C$_1$-C$_4$)(alkyl)aminocarbonyl, for instance dimethylaminocarbonyl;
- (C$_1$-C$_4$)(alkyl)arylaminocarbonyl;
- carboxyl;
- SO$_3^-$; M$^+$ with M$^+$ representing an alkali metal such as sodium or potassium, or alternatively a counterion of the cationic chromophore A and M$^+$ are absent;
- optionally substituted aryl such as phenyl, dibenzosuberyl or 1,3,5-cycloheptatrienyl;
  - optionally substituted heteroaryl; especially including the following cationic or non-cationic heteroaryl radicals comprising from 1 to 4 heteroatoms:
    - i) 5-, 6- or 7-membered monocyclic radicals such as furanyl or furyl, pyrrolyl or pyrryl, thiophenyl or thienyl, pyrazolyl, oxazolyl, oxazolium, isoxazolyl, isoxazolium, thiazolyl, thiazolium, isothiazolyl, isothiazolium, 1,2,4-triazolyl, 1,2,4-triazolium, 1,2,3-triazolyl, 1,2,3-triazolium, 1,2,4-oxazolyl, 1,2,4-oxazolium, 1,2,4-thiadiazolyl, 1,2,4-thiadiazolium, pyrylium, thiopyridyl, pyridinium, pyrimidinyl, pyrimidinium, pyrazinyl, pyrazinium, pyridazinyl, pyridazinium, triazinyl, triazinium, tetrazinyl, tetrazinium, azepine, azepinium, oxazepinyl, oxazepinium, thiepinyl, thiepinium, imidazolyl, imidazolium;
    - ii) 8- to 11-membered bicyclic radicals such as indolyl, indolinium, benzimidazolyl, benzimidazolium, benzoxazolyl, benzoxazolium, dihydrobenzoxazolinyl, benzothiazolyl, benzothiazolium, pyridoimidazolyl, pyridoimidazolium, thienocycloheptadienyl, these monocyclic or bicyclic groups being optionally substituted with one or more groups such as (C$_1$-C$_4$)alkyl, for instance methyl, or polyhalo(C$_1$-C$_4$)alkyl, for instance trifluoromethyl;
    - iii) or the following tricyclic ABC radical:

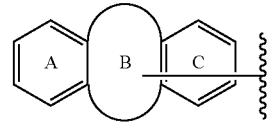

in which the two rings A and C optionally comprise a heteroatom, and ring B is a 5-, 6- or 7-membered ring, particularly a 6-membered ring, and contains at least one heteroatom, for instance piperidyl or pyranyl;
- optionally cationic, optionally substituted heterocycloalkyl, the heterocycloalkyl group especially represents a saturated or partially saturated 5-, 6- or 7-membered monocyclic group comprising from 1 to 4 heteroatoms chosen from oxygen, sulfur and nitrogen, such as di/tetrahydrofuryl, di/tetrahydrothiophenyl, di/tetrahydropyrrolyl, di/tetrahydropyranyl, di/tetra/hexahydrothiopyranyl, dihydropyridyl, piperazinyl, piperidinyl, tetramethylpiperidyl, morpholinyl, di/tetra/hexahydroazepinyl, di/tetrahydropyrimidinyl, these groups being optionally substituted with one or more groups such as (C$_1$-C$_4$) alkyl, oxo or thioxo; or the heterocycle represents the following group:

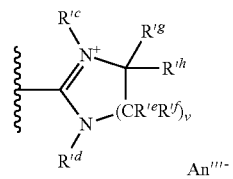

in which R$'^c$, R$'^f$, R$'^g$ and R$'^h$, which may be identical or different, represent a hydrogen atom or a (C$_1$-C$_4$) alkyl group, or alternatively two groups R$'^g$ with R$'^h$, and/or R$'^e$ with R$'^f$, form an oxo or thioxo group, or alternatively R$'^g$ with R$'^e$ together form a cycloalkyl; and v represents an integer between 1 and 3 inclusive; preferentially, R$'^c$ to R$'^h$ represent a hydrogen atom; and An'''$^-$ represents a counterion;
- —C(NR$'^c$R$'^d$)=N$^+$R$'^e$R$'^f$; An'''$^-$ with R$'^c$, R$'^d$, R$'^e$ and R$'^f$, which may be identical or different, representing a hydrogen atom or a (C$_1$-C$_4$)alkyl group; preferentially, R$'^c$ to R$'^f$ represent a hydrogen atom; and An'''$^-$ represents a counterion;
- —C(NR$'^c$R$'^d$)=NR$'^e$; with R$'^c$, R$'^d$ and R$'^e$ as defined previously;
- optionally substituted (di)aryl(C$_1$-C$_4$)alkyl such as 9-anthracenylmethyl, phenylmethyl or diphenylmethyl optionally substituted with one or more groups especially chosen from ($C_1$-$C_4$) alkyl, ($C_1$-$C_4$) alkoxy such as methoxy, hydroxyl, alkylcarbonyl or (di)($C_1$-$C_4$)(alkyl)amino such as dimethylamino;

optionally substituted (di)heteroaryl($C_1$-$C_4$)alkyl, the heteroaryl group especially being a cationic or non-cationic, 5- or 6-membered monocyclic radical comprising from 1 to 4 heteroatoms chosen from nitrogen, oxygen and sulfur, such as pyrrolyl, furanyl, thiophenyl, pyridyl, pyridyl N-oxide such as 4-pyridyl or 2-pyridyl-N-oxide, pyrylium, pyridinium or triazinyl groups, optionally substituted with one or more groups such as alkyl, particularly methyl; advantageously, the (di)heteroaryl($C_1$-$C_4$)alkyl is (di)heteroarylmethyl or (di)heteroarylethyl;

$CR^1R^2R^3$ with $R^1$, $R^2$ and $R^3$, which may be identical or different, representing a halogen atom or a group chosen from:
- ($C_1$-$C_4$)alkyl;
- ($C_1$-$C_4$)alkoxy;
- optionally substituted aryl such as phenyl optionally substituted with one or more groups, for instance ($C_1$-$C_4$)alkyl, ($C_1$-$C_4$)alkoxy or hydroxyl;
- optionally substituted heteroaryl such as thiophenyl, furanyl, pyrrolyl, pyranyl or pyridyl, optionally substituted with a ($C_1$-$C_4$)alkyl group;
- $P(Z^1)R'^1R'^2R'^3$ with $R'^1$ and $R'^2$, which may be identical or different, representing a hydroxyl, ($C_1$-$C_4$) alkoxy or alkyl group, $R'^3$ representing a hydroxyl or ($C_1$-$C_4$)alkoxy group, and $Z^1$ representing an oxygen or sulfur atom;

a sterically hindered ring; and optionally substituted alkoxyalkyl, such as methoxymethyl (MOM), ethoxyethyl (EOM) and isobutoxyethyl.

According to one particular embodiment, the thiol-protected dyes of formula (I) comprise a group Y chosen from i) aromatic cationic 5- or 6-membered monocyclic heteroaryl comprising from 1 to 4 heteroatoms chosen from oxygen, sulfur and nitrogen, such as oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinyl, pyridazinium, triazinium, tetrazinium, oxazepinium, thiepinyl, thiepinium, imidazolium; ii) cationic 8- to 11-membered bicyclic heteroaryl such as indolinium, benzimidazolium, benzoxazolium, benzothiazolium, these monocyclic or bicyclic heteroaryl groups optionally being substituted with one or more groups such as alkyls, for instance methyl, or polyhalo($C_1$-$C_4$)alkyl such as trifluoromethyl; iii) or the following heterocyclic:

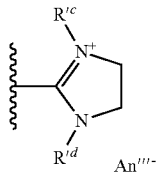

in which $R'^c$ and $R'^d$, which may be identical or different, represent a hydrogen atom or a group ($C_1$-$C_4$)alkyl; preferentially $R'^c$ to $R'^d$ represent a group ($C_1$-$C_4$)alkyl such as methyl; and $An'''^-$ represents a counterion.

In particular, Y represents a group chosen from oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinium, pyridazinium, triazinium and imidazolium, benzimidazolium, benzoxazolium, benzothiazolium, these groups being optionally substituted with one or more ($C_1$-$C_4$)alkyl groups, especially methyl.

In particular, Y represents a protecting group such as:
- ($C_1$-$C_4$)alkylcarbonyl, for instance methylcarbonyl or ethylcarbonyl;
- arylcarbonyl, for instance phenylcarbonyl;
- ($C_1$-$C_4$)alkoxycarbonyl;
- aryloxycarbonyl;
- aryl($C_1$-$C_4$)alkoxycarbonyl;
- (di)($C_1$-$C_4$)(alkyl)aminocarbonyl, for instance dimethylaminocarbonyl;
- ($C_1$-$C_4$)(alkyl)arylaminocarbonyl;
- optionally substituted aryl such as phenyl;
- 5- or 6-membered monocyclic heteroaryl such as imidazolyl or pyridyl;
- cationic 5- or 6-membered monocyclic heteroaryl such as pyrylium, pyridinium, pyrimidinium, pyrazinium, pyridazinium, triazinium, imidazolium; these groups being optionally substituted with one or more identical or different ($C_1$-$C_4$)alkyl groups such as methyl;
- cationic 8- to 11-membered bicyclic heteroaryl such as benzimidazolium or benzoxazolium; these groups being optionally substituted with one or more identical or different ($C_1$-$C_4$)alkyl groups such as methyl;
- cationic heterocycle having the following formula:

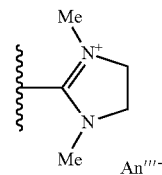

—$C(NH_2)=N^+H_2$; $An''''^-$; with $An''''^-$ being an anionic counterion as defined previously;

—$C(NH_2)=NH$;

$SO_3^-$, $M^+$ with $M^+$ representing an alkali metal such as sodium or potassium.

i). 2) $C_{sat}$ and $C'_{sat}$:

As indicated previously, in formula (I), $C_{sat}$ and $C'_{sat}$, independently of each other, represent a linear or branched or cyclic, optionally substituted $C_1$-$C_{18}$ alkylene chain.

Substituents that may be mentioned include the following groups: i) amino, ii) ($C_1$-$C_4$)alkylamino, iii) ($C_1$-$C_4$)dialkylamino, or the group iv) $R^a$—$Z^a$—$C(Z^b)$—$Z^c$—, in which $Z^a$, $Z^b$, which may be identical or different, represent an oxygen or sulfur atom, or a group $NR^{a'}$, $Z^c$, representing a bond, an oxygen or sulfur atom or a group $NR^a$ and $R^a$, represents an alkali metal, a hydrogen atom or a $C_1$-$C_4$ alkyl group and $R^{a'}$ represents a hydrogen atom or a $C_1$-$C_4$ alkyl group; more particularly, the groups iv) are chosen from carboxylate —C(O)O$^-$ or —C(O)OMetal (Metal=alkali metal), carboxyl —C(O)—OH, guanidino $H_2H$—C($NH_2$)—NH—, amidino $H_2H$—C($NH_2$)—, (thio)ureo $H_2N$—C(O)—NH— and $H_2N$—C(S)—NH—, aminocarbonyl —C(O)—$NRa'_2$ or aminothiocarbonyl —C(S)—$NRa'_2$; carbamoyl Ra'—C(O)—NRa'— or thiocarbamoyl Ra'—C(S)—NRa'— with Ra', which may be identical or different, representing a hydrogen atom or a ($C_1$-$C_4$) alkyl group; the said substituent(s) are preferably present on the carbon in the beta or gamma position relative to the sulfur atoms of the disulfide, thiol or protected-thiol group.

Preferably, in the case of formula (I), $C_{sat}$ and $C'_{sat}$ represent a chain —$(CH_2)_k$— with k being an integer between 1 and 8 inclusive.

i). 3) X and X':

In accordance with one particular embodiment of the invention, in the above-mentioned formula (I), when p and p' is equal to 1, the radicals X and X', which may be identical or different, represent the following sequence:

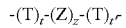

the said sequence being linked in formula (I) symmetrically as follows:

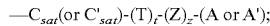

in which:
  T and T', which may be identical or different, represent one or more radicals or combinations thereof chosen from:
    —O—; —S—; —N(R)—; —N$^+$(R)(R°)—; —S(O)—; —S(O)$_2$—; —C(O)—; with R, R°, which may be identical or different, representing a hydrogen atom, a $C_1$-$C_4$ alkyl radical, $C_1$-$C_4$ hydroxyalkyl radical or an aryl($C_1$-$C_4$)alkyl radical; and a cationic or non-cationic, preferentially monocyclic heterocycloalkyl or heteroaryl radical, preferentially containing two heteroatoms (more preferentially two nitrogen atoms) and preferentially being 5- to 7-membered, more preferentially imidazolium;
  the indices t and t', which may be identical or different, are equal to 0 or 1;
  Z represents:
    —$(CH_2)_m$— radical with m being an integer between 1 and 8;
    —$(CH_2CH_2O)_q$— or —$(OCH_2CH_2)_q$— in which q is an integer between 1 and 5 inclusive;
    an aryl, alkylaryl or arylalkyl radical in which the alkyl radical is $C_1$-$C_4$ and the aryl radical is preferably $C_6$, being optionally substituted with at least one group $SO_3M$ with M representing a hydrogen atom, an alkali metal or an ammonium group substituted with one or more identical or different, linear or branched $C_1$-$C_{18}$ alkyl radicals optionally bearing at least one hydroxyl;
  z is 0 or 1.

Moreover, according to one particular embodiment of the invention, Z represents:

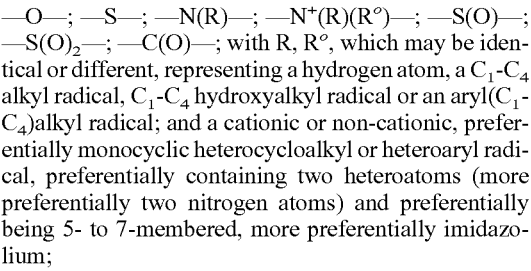

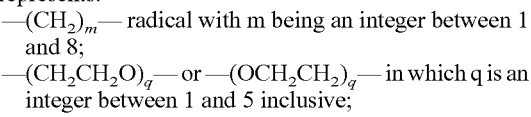

in which M represents a hydrogen atom, an alkali metal or an ammonium group or an ammonium group substituted with one or more identical or different, linear or branched $C_1$-$C_{10}$ alkyl radicals optionally bearing at least one hydroxyl; 0-4 represents an integer between 0 and 4 inclusive, and q represents an integer inclusively between 1 and 6.

i). 4). A and A':

The radicals A and/or A' of formula (I) contain at least one quaternized cationic chromophore or at least one chromophore bearing a quaternized or quaternizable cationic group.

According to one preferred embodiment of the invention, the dyes (I) according to the invention are disulfides and comprise identical quaternized cationic chromophores A and A'.

More particularly, the dyes of formula (I) according to the invention are symmetrical disulfides, i.e. they contain a $C_2$ axis of symmetry, i.e. formula (I) is such that:

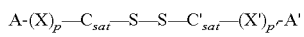

with A=A', X=X', p=p', $C_{sat}$=$C'_{sat}$.

As chromophores that are useful, mention may be made of those derived from the following dyes: acridines; acridones; anthrapyrimidines; anthranthrones; anthrapyrimidines; anthraquinones; azines; (poly)azos, hydrazono or hydrazones, in particular arylhydrazones; azomethines; benzanthrones; benzimidazoles; benzimidazolones; benzindoles; benzoxazoles; benzopyrans; benzothiazoles; benzoquinones; bisazines; bis-isoindolines; carboxanilides; coumarins; cyanins such as azacarbocyanins, diazacarbocyanins, diazahemicyanins, hemicyanin, or tetraazacarbocyanins; diazines; diketopyrrolopyrroles; dioxazines; diphenylamines; diphenylmethanes; dithiazines; flavonoids such as flavanthrones and flavones; fluorindines; formazans; indamines; indanthrones; indigoids and pseudo-indigoids; indophenols; indoanilines; isoindolines; isoindolinones; isoviolanthrones; lactones; (poly)methines such as dimethines of stilbene or styryl type; naphthalimides; naphthanilides; naphtholactams; naphthoquinones; nitro, especially nitro(hetero)aromatics; oxadiazoles; oxazines; perilones; perinones; perylenes; phenazines; phenoxazine; phenothiazines; phthalocyanin; polyenes/carotenoids; porphyrins; pyranthrones; pyrazolanthrones; pyrazolones; pyrimidinoanthrones; pyronines; quinacridones; quinolines; quinophthalones; squaranes; tetrazoliums; thiazines, thioindigo; thiopyronines; triarylmethanes, or xanthenes.

Among the cationic azo chromophores, mention may be made particularly of those derived from the cationic dyes described in the *Kirk Othmer Encyclopedia of Chemical Technology*, "Dyes, Azo", J. Wiley & Sons, updated on 19 Apr. 2010.

Among the azo chromophores A and/or A' that may be used according to the invention, mention may be made of the cationic azo dyes described in patent applications WO 95/15144, WO-95/01772 and EP-714954.

According to one preferred embodiment of the invention, the coloured chromophore A and/or A' is chosen from cationic chromophores, preferentially those derived from dyes known as "basic dyes".

Among the azo chromophores, mention may be made of those described in the Colour Index International 3rd edition, and especially the following compounds:
  Basic Red 22
  Basic Red 76
  Basic Yellow 57
  Basic Brown 16
  Basic Brown 17

Among the cationic quinone chromophores A and/or A', those mentioned in the abovementioned Colour Index Inter-

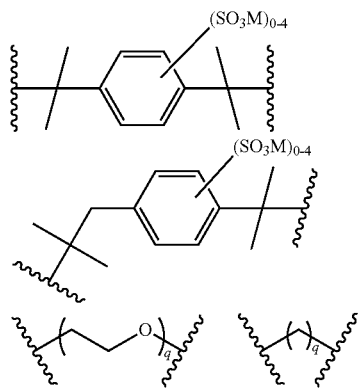

national are suitable for use, and among those, mention may be made, inter alia, of the radicals derived from the following dyes:
Basic Blue 22
Basic Blue 99

Among the cationic azine chromophores A and/or A', those listed in the Colour Index International are suitable for use, and among those, for example the radicals derived from the following dyes:
Basic Blue 17
Basic Red 2.

Among the cationic triarylmethane chromophores A and/or A' that may be used according to the invention, mention may be made, besides those listed in the Colour Index, of the radicals derived from the following dyes:
Basic Green 1
Basic Violet 3
Basic Violet 14
Basic Blue 7
Basic Blue 26.

Mention may also be made of the cationic chromophores derived from the dyes described in documents U.S. Pat. No. 5,888,252, EP 1 133 975, WO 03/029 359, EP 860 636, WO 95/01772, WO 95/15144 and EP 714 954. Mention may also be made of those listed in the encyclopaedia "The chemistry of synthetic dye" by K. Venkataraman, 1952, Academic press vol. 1 to 7, in Kirk Othmer's encyclopaedia "Chemical technology", in the chapter "Dyes and dye intermediates", 1993, Wiley and sons, and in various chapters of "Ullmann's Encyclopedia of Industrial Chemistry" 7th edition, Wiley and sons.

Preferably, the chromophores A and/or A' are chosen from those derived from dyes of azo and hydrazono type.

According to one particular embodiment, the cationic radicals A and/or A' in formula (I) comprise at least one cationic azo chromophore derived from a dye described in EP 850 636, FR 2 788 433, EP 920 856, WO 99/48465, FR 2 757 385, EP 85/0637, EP 91/8053, WO 97/44004, FR 2 570 946, FR 2 285 851, DE 2 538 363, FR 2 189 006, FR 1 560 664, FR 1 540 423, FR 1 567 219, FR 1 516 943, FR 1 221 122, DE 4 220 388, DE 4 137 005, WO 01/66646, U.S. Pat. No. 5,708,151, WO 95/01772, WO 515 144, GB 1 195 386, U.S. Pat. No. 3,524,842, U.S. Pat. No. 5,879,413, EP 1 062 940, EP 1 133 976, GB 738 585, DE 2 527 638, FR 2 275 462, GB 1974-27645, *Acta Histochem.* (1978), 61(1), 48-52; Tsitologiya (1968), 10(3), 403-5; Zh. Obshch. Khim. (1970), 40(1), 195-202; Ann. Chim. (Rome) (1975), 65(5-6), 305-14; Journal of the Chinese Chemical Society (Taipei) (1998), 45(1), 209-211; Rev. Roum. Chim. (1988), 33(4), 377-83; Text. Res. J. (1984), 54(2), 105-7; Chim. Ind. (Milan) (1974), 56(9), 600-3; Khim. Tekhnol. (1979), 22(5), 548-53; Ger. Monatsh. Chem. (1975), 106(3), 643-8; MRL Bull. Res. Dev. (1992), 6(2), 21-7; Lihua Jianyan, Huaxue Fence (1993), 29(4), 233-4; Dyes Pigm. (1992), 19(1), 69-79; Dyes Pigm. (1989), 11(3), 163-72.

According to one variant, A and/or A' of formula (I) contain at least one cationic radical borne by, or included in, at least one of the chromophores.

Preferably, the cationic radical is a quaternary ammonium; more preferentially, the cationic charge is endocyclic.

These cationic radicals are, for example, a cationic radical:
bearing an exocyclic (di/tri)($C_1$-$C_8$)alkylammonium charge, or
bearing an endocyclic charge, such as the following cationic heteroaryl groups: acridinium, benzimidazolium, benzobistriazolium, benzopyrazolium, benzopyridazinium, benzoquinolium, benzothiazolium, benzotriazolium, benzoxazolium, bipyridinium, bis-tetrazolium, dihydrothiazolium, imidazopyridinium, imidazolium, indolium, isoquinolium, naphthoimidazolium, naphthoxazolium, naphthopyrazolium, oxadiazolium, oxazolium, oxazolopyridinium, oxonium, phenazinium, phenoxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium or xanthylium.

Mention may be made of the hydrazono cationic chromophores of formulae (II) and (III'), and the azo cationic chromophores (IV), (IV'), (V) and (V') below:

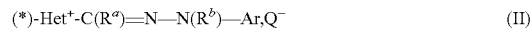  (II)

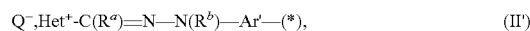  (II')

  (III)

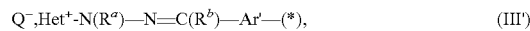  (III')

  (IV)

  (IV')

  (V)

  (V')

formulae (II) to (V') with:
Het$^+$ representing a cationic heteroaryl radical, preferentially bearing an endocyclic cationic charge, such as imidazolium, indolium or pyridinium, optionally substituted, preferentially with one or more ($C_1$-$C_8$) alkyl groups such as methyl;
Ar$^+$ represents an aralkyl radical, such as phenyl or naphthyl, bearing an exocyclic cationic charge, particularly tri($C_1$-$C_8$)alkylammonium such as trimethylammonium;
Ar represents an aryl group, especially phenyl, optionally substituted, preferentially with one or more electron-donating groups such as i) optionally substituted ($C_1$-$C_8$)alkyl, ii) optionally substituted ($C_1$-$C_8$)alkoxy, iii) (di)($C_1$-$C_8$)(alkyl)amino optionally substituted on the alkyl group(s) with a hydroxyl group, iv) aryl($C_1$-$C_8$) alkylamino, v) optionally substituted N—($C_1$-$C_8$)alkyl-N-aryl($C_1$-$C_8$)alkylamino or alternatively Ar represents a julolidine group;
Ar' is an optionally substituted divalent (hetero)alkylene group such as phenylene, particularly para-phenylene, or naphthalene, which are optionally substituted, preferentially with one or more groups ($C_1$-$C_8$)alkyl, hydroxyl or ($C_1$-$C_8$)alkoxy;
Ar" is an optionally substituted (hetero)aryl group such as phenyl or pyrazolyl, which are optionally substituted, preferentially with one or more groups ($C_1$-$C_8$)alkyl, hydroxyl, (di)($C_1$-$C_8$)(alkyl)amino, ($C_1$-$C_8$)alkoxy or phenyl;
R$^a$ and R$^b$, which may be identical or different, represent a hydrogen atom or a group ($C_1$-$C_8$)alkyl, which is optionally substituted, preferentially with a hydroxyl group; or alternatively the substituent R$^a$ with a substituent of Het$^+$ and/or R$^b$ with a substituent of Ar form, together with the atoms that bear them, a (hetero)cycloalkyl; particularly, R$^a$ and R$^b$ represent a hydrogen atom or a group ($C_1$-$C_4$) alkyl, which is optionally substituted with a hydroxyl group;

Q⁻ represents an organic or mineral anionic counterion such as a halide or an alkyl sulfate;

(*) represents the part of the chromophore linked to the rest of the molecule of formula (I).

In particular, mention may be made of the azo and hydrazono chromophores bearing an endocyclic cationic charge of formulae (II) to (IV') as defined previously. More particularly those of formulae (II) to (IV') derived from the dyes described in patent applications WO 95/15144, WO 95/01772 and EP-714954. Preferentially the following chromophores:

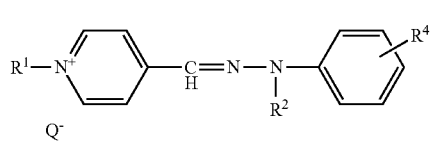

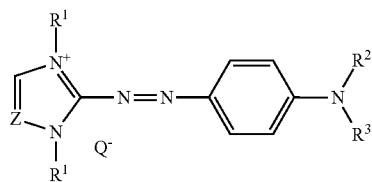

formulae (III-1) and (IV-1) with:

$R^1$ representing a group $(C_1-C_4)$alkyl such as methyl;

$R^2$ and $R^3$, which may be identical or different, representing a hydrogen atom or a group $(C_1-C_4)$alkyl such as methyl; and $R^4$ representing a hydrogen atom or an electron-donating group such as optionally substituted $(C_1-C_8)$alkyl, optionally substituted $(C_1-C_8)$alkoxy, or $(di)(C_1-C_8)$(alkyl)amino optionally substituted on the alkyl group(s) with a hydroxyl group; particularly, $R^4$ is a hydrogen atom, Z represents a group CH or a nitrogen atom, preferentially CH, Q⁻ is as defined previously;

it being understood that the chromophore (II-1) or (IV-1) is linked to the rest of the molecule of formula (I) by $R^2$, $R^1$ or $R^4$ in which case one of the hydrogen atoms of $R^2$, $R^1$ or $R^4$ is substituted with X or X' if p=1 or p'=1 or alternatively with $C_{sat}$ or $C_{sat'}$ if p=0 or p'=0.

Particularly, the chromophores (1'-1) and (IV-1) are derived from Basic Red 51, Basic Yellow 87 and Basic Orange 31 or derivatives thereof:

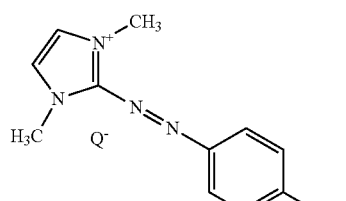

Basic Orange 31

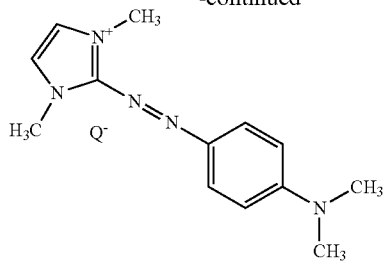

Basic Red 51

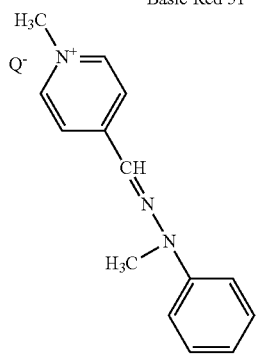

Basic Yellow 87 with Q' being an anionic counterion as defined previously, particularly a halide such as chloride or an alkyl sulfate such as methyl sulfate or mesityl.

According to one particular embodiment of the invention, the dyes of formula (I) are fluorescent, i.e. they contain at least one fluorescent chromophore as defined previously.

As fluorescent chromophores A and/or A' that are useful in the present invention, mention may be made of radicals derived from the following dyes: acridines, acridones, benzanthrones, benzimidazoles, benzimidazolones, benzindoles, benzoxazoles, benzopyrans, benzothiazoles, coumarins, difluoro{2-[(2H-pyrrol-2-ylidene-kN)methyl]-1H-pyrrolato-kN}bores (BODIPY®), diketopyrrolopyrroles, fluorindines, (poly)methines (especially cyanins and styryls/hemicyanins), naphthalimides, naphthanilides, naphthylamine (such as dansyls), oxadiazoles, oxazines, perilones, perinones, perylenes, polyenes/carotenoids, squaranes, stilbenes and xanthenes.

Mention may also be made of the fluorescent dyes A and/or A' described in documents EP 1 133 975, WO 03/029 359, EP 860 636, WO 95/01772, WO 95/15144, EP 714 954 and those listed in the encyclopaedia *The chemistry of synthetic* dyes by K. Venkataraman, 1952, Academic Press, vol. 1 to 7, in Kirk Othmer's encyclopaedia *Chemical Technology*, in the chapter "Dyes and dye Intermediates", 1993, Wiley and Sons, and in various chapters of *Ullmann's Encyclopedia of Industrial Chemistry* 7th edition, Wiley and Sons, and in *The Handbook—A Guide to Fluorescent Probes and Labeling Technologies*, 10th Ed Molecular Probes/Invitrogen—Oregon 2005 circulated on the Internet or in the preceding printed editions.

According to one preferred variant of the invention, the fluorescent chromophore A and/or A' is cationic and comprises at least one quaternary ammonium radical such as those derived from the polymethine dyes of formulae (VI) and (VI') below:

W⁺—[C(Rᶜ)═C(Rᵈ)]ₘ—Ar'—(*)Q- (VI)

Ar—[C(Rᵈ)═C(Rᶜ)]ₘ—W'⁺—(*)Q⁻ (VI')

formula (VI) or (VI') with:
W+ representing a cationic heterocyclic or heteroaryl group, particularly comprising a quaternary ammonium group optionally substituted with one or more groups ($C_1$-$C_8$) alkyl optionally substituted especially with one or more hydroxyl groups;
representing a divalent heterocyclic or heteroaryl radical as defined for W+;
Ar representing an aryl group such as phenyl or naphthyl, optionally substituted preferentially with i) one or more halogen atoms such as chlorine or fluorine; ii) one or more groups ($C_1$-$C_8$)alkyl, preferably of $C_1$-$C_4$ such as methyl; iii) one or more hydroxyl groups; iv) one or more ($C_1$-$C_8$)alkoxy groups such as methoxy; v) one or more hydroxy($C_1$-$C_8$)alkyl groups such as hydroxyethyl, vi) one or more amino groups or (di)($C_1$-$C_8$)alkylamino, preferably with the $C_1$-$C_4$ alkyl part optionally substituted with one or more hydroxyl groups, such as (di)hydroxyethylamino, vii) with one or more acylamino groups; viii) one or more heterocycloalkyl groups such as piperazinyl, piperidyl or 5- or 6-membered heteroaryl such as pyrrolidinyl, pyridyl and imidazolinyl;
Ar' is a divalent aryl radical as defined for Ar;
m' represents an integer between 1 and 4 inclusive, and in particular m is 1 or 2; more preferentially 1;
$R^c$ and $R^d$, which may be identical or different, represent a hydrogen atom or an optionally substituted group ($C_1$-$C_8$)alkyl, preferentially of $C_1$-$C_4$, or alternatively $R^c$ contiguous with W+ or W'+ and/or $R^d$ contiguous with Ar or Ar' form, with the atoms that bear them, a (hetero)cycloalkyl, particularly $R^c$ is contiguous with W+ or W'+ and forms a (hetero)cycloalkyl such as cyclohexyl;
Q− is an organic or mineral anionic counterion as defined previously;
(*) represents the part of the chromophore linked to the rest of the molecule of formula (I).

According to another variant, the disulfide, thiol or protected-thiol dye is a quaternized or quaternizable fluorescent dye such that, in formula (I) with p and p' equal to 1 and A and/or A' representing a naphthalimidyl radical optionally bearing an exocyclic cationic charge of formula (VII) or (VII'):

(VII)

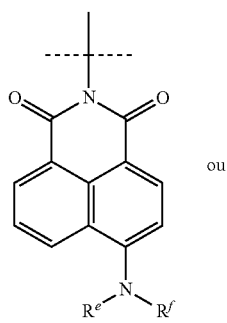

ou (VII')

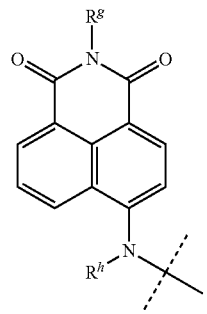

in which formulae (VII) and (VII'):
$R^e$, $R^f$, $R^g$ and $R^h$, which may be identical or different, representing a hydrogen atom or a ($C_1$-$C_6$) alkyl group which is optionally substituted, preferentially with a di($C_1$-$C_6$)alkylamino or tri($C_1$-$C_6$)alkyl ammonium group such as trimethylammonium;

┼ representing the bond the links the naphthalimidyl radical to the rest of the molecule via X or X', if p=1 or p'=1 or alternatively via Csat or Csat' if p=0 or p'=0.

According to one embodiment of the invention, p=1, z=f=0, t=1 and T represents —N(R)—, preferably in the para position on Ar relative to the olefin function —C($R^c$)═C($R^d$)—.

Particularly, in one variant, p=1, z=t'=0, t=1 and T represents —N(R)—, preferably in the para position on Ar relative to the styryl function —C(Rc)═C(Rd)- and T' represents a group —N(R)— or —N+(R)($R^o$)— or an imidazolium.

Preferably, W+ or W'+ is an imidazolium, pyridinium, benzimidazolium, pyrazolium, benzothiazolium or quinolinium optionally substituted with one or more identical or different $C_1$-$C_4$ alkyl radicals.

According to one particularly preferred embodiment of the invention, A and/or A' represent the chromophore (VI') as defined previously with m'=1, Ar representing a phenyl group substituted para to the styryl group —C($R^d$)═C($R^c$)— with a group (di)(hydroxy)($C_1$-$C_6$)(alkyl)amino such as dihydroxy($C_1$-$C_4$)alkylamino, and representing an imidazolium or pyridinium group, preferentially ortho- or para-pyridinium.

As examples of dyes of the invention, mention may be made of the disulfide dyes chosen from formulae (VIII) to (XIV) and the thiol or protected-thiol dyes chosen from formulae (VIII') to (XIV') below:

(VIII)

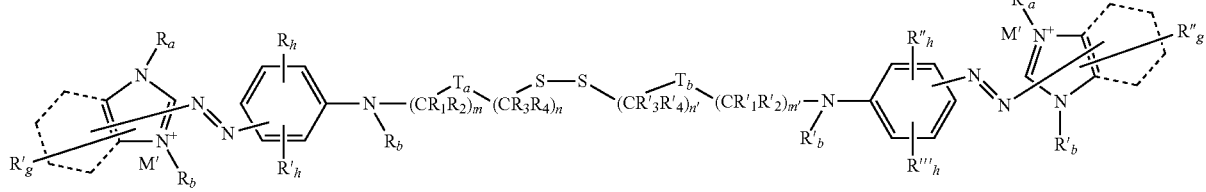

-continued
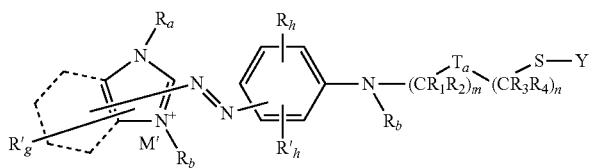
(VIII')
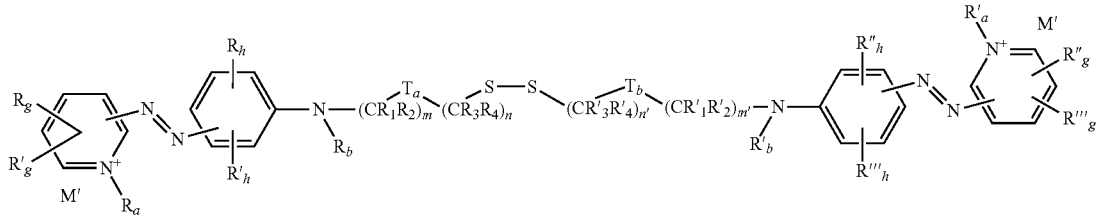
(IX)
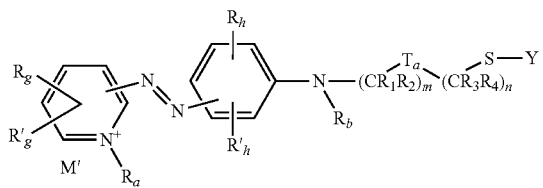
(IX')
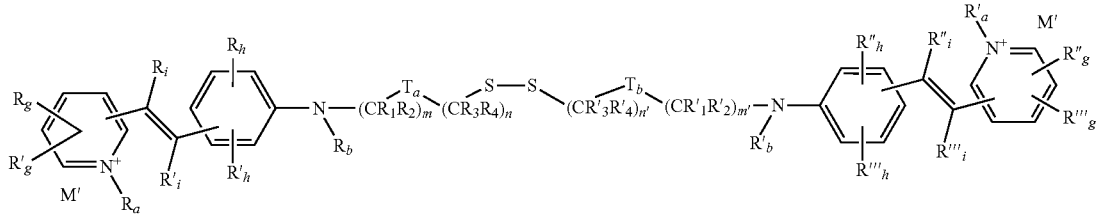
(X)
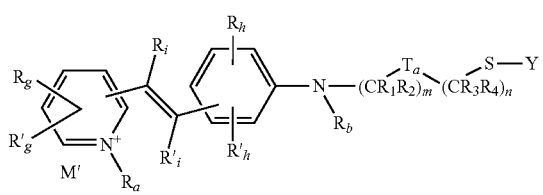
(X')
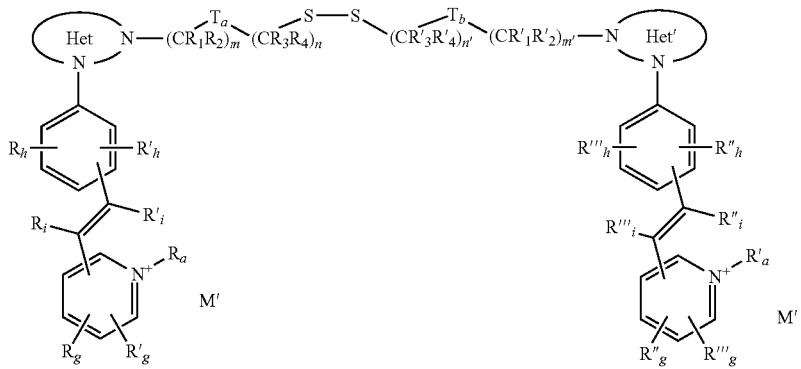
(XI)

-continued
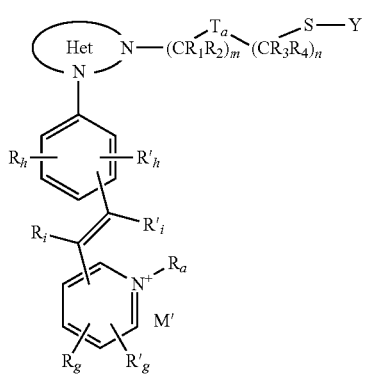
(XI')
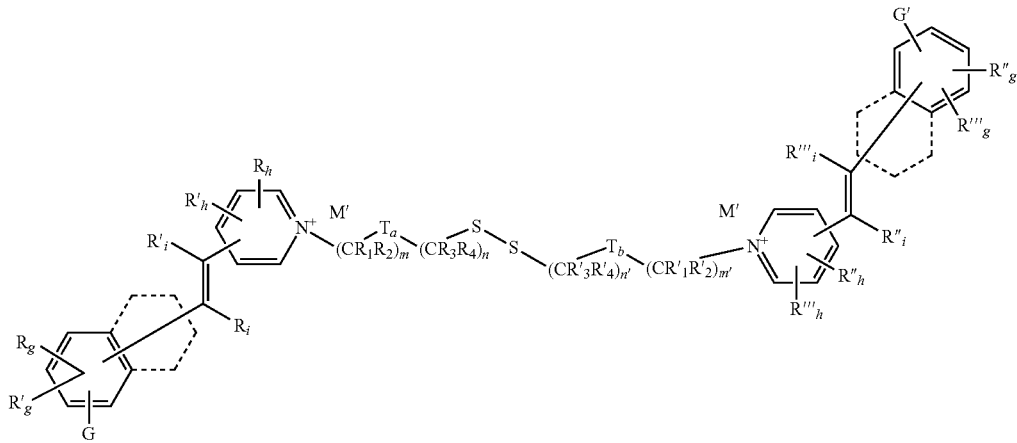
(XII)
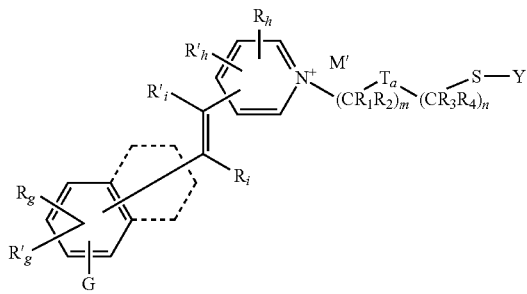
(XII')
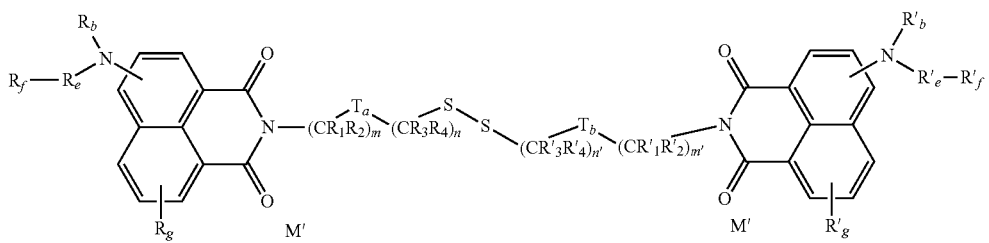
(XIII)
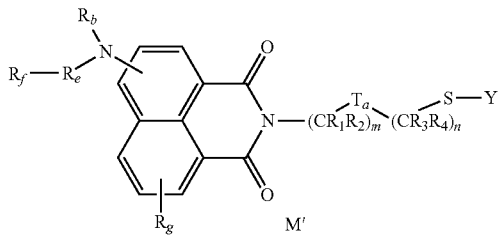
(XIII')

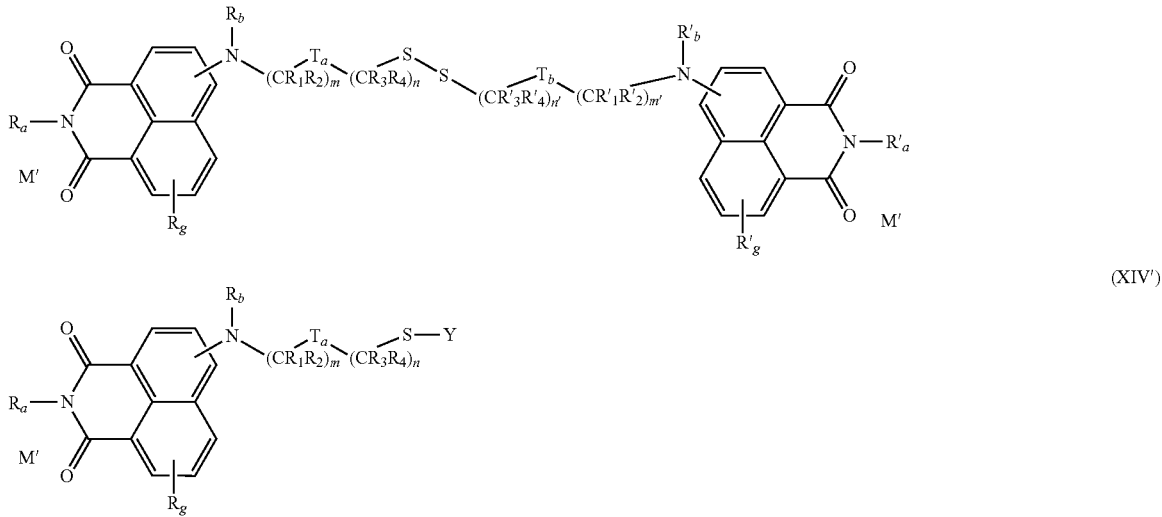

in which formulae (VIII) to (XIV) and (VIII') to (XIV'):

- G and G', which may be identical or different, represent a group —$NR_cR_d$, —$NR'_cR'_d$ or $C_1$-$C_6$ alkoxy which is optionally substituted, preferentially unsubstituted; preferentially, G and G' represent a group —$NR_cR_d$ or —$NR'_cR'_d$, respectively;
- $R^1$, $R^2$, $R^3$ and $R^4$, which may be identical or different, represent a hydrogen atom or a $C_1$-$C_6$ alkyl group; preferentially a hydrogen atom;
- $R_a$ and $R'_a$, which may be identical or different, represent an aryl($C_1$-$C_4$)alkyl group or a $C_1$-$C_6$ alkyl group optionally substituted with a hydroxyl or amino, $C_1$-$C_4$ alkylamino or $C_1$-$C_4$ dialkyl amino group, the said alkyl radicals possibly forming, with the nitrogen atom that bears them, a 5- to 7-membered heterocycle, optionally comprising another nitrogen or non-nitrogen heteroatom; preferentially, $R_a$ and $R'_a$ represent a $C_1$-$C_3$ alkyl group optionally substituted with a hydroxyl group, or a benzyl group;
- $R_b$ and $R'_b$, which may be identical or different, represent a hydrogen atom, an aryl($C_1$-$C_4$)alkyl group or a $C_1$-$C_6$ alkyl group that is optionally substituted; preferentially, $R_b$ and $R'_b$ represent a hydrogen atom or a $C_1$-$C_3$ alkyl or benzyl group;
- $R_c$, $R'_c$, $R_d$ and $R'_d$, which may be identical or different, represent a hydrogen atom, an aryl($C_1$-$C_4$)alkyl or $C_1$-$C_6$ alkoxy group or a $C_1$-$C_6$ alkyl group that is optionally substituted; $R_c$, $R'_c$, $R_d$ and $R'_d$ preferentially represent a hydrogen atom, a hydroxyl, $C_1$-$C_3$ alkoxy, amino or $C_1$-$C_3$ (di)alkylamino group, or a $C_1$-$C_3$ alkyl group that is optionally substituted with i) a hydroxyl group, ii) amino, iii) $C_1$-$C_3$ (di)alkylamino, or iv) quaternary ammonium $(R'')(R''')(R'''')N^+$—;
- or alternatively two adjacent radicals $R_c$ and $R_d$, $R'_c$ and $R'_d$ borne by the same nitrogen atom together form a heterocyclic or heteroaryl group; preferentially, the heterocycle or heteroaryl is monocyclic and 5- to 7-membered; more preferentially, the groups are chosen from imidazolyl and pyrrolidinyl;
- $R_e$ and $R'_e$, which may be identical or different, represent a linear or branched $C_1$-$C_6$ alkylene or $C_2$-$C_6$ alkenylene hydrocarbon-based chain;
- $R_f$ and $R'_f$, which may be identical or different, represent a group di($C_1$-$C_4$)alkylamino, $(R'')(R''')N$— or a quaternary ammonium group $(R'')(R''')(R'''')N^+$— in which R'', R''' and R'''', which may be identical or different, represent a hydrogen atom or a $C_1$-$C_4$ alkyl group or alternatively $(R'')(R''')(R'''')N^+$— represent an optionally substituted cationic heteroaryl group, preferentially an imidazolinium group optionally substituted with a $C_1$-$C_3$ alkyl group;
- $R_g$, $R'_g$, $R''_g$, $R'''_g$, $R_h$, $R'_h$, $R''_h$, and $R'''_h$, which may be identical or different, represent a hydrogen atom, a halogen atom, an amino, $C_1$-$C_4$ alkylamino, $C_1$-$C_4$ dialkylamino, cyano, carboxyl, hydroxyl or trifluoromethyl group, an acylamino, $C_1$-$C_4$ alkoxy, (poly)hydroxy($C_2$-$C_4$)alkoxy, alkylcarbonyloxy, alkoxycarbonyl or alkylcarbonylamino radical, an acylamino, carbamoyl or alkylsulfonylamino radical, an aminosulfonyl radical, or a $C_1$-$C_{16}$ alkyl radical optionally substituted with a group chosen from $C_1$-$C_{12}$ alkoxy, hydroxyl, cyano, carboxyl, amino, $C_1$-$C_4$ alkylamino and $C_1$-$C_4$ dialkylamino, or alternatively two alkyl radicals borne by the nitrogen atom of the amino group form a 5- to 7-membered heterocycle optionally comprising another nitrogen or non-nitrogen heteroatom; preferentially, $R_g$, $R'_g$, $R''_h$, $R'''_g$, $R_h$, $R'_h$, $R''_h$, and $R'''_h$ represent a hydrogen or halogen atom or a $C_1$-$C_3$ alkyl group;
- or alternatively two groups $R_g$ and $R'_g$, $R''_g$ and $R'''_g$, $R_h$, and $R'_h$; $R''_h$ and $R'''_h$ borne by two adjacent carbon atoms together form a benzo or indeno ring, a fused heterocycloalkyl or fused heteroaryl group; the benzo, indeno, heterocycloalkyl or heteroaryl ring being optionally substituted with a halogen atom, an amino, $C_1$-$C_4$ alkylamino, $C_1$-$C_4$ dialkylamino, nitro, cyano, carboxyl, hydroxyl or trifluoromethyl group, an acylamino, $C_1$-$C_4$ alkoxy, (poly)hydroxy($C_2$-$C_4$)alkoxy, alkylcarbonyloxy, alkoxycarbonyl or alkylcarbonylamino radical, an acylamino, carbamoyl or alkylsulfonylamino radical, an aminosulfonyl radical, or a $C_1$-$C_{16}$ alkyl radical optionally substituted with: a group chosen from $C_1$-$C_{12}$ alkoxy, hydroxyl, cyano, carboxyl, amino, $C_1$-$C_4$ alkylamino, $C_1$-$C_4$ dialkylamino, or alternatively two alkyl radicals borne by the nitrogen atom of the amino group form a 5- to 7-membered heterocycle optionally comprising another nitrogen or non-nitrogen heteroatom; preferentially, $R_g$ and $R'_g$, $R''_g$ and $R'''_g$ together form a benzo group;

or alternatively two groups $R_i$ and $R_g$, $R'''_i$ and $R'''_g$, $R'_i$ and $R'_h$; and/or $R''_i$ and $R''_h$ together form a fused (hetero)cycloalkyl, preferentially cycloalkyl such as cyclohexyl;

or alternatively when G represents —$NR_cR_d$ and G' represents —$NR'_cR'_d$, two groups $R_c$ and $R'_g$; and $R''_g$; $R_d$ and $R_g$, $R'_d$ and $R'''_g$ together form a saturated heteroaryl or heterocycle, optionally substituted with one or more groups ($C_1$-$C_6$)alkyl, preferentially a 5- to 7-membered heterocycle containing one or two heteroatoms chosen from nitrogen and oxygen; more preferentially the heterocycle is chosen from morpholinyl, piperazinyl, piperidyl and pyrrolidinyl groups;

$R_i$, $R'_i$, $R''_i$, and $R'''_i$, which may be identical or different, represent a hydrogen atom or a $C_1$-$C_4$ alkyl group;

$R_1$, $R_2$, $R_3$, $R_4$, $R'_1$, $R'_2$, $R'_3$, and $R'_4$, which may be identical or different, represent a hydrogen atom or a $C_1$-$C_4$ alkyl, $C_1$-$C_{12}$ alkoxy, hydroxyl, cyano, carboxyl, amino, $C_1$-$C_4$ alkylamino or $C_1$-$C_4$ dialkylamino group, the said alkyl radicals possibly forming with the nitrogen that bears them a 5- to 7-membered heterocycle optionally comprising another nitrogen or non-nitrogen heteroatom; preferentially, $R_1$, $R_2$, $R_3$, $R_4$, $R'_1$, $R'_2$, $R'_3$, and $R'_4$ are hydrogen atoms or an amino group; more preferentially, $R_1$, $R_2$, $R_3$, $R_4$, $R'_1$, $R'_2$, $R'_3$, and $R'_4$ represent a hydrogen atom;

$T_a$, $T_b$, which may be identical or different, represent i) either a covalent bond, ii) or one or more radicals or combinations thereof chosen from —$SO_2$—, —O—, —S—, —N(R)—, —$N^+(R)(R^o$—, —CO—, with R, $R^o$, which may be identical or different, representing a hydrogen atom, a $C_1$-$C_4$ alkyl or $C_1$-$C_4$ hydroxyalkyl radical; or an aryl($C_1$-$C_4$)alkyl, preferentially, $T_a$ is identical to $T_b$ and represent a covalent bond or a group chosen from —N(R)—, —C(O)—N(R)—, —N(R)—C(O)—, —O—C(O)—, —C(O)—O— and —$N^+(R)(R^o$—, with R, $R^o$, which may be identical or different, representing a hydrogen atom or a $C_1$-$C_4$ alkyl group; more preferentially, $T_a$ and $T_b$ represent a bond; iii) or a cationic or non-cationic, preferentially monocyclic, preferentially identical heterocycloalkyl or heteroaryl radical, preferentially containing two heteroatoms (more preferentially two nitrogen atoms) and preferentially being 5- to 7-membered, such as imidazolium;

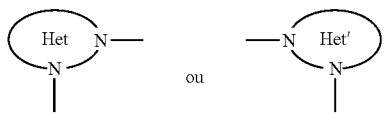

ou identical or different, represent an optionally substituted heterocyclic group; preferentially, the heterocycles are identical, monocyclic, saturated and 5- to 8-membered and comprise in total two nitrogen atoms;

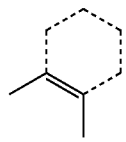

represent an aryl or heteroaryl group fused to the imidazolium or phenyl ring; or alternatively is absent from the imidazolium or phenyl ring; preferentially, when the ring is present, the ring is a benzo;

m, m', n and n', which may be identical or different, represent an integer between 0 and 6 inclusive, with m+n and m'+n', which may be identical or different, represents an integer between 1 and 10 inclusive; preferentially, m+n=m'+n'=an integer between 2 and 4 inclusive; more preferentially, m+n=m'+n'=an integer equal to 2;

Y is as defined previously; in particular, Y represents a hydrogen atom or a protecting group such as:
($C_1$-$C_4$)alkylcarbonyl, for instance methylcarbonyl or ethylcarbonyl;
arylcarbonyl, for instance phenylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl, for instance dimethylaminocarbonyl;
($C_1$-$C_4$)(alkyl)arylaminocarbonyl;
optionally substituted aryl such as phenyl;
5- or 6-membered monocyclic heteroaryl such as imidazolyl or pyridyl;
cationic 5- or 6-membered monocyclic heteroaryl such as pyrylium, pyridinium, pyrimidinium, pyrazinium, pyridazinium, triazinium, imidazolium; these groups being optionally substituted with one or more identical or different ($C_1$-$C_4$)alkyl groups such as methyl;
cationic 8- to 11-membered bicyclic heteroaryl such as benzimidazolium or benzoxazolium; these groups being optionally substituted with one or more identical or different ($C_1$-$C_4$)alkyl groups such as methyl;
cationic heterocycle having the following formula:

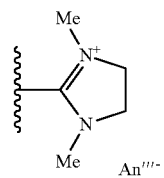

—$C(NH_2)$=$N^+H_2$; $An''''$; with $An''''^-$ being an anionic counterion as defined previously;
—$C(NH_2)$=NH;
$SO_3^-$, $M^+$ with $M^+$ representing an alkali metal such as sodium or potassium. and
M' representing an anionic counterion, derived from a salt of an organic or mineral acid, or from an organic or mineral base that ensures the electrical neutrality of the molecule.

In particular, the dyes of formula (I) are chosen from dyes with a naphthalimidyl disulfide, thiol or protected-thiol chromophore, chosen from formulae (XIII), (XIII'), (XIV) and (XIV') as defined previously.

According to one preferred mode of the invention, the dyes of formula (I) are chosen from disulfide, thiol or protected-thiol dyes chosen from formulae (XV) to (XV') below:

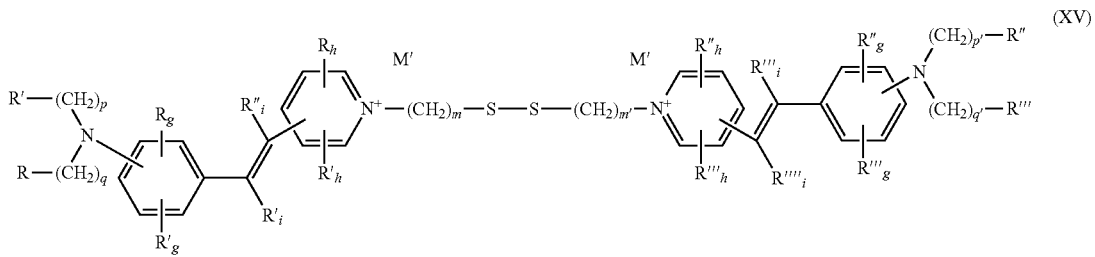

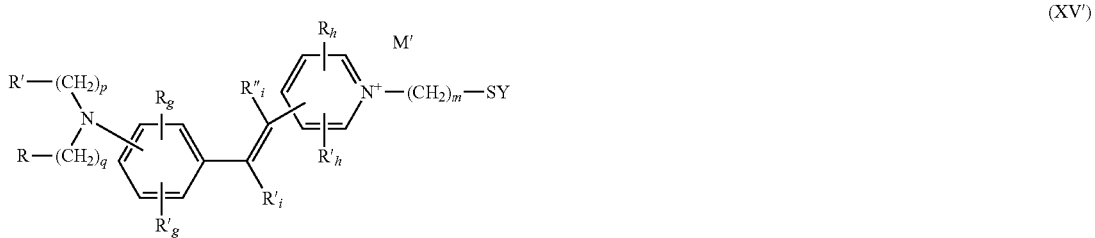

the organic or mineral acid salts, optical isomers, geometrical isomers, and solvates such as hydrates thereof;

in which formulae (XV) and (XV'):

- R and R''', which may be identical or different, represent a hydroxyl group, an amino group ($NR_aR_b$) or an ammonium group ($N^+R_aR_bR_c$), $An^-$; preferentially hydroxyl; with $R_a$, $R_b$ and $R_c$, which may be identical or different, representing a hydrogen atom or a ($C_1$-$C_4$)alkyl group;
  or alternatively two alkyl groups $R_a$ and $R_b$ of the amino or ammonium group form a 5- to 7-membered heterocycle optionally comprising another nitrogen or non-nitrogen heteroatom, such as morpholinyl, piperazinyl, piperidyl, pyrrolyl, morpholinium, piperazinium, piperidinium or pyrrolinium, and $An^-$ representing an anionic counterion;
- R' and R'', which may be identical or different, represent a hydrogen atom or a group as defined for R and R''', respectively;
- $R_g$, $R'_g$, $R''_g$, $R'''_g$, $R_h$, $R'_h$, $R''_h$ and $R'''_h$, which may be identical or different, represent a hydrogen or halogen atom, an amino, (di)($C_1$-$C_4$)alkylamino, cyano, carboxyl, hydroxyl, trifluoromethyl, acylamino, $C_1$-$C_4$ alkoxy, $C_2$-$C_4$ (poly)hydroxyalkoxy, ($C_1$-$C_4$)alkylcarbonyloxy, ($C_1$-$C_4$)alkoxycarbonyl, ($C_1$-$C_4$)alkylcarbonylamino, acylamino, carbamoyl or ($C_1$-$C_4$)alkylsulfonylamino group, an aminosulfonyl radical or a radical ($C_1$-$C_{16}$)alkyl optionally substituted with a group chosen from ($C_1$-$C_{12}$)alkoxy, hydroxyl, cyano, carboxyl and (di)($C_1$-$C_4$)alkylamino, or alternatively the two alkyl radicals borne by the nitrogen atom of the amino group form a 5- to 7-membered heterocycle optionally comprising another nitrogen or non-nitrogen heteroatom; in particular, $R_g$, $R'_g$, $R''_g$, $R'''_g$, $R_h$, $R'_h$, $R''_h$ and $R'''_h$ represent a hydrogen atom or a ($C_1$-$C_4$) alkyl group;
- $R'_i$, $R''_i$, $R'''_i$ and $R''''_i$, which may be identical or different, represent a hydrogen atom or a ($C_1$-$C_4$)alkyl group; in particular $R'_i$, $R''_i$, $R'''_i$, and $R''''_i$ represent a hydrogen atom;
- m, m', which may be identical or different, represent an integer between 1 and 10 inclusive; in particular an integer between 2 and 4 inclusive; preferentially, m and m' are equal to 2;
- p, p', q and q', which may be identical or different, represent an integer between 1 and 6 inclusive;
- M' representing an anionic counterion; and
- Y is as defined previously;
- it being understood that when the compound of formula (XV) or (XV') contains other cationic parts, it is combined with one or more anionic counterions that afford formula (XV) or (XV') electrical neutrality.

According to one particular mode of the invention, the dyes of the invention belong to formula (XVa) or (XV'a) which bear an ethylene group connecting the pyridinium part to the phenyl ortho or para to the pyridinium, i.e. 2-4', 4-2', 4-4':

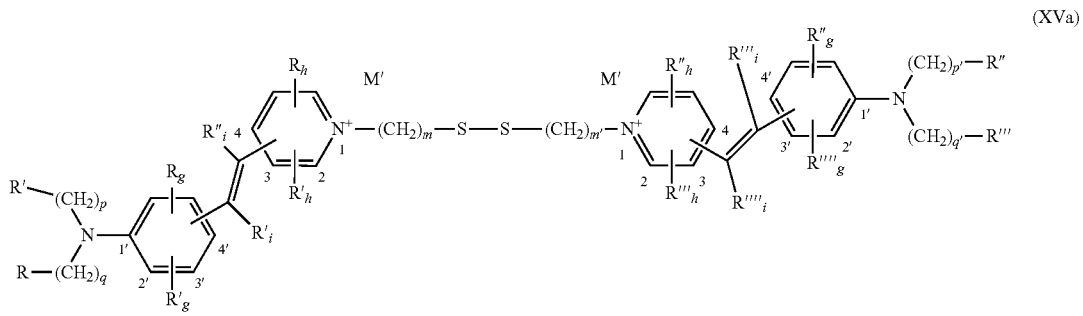

(XV'a)

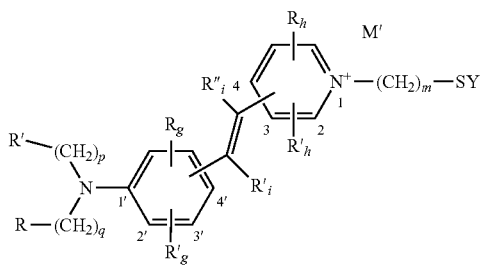

with R, R', R", R''', $R_g$, $R'_g$, $R''_g$, $R'''_g$, $R_h$, $R'_h$, $R''_h$, $R'''_h$, $R'_i$, $R''_i$, $R'''_i$, $R''''_i$, m, m', p, p', q, q', Y and M' as defined previously in formulae (XV) and (XV'). In particular, $R_h$ and $R''_h$ are ortho to the pyridinium group and $R'_h$ and $R'''_h$ represent a hydrogen atom. Another aspect of the invention concerns the dyes of formula (XVa) or (XV'a) bearing groups $R_g$, $R''_g$ in position 3' and $R'_g/R'''_g$ which represent a hydrogen atom.

Advantageously, the dyes of formulae (XVa) and (XV'a) bear their ethylene group para to the phenyl bearing the amino group: $R'(CH_2)_p$—N—$(CH_2)_q$—R and/or $R'''(CH_2)_{p'}$—N—$(CH_2)_{q'}$—R''', i.e. in position 4', preferentially bear an ethylene or styryl group linking the pyridinium part to the phenyl ortho to the pyridinium, i.e. 2-4'.

According to another particular mode of the invention, the dyes of the invention belong to formula (XVI) or (XVI'):

hydroxy($C_1$-$C_4$)alkyl and/or —C(O)OR' group with R' representing a hydrogen atom, a $C_1$-$C_4$ alkyl group or a group —C(O)—O⁻ and, in the latter case, an anionic counterion An⁻ is absent; such as pyrrolidinyl and piperidyl;

$R_3$ represents a hydrogen atom or a group —C(O)OR" with R" representing a hydrogen atom, an alkali metal or a $C_1$-$C_6$ alkyl group or alternatively $R_3$ represents a group —C(O)—O⁻ and, in the latter case, an anionic counterion An⁻ is absent;

Z represents a divalent amido group —C(O)—N(R)—, —N(R)—C(O)—, or a divalent $C_1$-$C_{10}$ alkylene group interrupted with an amido group —C(O)—N(R)—, —N(R)—C(O)— such as —$(CH_2)_{n'}$—C(O)—N(R)—$(CH_2)_p$—, —$(CH_2)_{n''}$—N(R)—C(O)—$(CH_2)_p$—, with (XVI)

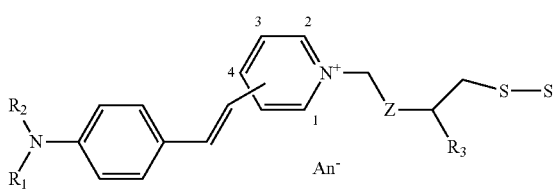

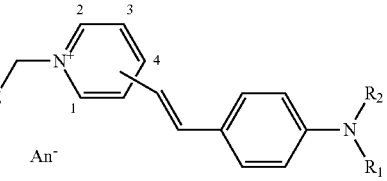

(XVI')

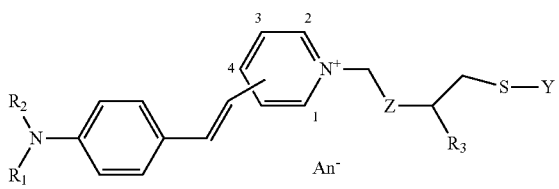

in which formula (XVI) or (XVI'):
$R_1$ represents a $C_1$-$C_6$ alkyl group substituted with one or more hydroxyl groups or —C(O)OR' with R' representing a hydrogen atom, a $C_1$-$C_4$ alkyl group or a group —C(O)—O⁻ and, in the latter case, an anionic counterion An⁻ is absent; in particular $R_1$ represents a $C_1$-$C_6$ alkyl group substituted with one or more hydroxyl groups and more specifically with only one hydroxyl group;

$R_2$ represents a $C_1$-$C_6$ alkyl group optionally substituted with one or more hydroxyl groups;

or alternatively the groups $R_1$ and $R_2$ form, together with the nitrogen atom that bears them, a saturated heterocyclic radical substituted with at least one hydroxyl, (poly)

n' representing an integer between 0 and 3 inclusive; preferentially, n' is equal to 0, 2, 3; p representing an integer between 0 and 4 inclusive, n" representing an integer between 0 and 3 inclusive and especially n'=n"=p=0 and R representing a hydrogen atom or a $C_1$-$C_6$ alkyl group;

An⁻ represents an anionic counterion;

Y is as defined previously;

it being understood that when the compound of formula (XVI) or (XVI') contains other cationic parts, it is combined with one or more anionic counterions that afford formula (XVI) or (XVI') electrical neutrality.

According to another particular mode of the invention, the dyes of the invention belong to formula (XVIa) or (XVI'a):

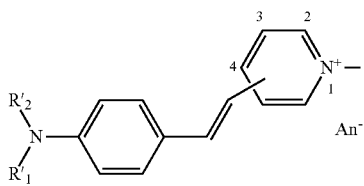 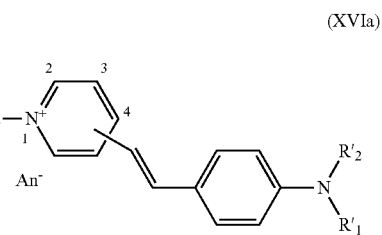

(XVIa)

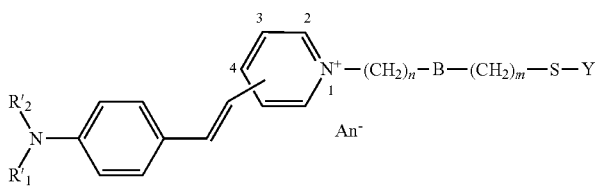

(XVI'a)

in which formulae (Ia) and (Ib):

- $R'_1$ represents a $C_1$-$C_4$ alkyl group substituted with one or more hydroxyl groups, particularly with only one hydroxyl group, or —C(O)OR' with R' representing a hydrogen atom, a $C_1$-$C_4$ alkyl group or a group —C(O)—O⁻ and, in the latter case, an anionic counterion An⁻ is absent; preferentially, $R'_1$ represents a $C_1$-$C_4$ alkyl group substituted with a hydroxyl group;
- $R'_2$ represents a $C_1$-$C_4$ alkyl group optionally substituted with one or more hydroxyl groups, particularly with only one hydroxyl group; more particularly, $R'_1$ and $R'_2$ are identical;
- An⁻ represents an anionic counterion as defined previously;
- B represents a divalent amido group —C(O)—N(R)—, —N(R)—C(O)—, with R representing a hydrogen atom or a group ($C_1$-$C_6$)alkyl; preferentially, R=H;
- n and m, which may be identical or different, represent an integer between 1 and 4 inclusive; preferentially, n is equal to 3 and m is equal to 2;
- Y is as defined previously;

it being understood that the bond between the pyridinium ring and the double bond of the ethylene or styryl group is located in position 2 or 4 of the pyridinium, preferentially at 4.

As examples of disulfide, thiol and protected-thiol direct dyes of formula (I) of the invention, mention may be made of those having the following chemical structures:

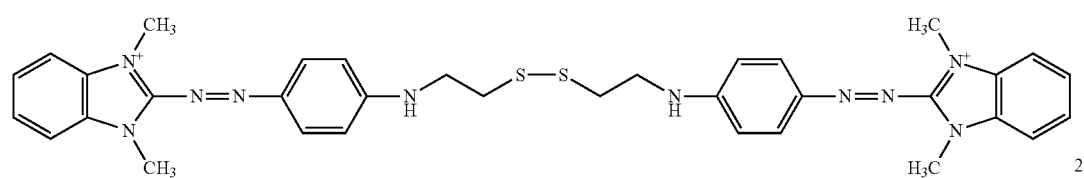 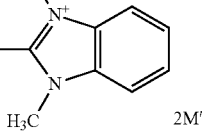

1

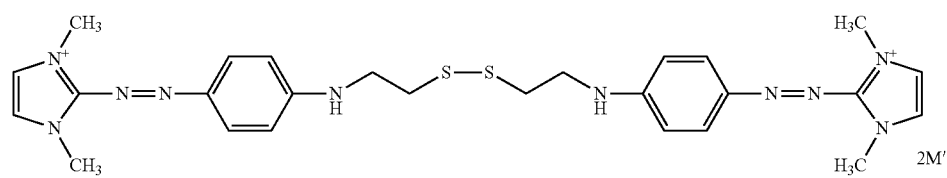 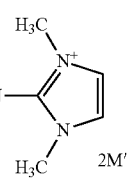

2

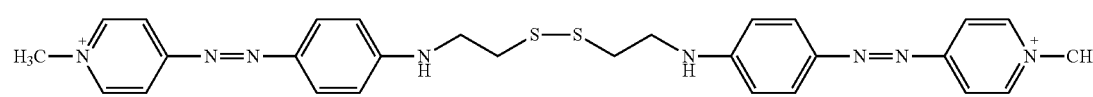

3

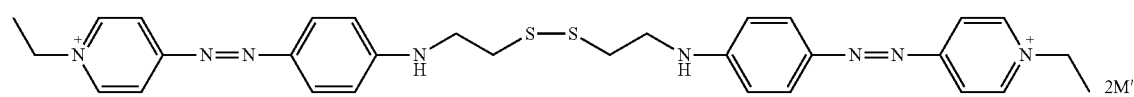 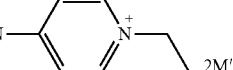

4

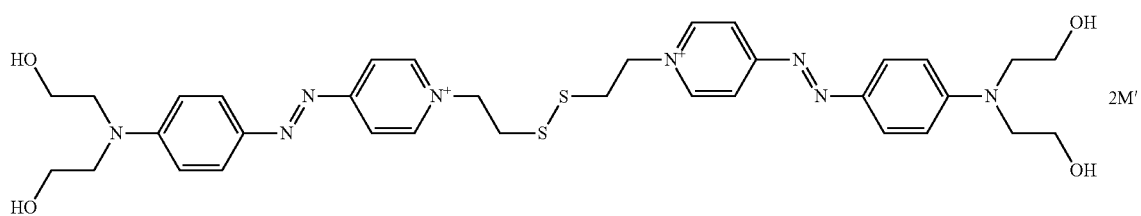
5
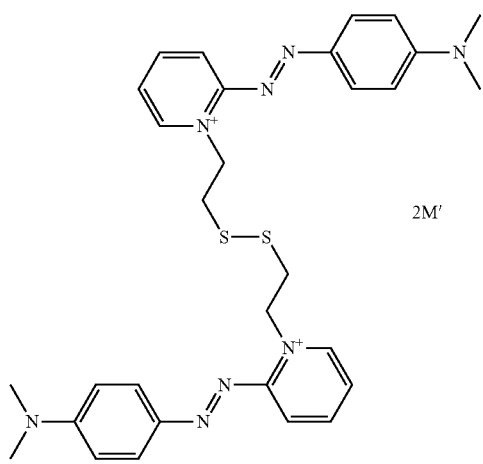
6
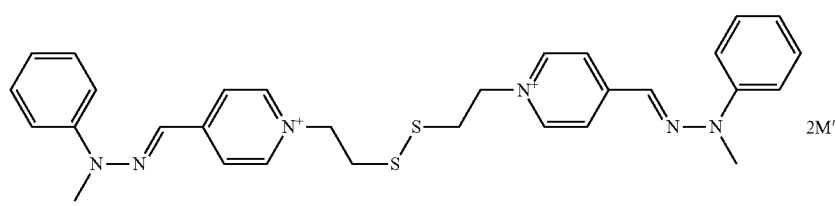
7
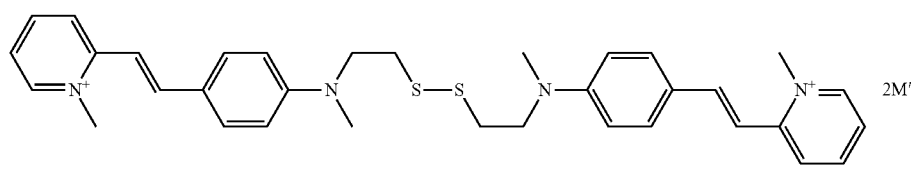
8
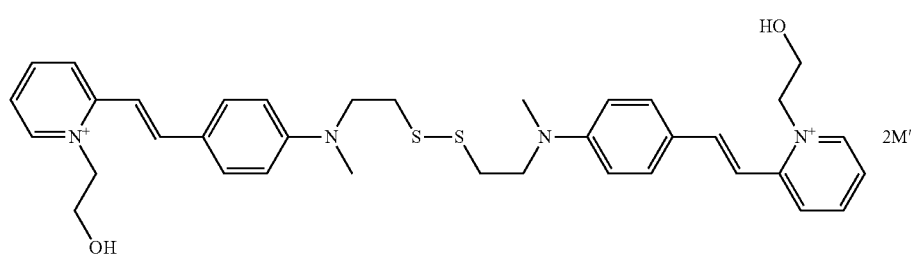
9
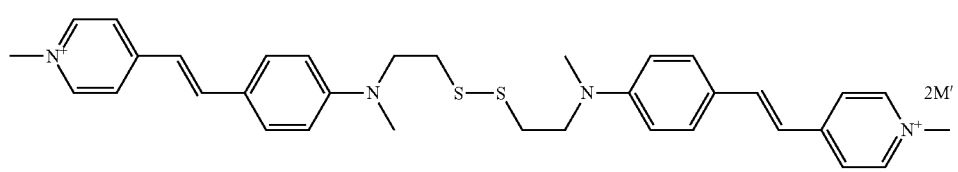
10

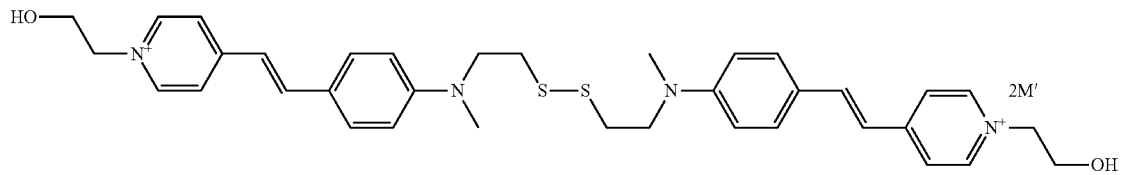
11
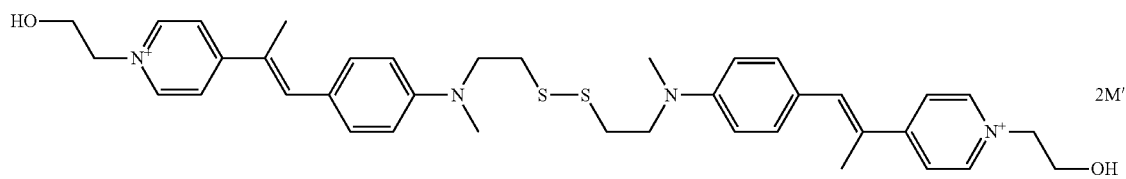
12
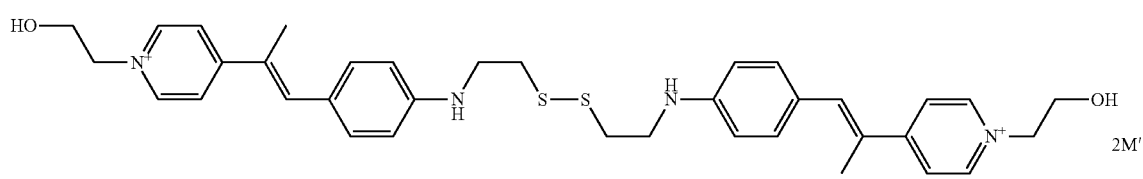
13
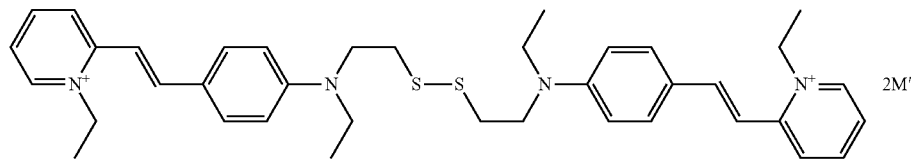
14
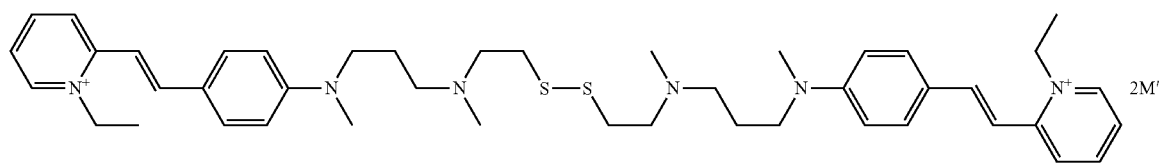
15
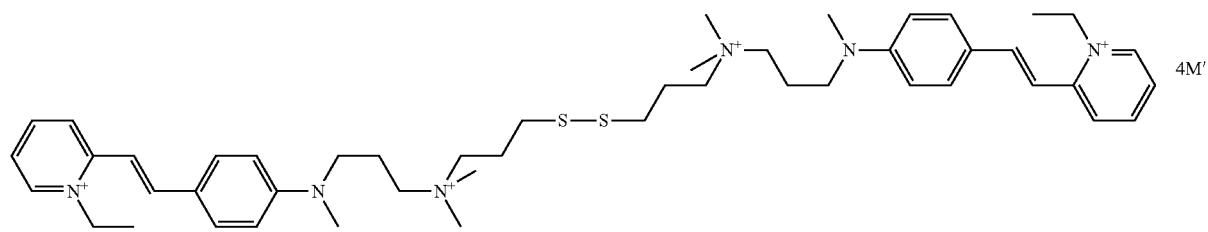
16
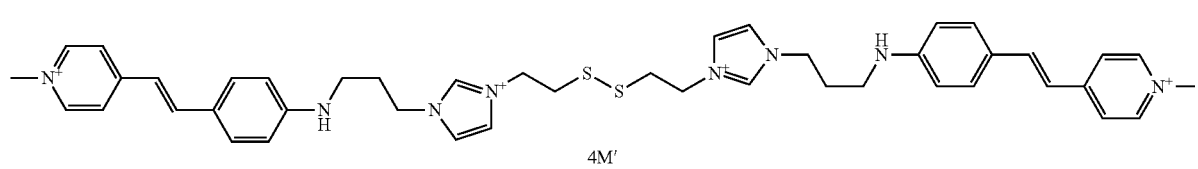
17
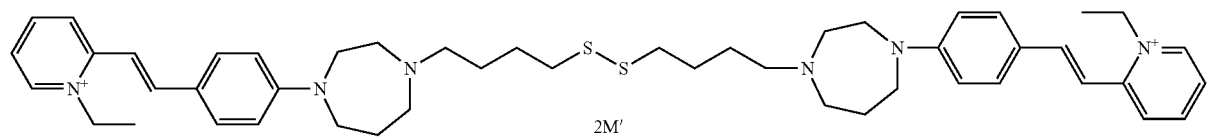
18

19
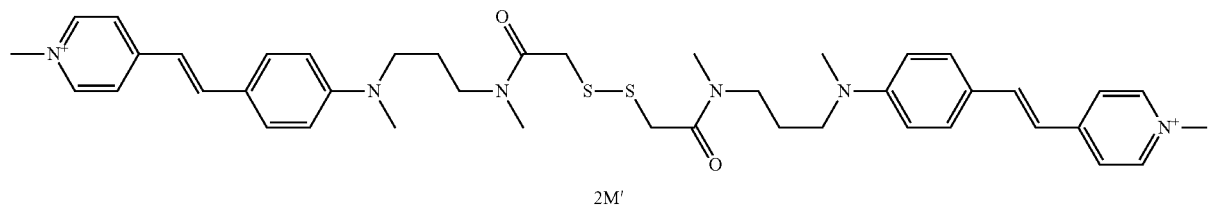
2M'
20
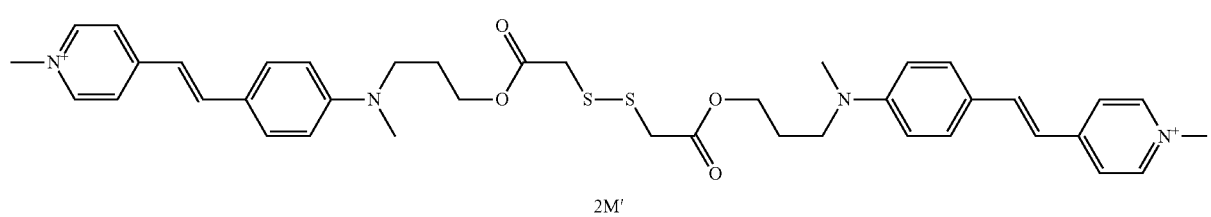
2M'
21
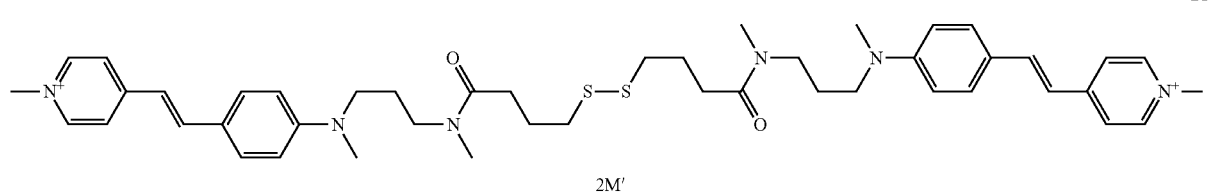
2M'
22
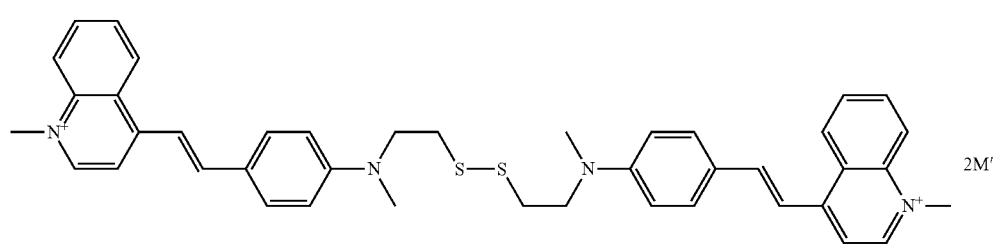
2M'
23
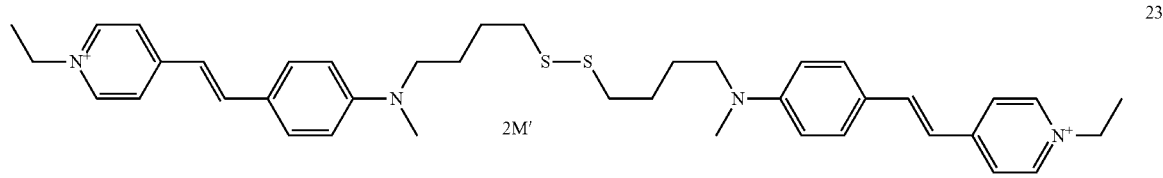
2M'
24
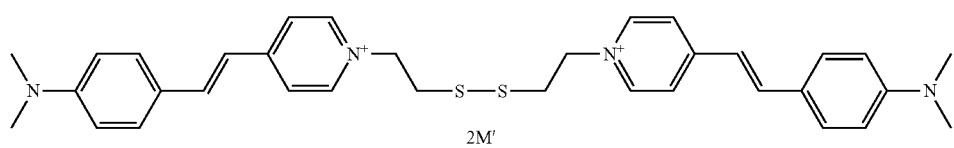
2M'
25
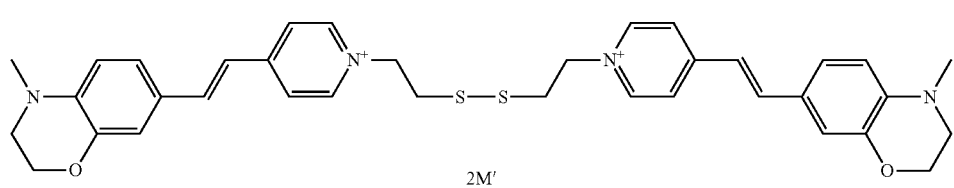
2M'
26
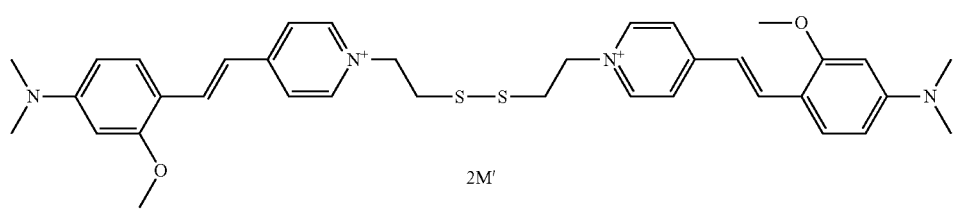
2M'

-continued
27
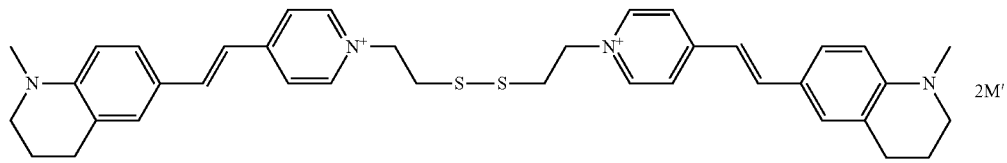
2M′
28
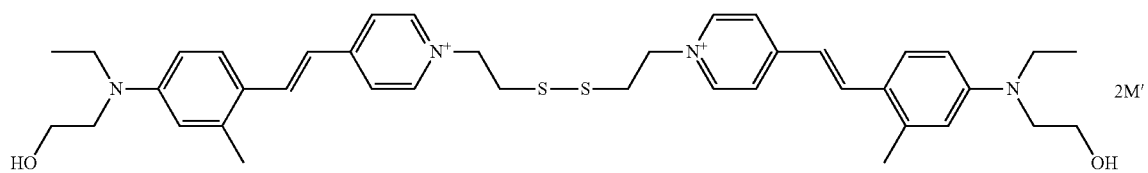
2M′
29
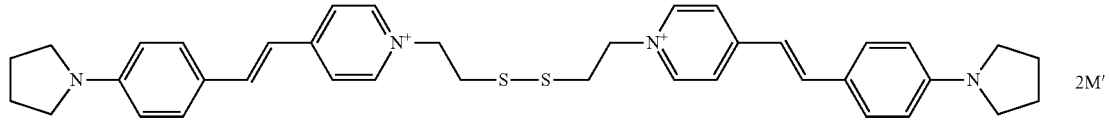
2M′
30
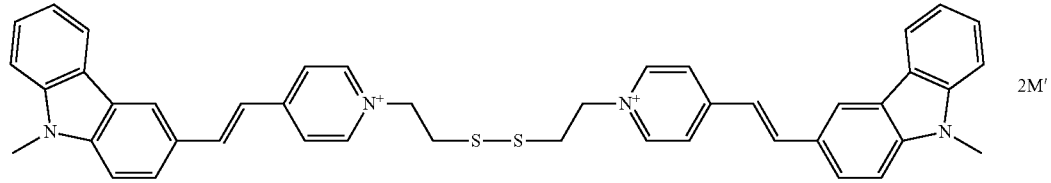
2M′
31
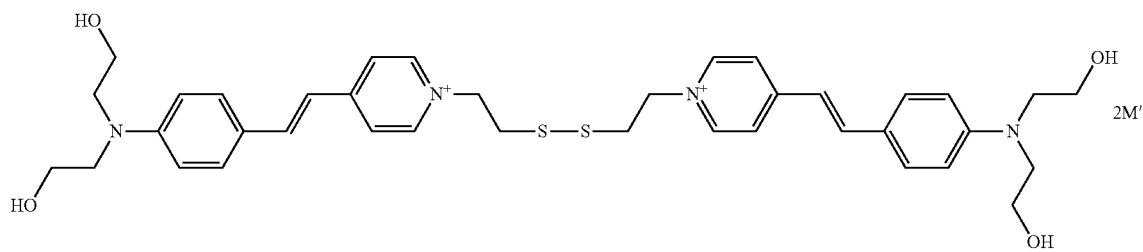
2M′
32
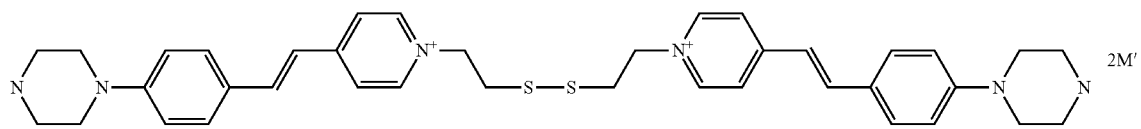
2M′
33
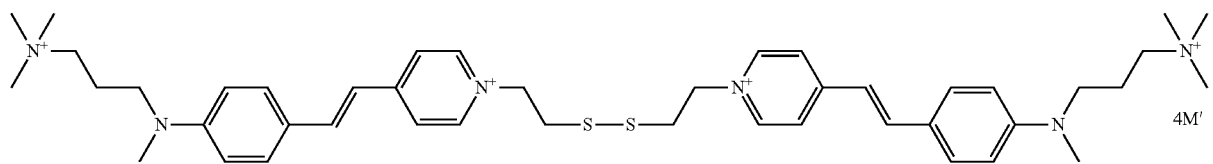
4M′
34
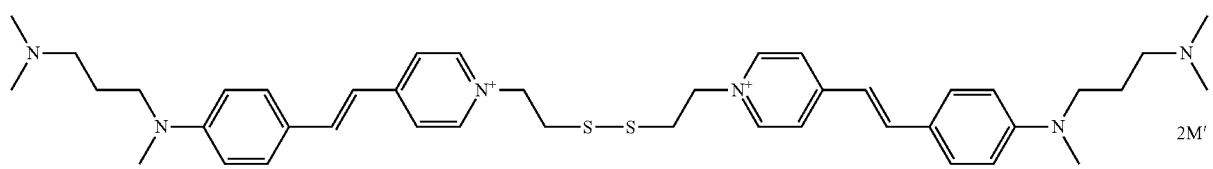
2M′

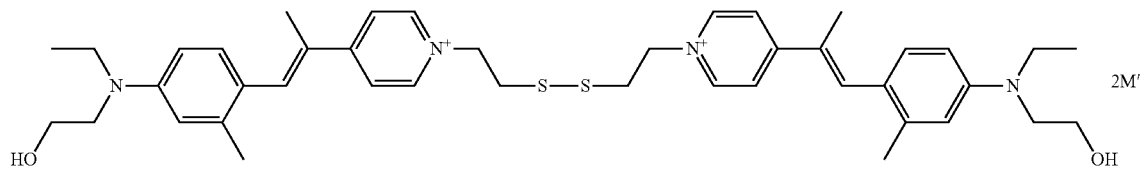
35
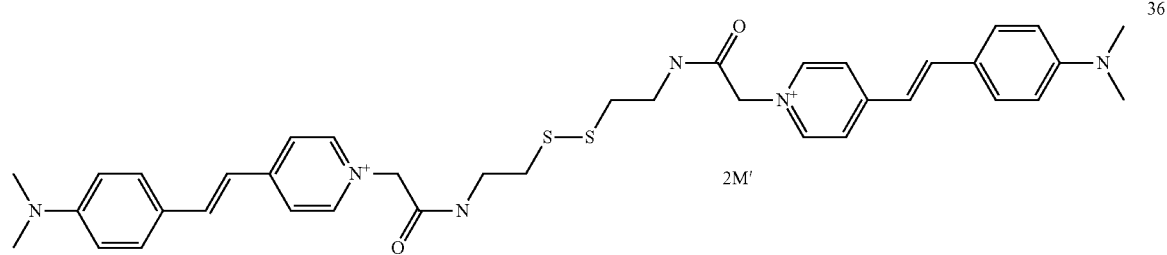
36
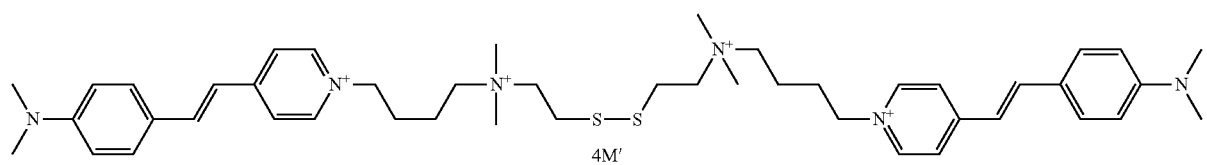
37
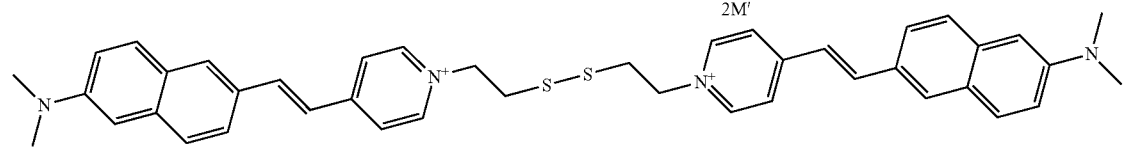
38
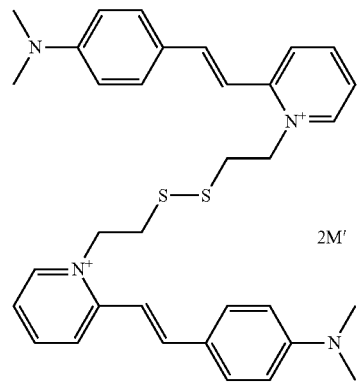
39
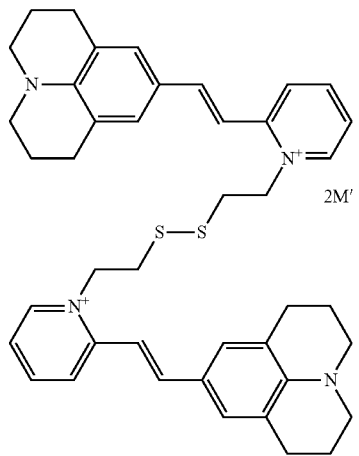
40

-continued
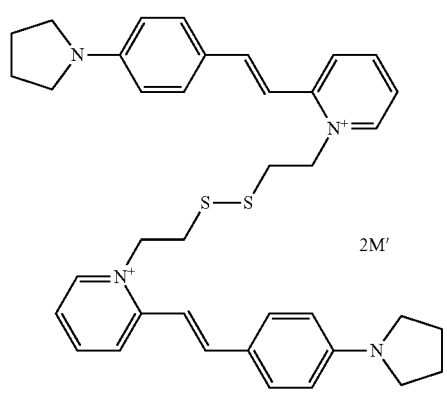
41
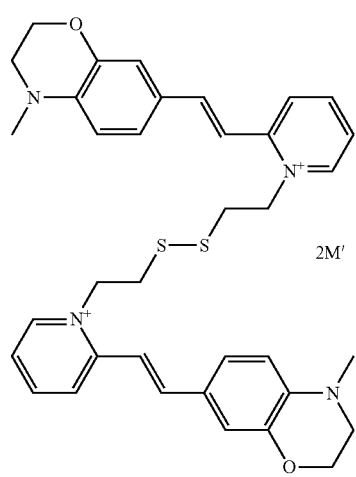
42
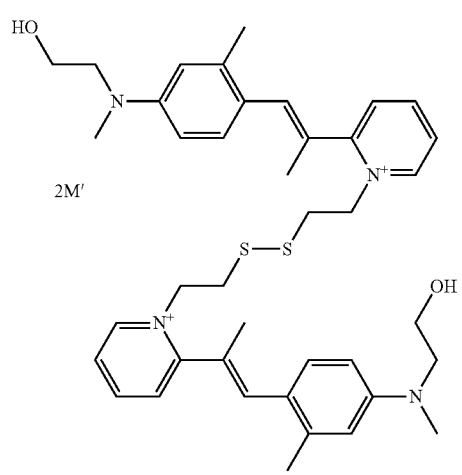
43
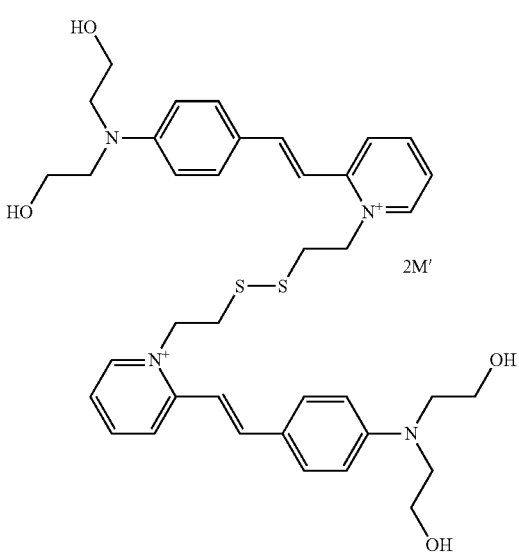
44
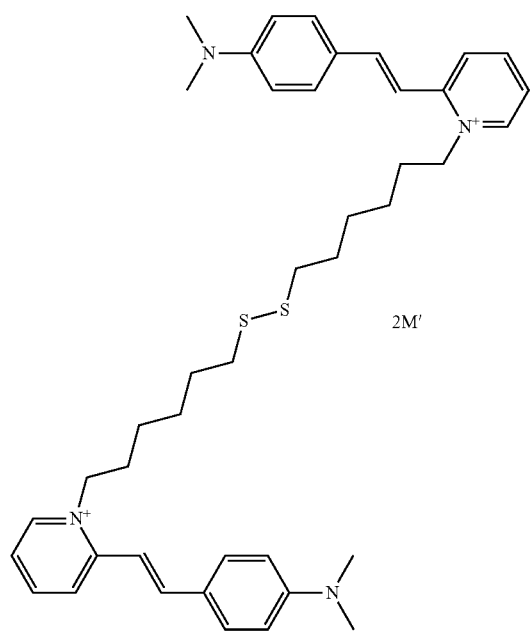
45

46
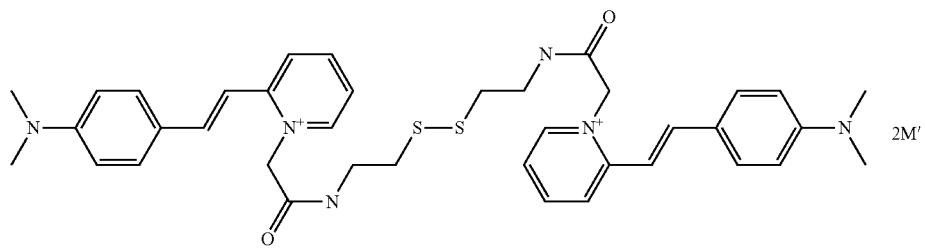
2M'
47
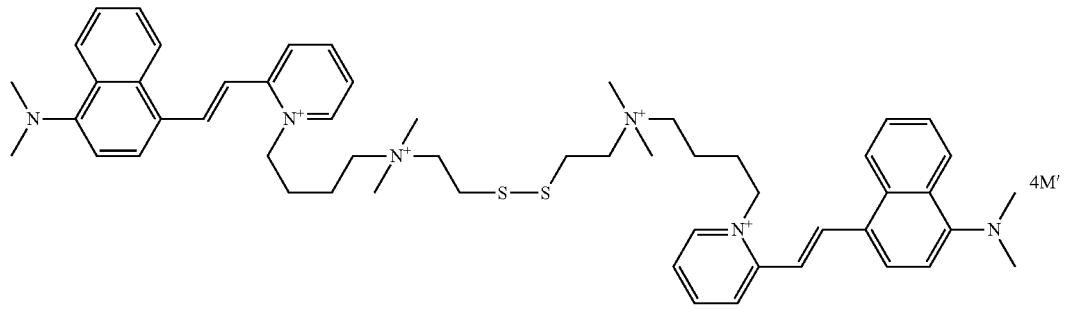
4M'
48
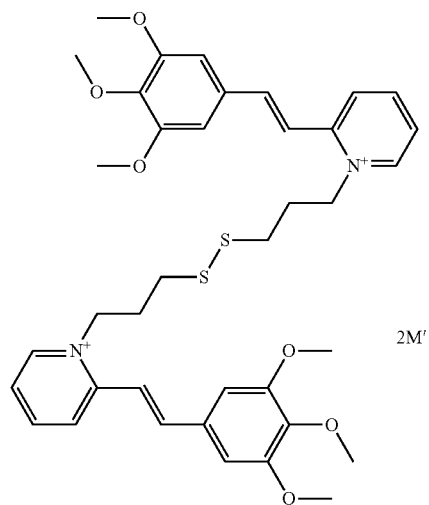
2M'
49
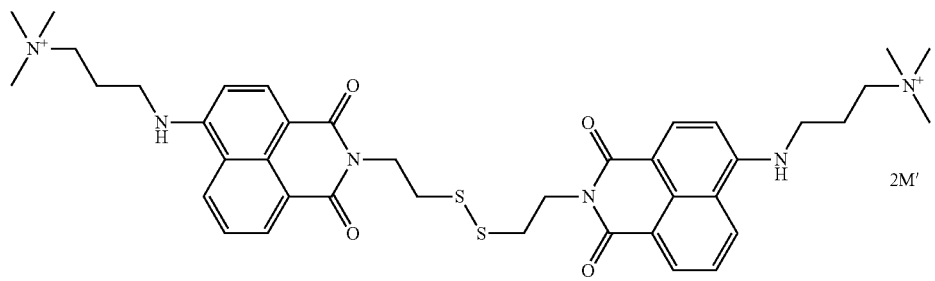
2M'
49a
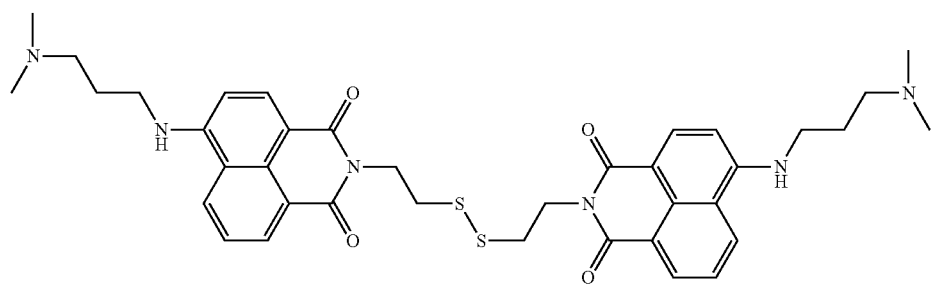

51 52
-continued
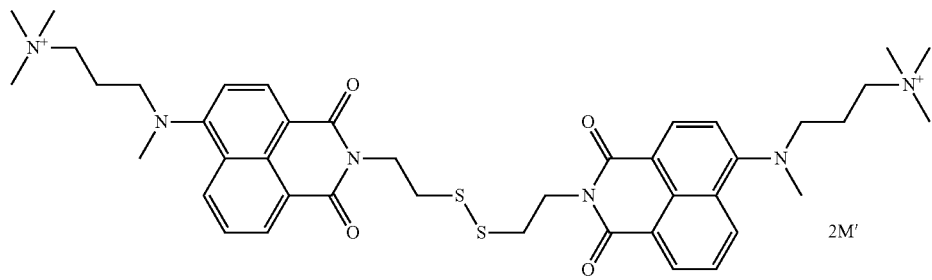
50
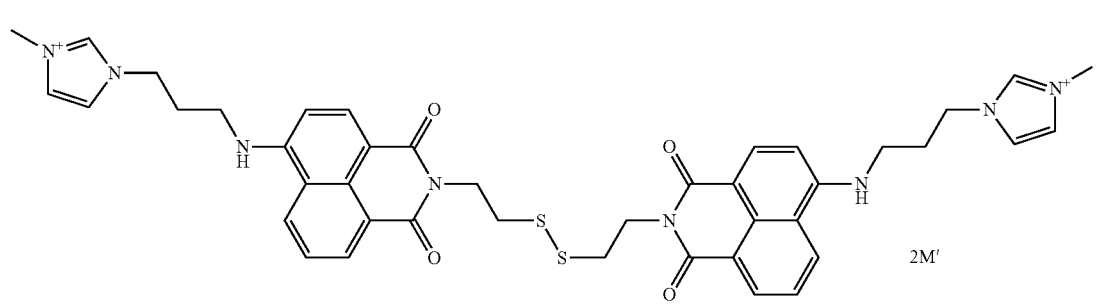
51
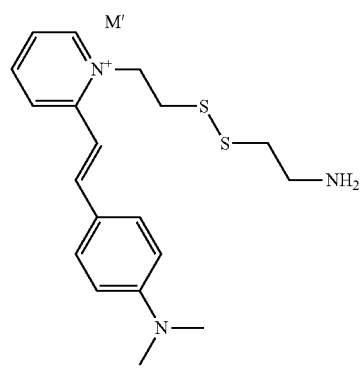
52
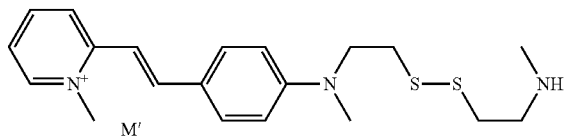
53
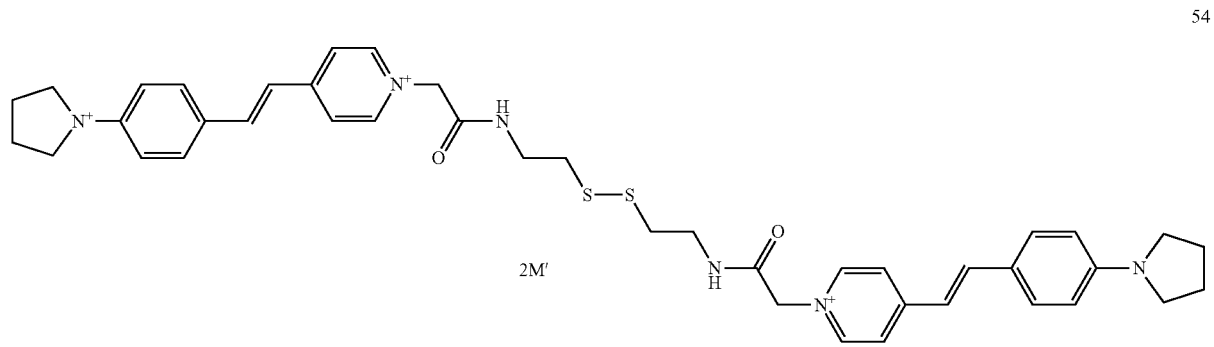
54
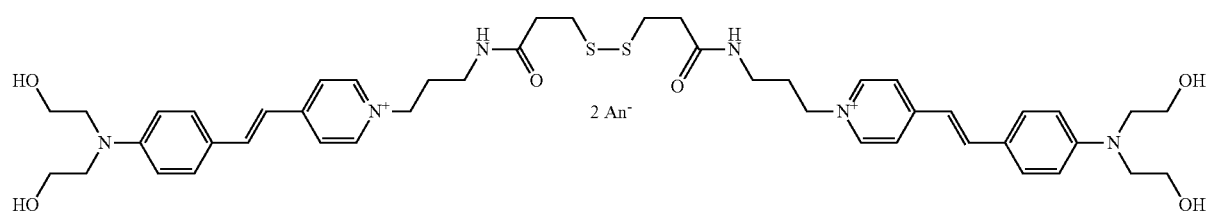
55

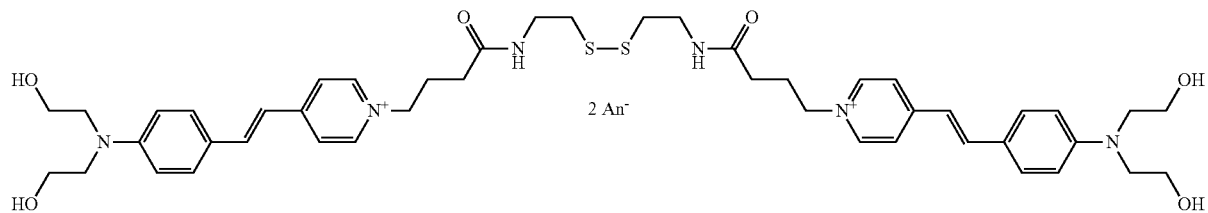
56
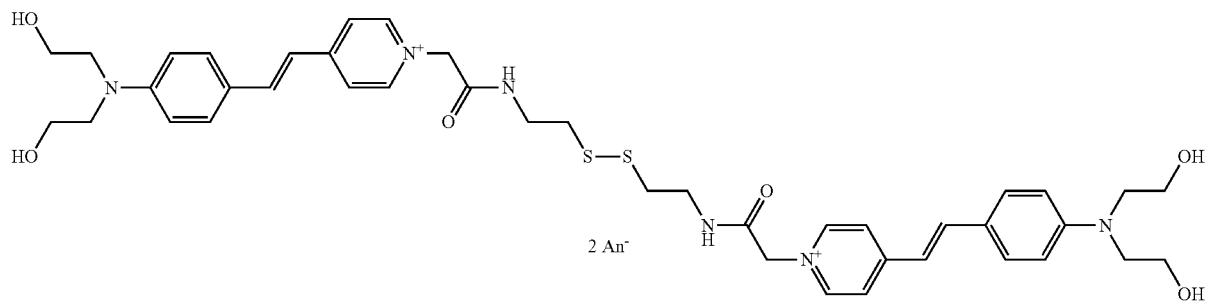
57
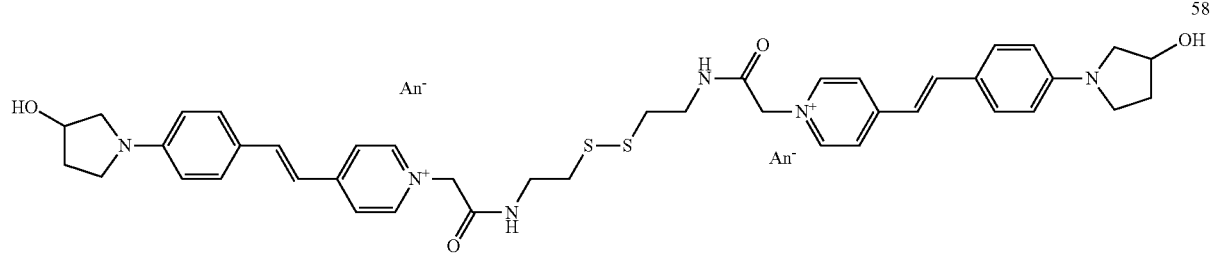
58
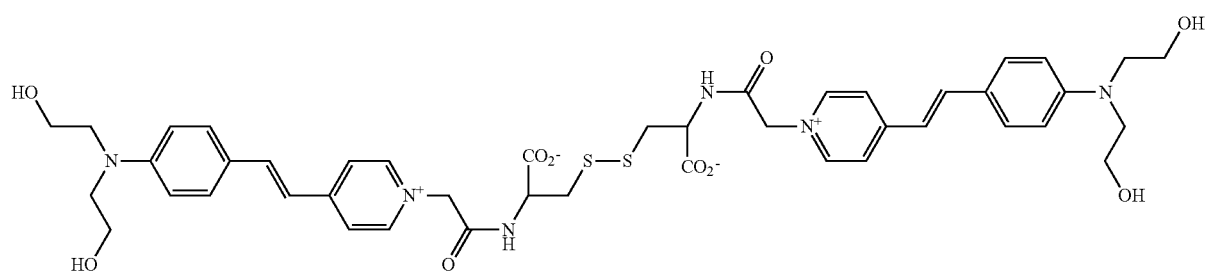
59
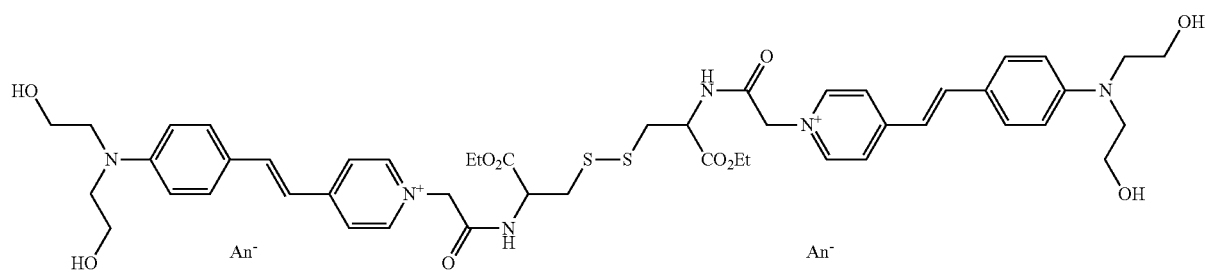
60

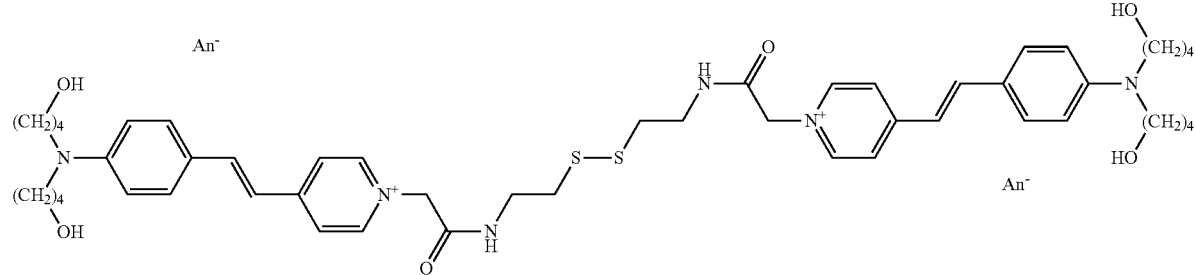
61
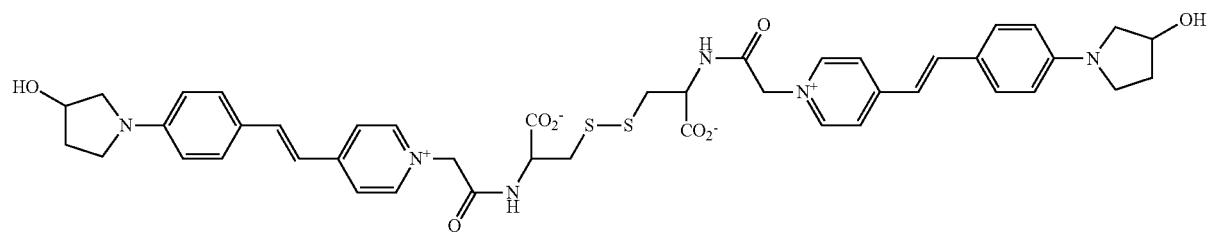
62
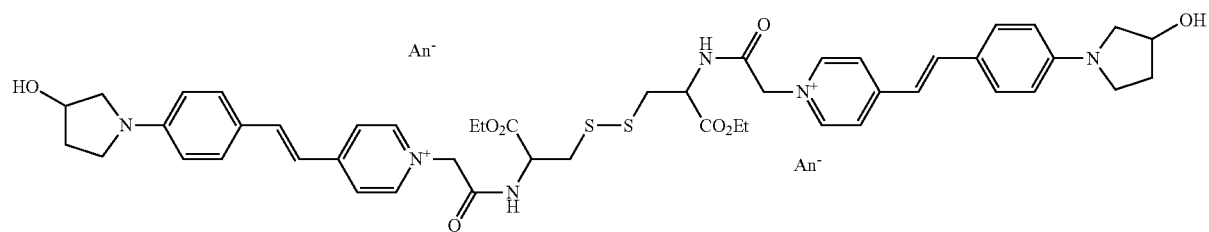
63
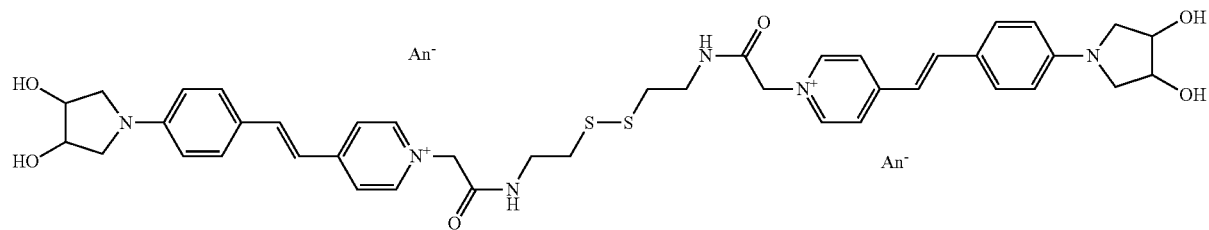
64
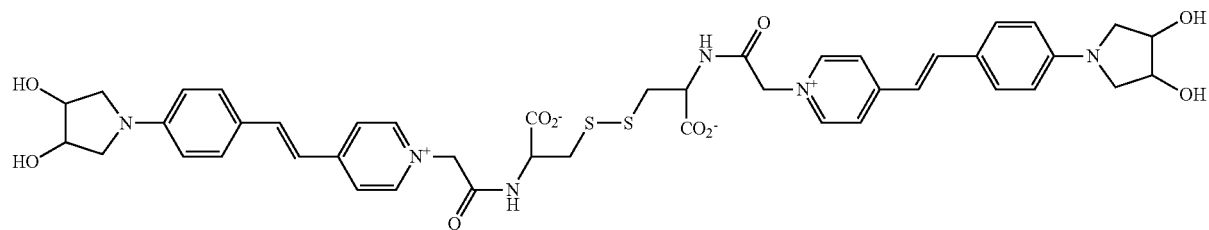
65

-continued
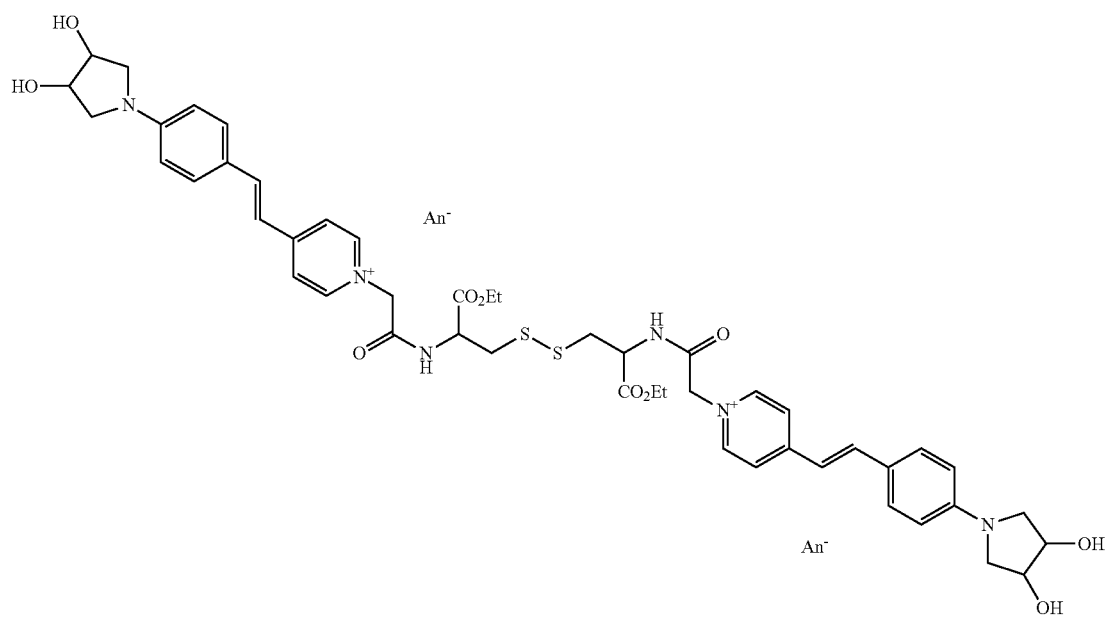
66
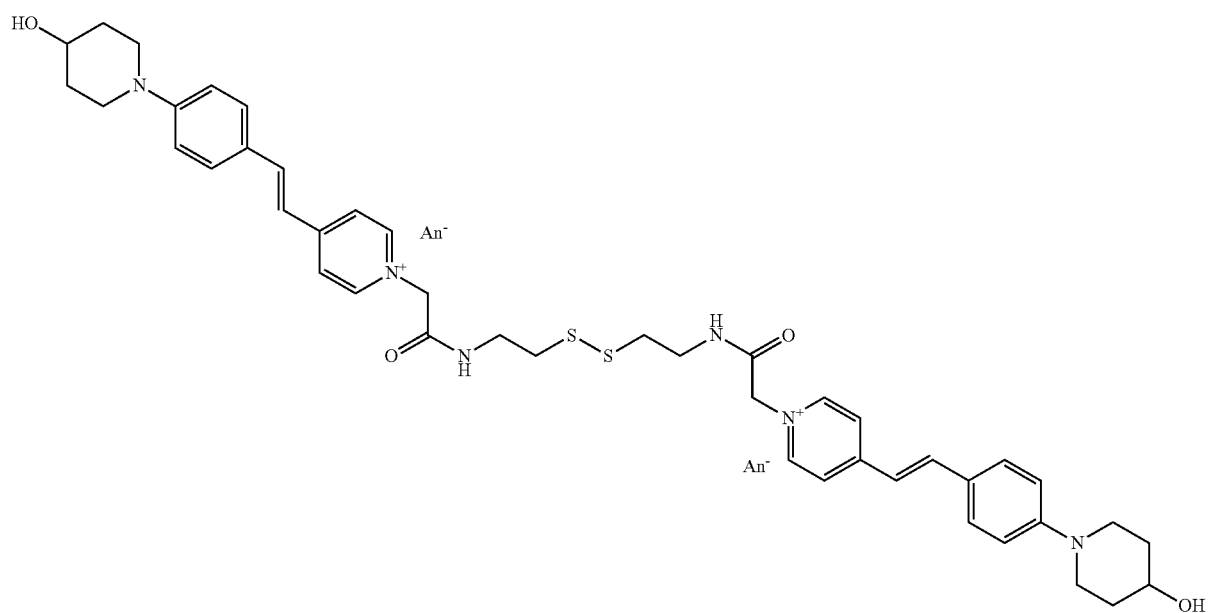
67
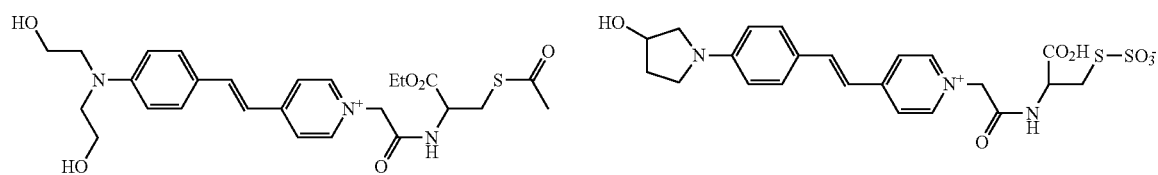
68 69

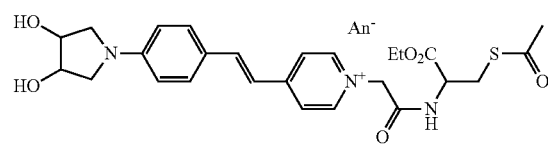
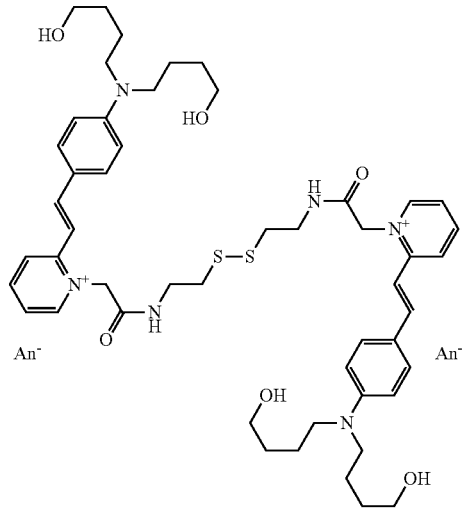
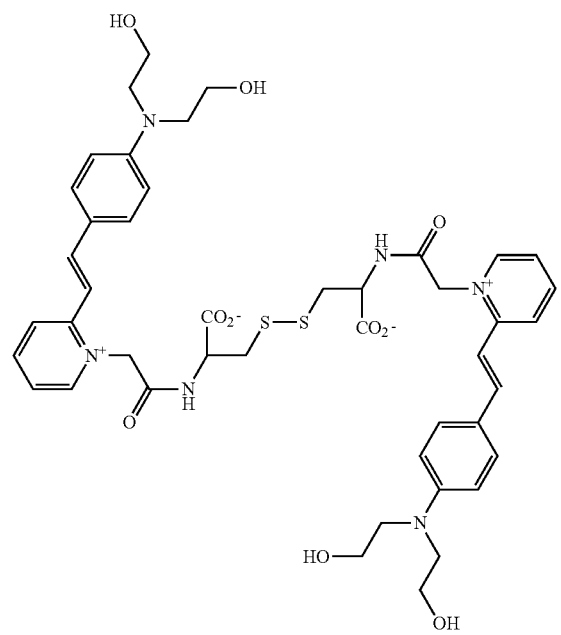
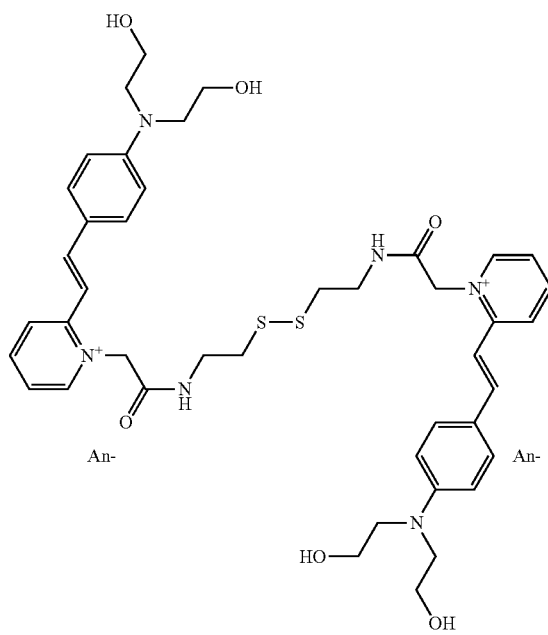

-continued
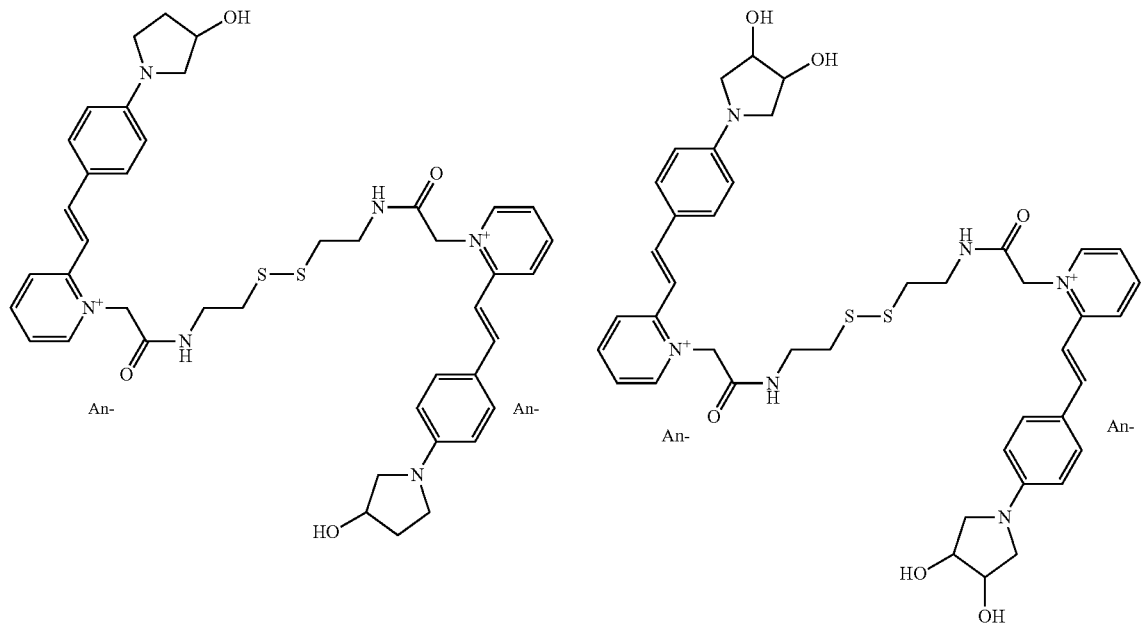
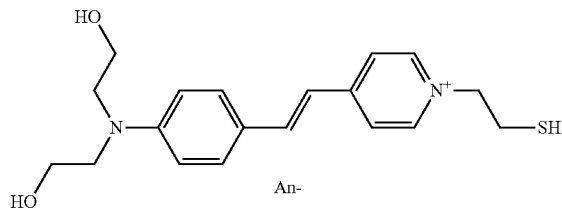
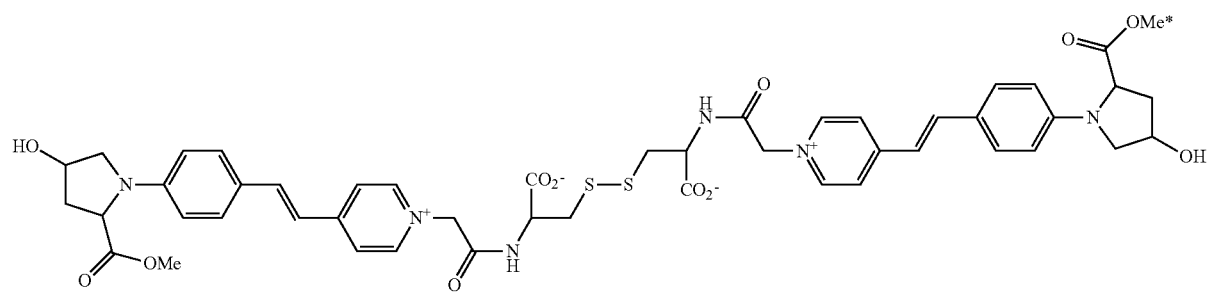
Me⁺ represents an alkali metal or an alkaline-earth metal; or a methyl
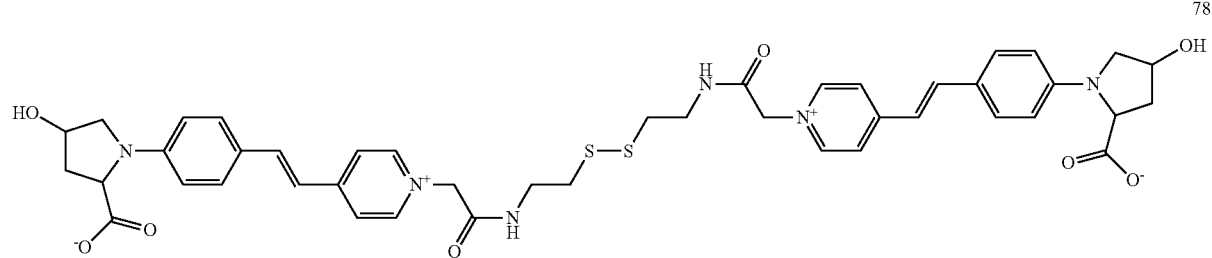

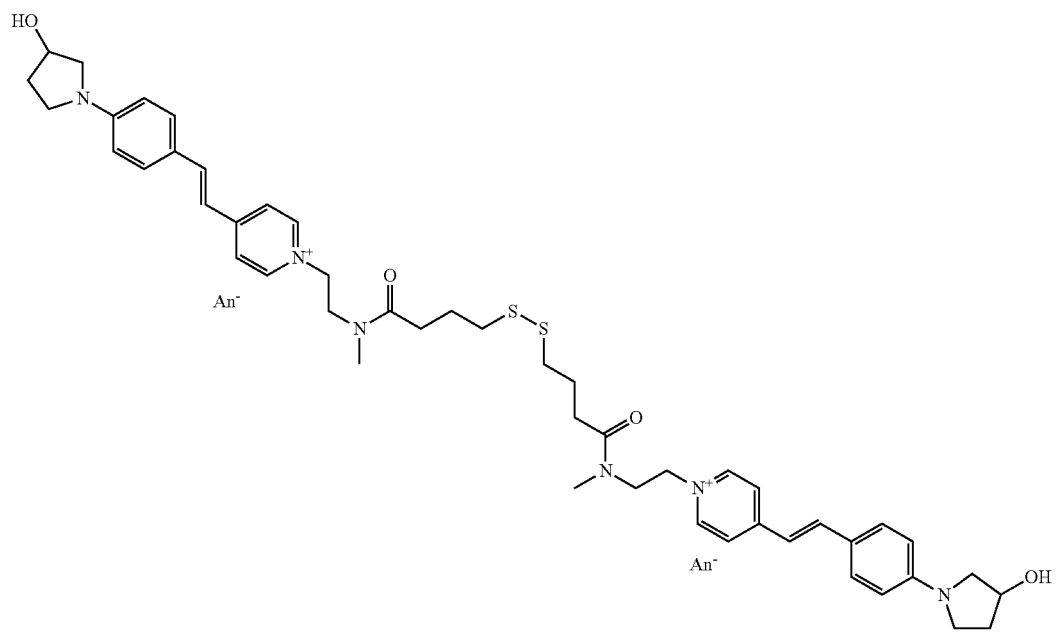
79
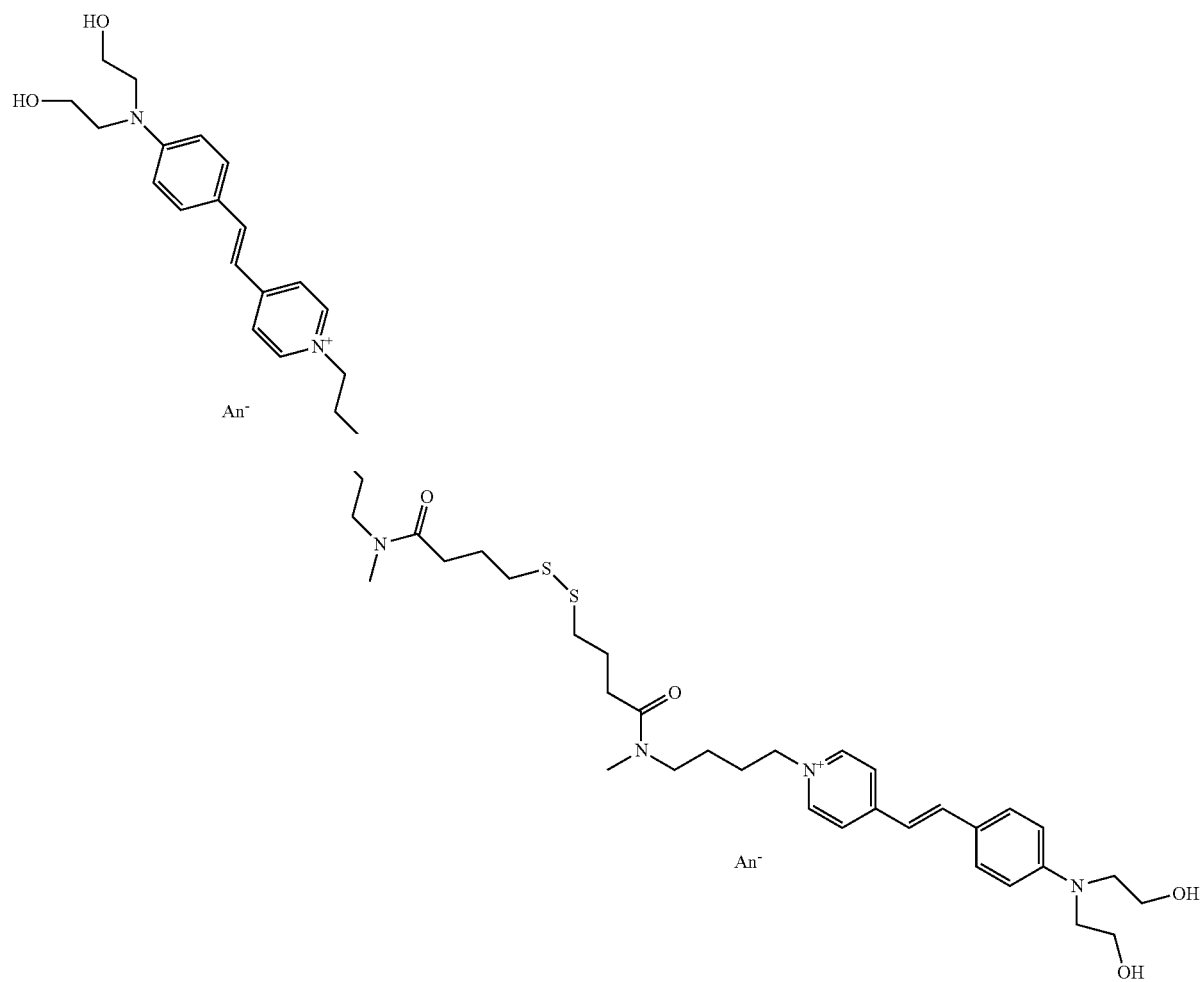
80

81
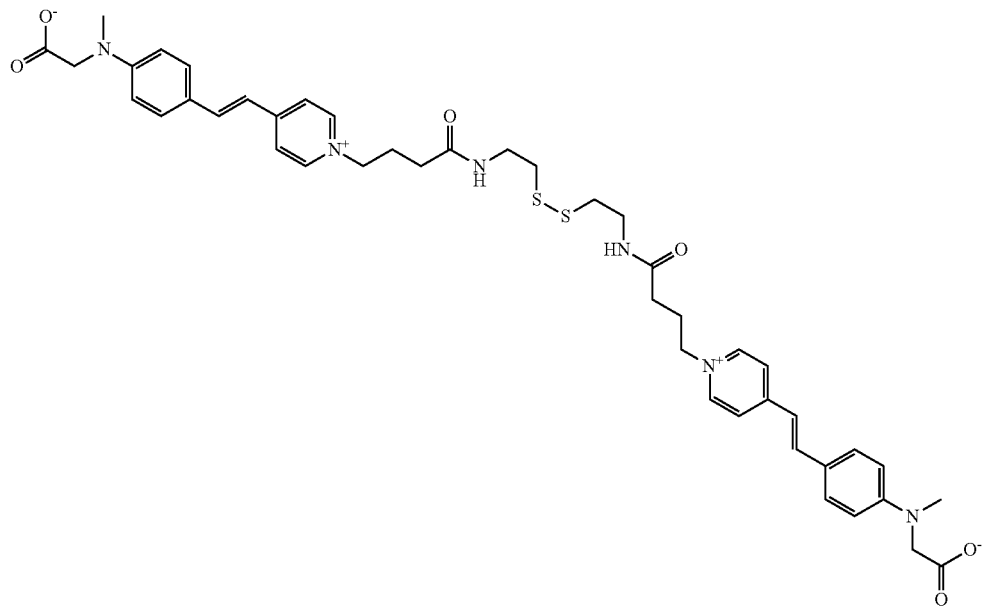
82
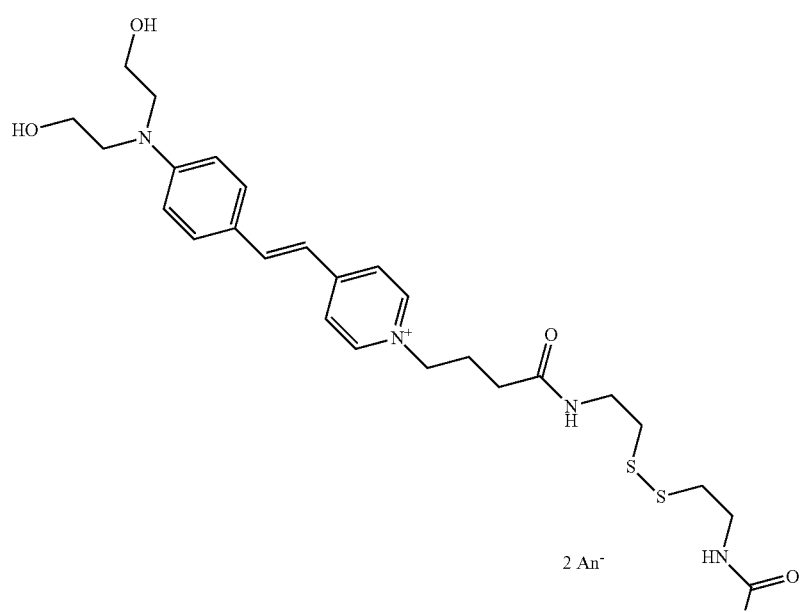
2 An⁻

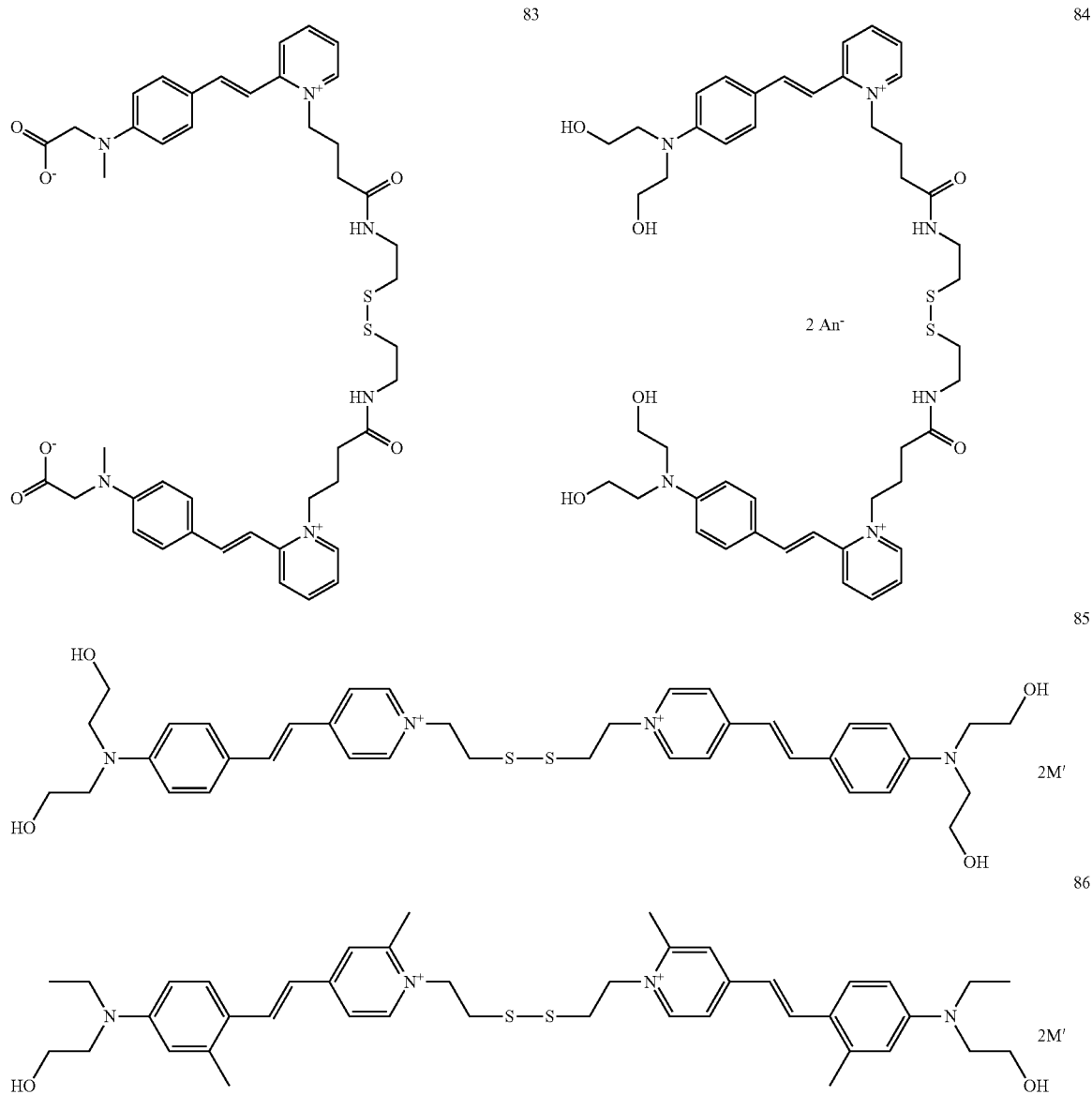

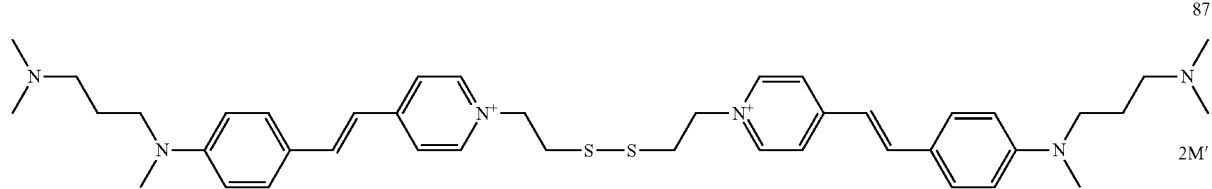
87
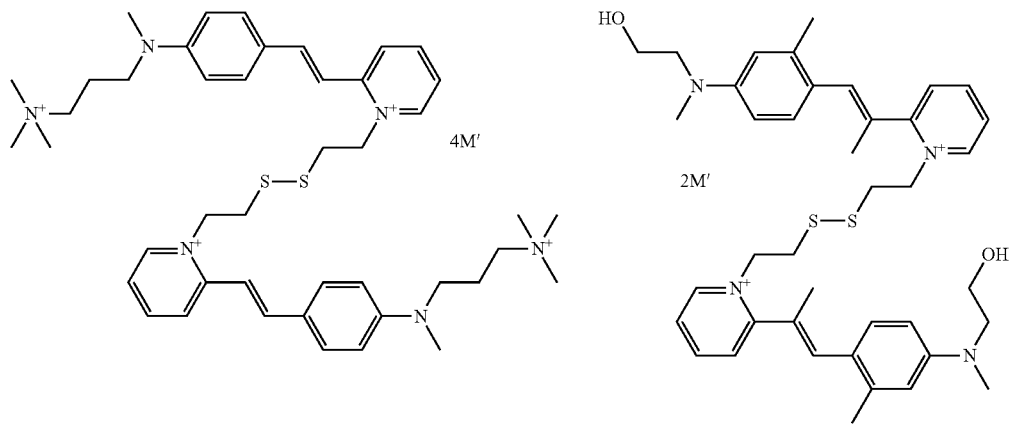
88
89
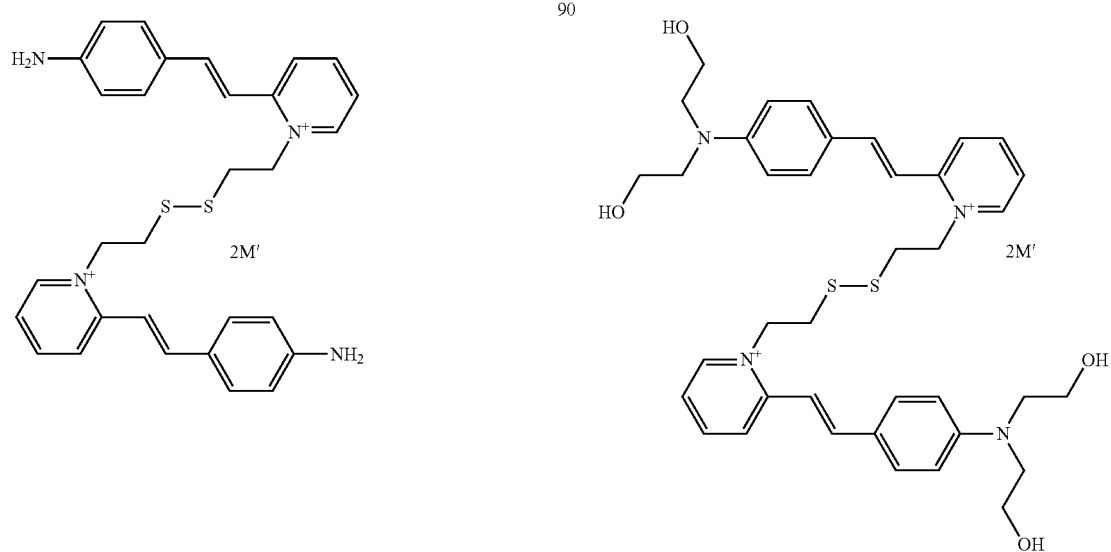
90
91
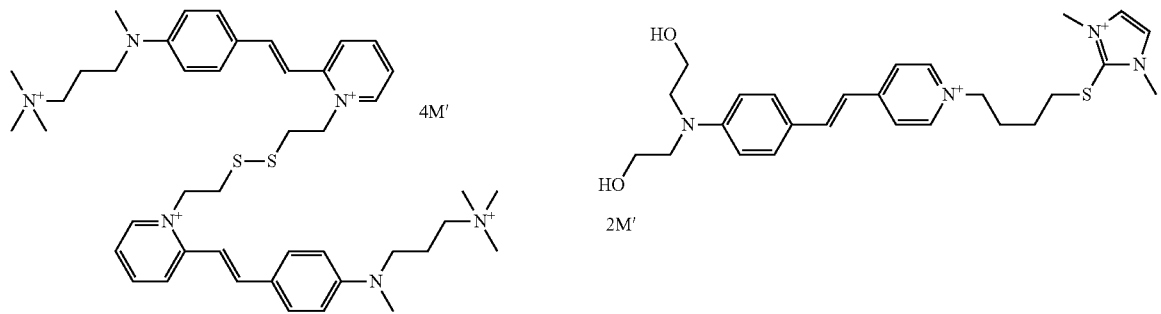
92
93

-continued
94
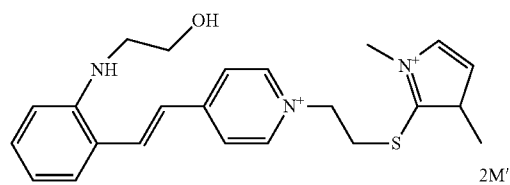
2M′
95
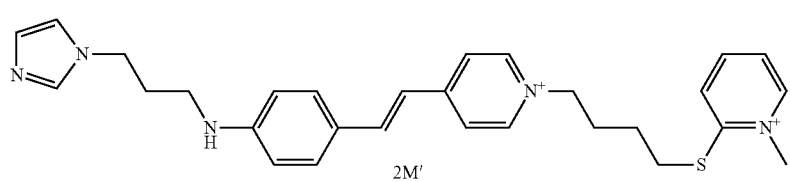
2M′
96
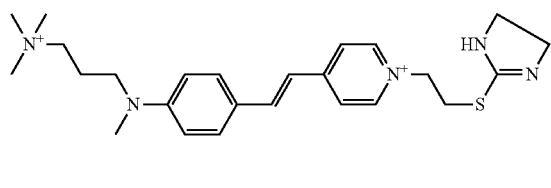
97
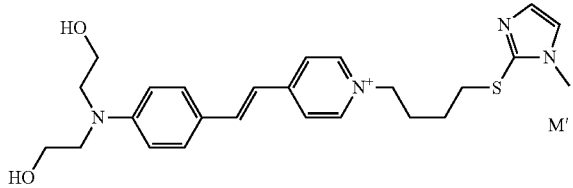
M′
98
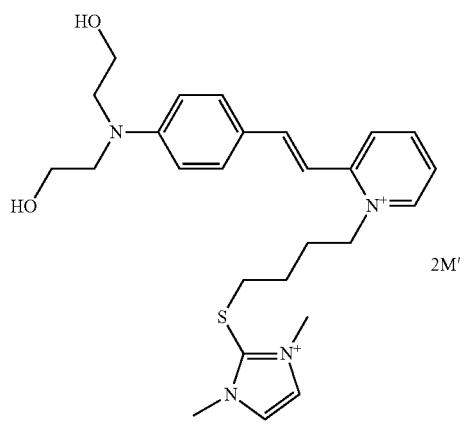
2M′
99
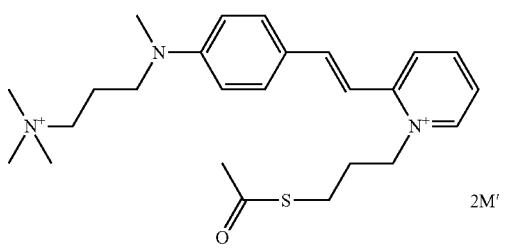
2M′
100
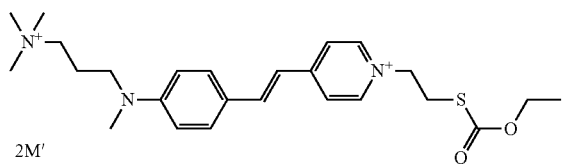
2M′
101
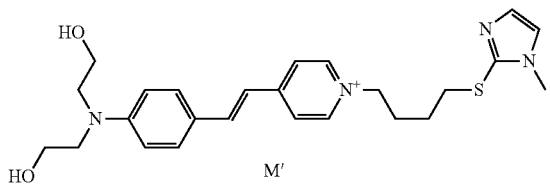
M′
102
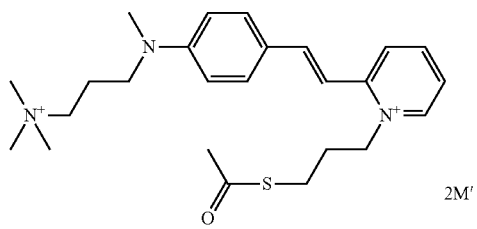
2M′
102
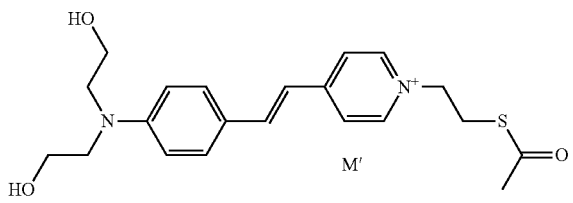
M′

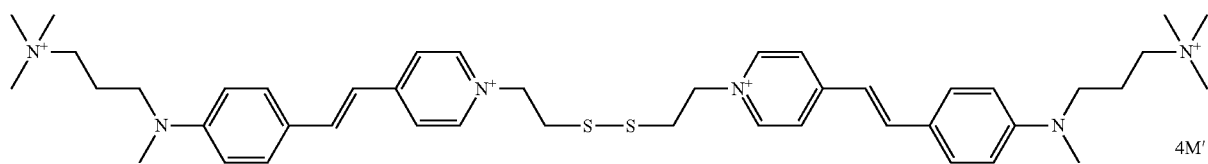
103
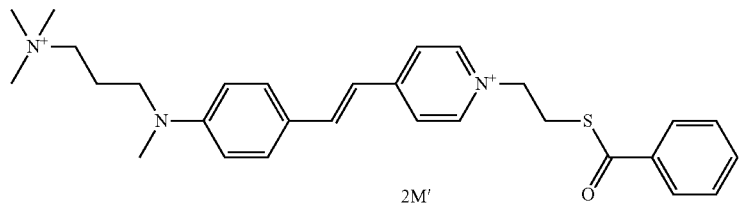
104
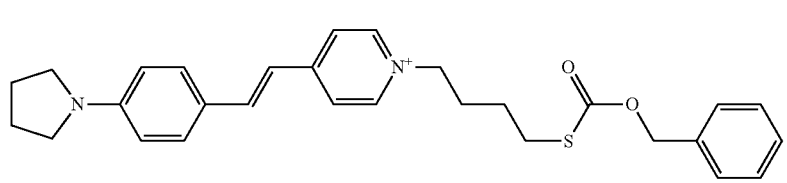
105
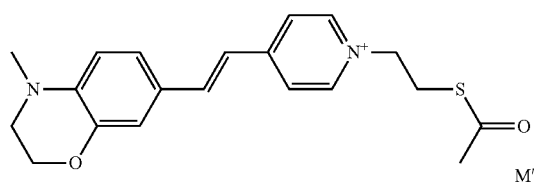
106
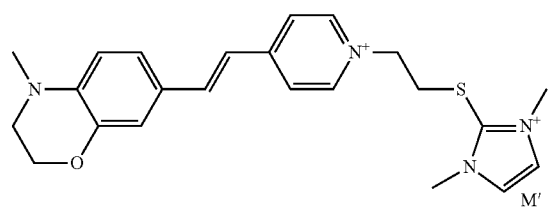
107
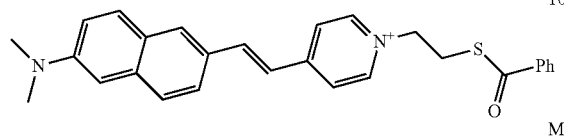
108
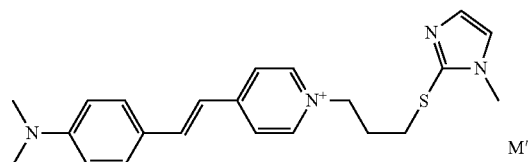
109
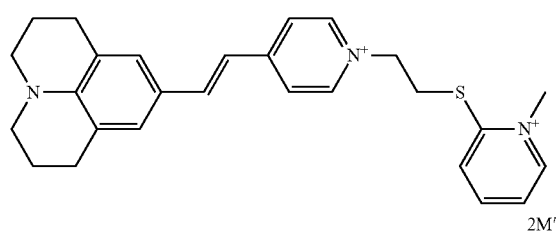
110
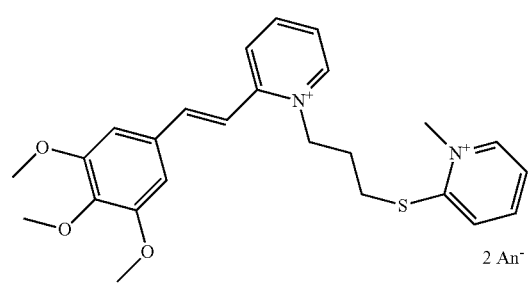
111

-continued
112
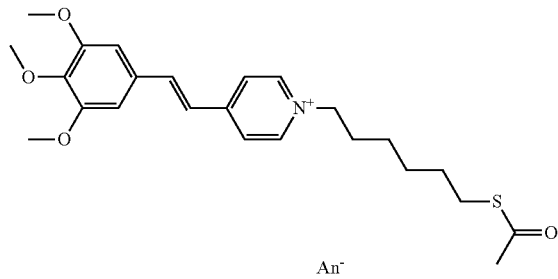
113
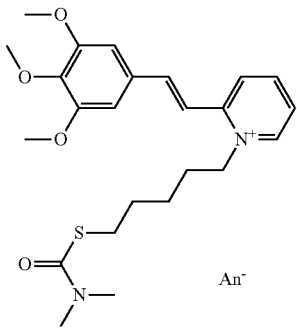
114
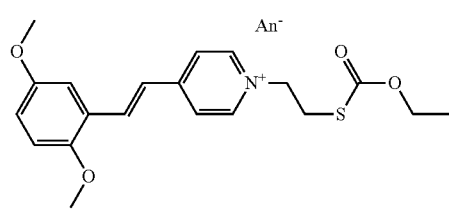
115
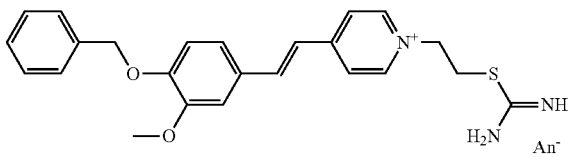
116
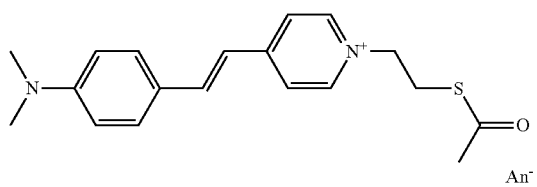
117
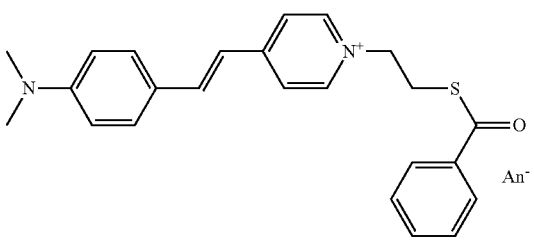
118
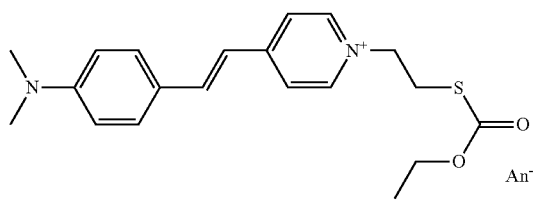
119
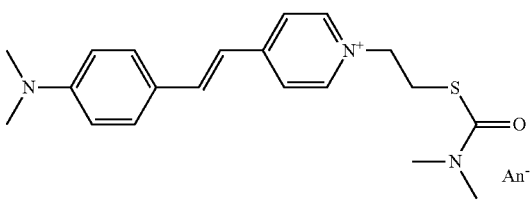
120
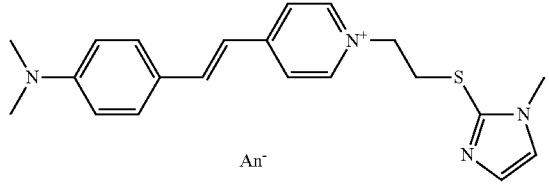
121
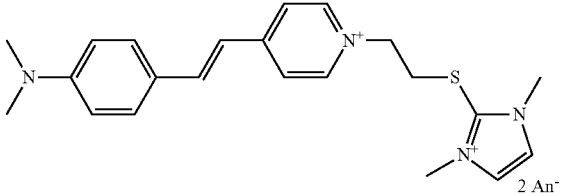
122
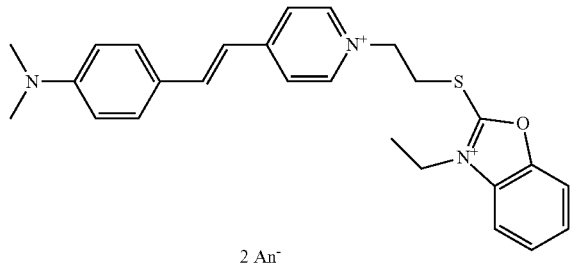

with An⁻ and M', which may be identical or different, preferentially identical, representing anionic counterions. More particularly, the anionic counterion is chosen from halides such as chloride, alkyl sulfates such as methyl sulfate, mesylate and ½(O=)$_2$SO$^{2-}$ or ½ SO$_4^{2-}$.

More preferentially, the dyes i) as defined previously are chosen from compounds 44, 49, 49a and 55, especially 44, 49 and 55.

According to one particularly advantageous embodiment of the invention, the dye 0 is a dye comprising a "permanent" cationic charge, i.e. containing in its structure at least one quaternized nitrogen atom (ammonium) or quaternized phosphorus atom (phosphonium); preferentially quaternized nitrogen.

The composition according to the invention contains, in a cosmetic medium, an amount of dyes bearing a disulfide, thiol or protected-thiol function as defined previously, especially of formula (I) as defined previously, generally inclusively between 0.001% and 30% relative to the total weight of the composition.

Preferably, the amount of dyes bearing a disulfide, thiol or protected-thiol function as defined previously, especially of formula (I), is inclusively between 0.01% and 5% by weight relative to the total weight of the composition. By way of example, the dye(s) are in an amount of between 0.01% and 2%.

i). 5). The Cosmetically Acceptable Organic or Mineral Acid Salt and Counterion of the Dyes of the Invention They are chosen from the "organic or mineral acid salt" and "anionic counterion" as defined previously.

Moreover, the addition salts that may be used in the context of the invention may be chosen from addition salts with a cosmetically acceptable base such as basifying agents as defined below, for instance alkali metal hydroxides such as sodium hydroxide, potassium hydroxide, aqueous ammonia, amines or alkanolamines.

ii) At Least One Fatty Alcohol;

The composition of the invention comprises one or more sparingly ethoxylated or non-ethoxylated fatty alcohols.

The sparingly ethoxylated fatty alcohols that are suitable for performing the invention are chosen more particularly from saturated or unsaturated alcohols containing from 8 to 40 carbon atoms and preferably from 12 to 22 carbon atoms, and from 1 to 6 and preferably from 1 to 3 ethylene oxide units.

If they are unsaturated, these compounds may comprise one to three conjugated or non-conjugated carbon-carbon double bonds.

The sparingly ethoxylated fatty alcohol(s) preferably have the following formula:

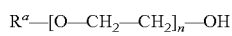

with
R$^a$ representing a linear or branched C$_8$-C$_{40}$ alkyl or linear or branched C$_8$-C$_{40}$ and preferably C$_8$-C$_{30}$ alkenyl group, optionally substituted with one or more hydroxyl groups, and n is an integer between 1 and 6 inclusive, preferentially between 1 and 3 and more particularly between 1 and 2 inclusive.

Among the sparingly ethoxylated fatty alcohols, mention may be made more particularly of lauryl alcohol containing 2 OE, lauryl alcohol containing 3 OE, decyl alcohol containing 3 OE, decyl alcohol containing 5 OE, stearyl alcohol containing 2 OE, stearyl alcohol containing 3 OE, stearyl alcohol containing 4 OE, stearyl alcohol containing 5 OE, cetyl alcohol containing 2 OE, cetyl alcohol containing 3 OE, cetyl alcohol containing 4 OE and cetyl alcohol containing 5 OE, and mixtures thereof, such as cetearyl alcohol containing 3 OE, cetearyl alcohol containing 4 OE and cetearyl alcohol containing 5 OE.

Advantageously, the ethoxylated fatty alcohol is solid or pasty at a temperature of 25° C. For the purposes of the present invention, the term "fatty alcohol that is solid or pasty at 25° C." means a fatty alcohol that has a viscosity, measured with a rheometer (for example an R$^{600}$ rheometer) at a shear rate of 1 s$^{-1}$, of greater than or equal to 1 Pa·s.

Preferably, the sparingly ethoxylated fatty alcohols are saturated, linear sparingly ethoxylated fatty alcohols.

The fatty alcohols of the invention may be "non-ethoxylated", i.e. they do not comprise in their structure any ethylene oxide groups —CH$_2$—CH$_2$—O—.

In this case, the fatty alcohol has the structure R—OH, in which R denotes a saturated or unsaturated, linear or branched radical comprising from 8 to 40 and preferably from 8 to 30 carbon atoms; R may be substituted with one or more hydroxyl groups and preferably with one or two hydroxyl groups.

Examples that may be mentioned include lauryl alcohol, cetyl alcohol, stearyl alcohol, oeyl alcohol, behenyl alcohol, linoleyl alcohol, undecylenyl alcohol, palmitoleyl alcohol, arachidonyl alcohol and erucyl alcohol, and mixtures thereof.

The fatty alcohol may represent a mixture of fatty alcohols, which means that several species of fatty alcohol may coexist, in the form of a mixture, in a commercial product.

Advantageously, the fatty alcohol is solid or pasty at a temperature of 25° C. For the purposes of the present invention, the term "fatty alcohol that is solid or pasty at 25° C." means a fatty alcohol that has a viscosity, measured with a rheometer (for example an R600 rheometer) at a shear rate of 1 s$^{-1}$, of greater than or equal to 1 Pa·s.

Preferentially, the fatty alcohol used in the cosmetic composition according to the invention is chosen from myristyl alcohol, cetyl alcohol, stearyl alcohol and palmityl alcohol, and mixtures thereof, such as cetylstearyl alcohol.

Even more preferentially, the fatty alcohols used in the cosmetic composition according to the invention are stearyl alcohol or cetyl alcohol and mixtures thereof, such as cetylstearyl alcohol especially at 50/50.

Preferably, the non-ethoxylated fatty alcohols are saturated, linear non-ethoxylated fatty alcohols.

Preferably, the sparingly ethoxylated or non-ethoxylated fatty alcohol according to the invention is a non-ethoxylated fatty alcohol.

The sparingly ethoxylated or non-ethoxylated fatty alcohol(s) used in the composition according to the present invention may be present in the composition in an amount ranging from 0.01% to 30%, preferably in an amount ranging from 0.1% to 20% and even more preferentially in an amount ranging from 0.5% to 10% by weight relative to the total weight of the composition.

iii) At Least One Cationic Surfactant;

The oxidizing composition comprises one or more cationic surfactants. Mention may be made, for example, of optionally polyoxyalkylenated primary, secondary or tertiary fatty amine salts, quaternary ammonium salts, and mixtures thereof.

Examples of quaternary ammonium salts that may especially be mentioned include:

a) those corresponding to the general formula (XVII) below:

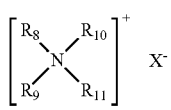

(XVII)

in which formula (XVII) the groups $R_8$ to $R_{11}$, which may be identical or different, represent a linear or branched aliphatic group comprising from 1 to 30 carbon atoms or an aromatic group such as aryl or alkylaryl, at least one of the groups $R_8$ to $R_{11}$ comprising from 8 to 30 carbon atoms and preferably from 12 to 24 carbon atoms. The aliphatic groups may comprise heteroatoms such as, in particular, oxygen, nitrogen, sulfur and halogens.

The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkylacetate, $C_1$-$C_{30}$ hydroxyalkyl, $X^-$ is an anionic counterion chosen from halides, phosphates, acetates, lactates, ($C_1$-$C_4$) alkyl sulfates, and ($C_1$-$C_4$)alkyl- or ($C_1$-$C_4$)alkylarylsulfonates.

Among the quaternary ammonium salts of formula (XVII), preference is given firstly to tetraalkylammonium halides such as tetraalkylammonium chlorides, for instance tetraalkylammonium or alkyltrimethylammonium halides such as dialkyldimethylammonium or alkyltrimethylammonium chlorides in which the alkyl group contains from approximately 12 to 22 carbon atoms, in particular halides such as behenyltrimethylammonium chloride, distearyldimethylammonium chloride, cetyltrimethylammonium chloride, benzyldimethylstearylammonium chloride, or else, secondly, alkoxy sulfates, especially distearoylethylhydroxyethylmethylammonium methosulfate, dipalmitoylethylhydroxyethylammonium methosulfate or distearoylethylhydroxyethylammonium methosulfate, or else, lastly, palmitylamidopropyltrimethylammonium halide, particularly the chloride or stearamidopropyldimethyl(myristyl acetate)ammonium chloride, sold under the name Ceraphyl® 70 by the company Van Dyk;

b) quaternary ammonium salts of imidazoline, for instance those of formula (XVIII) below:

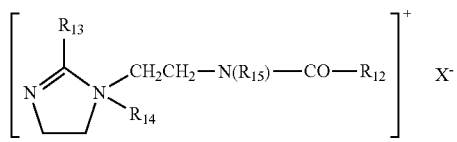

(XVIII)

in which formula (XVIII):
  $R_{12}$ represents an alkenyl or alkyl group comprising from 8 to 30 carbon atoms, for example fatty acid derivatives of tallow;
  $R_{13}$ represents a hydrogen atom, a $C_1$-$C_4$ alkyl group or an alkenyl or alkyl group comprising from 8 to 30 carbon atoms;
  $R_{14}$ represents a $C_1$-$C_4$ alkyl group;
  $R_{15}$ represents a hydrogen atom or a $C_1$-$C_4$ alkyl group;
  $X^-$ represents an anionic counterion chosen in particular from halides, phosphates, acetates, lactates, ($C_1$-$C_4$) alkyl sulfates, ($C_1$-$C_4$)alkyl- or ($C_1$-$C_4$)alkylarylsulfonates.
  $R_{12}$ and $R_{13}$ preferably denote a mixture of alkyl or alkenyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name Rewoquat® W 75 by the company Rewo;

c) quaternary diammonium or triammonium salts, particularly of formula (XIX) below:

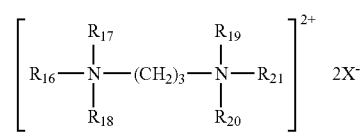

(XIX)

in which formula (XIX):
  $R_{16}$ denotes an alkyl group comprising from about 16 to 30 carbon atoms, which is optionally hydroxylated and/or interrupted with one or more oxygen atoms;
  $R_{17}$ is chosen from hydrogen, an alkyl group comprising from 1 to 4 carbon atoms or a group —$(CH_2)_3$—$N^+$ ($R_{16a}$)($R_{17a}$)($R_{18a}$); $R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms, and
  $X^-$ represents an anionic counterion chosen in particular from halides, acetates, phosphates, nitrates, ($C_1$-$C_4$) alkyl sulfates, ($C_1$-$C_4$)alkyl- or ($C_1$-$C_4$)alkylarylsulfonates, in particular methyl sulfate and ethyl sulfate. Such compounds are, for example, Finquat CT-P, available from the company Finetex (Quaternium 89), and Finquat CT, available from the company Finetex (Quaternium 75);

d) quaternary ammonium salts containing one or more ester functions, such as those of formula (XX) below:

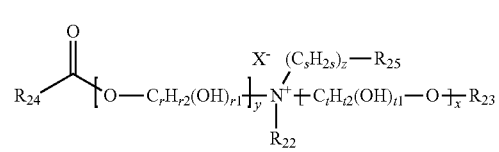

(XX)

in which formula (XX):
  $R_{22}$ is chosen from $C_1$-$C_6$ alkyl and $C_1$-$C_6$ hydroxyalkyl or dihydroxyalkyl groups;
  $R_{23}$ is chosen from:
    the group

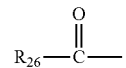

linear or branched, saturated or unsaturated $C_1$-$C_{22}$ hydrocarbon-based groups $R_{27}$,
    a hydrogen atom;
  $R_{25}$ is chosen from:
    the group

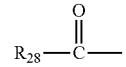

linear or branched, saturated or unsaturated $C_1$-$C_6$ hydrocarbon-based groups $R_{29}$,
a hydrogen atom;

$R_{24}$, $R_{26}$ and $R_{28}$, which may be identical or different, are chosen from linear or branched, saturated or unsaturated $C_7$-$C_{21}$ hydrocarbon-based groups;

r, s and t, which may be identical or different, are integers ranging from 2 to 6;

r1 and t1, which may be identical or different, are equal to 0 or 1, with r2+r1=2r and t1+t2=2t, y is an integer ranging from 1 to 10;

x and z, which may be identical or different, are integers ranging from 0 to 10;

$X^-$ represents an organic or inorganic anionic counterion; with the proviso that the sum x+y+z is from 1 to 15, that when x is 0, then $R_{23}$ denotes $R_{27}$ and that when z is 0, then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and may contain from 12 to 22 carbon atoms, or may be short and may contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anionic counterion $X^-$ is preferably a halide, preferably such as chloride, bromide or iodide, a ($C_1$-$C_4$)alkyl sulfate or a ($C_1$-$C_4$)alkyl- or ($C_1$-$C_4$)alkylaryl-sulfonate. However, use may be made of methanesulfonate, phosphate, nitrate, tosylate, an anion derived from an organic acid, such as acetate or lactate, or any other anion compatible with the ammonium containing an ester function.

The anionic counterion $X^-$ is even more particularly chloride, methyl sulfate or ethyl sulfate.

Use is made more particularly, in the composition according to the invention, of the ammonium salts of formula (XX) in which:

$R_{22}$ denotes a methyl or ethyl group, x and y are equal to 1, z is equal to 0 or 1, r, s and t are equal to 2, $R_{23}$ is chosen from:
the group

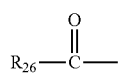

methyl, ethyl or $C_{14}$-$C_{22}$ hydrocarbon-based groups,
a hydrogen atom, $R_{25}$ is chosen from:
the group

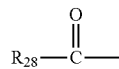

a hydrogen atom, $R_{24}$, $R_{26}$ and $R_{28}$, which may be identical or different, are chosen from linear or branched, saturated or unsaturated $C_{13}$-$C_{17}$ hydrocarbon-based groups, and more particularly from linear or branched, saturated or unsaturated $C_{13}$-$C_{17}$ alkyl and alkenyl groups.

Advantageously, the hydrocarbon-based radicals are linear.

Among the quaternary ammonium salts containing one or more ester functions of formula (XX), examples that may be mentioned include salts, especially the chloride or methyl sulfate, of diacyloxyethyldimethylammonium, diacyloxyethylhydroxy-ethylmethylammonium, monoacyloxyethyldihydroxyethylmethylammonium, triacyloxy-ethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably methyl or ethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium salts of mono-, di- and triesters with a weight majority of diester salts.

It is also possible to use the ammonium salts containing at least one ester function that are described in U.S. Pat. No. 4,874,554 and U.S. Pat. No. 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the cationic surfactants that may be present in the composition according to the invention, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

According to the present invention, the cationic surfactant(s) are preferably present in the composition in an amount ranging from 0.01% to 40% by weight, preferably from 0.1% to 20% by weight and better still from 0.2% to 10% by weight, relative to the total weight of the composition.

iv) At Least One Alkaline Agent;

The composition according to the invention comprises one or more alkaline agents. This agent may be chosen from mineral or organic or hybrid alkaline agents, or mixtures thereof.

The mineral alkaline agent(s) are preferably chosen from aqueous ammonia, alkali carbonates or bicarbonates such as sodium or potassium carbonates and sodium or potassium bicarbonates, sodium hydroxide or potassium hydroxide, or mixtures thereof.

According to one advantageous embodiment of the invention, the alkaline agent(s) are organic amines, i.e. they contain at least one substituted or unsubstituted amino group.

The organic alkaline agent(s) are preferentially chosen from organic amines with a $pK_b$ at 25° C. of less than 12, preferably less than 10 and even more advantageously less than 6. It should be noted that it is the $pK_b$ corresponding to the function of highest basicity.

Hybrid compounds that may be mentioned include the salts of the amines mentioned previously with acids such as carbonic acid or hydrochloric acid.

The organic alkaline agent(s) are chosen, for example, from alkanolamines, oxyethylenated and/or oxypropylenated ethylenediamines, amino acids and the compounds of formula (XXI) below:

$$R^x\!\!\diagdown\!\!\underset{R^y}{\overset{}{N}}\!\!-\!W\!-\!\underset{R^t}{\overset{R^z}{N}}\!\!\diagup\quad\text{(XXI)}$$

in which formula (XXI):

W is a divalent $C_1$-$C_6$ alkylene radical optionally substituted with a hydroxyl group or a $C_1$-$C_6$ alkyl radical, and/or optionally interrupted with one or more heteroatoms such as oxygen or $NR^u$;

$R^x$, $R^y$, $R^z$ $R^t$ and $R^u$, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Alkanolamines such as monoalkanolamines, dialkanolamines or trialkanolamines comprising from one to three identical or different $C_1$-$C_4$ hydroxyalkyl radicals are in particular suitable for performing the invention.

Among compounds of this type, mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (XXII) below:

$$R-CH_2-CH\!\!\diagdown\!\!\underset{\underset{O}{\overset{\|}{C}}-OH}{\overset{NH_2}{}}\quad\text{(XXII)}$$

in which formula (XXII):

R denotes a group chosen from:

$$\underset{NH}{\diagdown}\!\!=\!\!\underset{}{\diagup}\!\!N,$$

aminoproml: —$(CH_2)_3$—$NH_2$, aminoethyl —$(CH_2)_2$—$NH_2$, —$(CH_2)_2$—$NH$—$C(O)$—$NH_2$ and $$-(CH_2)_2-NH-C\!\!\diagdown\!\!\underset{NH}{\overset{NH_2.}{}}$$

The compounds corresponding to formula (XXII) are histidine, lysine, arginine, ornithine and citrulline.

The organic amine may also be chosen from organic amines of heterocyclic type. Besides histidine that has already been mentioned in the amino acids, mention may be made in particular of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and baleine.

The organic amine is chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Mention may be made in particular of the use of guanidine carbonate or monoethanolamine hydrochloride as hybrid compounds.

The composition of the invention preferably contains one or more alkanolamines and/or one or more basic amino acids, more advantageously one or more alkanolamines. More preferentially still, the organic amine is monoethanolamine.

According to one particular embodiment, the composition of the invention comprises, as alkaline agent, one or more alkanolamines.

Preferably, the alkanolamine is ethanolamine (or monoethanolamine).

In one variant of the invention, the composition comprises, as alkaline agent, one or more alkanolamines (preferably ethanolamine) and aqueous ammonia. In this variant, the alkanolamine(s) are present in a predominant amount relative to the aqueous ammonia.

Advantageously, the composition according to the invention has a content of alkaline agent(s) ranging from 0.01% to 30% by weight, preferably from 0.1% to 20% by weight and better still from 1% to 10% by weight relative to the weight of the said composition.

v) At Least One Reducing Agent.

The composition of the invention comprises one or more reducing agents.

Preferably, the reducing agent(s) are chosen from thiols such as thioglycolic acid, thiolactic acid, 3-mercaptopropionic acid, thiomalic acid, 2,3-dimercaptosuccinic acid, cysteine, N-glycyl-L-cysteine, L-cysteinylglycine and also esters and salts thereof, thioglycerol, cysteamine and $C_1$-$C_4$ acyl derivatives thereof, N-mesylcysteamine, N-acetylcysteine, N-mercaptoalkylamides of sugars such as N-(mercapto-2-ethyl) gluconamide, pantetheine, N-(mercaptoalkyl)-ω-hydroxyalkylamides, for example those described in patent application EP-A-354 835, N-mono- or N,N-dialkylmercapto-4-butyramides, for example those described in patent application EP-A-368 763, aminomercaptoalkyl amides, for example those described in patent application EP-A-432 000, N-(mercaptoalkyl)succinamic acids and N-(mercaptoalkyl)succinimides, for example those described in patent application EP-A-465 342, alkylamino mercaptoalkyl amides, for example those described in patent application EP-A-514 282, the azeotropic mixture of 2-hydroxypropyl thioglycolate and of (2-hydroxy-1-methyl)ethyl thioglycolate as described in patent application FR-A-2 679 448, mercaptoalkylamino amides, for example those described in patent application FR-A-2 692 481, and N-mercaptoalkylalkanediamides, for example those described in patent application EP-A-653 202.

The reducing agent may alternatively be chosen from hydrides such as sodium or potassium borohydride or alkali metal or alkaline-earth metal sulfites or bisulfites; or alternatively from phosphorus derivatives such as phosphines or phosphites.

The reducing agent(s) are preferably chosen from thiols.

The preferred reducing agents are thioglycolic acid and cysteine, or salts thereof. The reducing agent is preferably used as an aqueous solution.

In general, the concentration of reducing agent(s) is inclusively between 0.01% and 30% by weight, preferably between 0.1% and 25% by weight and more particularly between 0.5% and 10% by weight relative to the total weight of the composition applied to the keratin fibres.

vi) Optionally at Least One Oxidizing Agent

The composition according to the invention may also comprise one or more chemical oxidizing agent(s). The term "chemical oxidizing agent" means an oxidizing agent other than atmospheric oxygen.

The chemical oxidizing agents are for example chosen from hydrogen peroxide, urea peroxide, alkali metal bromates or ferricyanides, peroxygenated salts, for instance persulfates, perborates, peracids and precursors thereof and percarbonates of alkali metals or alkaline-earth metals. Advantageously, the oxidizing agent is hydrogen peroxide.

The content of oxidizing agent(s) more particularly represents from 0.1% to 20% by weight and preferably from 0.5% to 10% by weight relative to the weight of the composition containing them.

vii) Optionally at Least One Thickening Organic Polymer;

The composition according to the invention may contain vii) one or more thickening organic polymers.

the term "thickening polymer" means a polymer which, when introduced at 1% by weight in an aqueous solution or an aqueous-alcoholic solution containing 30% ethanol, and at pH 7, or in an oil chosen from liquid petroleum jelly, isopropyl myristate or cyclopentadimethylsiloxane, makes it possible to achieve a viscosity of at least 100 cps and preferably of at least 500 cps, at 25° C. and at a shear rate of 1 $s^{-1}$. This viscosity may be measured using a cone/plate viscometer (Haake R600 rheometer or the like). The thickening polymers may thicken the aqueous phase and/or the fatty phase, preferentially the aqueous phase.

the term "organic thickening polymer" means a thickening polymer as defined previously, which is formed from carbon and hydrogen, and possibly nitrogen, oxygen, sulfur, halogens such as fluorine, chlorine or bromine, and also phosphorus, alkali metals such as sodium or potassium, or alkaline-earth metals such as magnesium or calcium. The organic polymers according to the invention do not comprise silicon.

The organic thickening polymers according to the invention may be of natural or synthetic origin.

The thickening polymers may be anionic, cationic, amphoteric or nonionic associative or non-associative polymers.

Aqueous-phase-thickening polymers that may be mentioned include non-associative thickening polymers bearing sugar units.

For the purposes of the present invention, the term "sugar unit" means a unit derived from a carbohydrate of formula $C_n(H_2O)_{n-1}$ or $(CH_2O)_n$, which may be optionally modified by substitution and/or by oxidation and/or by dehydration.

The sugar units that may be included the composition of the thickening polymers of the invention are preferably derived from the following sugars:
glucose;
galactose;
arabinose;
rhamnose;
mannose;
xylose;
fucose;
anhydrogalactose;
galacturonic acid;
glucuronic acid;
mannuronic acid;
galactose sulfate;
anhydrogalactose sulfate and
fructose.

Thickening polymers of the invention that may especially be mentioned include native gums such as:
a) tree or shrub exudates, including:
gum arabic (branched polymer of galactose, arabinose, rhamnose and glucuronic acid),
ghatti gum (polymer derived from arabinose, galactose, mannose, xylose and glucuronic acid);
karaya gum (polymer derived from galacturonic acid, galactose, rhamnose and glucuronic acid);
gum tragacanth (or tragacanth) (polymer of galacturonic acid, galactose, fucose, xylose and arabinose);

b) gums derived from algae, including:
  agar (polymer derived from galactose and anhydrogalactose);
  alginates (polymers of mannuronic acid and of glucuronic acid);
  carrageenans and furcellerans (polymers of galactose sulfate and of anhydrogalactose sulfate);
c) gums derived from seeds or tubers, including:
  guar gum (polymer of mannose and galactose);
  locust bean gum (polymer of mannose and galactose);
  fenugreek gum (polymer of mannose and galactose);
  tamarind gum (polymer of galactose, xylose and glucose);
  konjac gum (polymer of glucose and mannose);
d) microbial gums, including:
  xanthan gum (polymer of glucose, mannose acetate, mannose/pyruvic acid and glucuronic acid);
  gellan gum (polymer of partially acylated glucose, rhamnose and glucuronic acid);
  scleroglucan gum (glucose polymer);
e) plant extracts, including:
  cellulose (glucose polymer);
  starch (glucose polymer).
  inulin.

These polymers may be physically or chemically modified. A physical treatment that may especially be mentioned is the temperature.

Chemical treatments that may be mentioned include esterification, etherification, amidation and oxidation reactions. These treatments can lead to polymers that may especially be nonionic, anionic or amphoteric.

Preferably, these chemical or physical treatments are applied to guar gums, locust bean gums, starches and celluloses.

The nonionic guar gums that may be used according to the invention may be modified with $C_1$-$C_6$ (poly)hydroxyalkyl groups.

Among the $C_1$-$C_6$ (poly)hydroxyalkyl groups that may be mentioned, for example, are hydroxymethyl, hydroxyethyl, hydroxypropyl and hydroxybutyl groups.

These guar gums are well known in the prior art and can be prepared, for example, by reacting the corresponding alkene oxides such as, for example, propylene oxides, with the guar gum so as to obtain a guar gum modified with hydroxypropyl groups.

The degree of hydroxyalkylation preferably ranges from 0.4 to 1.2, and corresponds to the number of alkylene oxide molecules consumed by the number of free hydroxyl functions present on the guar gum.

Such nonionic guar gums optionally modified with hydroxyalkyl groups are sold, for example, under the trade names Jaguar HP8, Jaguar HP60 and Jaguar HP120 by the company Rhodia Chimie.

The botanical origin of the starch molecules used in the present invention may be cereals or tubers. Thus, the starches are chosen, for example, from corn starch, rice starch, cassava starch, barley starch, potato starch, wheat starch, sorghum starch and pea starch.

The starches may be chemically or physically modified especially by one or more of the following reactions: pregelatinization, oxidation, crosslinking, esterification, etherification, amidation, heat treatments.

Distarch phosphates or compounds rich in distarch phosphate will preferentially be used, for instance the products sold under the references Prejel VA-70-T AGGL (gelatinized hydroxypropyl cassava distarch phosphate), Prejel TK1 (gelatinized cassava distarch phosphate) and Prejel 200 (gelatinized acetyl cassava distarch phosphate) by the company Avebe, or Structure Zea from National Starch (gelatinized corn distarch phosphate).

According to the invention, amphoteric starches may also be used, these amphoteric starches comprising one or more anionic groups and one or more cationic groups. The anionic and cationic groups may be linked to the same reactive site of the starch molecule or to different reactive sites; they are preferably linked to the same reactive site. The anionic groups may be of carboxylic, phosphate or sulfate type, preferably carboxylic. The cationic groups may be of primary, secondary, tertiary or quaternary amine type.

The starch molecules may be derived from any plant source of starch, especially such as corn, potato, oat, rice, tapioca, sorghum, barley or wheat. It is also possible to use the starch hydrolysates mentioned above. The starch is preferably derived from potato.

The non-associative thickening polymers of the invention may be cellulose-based polymers not comprising any $C_{10}$-$C_{30}$ fatty chains in their structure.

According to the invention, the term "cellulose-based polymer" means any polysaccharide compound bearing in its structure sequences of glucose residues connected via β-1,4 bonds; besides unsubstituted celluloses, the cellulose derivatives may be anionic, cationic, amphoteric or nonionic;

Thus, the cellulose-based polymers of the invention may be chosen from unsubstituted celluloses, including those in a monocrystalline form, and cellulose ethers.

Among these cellulose-based polymers, cellulose ethers, cellulose esters and cellulose ester ethers are distinguished.

Among the cellulose esters are inorganic esters of cellulose (cellulose nitrates, sulfates, phosphates, etc.), organic cellulose esters (cellulose monoacetates, triacetates, amidopropionates, acetatebutyrates, acetatepropionates and acetatetrimellitates, etc.), and mixed organic/inorganic esters of cellulose, such as cellulose acetatebutyrate sulfates and cellulose acetatepropionate sulfates. Among the cellulose ester ethers, mention may be made of hydroxypropylmethylcellulose phthalates and ethylcellulose sulfates.

Among the nonionic cellulose ethers not containing a $C_{10}$-$C_{30}$ fatty chain, i.e. "Non-associative", mention may be made of ($C_1$-$C_4$)alkylcelluloses such as methylcelluloses and ethylcelluloses (for example Ethocel Standard 100 Premium from Dow Chemical); (poly)hydroxy($C_1$-$C_4$)alkylcelluloses such as hydroxymethylcelluloses, hydroxyethylcelluloses (for example Natrosol 250 HHR sold by Aqualon) and hydroxypropylcelluloses (for example Klucel EF from Aqualon); mixed celluloses (poly) hydroxy($C_1$-$C_4$)alkyl($C_1$-$C_4$) alkylcelluloses such as hydroxypropyl methylcelluloses (for example Methocel E4M from Dow Chemical), hydroxyethyl methylcelluloses, hydroxyethyl methylcelluloses (for example Bermocoll E 481 FQ from Akzo Nobel) and hydroxybutyl methylcelluloses.

Among the anionic cellulose ethers not containing a fatty chain, mention may be made of (poly)carboxy($C_1$-$C_4$)alkylcelluloses, and salts thereof. Examples that may be mentioned include carboxymethylcelluloses, carboxymethylmethylcelluloses (for example Blanose 7M from the company Aqualon) and carboxymethylhydroxyethylcelluloses, and the sodium salts thereof.

Among the cationic cellulose ethers not containing a fatty chain, mention may be made of cationic cellulose derivatives grafted with a water-soluble quaternary ammonium monomer, and disclosed in particular in U.S. Pat. No. 4,131,576, such as (poly)hydroxy($C_1$-$C_4$)alkyl celluloses, for instance hydroxymethyl, hydroxyethyl or hydroxypropyl celluloses grafted in particular with a methacryloylethyltrimethylammonium, methacrylamidopropyltrimethylammonium or dimethyldiallylammonium salt. The commercial products corresponding to this definition are more particularly the products sold under the names Celquat® L 200 and Celquat® H 100 by the company National Starch.

Among the nonassociative thickening polymers not bearing sugar units that may be used, mention may be made of crosslinked acrylic or methacrylic acid homopolymers or copolymers, crosslinked 2-acrylamido-2-methylpropanesulfonic acid homopolymers and crosslinked acrylamide copolymers thereof, ammonium acrylate homopolymers, or copolymers of ammonium acrylate and of acrylamide, alone or mixtures thereof.

A first family of nonassociative thickening polymers that is suitable for use is represented by crosslinked acrylic acid homopolymers.

Among the homopolymers of this type, mention may be made of those crosslinked with an allyl alcohol ether of the sugar series, such as, for example, the products sold under the names Carbopol 980, 981, 954, 2984 and 5984 by the company Noveon or the products sold under the names Synthalen M and Synthalen K by the company 3 VSA.

The nonassociative thickening polymers may also be crosslinked (meth)acrylic acid copolymers, such as the polymer sold under the name Aqua SF1 by the company Noveon.

The nonassociative thickening polymers may be chosen from crosslinked 2-acrylamido-2-methylpropanesulfonic acid homopolymers and the crosslinked acrylamide copolymers thereof.

Among the partially or totally neutralized crosslinked copolymers of 2-acrylamido-2-methylpropanesulfonic acid and of acrylamide, mention may be made in particular of the product described in Example 1 of document EP 503 853, and reference may be made to said document as regards these polymers.

The composition may similarly comprise, as nonassociative thickening polymers, ammonium acrylate homopolymers or copolymers of ammonium acrylate and of acrylamide.

Among the ammonium acrylate homopolymers that may be mentioned is the product sold under the name Microsap PAS 5193 by the company Hoechst. Among the copolymers of ammonium acrylate and of acrylamide that may be mentioned is the product sold under the name Bozepol C Nouveau or the product PAS 5193 sold by the company Hoechst. Reference may be made especially to documents FR 2 416 723, U.S. Pat. No. 2,798,053 and U.S. Pat. No. 2,923,692 as regards the description and preparation of such compounds.

Among the aqueous-phase thickening polymers, mention may also be made of the non-cellulose-based associative polymers that are well known to those skilled in the art and especially of nonionic, anionic, cationic or amphoteric nature.

It is recalled that "associative polymers" are polymers that are capable, in an aqueous medium, of reversibly associating with each other or with other molecules.

Their chemical structure more particularly comprises at least one hydrophilic region and at least one hydrophobic region.

The term "hydrophobic group" means a radical or polymer with a saturated or unsaturated, linear or branched hydrocarbon-based chain, comprising at least 10 carbon atoms, preferably from 10 to 30 carbon atoms, in particular from 12 to 30 carbon atoms and more preferentially from 18 to 30 carbon atoms.

Preferentially, the hydrocarbon-based group is derived from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

Among the associative polymers of anionic type that may be mentioned are:

(a) those comprising at least one hydrophilic unit and at least one fatty-chain allyl ether unit, more particularly those whose hydrophilic unit is formed by an ethylenic unsaturated anionic monomer, more particularly a vinylcarboxylic acid and most particularly an acrylic acid or a methacrylic acid or mixtures thereof.

Among these anionic associative polymers, those that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether, and from 0 to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl alcohol ether (Steareth-10), in particular those sold by the company Ciba under the names Salcare SC 80® and Salcare SC 90®, which are aqueous 30% emulsions of a crosslinked terpolymer of methacrylic acid, of ethyl acrylate and of steareth-10 allyl ether (40/50/10);

(b) polymers comprising i) at least one hydrophilic unit of unsaturated olefinic carboxylic acid type, and ii) at least one hydrophobic unit of the type such as a ($C_{10}$-$C_{30}$) alkyl ester of an unsaturated carboxylic acid.

($C_{10}$-$C_{30}$)alkyl esters of unsaturated carboxylic acids that are useful in the invention comprise, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to U.S. Pat. No. 3,915,921 and U.S. Pat. No. 4,509,949.

Among the anionic associative polymers of this type, use will be made more particularly of those formed from 95% to 60% by weight of acrylic acid (hydrophilic unit), 4% to 40% by weight of $C_{10}$-$C_{30}$ alkyl acrylate (hydrophobic unit) and 0 to 6% by weight of crosslinking polymerizable monomer, or alternatively those formed from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described previously.

Among the said above polymers, those most particularly preferred according to the present invention are the products sold by the company Goodrich under the trade names Pemulen TR1®, Pemulen TR2® and Carbopol 1382®, and even more preferentially Pemulen TR1®, and the product sold by the company SEPPIC under the name Coatex SX®.

Mention may also be made of the acrylic acid/lauryl methacrylate/vinylpyrrolidone terpolymer sold under the name Acrylidone LM by the company ISP.

(c) maleic anhydride/$C_{30}$-$C_{38}$ α-olefin/alkyl maleate terpolymers, such as the product (maleic anhydride/$C_{30}$-$C_{38}$ α-olefin/isopropyl maleate) sold under the name Performa V 1608® by the company Newphase Technologies.

(d) acrylic terpolymers comprising:
   i) about 20% to 70% by weight of an α,β-monoethylenically unsaturated carboxylic acid [A],
   ii) about 20% to 80% by weight of an α,β-monoethylenically unsaturated non-surfactant monomer other than [A],
   iii) about 0.5% to 60% by weight of a nonionic monourethane which is the product of reaction of a monohydric surfactant with a monoisocyanate containing monoethylenic unsaturation, such as those described in patent application EP-A-0 173 109 and more particularly the terpolymer described in Example 3, namely a methacrylic acid/methyl acrylate/behenyl alcohol dimethyl-meta-isopropenylbenzylisocyanate ethoxylated (40 EO) terpolymer, as an aqueous 25% dispersion.

(e) copolymers comprising among their monomers an α,β-monoethylenically unsaturated carboxylic acid and an ester of an α,β-monoethylenically unsaturated carboxylic acid and of an oxyalkylenated fatty alcohol.

Preferentially, these compounds also comprise as monomer an ester of an α,β-monoethylenically unsaturated carboxylic acid and of a $C_1$-$C_4$ alcohol.

An example of a compound of this type that may be mentioned is Aculyn 22® sold by the company Röhm & Haas, which is a methacrylic acid/ethyl acrylate/oxyalkylenated stearyl methacrylate terpolymer.

(f) amphiphilic polymers comprising at least one ethylenically unsaturated monomer bearing a sulfonic group, in free or partially or totally neutralized form and comprising at least one hydrophobic part. These polymers may be crosslinked or noncrosslinked. They are preferably crosslinked.

The ethylenically unsaturated monomers bearing a sulfonic group are especially chosen from vinylsulfonic acid, styrenesulfonic acid, (meth)acrylamido($C_1$-$C_{22}$)alkylsulfonic acids, N—($C_1$-$C_{22}$)alkyl(meth)acrylamido($C_1$-$C_{22}$)alkylsulfonic acids such as undecylacrylamidomethanesulfonic acid, and also partially or totally neutralized forms thereof.

Use will more preferably be made of (meth)acrylamido ($C_1$-$C_{22}$)alkylsulfonic acids, such as, for example, acrylamidomethanesulfonic acid, acrylamidoethanesulfonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid, 2-acrylamido-2,6-dimethyl-3-heptanesulfonic acid, and also partially or totally neutralized forms thereof.

2-Acrylamido-2-methylpropanesulfonic acid (AMPS), and also partially or totally neutralized forms thereof, will more particularly be used.

The amphiphilic polymers in accordance with the invention may be chosen especially from random amphiphilic AMPS polymers modified by reaction with a $C_6$-$C_{22}$ n-monoalkylamine or di-n-alkylamine, and such as those described in Patent Application WO 00/31154. These polymers may also contain other ethylenically unsaturated hydrophilic monomers selected, for example, from (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

The preferred polymers of this family are chosen from amphiphilic copolymers of AMPS and of at least one ethylenically unsaturated hydrophobic monomer.

These same copolymers may also contain one or more ethylenically unsaturated monomers not comprising a fatty chain, such as (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described especially in patent application EP-A-750 899, U.S. Pat. No. 5,089,578 and in the following Yotaro Morishima publications:

*Self-assembling amphiphilic polyelectrolytes and their nanostructures*—Chinese Journal of Polymer Science Vol. 18, No. 40 (2000), 323-336;

*Micelle formation of random copolymers of sodium 2-(acrylamido)-2-methylpropanesulfonate and a nonionic surfactant macromonomer in water as studied by fluorescence and dynamic light scattering*—Macromolecules, Vol. 33, No. 10 (2000), 3694-3704;

*Solution properties of micelle networks formed by nonionic moieties covalently bound to a polyelectrolyte: salt effects on rheological behavior*—Langmuir, Vol. 16, No. 12, (2000) 5324-5332;

*Stimuli responsive amphiphilic copolymers of sodium 2-(acrylamido)-2-methylpropanesulfonate and associative macromonomers*—Polym. Preprint, Div. Polym. Chem., 40(2), (1999), 220-221.

Among these polymers, mention may be made of:

copolymers, which may or may not be crosslinked and which may or may not be neutralized, comprising from 15 to 60% by weight of AMPS units and from 40 to 85% by weight of ($C_8$-$C_{16}$)alkyl(meth)acrylamide units or of ($C_8$-$C_{16}$)alkyl(meth)acrylate units, with respect to the polymer, such as those described in Application EP-A-750 899;

terpolymers comprising from 10 mol % to 90 mol % of acrylamide units, from 0.1 mol % to 10 mol % of AMPS units and from 5 mol % to 80 mol % of n-($C_6$-$C_{18}$) alkylacrylamide units, such as those described in U.S. Pat. No. 5,089,578.

Mention may also be made of copolymers of totally neutralized AMPS and of dodecyl methacrylate, and also crosslinked and non-crosslinked copolymers of AMPS and of n-dodecylmethacrylamide, such as those described in the Morishima articles mentioned above.

Among the cationic associative polymers that may be mentioned are:

(I) cationic associative polyurethanes;

(II) the compound sold by the company Noveon under the name Aqua CC and which corresponds to the INCI name Polyacrylate-1 Crosspolymer.

Polyacrylate-1 Crosspolymer is the product of polymerization of a monomer mixture comprising:

a di($C_1$-$C_4$ alkyl)amino($C_1$-$C_6$ alkyl) methacrylate, one or more $C_1$-$C_{30}$ alkyl esters of (meth)acrylic acid, a polyethoxylated $C_{10}$-$C_{30}$ alkyl methacrylate (20-25 mol of ethylene oxide units), a 30/5 polyethylene glycol/polypropylene glycol allyl ether, a hydroxy($C_2$-$C_6$ alkyl) methacrylate, and an ethylene glycol dimethacrylate.

(III) quaternized (poly)hydroxyethylcelluloses modified with groups comprising at least one fatty chain, such as alkyl, arylalkyl or alkylaryl groups comprising at least 8 carbon atoms, or mixtures thereof. The alkyl radicals borne by the above quaternized celluloses or hydroxyethylcelluloses preferably comprise from 8 to 30 carbon atoms. The aryl radicals preferably denote phenyl, benzyl, naphthyl or anthryl groups.

Examples of quaternized alkylhydroxyethylcelluloses containing $C_8$-$C_{30}$ fatty chains that may be mentioned include the products Quatrisoft LM 200®, Quatrisoft LM-X 529-18-A®, Quatrisoft LM-X 529-18B® ($C_{12}$ alkyl) and Quatrisoft LM-X 529-8® ($C_{18}$ alkyl) sold by the company Aqualon, and the products Crodacel QM®, Crodacel QL® ($C_{12}$ alkyl) and Crodacel QS® ($C_{18}$ alkyl) sold by the company Croda, and the product Softcat SL 100® sold by the company Aqualon.

(IV) cationic polyvinyllactam polymers.

Such polymers are described, for example, in patent application WO-00/68282.

As cationic poly(vinyllactam) polymers according to the invention, vinylpyrrolidone/dimethylaminopropylmethacrylamide/dodecyldimethylmethacrylamidopropylammonium tosylate terpolymers, vinyl pyrrolidone/dimethylaminopropylmethacrylamide/cocoyldimethylmethacrylamidopropyl ammonium tosylate terpolymers, vinylpyrrolidone/dimethylaminopropylmethacrylamide/lauryldimethylmethacrylamidopropylammonium tosylate or chloride terpolymers are used in particular.

The amphoteric associative polymers are preferably chosen from those comprising at least one non-cyclic cationic unit. Even more particularly, the ones that are preferred are those prepared from or comprising 1 to 20 mol %, preferably 1.5 to 15 mol % and even more particularly 1.5 to 6 mol % of fatty-chain monomer relative to the total number of moles of monomers.

Amphoteric associative polymers according to the invention are described and prepared, for example, in patent application WO 98/44012.

Among the amphoteric associative polymers according to the invention, the ones that are preferred are acrylic acid/(meth)acrylamidopropyltrimethylammonium chloride/stearyl methacrylate terpolymers.

The associative polymers of nonionic type that may be used according to the invention are preferably chosen from:
(a) copolymers of vinylpyrrolidone and of fatty-chain hydrophobic monomers, of which examples that may be mentioned include:
  the products Antaron V216® and Ganex V216® (vinylpyrrolidone/hexadecene copolymer) sold by the company ISP,
  the products Antaron V220® and Ganex V220® (vinylpyrrolidone/eicosene copolymer) sold by the company ISP.
(b) copolymers of $C_1$-$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208®.
(c) copolymers of hydrophilic methacrylates or acrylates and of hydrophobic monomers comprising at least one fatty chain, for instance the polyethylene glycol methacrylate/lauryl methacrylate copolymer.
(d) polyurethane polyethers comprising in their chain both hydrophilic blocks usually of polyoxyethylenated nature and hydrophobic blocks, which may be aliphatic sequences alone and/or cycloaliphatic and/or aromatic sequences.
(e) polymers with an aminoplast ether backbone containing at least one fatty chain, such as the Pure Thix® compounds sold by the company Sud-Chemie.
(f) celluloses or derivatives thereof, modified with groups comprising at least one fatty chain, such as alkyl, arylalkyl or alkylaryl groups or mixtures thereof in which the alkyl groups are of $C_8$, and in particular:
  nonionic alkylhydroxyethylcelluloses such as the products Natrosol Plus Grade 330 CS and Polysurf 67 ($C_{16}$ alkyl) sold by the company Aqualon;
  nonionic nonoxynylhydroxyethylcelluloses such as the product Amercell HM-1500 sold by the company Amerchol;
  nonionic alkylcelluloses such as the product Bermocoll EHM 100 sold by the company Berol Nobel;
(g) associative guar derivatives, for instance hydroxypropyl guars modified with a fatty chain, such as the product Esaflor HM 22 (modified with a $C_{22}$ alkyl chain) sold by the company Lamberti; the product Miracare XC 95-3 (modified with a $C_{14}$ alkyl chain) and the product RE 205-146 (modified with a $C_{20}$ alkyl chain) sold by Rhodia Chimie.

Preferably, the polyurethane polyethers comprise at least two hydrocarbon-based lipophilic chains containing from 6 to 30 carbon atoms, separated by a hydrophilic block, the hydrocarbon-based chains possibly being pendent chains or chains at the end of the hydrophilic block. In particular, it is possible for one or more pendent chains to be included. In addition, the polymer may comprise a hydrocarbon-based chain at one end or at both ends of a hydrophilic block.

The polyurethane polyethers may be multiblock, in particular in triblock form. The hydrophobic blocks may be at each end of the chain (for example: triblock copolymer containing a hydrophilic central block) or distributed both at the ends and in the chain (for example multiblock copolymer). These same polymers may also be graft polymers or star polymers.

The nonionic fatty-chain polyurethane polyethers may be triblock copolymers in which the hydrophilic block is a polyoxyethylenated chain comprising from 50 to 1000 oxyethylene groups. The nonionic polyurethane polyethers comprise a urethane bond between the hydrophilic blocks, whence arises the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, it is also possible to use Rheolate 205® containing a urea function, sold by the company Rheox, or Rheolate® 208, 204 or 212, and also Acrysol RM 184®.

Mention may also be made of the product Elfacos T210® containing a $C_{12-14}$ alkyl chain, and the product Elfacos T212® containing a $C_{18}$ alkyl chain, from Akzo.

The product DW 1206B® from Röhm & Haas containing a $C_{20}$ alkyl chain and a urethane bond, sold at a solids content of 20% in water, may also be used.

It is also possible to use solutions or dispersions of these polymers, especially in water or in aqueous-alcoholic medium. Examples of such polymers that may be mentioned are Rheolate® 255, Rheolate® 278 and Rheolate® 244 sold by the company Rheox. The products DW 1206F and DW 1206J sold by the company Röhm & Haas may also be used.

The polyurethane polyethers that may be used according to the invention are in particular those described in the article by G. Formum, J. Bakke and Fk. Hansen—*Colloid Polym. Sci.* 271, 380.389 (1993).

It is even more particularly preferred to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold especially by the company Röhm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%)].

Use may also be made of fatty-phase-thickening polymers.

Preferably, the polymers for structuring the oily phase via physical interactions are chosen from polyamides, silicone polyamides, saccharide or polysaccharide mono- or poly-alkyl esters, N-acylamino acid amide derivatives, and copolymers comprising an alkylene or styrene block, these copolymers possibly being diblock, triblock, multiblock or radial-block polymers, also known as star copolymers, or alternatively comb polymers.

1) Polymers Bearing at Least One Crystallizable Block in the Backbone

These are also polymers that are soluble or dispersible in the oil or fatty phase by heating above their melting point m.p. These polymers are especially block copolymers consisting of at least two blocks of different chemical nature, one of which is crystallizable.

As polymers bearing in the backbone at least one crystallizable block that are suitable for use in the invention, mention may be made of:

i). the polymers defined in document U.S. Pat. No. 5,156, 911;

ii). block copolymers of olefin or of cycloolefin containing a crystallizable chain, for instance those derived from the block polymerization of:

cyclobutene, cyclohexene, cyclooctene, norbornene (i.e. bicyclo(2,2,1)-2-heptene), 5-methylnorbornene, 5-ethylnorbornene, 5,6-dimethyl-norbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-octahydro-naphthalene, dicyclopentadiene, and mixtures thereof, with ethylene, propylene, 1-butene, 3-methyl-1-butene, 1-hexene, 4-methyl-1-pentene, 1-octene, 1-decene or 1-eicosene, or mixtures thereof. These block copolymers may be in particular (ethylene/norbornene) block copolymers and (ethylene/propylene/ethylidenenorbornene) block terpolymers.

Those resulting from the block copolymerization of at least two $C_2$-$C_{16}$, and better still $C_2$-$C_{12}$, α-olefins such as those mentioned above and in particular block bipolymers of ethylene and of 1-octene may also be used.

Copolymers containing at least one crystallizable block, the rest of the copolymer being amorphous (at room temperature). These copolymers may also contain two crystallizable blocks of different chemical nature. The preferred copolymers are those that simultaneously contain at room temperature a crystallizable block and an amorphous block that are both hydrophobic and lipophilic, sequentially distributed; mention may be made, for example, of polymers containing one of the crystallizable blocks and one of the amorphous blocks below:

Block that is crystallizable by nature: a) of polyester type, for instance poly(alkylene terephthalate), b) of polyolefin type, for instance polyethylenes or polypropylenes.

Amorphous and lipophilic block, for instance: amorphous polyolefins or copoly(olefin)s such as poly(isobutylene), hydrogenated polybutadiene or hydrogenated poly(isoprene).

As examples of such copolymers containing a crystallizable block and an amorphous block, mention may be made of:

a) poly(δ-caprolactone)-b-poly(butadiene) block copolymers, preferably used hydrogenated, such as those described in the article Melting behaviour of poly(δ-caprolactone)-block-polybutadiene copolymers from S. Nojima, Macromolecules, 32, 3727-3734 (1999), b) the hydrogenated block or multiblock poly(butylene terephthalate)-b-poly(isoprene) block copolymers cited in the article Study of morphological and mechanical properties of PP/PBT by B. Boutevin et al., Polymer Bulletin, 34, 117-123 (1995), c) the poly(ethylene)-b-copoly(ethylene/propylene) block copolymers cited in the articles Morphology of semi-crystalline block copolymers of ethylene-(ethylene-alt-propylene) by P. Rangarajan et al., Macromolecules, 26, 4640-4645 (1993) and *Polymer aggregates with crystalline cores: the system poly(ethylene)poly(ethylene-propylene)* P. Richter et al., Macromolecules, 30, 1053-1068 25 (1997).

d) the poly(ethylene)-b-poly(ethylethylene) block copolymers mentioned in the general article *Crystallization in block copolymers* by I. W. Hamley, *Advances in Polymer Science*, vol. 148, 113-137 (1999).

The semi-crystalline polymers that may be used in the context of the invention may be non-crosslinked or partially crosslinked, provided that the degree of crosslinking does not impede their dissolution or dispersion in the liquid oily phase by heating above their melting point. It may then be a case of chemical crosslinking, by reaction with a multifunctional monomer during the polymerization. It may also be a case of physical crosslinking, which may then be due either to the establishment of bonds of hydrogen or dipolar type between groups borne by the polymer, for instance dipolar interactions between carboxylate ionomers, these interactions being in small amount and borne by the polymer backbone; or due to a phase separation between the crystallizable blocks and the amorphous blocks borne by the polymer.

Preferably, the semi-crystalline polymers that are suitable for the invention are non-crosslinked.

As particular examples of semi-crystalline polymers that may be used in the composition according to the invention, mention may be made of the Intelimer® products from the company Landec described in the brochure "Intelimer® polymers". These polymers are in solid form at room temperature (25° C.). They bear crystallizable side chains and contain the monomer. Mention may be made especially of "Landec IP22®", with a melting point m.p. of 56° C., which is a viscous, impermeable, non-tacky product at room temperature.

It is also possible to use the semi-crystalline polymers described in Examples 3, 4, 5, 7 and 9 of U.S. Pat. No. 5,156,911, resulting from the copolymerization of acrylic acid and of $C_5$ to $C_{16}$ alkyl (meth)acrylate, such as those resulting from the copolymerization:

of acrylic acid, of hexadecyl acrylate and of isodecyl acrylate in a 1/16/3 ratio, of acrylic acid and of pentadecyl acrylate in a 1/19 ratio, of acrylic acid, of hexadecyl acrylate and of ethyl acrylate in a 2.5/76.5/20 ratio, of acrylic acid, of hexadecyl acrylate and of methyl acrylate in a 5/85/10 ratio, of acrylic acid and of octadecyl (meth)acrylate in a 2.5/97.5 ratio.

It is also possible to use the polymer "Structure O" sold by the company National Starch, such as the product described in document U.S. Pat. No. 5,736,125, of m.p. 44° C., and also semi-crystalline polymers containing crystallizable side chains comprising fluoro groups as described in Examples 1, 4, 6, 7 and 8 of document WO-A-01/19333.

It is also possible to use the semi-crystalline polymers obtained by copolymerization of stearyl acrylate and of acrylic acid or of NVP, or by copolymerization of behenyl acrylate and of acrylic acid or NVP, as described in document U.S. Pat. No. 5,519,063 or EP-A-0 550 745.

According to one particular embodiment variant, the semi-crystalline polymers that are suitable for use in the present invention are especially alkyl acrylates, among which mention may be made of the Landec copolymers:

Doresco IPA 13-10: polystearyl acrylate, m.p. of 49° C. and MW of 145 000;
Doresco IPA 13-3®: polyacrylate/methacrylic acid, m.p. of 65° C. and MW of 114 000;
Doresco IPA 13-4®: polyacrylate/vinylpyrrolidone, m.p. of 44° C. and MW of 387 000;
Doresco IPA13-5®: polyacrylate/hydroxyethyl methacrylate, m.p. of 47° C. and MW of 397 600;
Doresco IPA 13-6®: polybehenyl acrylate, m.p. of 66° C.

2) Non-Silicone Polyamides

The particular polyamides used in the composition according to the invention are preferably those described in document U.S. Pat. No. 5,783,657 from the company Union Camp.

Each of these polyamides especially satisfies formula (XXXVII) below:

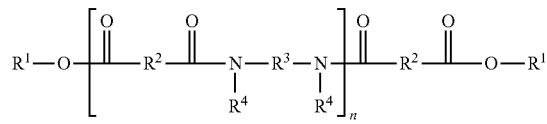

(XXII)

in which formula (XXII):

n denotes a whole number of amide units such that the number of ester groups represents from 10% to 50% of the total number of ester and amide groups;

$R^1$ is independently in each case an alkyl or alkenyl group containing at least 4 carbon atoms and especially from 4 to 24 carbon atoms;

$R^2$ represents independently in each case a $C_4$ to $C_{55}$ hydrocarbon-based group, on condition that 50% of the groups $R_2$ represent a $C_{30}$ to $C_{55}$ hydrocarbon-based group;

$R^3$ represents independently in each case an organic group bearing at least two carbon atoms, hydrogen atoms and optionally one or more oxygen or nitrogen atoms; and $R^4$ represents independently in each case a hydrogen atom, a $C_1$ to $C_{10}$ alkyl group or a direct bond to $R_3$ or to another $R_4$ such that the nitrogen atom to which are attached both $R_3$ and $R_4$ forms part of a heterocyclic structure defined by $R_4$—N—$R_3$, with at least 50% of the groups $R_4$ representing a hydrogen atom.

In particular, the ester groups of this polyamide represent from 15% to 40% and at best from 20% to 35% of the total number of ester and amide groups. Furthermore, n advantageously represents an integer ranging from 1 to 10 and better still from 1 to 5, limits inclusive.

Preferably, $R^1$ is a $C_{12}$ to $C_{22}$ and preferably $C_{16}$ to $C_{22}$ alkyl group. Advantageously, $R^2$ may be a $C_{10}$ to $C_{42}$ hydrocarbon-based (alkylene) group. Preferably, at least 50% and better still at least 75% of the groups $R^2$ are groups containing from 30 to 42 carbon atoms. The other groups $R^2$ are $C_4$ to $C_{19}$ and better still $C_4$ to $C_{12}$ hydrogen-containing groups. Preferably, $R^3$ represents a $C_2$ to $C_{36}$ hydrocarbon-based group or a polyoxyalkylene group and $R^4$ represents a hydrogen atom. Preferably, $R^3$ represents a $C_2$ to $C_{12}$ hydrocarbon-based group. The hydrocarbon-based groups may be linear, cyclic or branched, and saturated or unsaturated groups. Moreover, the alkyl and alkylene groups may be linear or branched, and saturated or unsaturated groups.

The thickening of the oily phase may be obtained by means of one or more polyamides defined above. In general, these polyamides are in the form of mixtures, these mixtures also possibly containing a synthetic product corresponding to a polyamide as defined above with n being 0, i.e. a diester.

As structuring polyamides that may be used in the invention, mention may also be made of polyamide resins resulting from the condensation of an aliphatic dicarboxylic acid and a diamine (including compounds containing, respectively, more than two carboxyl groups and more than two amine groups), the carboxyl and amine groups of adjacent individual units being condensed in the form of an amide bond. These polyamide resins are especially the products sold under the brand name Versamid® by the companies General Mills, Inc. and Henkel Corp., under the brand name Onamid®, especially Onamid S or C. These resins have a weight-average molecular mass ranging from 6000 to 9000. For further information regarding these polyamides, reference may be made to U.S. Pat. No. 3,645,705 and U.S. Pat. No. 3,148,125. Use is made more especially of Versamid® 30 or 744.

It is also possible to use the polyamides sold or manufactured by the company Arizona under the references Uni-Rez (2658, 2931, 2970, 2621, 2613, 2624, 2665, 1554, 2623, 2662) and the product sold under the reference Macromelt 6212 by the company Henkel. For further information regarding these polyamides, reference may be made to document U.S. Pat. No. 5,500,209.

As examples of structuring polyamides that may be used in the composition according to the invention, mention may also be made of the commercial products sold or manufactured by the company Arizona Chemical under the names Uniclear 80 and Uniclear 100. They are sold, respectively, in the form of an 80% (active material) gel and a 100% (active material) gel in a mineral oil. They have a softening point of from 88 to 105° C. These commercial products are a mixture of copolymers of a C36 diacid coupled with ethylenediamine, having an average molecular mass of about 6000. The terminal ester groups result from the esterification of the remaining acid end groups with cetyl alcohol, stearyl alcohol or mixtures thereof (also known as cetylstearyl alcohol).

2) Saccharide or Polysaccharide Mono- or Polyalkyl Esters

Among the saccharide or polysaccharide monoalkyl or polyalkyl esters that are suitable for use in the invention, mention may be made of dextrin or inulin alkyl or polyalkyl esters.

It may especially be a dextrin mono- or polyester of at least one fatty acid corresponding especially to formula (XXIII) below:

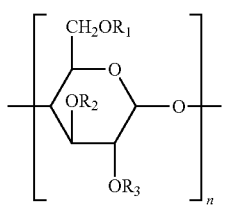

(XXIII)

in which formula (XXIII):
n is an integer ranging from 3 to 200, especially ranging from 20 to 150 and in particular ranging from 25 to 50,
$R_1$, $R_2$ and $R_3$, which may be identical or different, are chosen from hydrogen and an acyl group (R—C(O)—) in which the radical R is a linear or branched, saturated or unsaturated hydrocarbon-based group containing from 7 to 29, in particular from 7 to 21, especially from 11 to 19, more particularly from 13 to 17, or even 15, carbon atoms, with the proviso that at least one of the said radicals $R_1$, $R_2$ or $R_3$ is other than hydrogen.

In particular, $R_1$, $R_2$ and $R_3$ may represent hydrogen or an acyl group (R—C(O)—) in which R is a hydrocarbon-based radical as defined above, with the proviso that at least two of the said radicals $R_1$, $R_2$ and $R_3$ are identical and other than hydrogen.

The radicals $R_1$, $R_2$ and $R_3$ may all contain an acyl group (R—C(O)), which is identical or different and especially identical.

In particular, n mentioned above advantageously ranges from 25 to 50 and is especially equal to 38 in the general formula of the saccharide ester that may be used in the present invention.

When the radicals $R_1$, $R_2$ and/or $R_3$, which may be identical or different, contain an acyl group (R—C(O)), these radicals may be chosen especially from caprylic, capric, lauric, myristic, palmitic, stearic, arachic, behenic, isobutyric, isovaleric, 2-ethylbutyric, ethylmethylacetic, isoheptanoic, 2-ethylhexanoic, isononanoic, isodecanoic, isotridecanoic, isomyristic, isopalmitic, isostearic, isoarachic, isohexanoic, decenoic, dodecenoic, tetradecenoic, myristoleic, hexadecenoic, palmitoleic, oleic, elaidic, asclepinic, gondoleic, eicosenoic, sorbic, linoleic, linolenic, punicic, stearidonic, arachidonic and stearolic radicals, and mixtures thereof.

Preferably, at least one dextrin palmitate is used as fatty acid ester of dextrin. This ester may be used alone or as a mixture with other esters.

Advantageously, the fatty acid ester of dextrin has a degree of substitution of less than or equal to 2.5, especially ranging from 1.5 to 2.5 and preferably from 2 to 2.5 on the basis of one glucose unit. The weight-average molecular weight of the dextrin ester may in particular be from 10 000 to 150 000, especially from 12 000 to 100 000 and even from 15 000 to 80 000.

Dextrin esters, in particular dextrin palmitates, are commercially available under the name Rheopearl TL or Rheopearl KL by the company Chiba Flour.

3) N-Acylamino Acid Amide Derivatives

The N-acylamino acid amides that may be used are, for example, diamides from the combination of an N-acylamino acid with amines comprising from 1 to 22 carbon atoms, such as those described in document FR 2 281 162. They are, for example, alkylglutamic acid amide derivatives such as the laurylglutamic acid dibutylamide sold by the company Ajinomoto under the name Gelling Agent GP-1, or alternatively the 2-ethylhexylglutamic acid dibutylamide sold by the company Ajinomoto under the name Gelling Agent GA-01.

4) Copolymers Comprising an Alkylene or Styrene Block

The copolymers may have a comb or the block structure of diblock, triblock, multiblock and/or radial or star type and may comprise at least two thermodynamically incompatible segments.

The structuring agent may comprise, for example, a styrene segment as described in patent applications EP 0 497 144, WO 98/42298, U.S. Pat. No. 6,225,690, U.S. Pat. No. 6,174,968 and U.S. Pat. No. 6,225,390, an ethylene/butylene segment or an ethylene/propylene segment as described in U.S. Pat. No. 6,225,690, U.S. Pat. No. 6,174,968 and U.S. Pat. No. 6,225,390, a butadiene segment, an isoprene segment, a polyvinyl segment, for instance polyalkyl (meth)acrylate or polyvinyl alcohol or polyvinyl acetate, a silicone segment as described in U.S. Pat. No. 5,468,477 and U.S. Pat. No. 5,725,882, or a combination of these segments.

A diblock copolymer is usually defined as being of A-B type in which a hard segment (A) is followed by a soft segment (B).

A triblock copolymer is usually defined as being of A-B-A type or as a ratio of a hard segment, a soft segment and a hard segment.

A multiblock, radial or star copolymer may comprise any type of combination of hard segments and soft segments, with the proviso that the characteristics of the hard segments and of the soft segments are conserved.

An example of hard segments of block copolymers that may be mentioned is styrene, and examples of soft segments of block copolymers that may be mentioned include ethylene, propylene and butylene, and a combination thereof.

The triblock copolymers, and especially those of polystyrene/polyisoprene or polystyrene/polybutadiene type, which are suitable for use in the invention may be those sold under the reference Luvitol HSB by the company BASF. Mention may also be made of triblock copolymers of polystyrene/copoly(ethylene-propylene) or polystyrene/copoly(ethylene-butylene) type, such as those sold under the reference Kraton by the company Shell Chemical Co., or under the reference Gelled Permethyl 99 A by the company Penreco. Such triblock copolymers are particularly preferred according to the invention.

As a further example of block copolymers that may be suitable for use in the present invention, mention may also be made of the block copolymers sold under the reference Versagel by the company Penreco, those sold under the reference Kraton by the company Shell and those sold under the reference Gel Base by the company Brooks Industries.

Among the fatty-phase thickening polymers, polymers bearing in the backbone at least one crystallizable block are preferred.

The aqueous-phase or fatty-phase thickening polymers may be used alone or as mixtures in all proportions.

Preferably, the thickeners are aqueous-phase thickeners.

Preferably, the polymers in the cosmetic compositions in accordance with the present invention advantageously have in solution or in dispersion, at 1% active material in water, a viscosity, measured using a Rheomat RM 180 rheometer at 25° C., of greater than 0.1 ps and even more advantageously greater than 0.2 cp, at a shear rate of 200 $s^{-1}$.

According to one particular embodiment of the invention, the organic thickening polymer(s) are chosen from cellulose-based polymers.

The organic thickening polymer(s) are present in the composition according to the invention in a content ranging from 0.01% to 10% by weight and preferably from 0.1% to 5% by weight relative to the total weight of the composition.

viii) Adjuvants:

The composition comprising the ingredients i) to v) as defined previously may also contain various adjuvants conventionally used in hair dye compositions, such as anionic surfactants, nonionic surfactants other than the ethoxylated fatty alcohols ii), amphoteric or zwitterionic surfactants, or mixtures thereof, anionic, cationic, nonionic, amphoteric or zwitterionic polymers or mixtures thereof, mineral thickeners, penetrants, sequestrants, fragrances, buffers, dispersants, conditioning agents, for instance volatile or non-volatile, modified or unmodified silicones, film-forming agents, ceramides, preserving agents and opacifiers.

The above adjuvants are generally present in an amount, for each of them, inclusively between 0.01% and 20% by weight relative to the weight of the composition.

Needless to say, a person skilled in the art will take care to select this or these optional additional compound(s) such that the advantageous properties intrinsically associated with the dye composition in accordance with the invention are not, or are not substantially, adversely affected by the envisaged addition(s).

ix) Additional Dyes:

The composition comprising the dye(s) bearing a disulfide, thiol or protected-thiol function especially of formula (I) as defined previously of the process of the invention may also contain one or more additional direct dyes other than the disulfide, thiol or protected-thiol direct dyes of formula (I) according to the invention. These direct dyes are chosen, for example, from those conventionally used in direct dyeing, and among which mention may be made of any commonly used aromatic and/or non-aromatic dye such as neutral, acidic or cationic nitrobenzene direct dyes, neutral, acidic or cationic azo direct dyes, natural direct dyes, neutral, acidic or cationic quinone and in particular anthraquinone direct dyes, azine, triarylmethane, indoamine, methine, styryl, porphyrin, metalloporphyrin, phthalocyanine, cyanine and methine direct dyes, and fluorescent dyes, other than the dyes of formula (I).

The composition comprising the dye(s) bearing a disulfide, thiol or protected thiol function especially of formula (I) as defined previously of the process of the invention may also contain one or more oxidation bases and/or one or more couplers conventionally used for the dyeing of keratin fibres.

Among the oxidation bases, mention may be made of para-phenylenediamines, bis(phenyl)alkylenediamines, para-aminophenols, bis-para-aminophenols, ortho-aminophenols and heterocyclic bases, and the addition salts thereof.

Among these couplers, mention may be made especially of meta-phenylenediamines, meta-aminophenols, meta-diphenols, naphthalene-based couplers and heterocyclic couplers, and the addition salts thereof.

The coupler(s) are each generally present in an amount inclusively between 0.001% and 10% by weight and preferably between 0.005% and 6% by weight relative to the total weight of the dye composition.

The oxidation base(s) present in the dye composition are each generally present in an amount inclusively between 0.001% and 10% by weight and preferably between 0.005% and 6% by weight relative to the total weight of the dye composition.

In general, the addition salts of the oxidation bases and couplers used in the context of the invention are especially chosen from the salts of addition with an acid, such as the hydrochlorides, hydrobromides, sulfates, citrates, succinates, tartrates, lactates, tosylates, benzenesulfonates, phosphates and acetates, and the salts of addition with a base, such as alkali metal hydroxides, for instance sodium hydroxide, potassium hydroxide, ammonia, amines or alkanolamines.

According to one particular embodiment, the composition of the process of the invention contains at least one oxidation base and optionally at least one coupler as defined above.

This embodiment may be implemented in the presence of one or more chemical oxidizing agents. The term "chemical oxidizing agent" means chemical oxidizing agents other than atmospheric oxygen, such as those described previously.

The use of hydrogen peroxide is particularly preferred.

The content of oxidizing agent(s) is generally inclusively between 1% and 40% by weight relative to the weight of the composition and preferably between 1% and 20% by weight relative to the weight of the composition containing them.

The pH:

The pH of the composition according to the invention is generally inclusively between 2 and 12 approximately and preferably between 3 and 11 approximately. It may be adjusted to the desired value by means of acidifying or basifying agents usually used in the dyeing of keratin fibres, or alternatively using standard buffer systems.

The pH of the composition is preferentially inclusively between 6 and 9, particularly between 7 and 9, and more particularly between 7.5 and 9.

Among the acidifying agents that may be mentioned, for example, are mineral or organic acids, for instance hydrochloric acid, orthophosphoric acid or sulfuric acid, carboxylic acids, for instance acetic acid, tartaric acid, citric acid and lactic acid, and sulfonic acids.

Among the alkaline agents that may be mentioned, for example, are aqueous ammonia, alkali metal carbonates, alkanolamines such as monoethanolamine, diethanolamine and triethanolamine, and other alkaline agents iv) as defined previously.

Forms of the Composition:

The dye composition comprising i) the dye(s) bearing a disulfide, thiol or protected-thiol function especially of formula (I) as defined previously and the ingredients ii), iii), iv) and v) as defined previously may be in various galenical forms, such as in the form of liquids, lotions, creams or gels, or in any other form that is suitable for dyeing keratin fibres. They may also be conditioned under pressure in an aerosol can in the presence of a propellant or in a non-aerosol can, and form a mousse.

2). DYEING PROCESSES OF THE INVENTION

The process for dyeing keratin fibres, especially dark keratin fibres, according to the invention comprises the step of applying to the keratin fibres:
   i) at least one cationic direct dye bearing a disulfide function, a thiol function or a protected-thiol function as defined previously;
   ii) at least one sparingly ethoxylated or non-ethoxylated fatty alcohol as defined previously;
   iii) at least one cationic surfactant as defined previously;
   iv) at least one alkaline agent as defined previously;
   v) at least one reducing agent as defined previously; and
   vii) optionally at least one organic thickening polymer as defined previously; the ingredients i) to v) and vii) possibly being applied either together onto the said fibres or separately.

When it is desired to lighten dark keratin fibres without the use of a chemical oxidizing agent, an ingredient i) that is fluorescent is used in the dye composition or the dyeing process. Preferentially, the fluorescent dyes of formula (I) are chosen from the dyes of formulae (XIII), (XIII'), (XIV), (XIV'), (XVa), (XV'a), (XV) to (XV'), (XVI), (XVI'), (XVIa) and (XVI'a) as defined previously. More particularly, the fluorescent dyes i) as defined previously used for lightening keratin fibres are chosen from compounds 44, 49, 49a and 55.

The dyeing process according to the invention may be performed in one step by applying to the keratin fibres the composition according to the invention comprising the ingredients i) to v) and optionally vii) as defined previously, in one or more steps.

According to one particular embodiment of the process of the invention, the reducing agent v) as defined previously may be applied as a pretreatment before the application of the dye composition containing the ingredients i) to iv) and optionally vii).

According to another interesting variant, the reducing composition comprising the reducing agent v) and the ingredients iv) and iii) as defined previously is applied to the keratin fibres as a pretreatment before the application of the dye composition comprising the ingredients i) and ii) and optionally vii) as defined previously.

According to another variant of the invention, the reducing composition comprising the reducing agent v) and the ingredient iv) as defined previously is applied to the keratin fibres as a pretreatment before the application of the dye composition comprising the ingredients i), ii) and iii) and optionally vii) as defined previously.

According to another variant of the invention, the reducing composition comprising the reducing agent v) and the ingredient iii) as defined previously is applied to the keratin fibres as a pretreatment before the application of the dye composition comprising the ingredients i), ii) and iv) and optionally vii) as defined previously.

According to another variant of the invention, the reducing composition comprising the reducing agent v) and the ingredient ii) as defined previously is applied to the keratin fibres as a pretreatment before the application of the dye composition comprising the ingredients i), iii) and iv) and optionally vii) as defined previously.

According to another particularly advantageous embodiment, the process of the invention comprises a first step of reducing pretreatment with a reducing composition that is applied to the keratin fibres, comprising the ingredients iv), v) and optionally ii) as defined previously, followed, in a second step, by the application of a dye composition comprising the ingredients i), ii) and iii) and optionally vii) as defined previously.

The reducing pretreatment may be of short duration, especially from 1 second to 30 minutes and preferably from 1 minute to 15 minutes, with one or more reducing agents as mentioned previously.

Between the reducing pretreatment step and the dyeing step using the composition comprising the ingredient i) as defined previously, the keratin fibres are preferentially rinsed with water.

The leave-on time of the dye composition, i.e. comprising the ingredient i) as defined previously, is inclusively between 5 minutes and 1 hour and preferably between 10 minutes and 40 minutes.

The dye composition, i.e. the composition comprising the ingredient i), is generally applied at room temperature. However, it may be applied at temperatures ranging from 20 to 180° C.

According to another variant, instead of using the reducing agent as a pretreatment, it is used as a post-treatment, after the application of the dye composition.

According to another particular dyeing process of the invention, the dyeing process does not comprise any reducing pretreatment or post-treatment step. In this case, the dyeing process comprises the step of applying the composition according to the invention, which comprises the ingredients i) to v) and optionally vii) as defined previously.

When the ingredient i) is a protected-thiol dye, i.e. the thiol dye of formula (I) as defined previously in which U═Y with Y being a protecting group, the process of the invention may be preceded by a deprotection step for restoring the SH function in situ.

By way of example, it is possible to deprotect the function S—Y of the dyes of the invention with Y being a protecting group, by adjusting the pH as follows:

| Y: protecting group | deprotection |
| --- | --- |
| alkylcarbonyl, | pH > 9 |
| arylcarbonyl, | pH > 9 |
| alkoxycarbonyl, | pH > 9 |
| aryloxycarbonyl, | pH > 9 |
| arylalkoxycarbonyl, | pH > 9 |
| (di)(alkyl)aminocarbonyl, | pH > 9 |
| (alkyl)arylaminocarbonyl, | pH > 9 |
| optionally substituted aryl such as phenyl, | pH > 9 |
| 5-, 6- or 7-membered monocyclic heteroaryl such as oxazolium, | pH > 9 |
| 8- to 11-membered bicyclic heteroaryl such as benzimidazolium or benzoxazolium | pH > 9 |

The deprotection step may also be performed during a step of pretreatment of the hair, for instance the hair-reducing pretreatment.

A treatment with one or more chemical oxidizing agents may optionally be performed after the application of ingredients i) to iv) and optionally vii) as defined previously to the keratin fibres. To do this, a fixing composition comprising at least one cosmetic chemical oxidizing agent such as the ingredient vi) as defined previously and optionally the ingredient vii) as defined previously may be used. Thus, it may be chosen especially from hydrogen peroxide, urea peroxide, alkali metal bromates, persalts such as perborates and persulfates, and also enzymes, among which mention may be made of peroxidases, 2-electron oxidoreductases such as uricases, and 4-electron oxygenases such as laccases. The use of hydrogen peroxide is particularly preferred.

The leave-on time of the oxidizing (fixing) composition is inclusively between 1 second and 40 minutes and preferably between 15 seconds and 15 minutes.

Preferentially, the application of the oxidizing composition takes place after the application of the dye composition, i.e. the composition comprising the ingredient i) as defined previously and optionally the ingredient vii) as defined previously.

Between the dyeing step using the composition comprising the ingredient i) as defined previously and the fixing step, the keratin fibres are preferentially rinsed with water.

When the ingredients i) and v) and optionally vii) as defined previously are not in the same composition, the pH of the composition that contains i) is preferentially inclusively between 4 and 10 and particularly between 5 and 7; and the pH of the composition that contains v) is preferentially inclusively between 4 and 10 and particularly between 7 and 10.

The dyeing and/or lightening process according to the invention may be followed by shampooing with a standard shampoo and/or drying of the keratin fibres.

According to particularly advantageous embodiments, the process is performed in three different ways using compositions A, B and C in which:

the dye composition A contains:
i) at least one fluorescent disulfide dye in a concentration inclusively between 0.01 g % and 5 g % and preferably between 0.05 g % and 2 g %;
ii) at least one fatty alcohol preferentially chosen from myristyl alcohol, stearyl alcohol and palmityl alcohol, in a concentration inclusively between 0.05 g % and 10 g % and preferably inclusively between 0.5 g % and 5 g %;
iii) at least one cationic surfactant preferably chosen from quaternary ammonium salts containing one or more ester functions, such as those of formula (XX) as defined previously, in a concentration inclusively between 0.1 g % and 40 g % and preferably between 1 g % and 15 g %;
the pH of composition A preferably being inclusively between 4 and 10, and more particularly between 5 and 7;

the reducing composition B comprises:
v) at least one thiol reducing agent in a concentration preferably inclusively between 0.5 g % and 50 g % and more particularly inclusively between 10 g % and 30 g %;
iv) at least one alkaline agent preferably comprising an amine group, in a concentration preferably inclusively between 0.1 g % and 30 g % and more particularly between 0.5 g % and 5 g %;
and optionally at least one fragrance in a concentration preferably inclusively between 0.01 g % and 10 g % and more particularly between 0.2 g % and 2 g %;

the pH of composition B preferably being inclusively between 5 and 12, and more particularly inclusively between 7 and 10;

the fixing composition C comprises: vi) at least one oxidizing agent in a concentration preferably inclusively between 0.01 g % and 30 g % and more particularly between 0.5 g % and 5 g %, the pH of composition C preferably being inclusively between 1.5 and 7 and more particularly between 2 and 5;
it being understood that the fixing composition may also comprise a thickening organic polymer vii) as defined previously; just like compositions A and/or B.

Variant 1:
The dye composition A is mixed with the reducing composition B in the following proportions: 9 volumes of composition A are mixed with 1 volume of composition B in a bowl. The mixture is applied to the hair with a leave-on time preferably inclusively between 5 minutes and 1 hour and preferably between 10 minutes and 40 minutes. The hair is rinsed and is then optionally shampooed, shampooing preferably being performed, and the hair is then dried.

Variant 2:
The dyeing formula A is mixed with the reducing composition B in the following proportions: 9 volumes of composition A are mixed with 1 volume of composition B in a bowl. The mixture is applied to the hair with a leave-on time preferably inclusively between 5 minutes and 1 hour and more particularly inclusively between 10 minutes and 40 minutes.

The hair is optionally rinsed, preferably rinsed. The fixing composition C is then applied to the hair with a leave-on time preferably inclusively between 1 minutes and 30 hour and more particularly inclusively between 3 minutes and 10 minutes.

The hair is rinsed and is then optionally shampooed, shampooing preferably being performed, and the hair is then dried.

Variant 3:
The reducing formula is applied to the hair with a leave-on time preferably inclusively between 5 minutes and 1 hour and more particularly inclusively between 10 minutes and 40 minutes. The hair is optionally rinsed, preferably rinsed. The dye formula is applied to the hair with a leave-on time preferably inclusively between 5 minutes and 1 hour and more particularly inclusively between 10 minutes and 40 minutes. The hair is optionally rinsed, preferably rinsed. The fixing composition C is then applied to the hair with a leave-on time preferably inclusively between 1 minutes and 30 hour and more particularly between 3 minutes and 10 minutes. The hair is rinsed and is then optionally shampooed, shampooing preferably being performed, and the hair is then dried.

3). DYEING KIT OF THE INVENTION

A subject of the invention is also a multi-compartment dyeing device or "kit" comprising a first compartment containing a dye composition comprising the composition containing the ingredient i); a second compartment which contains a reducing agent v) as defined previously; the ingredients ii) to iv) as defined previously being divided among the first two compartments, and optionally a third compartment comprising vi) at least one oxidizing agent vii) as defined previously.

According to one variant, the device comprises a first compartment containing a dye composition comprising the composition containing the ingredients i) to iv) as defined previously; a second compartment which contains at least one reducing agent v) as defined previously and optionally a third compartment comprising at least one oxidizing agent vi) and optionally vii) as defined previously.

Alternatively, the dyeing device contains a first compartment containing a dye composition that comprises at least i) a protected-thiol dye, and the ingredients ii) to iv), a second compartment containing an agent capable of deprotecting the protected thiol to liberate the thiol, a third compartment that contains at least one reducing agent v) as defined previously, and optionally a fourth compartment comprising an oxidizing agent vi) and optionally vii) as defined previously.

According to other variants:
the first compartment contains i) and ii) as defined previously and the second compartment comprises the ingredients v), iv) and iii) as defined previously;
or alternatively the first compartment contains the ingredients i), ii) and iii) as defined previously and the second compartment comprises the ingredients v) and iv);
or alternatively the first compartment contains the ingredients i), iii) and iv) as defined previously and the second compartment comprises the ingredients v) and ii).

For these variants, a third compartment may be present, which contains an oxidizing agent vi) and optionally vii) as defined previously, and optionally a fourth compartment containing an agent that is capable of deprotecting the protected thiol to liberate the thiol if the ingredient i) of the first compartment is a protected thiol.

Each of the devices mentioned above may be equipped with a means for applying the desired mixture to the hair, for instance the devices described in patent FR 2 586 913.

The examples that follow serve to illustrate the invention without, however, being limiting in nature.

The direct thiol, protected thiol or disulfide dyes of formula (I) that are useful in the present invention are known compounds and may be prepared according to methods known to those skilled in the art, especially from the methods described in patent applications EP 1 647 580, EP 2 004 759, WO 2007/110 541, WO 2007/110 540, WO 2007/110 539, WO 2007/110 538, WO 2007/110 537, WO 2007/110 536, WO 2007/110 535, WO 2007/110 534, WO 2007/110 533, WO 2007/110 532, WO 2007/110 531, EP 2 070 988 and WO 2009/040 354.

Examples of Dyeing

Concentration of the Starting Materials in Unmodified Form

Composition A:

| Ingredient | Commercial name | Supplier | Amount |
|---|---|---|---|
| Disulfide dye of formula 44 having as counterion the disulfate ion $SO_4^{2-}$ (ingredient i)) | | | 0.5 g % |
| Cetylstearyl alcohol (50/50 $C_{16}/C_{18}$) (ingredient ii)) | Ecorol 68/50 P | Cognis | 2.5 g % |
| Myristyl/cetyl/stearyl myristate/palmitate/stearate mixture | Crodamol MS-PA-(MH) | Croda | 0.5 g % |
| Dipalmitoylethyl-hydroxyethylmethylammonium methosulfate/cetearyl alcohol (ingredients ii) and iii)) | Dehyquart F 30 | Cognis | 4.5 g % |
| Water | | | qs 100% |

Composition B

| Ingredient | Commercial name | Supplier | Amount |
|---|---|---|---|
| Ammonium thioglycolate as a 71% aqueous solution (pH 6) (ingredient iv)) | 71% Ammonium thioglycolate | Bruno bock | 20 g % |
| Diethylenetriamine-pentaacetic acid, pentasodium salt as a 40% aqueous solution | Versenex 80 | Univar | 0.4 g % |
| Fragrance | Fresh mint | Mane | 0.8 g % |
| Monoethanolamine (ingredient v)) | Monoethanolamine Care | Univar | 1.21 g % |
| Oxyethylenated oleyl alcohol (20 OE) (ingredient ii)) | Brij O20-SO-(MV) | Croda | 6 g % |
| Water | | | qs 100% |

Composition C

| Ingredient | Commercial name | Supplier | Amount |
|---|---|---|---|
| Hydrogen peroxide as a 50% aqueous solution (200 vol. aqueous hydrogen peroxide solution) | $H_2O_2$ Interox ST-50 | Brenntag | 0.48 g % |
| Etidronic acid, tetrasodium salt, as a 30% aqueous solution | Turpinal 4 NL | Brenntag | 0.02 g % |
| Sodium salicylate | Sodium salicylate | Merck | 0.0035 g % |
| Tetrasodium pyrophosphate | Tetrasodium pyrophosphate | Penreac | 0.004 g % |
| decahydrate | decahydrate PRS | | |
| Polydimethyl-diallylammonium chloride at 40% in water | Merquat 100 | Nalco | 0.125 g % |
| Phosphoric acid | Prayphos P5 85 | Prayon | 0.012 g % |
| Crosslinked ethyltrimeth-ylammonium methacrylate chloride homopolymer as a 50% inverse emulsion in mineral oil | Salcare SC 95 | Ciba | 1.3 g % |
| Water | | | qs 100% |

9 parts of composition A are mixed with 1 part of composition B in a bowl.

The mixture is applied to brown hair (dark hair having a tone height of 4 (TH4)), with a leave-on time of 20 minutes.

The hair is rinsed.

The fixing formula C is applied to the hair, with a leave-on time of 5 minutes.

The hair is rinsed and is then shampooed, then the hair is dried.

Colorimetric Evaluation Results in the L*a*b* System for Evaluating the Coloring of the Locks:

The color of the locks was evaluated in the L*a*b* system by means of a MINOLTA® CM 3600D spectrocolorimeter (Illuminant D65).

In this L*a*b* system, L* represents the lightness, a* indicates the green/red color axis and b* the blue/yellow color axis. The higher the value of L, the lighter or weaker the color. Conversely, the lower the value of L, the darker or much stronger the color. The higher the value of a*, the redder the shade, and the higher the value of b*, the more yellow the shade.

The variation in coloring between the TH4 dyed and treated locks of hair is measured by (ΔE) according to the following equation:

$$\Delta E = \sqrt{(L^*-L_0^*)^2+(a^*-a_0^*)^2+(b^*-b_0^*)^2}$$

In this equation, L*, a* and b* represent the values after treatment, and $L_0^*$, $a_0^*$ and $b_0^*$ represent the values measured before treatment.

The greater the value of ΔE, the greater the difference in color between the TH4 locks and the uncolored locks.

| | L* | a* | b* | ΔE* |
|---|---|---|---|---|
| TH4 reference | 24.27 | 3.96 | 4.72 | — |
| After treatment A + B + C | 25.1 | 8.11 | 8.12 | 5.43 |

It is noted that the ΔE value is significantly high after treatment with compositions A+B+C. A mahogany colouration is obtained which is intense and persistent (even after several washing operations).

On the other hand the colour changed very little after the shampooing operations, given the number of successive shampooing operations (even after more than 10 shampooing operations. It is also observed that the coloration is particularly resistant vs. perspiration.

The invention claimed is:
1. A cosmetic composition comprising:
    i) at least one direct dye chosen from dyes of formula (I) comprising at least one functional group chosen from disulfide, thiol, and protected-thiol functional groups:

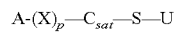

(I)

the salts thereof with an organic or mineral acid, optical or geometric isomers thereof, tautomers thereof, and solvates thereof,
wherein:
U is a radical chosen from:
a) —S—$C'_{sat}$—$(X')_{p'}$-A'; and
b) —Y;
A and A', which may be identical or different, are chosen polymethine radicals of formula (VI'), below:

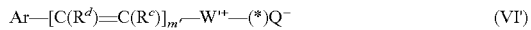

Ar—$[C(R^d)$=$C(R^c)]_{m'}$—$W'^+$—(*)$Q^-$    (VI')

wherein:
$W^+$ is chosen from cationic heterocyclic and heteroaryl groups;
Ar is an optionally substituted aryl group;
m' is an integer ranging from 1 to 4 inclusive;
$R^c$ and $R^d$, which may be identical or different, are chosen from hydrogen and optionally substituted ($C_1$-$C_8$) alkyl groups, or alternatively $R^c$ contiguous with $W'^+$ and/or $R^d$ contiguous with Ar form, with the atoms that bear them, a (hetero)cycloalkyl;
$Q^-$ is an anionic counterion;
(*) is the part of the chromophore linked to the rest of the molecule of formula (I);
Y is chosen from hydrogen and thiol-function protecting groups;
X and X', which may be identical or different, are chosen from linear or branched, saturated or unsaturated divalent $C_1$-$C_{30}$ hydrocarbon-based chains, optionally interrupted and/or optionally terminated at one or both ends with at least one divalent group chosen from:
—N(R)—, —$N^+$(R)(R)—, —O—, —S—, —CO—, and —$SO_2$—, wherein R, which may be identical or different, is chosen from hydrogen and $C_1$-$C_4$ alkyl, hydroxyalkyl and aminoalkyl radicals;
aromatic or non-aromatic, saturated or unsaturated, fused or non-fused (hetero)cyclic radicals optionally comprising at least one identical or different, optionally substituted heteroatom;
p and p', which may be identical or different, are equal to 0 or 1;
$C_{sat}$ and $C'_{sat}$, which may be identical or different, are chosen from optionally cyclic, optionally substituted linear or branched $C_1$-$C_{18}$ alkylene chains;
ii) at least one fatty alcohol chosen from sparingly ethoxylated and non-ethoxylated fatty alcohols;
iii) at least one cationic surfactant;
iv) at least one alkaline agent; and
v) at least one reducing agent chosen from thioglycolic acid, thiolactic acid, 3-mercaptopropionic acid, thiomalic acid, 2,3-dimercaptosuccinic acid, cysteine, N-glycyl-L-cysteine, L-cysteinylglycine, and esters and salts thereof; thioglycerol; cysteamine and $C_1$-$C_4$ acyl derivatives thereof; N-mesylcysteamine; N-acetylcysteine; N-(mercapto-2-ethyl) gluconamide; pantetheine, N-(mercaptoalkyl)-ω-hydroxyalkylamides; N-mono- or N,N-dialkylmercapto-4-butyramides; aminomercaptoalkyl amides; N-(mercaptoalkyl)succinamic acids and N-(mercaptoalkyl)succinimides; alkylamino mercaptoalkyl amides; the azeotropic mixture of 2-hydroxypropyl thioglycolate and of (2-hydroxy-1-methyl)ethyl thioglycolate; ammonium thioglycolate; mercaptoalkylamino amides; and N-mercaptoalkylalkanediamides.

2. The composition according to claim 1, wherein the radicals A and/or A' of the at least one direct dye of formula (I),
which may be identical or different, are chosen from radicals comprising at least one quaternized cationic chromophore.

3. The composition according to claim 1, wherein which the at least one direct dye of formula (I) is a disulfide dye, wherein U is a radical chosen from a) —S—$C'_{sat}$—$(X')_{p'}$-A'.

4. The composition according to claim 3, wherein the at least one direct dye of formula (I) is a symmetrical disulfide dye of the following formula (Ia):

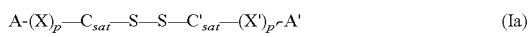

A-$(X)_p$—$C_{sat}$—S—S—$C'_{sat}$—$(X')_{p'}$-A'    (Ia)

wherein A=A', X=X', p=p', and $C_{sat}$=$C'_{sat}$.

5. The composition according to claim 1, wherein the at least one direct dye of formula (I) is a dye comprising a thiol or protected-thiol function, wherein U is the radical b) Y, chosen from hydrogen and the following radicals:
($C_1$-$C_4$)alkylcarbonyl;
($C_1$-$C_4$)alkylthiocarbonyl;
($C_1$-$C_4$)alkoxycarbonyl;
($C_1$-$C_4$)alkoxythiocarbonyl;
($C_1$-$C_4$)alkylthio-thiocarbonyl;
(di)($C_1$-$C_4$)(alkyl)aminocarbonyl;
(di)($C_1$-$C_4$)(alkyl)aminothiocarbonyl;
arylcarbonyl;
aryloxycarbonyl;
aryl($C_1$-$C_4$)alkoxycarbonyl;
(di)($C_1$-$C_4$)(alkyl)aminocarbonyl;
($C_1$-$C_4$)(alkyl)arylaminocarbonyl;
carboxyl;
$SO_3^-M^+$, wherein $M^+$ is chosen from alkali metal ions, or alternatively a counterion of the cationic chromophore A and $M^+$ are absent;
optionally substituted aryl;
optionally substituted heteroaryl;
optionally cationic, optionally substituted heterocycloalkyl;
—C($NR'^cR'^d$)=$N^+R'^eR'^f$; $An'''^-$, wherein $R'^c$, $R'^d$, $R'^e$ and $R'^f$, which may be identical or different, are chosen from hydrogen and ($C_1$-$C_4$)alkyl groups and $An'''^-$ is a counterion;
—C($NR'^cR'^d$)=$NR'^e$; wherein $R'^c$, $R'^d$ and $R'^e$ are defined above;
optionally substituted (di)aryl($C_1$-$C_4$)alkyl;
optionally substituted (di)heteroaryl($C_1$-$C_4$)alkyl;
$CR^1R^2R^3$, wherein $R^1$, $R^2$ and $R^3$, which may be identical or different, are chosen from halogen and the following groups:
($C_1$-$C_4$)alkyl;
($C_1$-$C_4$)alkoxy;
optionally substituted aryl;
optionally substituted heteroaryl;
—P($Z^1$)$R'^1R'^2R'^3$, wherein $R'^1$ and $R'^2$, which may be identical or different, are chosen from hydroxyl, ($C_1$-$C_4$)alkoxy and alkyl groups, $R'^3$ is chosen from hydroxyl and ($C_1$-$C_4$)alkoxy groups, and $Z^1$ is chosen from oxygen and sulfur;
sterically hindered rings; and
optionally substituted alkoxyalkyl.

6. The composition according to claim 1, wherein, in formula (I), $C_{sat}$ and $C'_{sat}$, which may be identical or different, are chosen from —$(CH_2)_k$— chains, wherein k is an integer ranging from 1 to 8 inclusive.

7. The composition according to claim 1, wherein, in formula (I), p and p' are equal to 1, and X and X', which may be identical or different, are chosen from the following sequence:

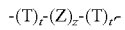

-$(T)_{t'}$-$(Z)_z$-$(T)_{t'}$- wherein the sequence is linked in formula (I) symmetrically as follows:

—C$_{sat}$(or C'sat)-(T)$_t$-(Z)$_z$-(T')$_{t'}$-(A or A');

wherein:

T and T', which may be identical or different, are chosen from at least one of: —O—; —S—; —N(R)—; —N+(R)(R°)—; —S(O)—; —S(O)$_2$—; —C(O)—; wherein R, R°, which may be identical or different, are chosen from hydrogen, C$_1$-C$_4$ alkyl radicals, C$_1$-C$_4$ hydroxyalkyl radicals and aryl(C$_1$-C$_4$)alkyl radicals; and cationic or non-cationic heterocycloalkyl or heteroaryl radicals, optionally monocyclic and optionally comprising two heteroatoms;

t and t', which may be identical or different, are equal to 0 or 1;

Z is chosen from:
—(CH$_2$)$_m$—, wherein m is an integer ranging from 1 to 8 inclusive;
—(CH$_2$CH$_2$O)$_q$— and —(OCH$_2$CH$_2$)$_q$—, wherein q is an integer ranging from 1 to 5 inclusive;
aryl, alkylaryl and arylalkyl radicals, wherein the alkyl radical is chosen from C$_1$-C$_4$ alkyl radicals, optionally substituted with at least one group SO$_3$M, wherein M is chosen from hydrogen, alkali metals and ammonium groups substituted with at least one radical, which may be identical or different, chosen from linear or branched C$_1$-C$_{18}$ alkyl radicals optionally bearing at least one hydroxyl group; and z is 0 or 1.

8. The composition according to claim 1, wherein the at least one dye of formula (I) is chosen from disulfide dyes of formulae XII and thiol or protected-thiol dyes of formulae XII' below:

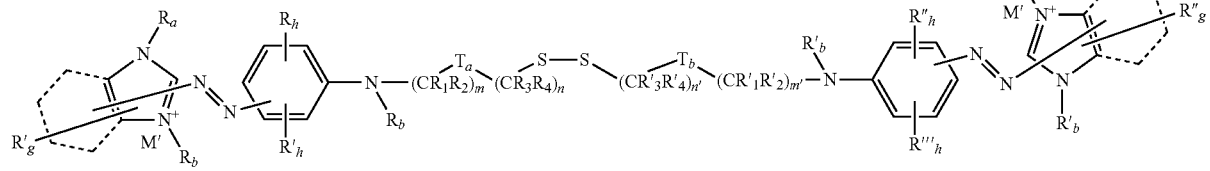

(VIII)

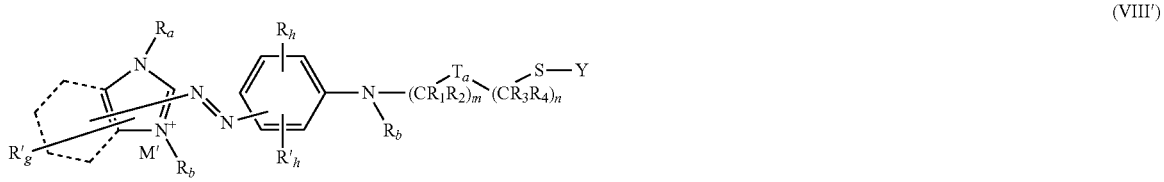

(VIII')

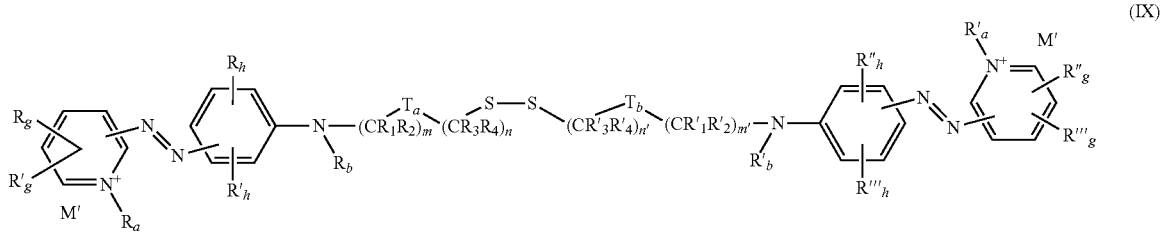

(IX)

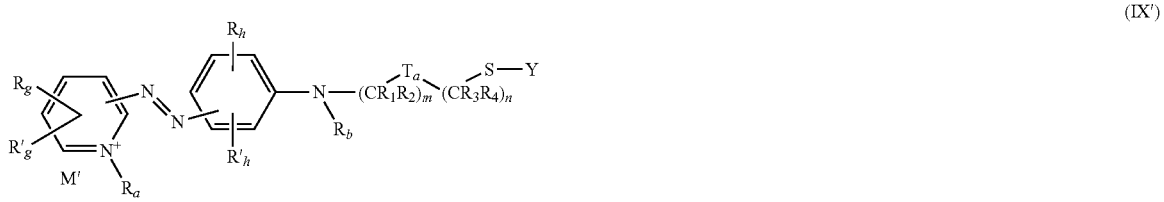

(IX')

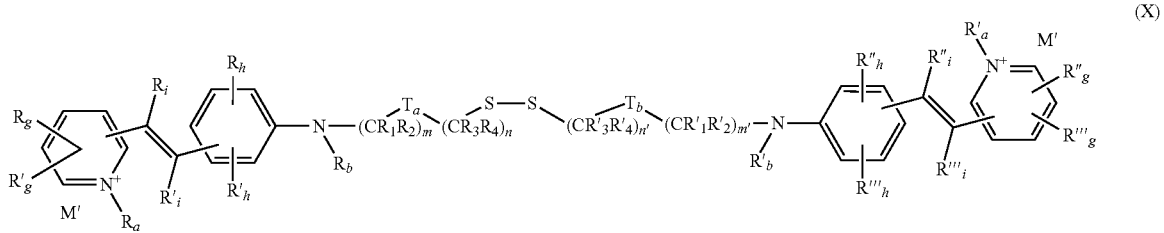

(X)

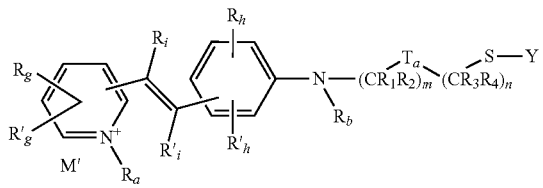
(X')
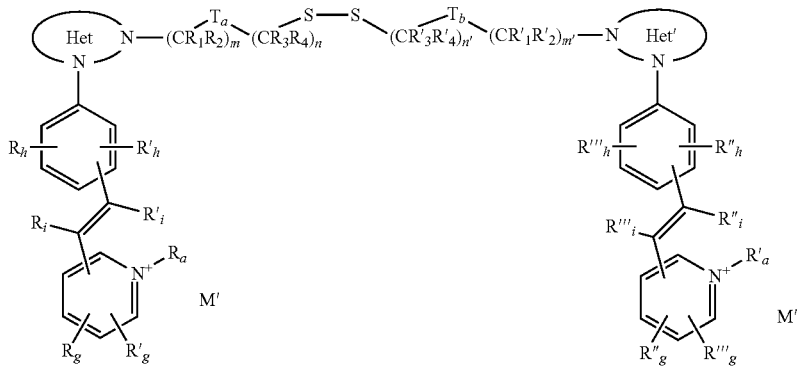
(XI)
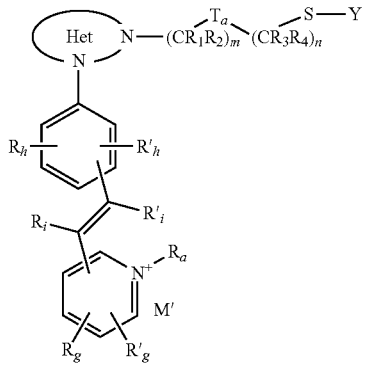
(XI')
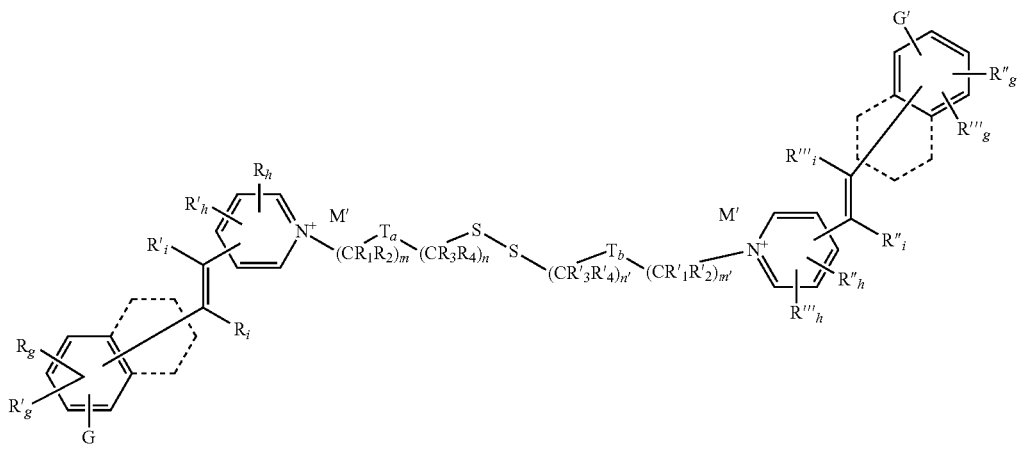
(XII)

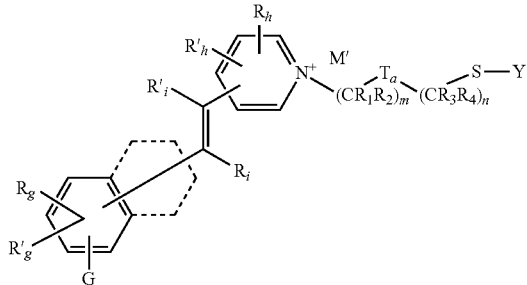
(XII')

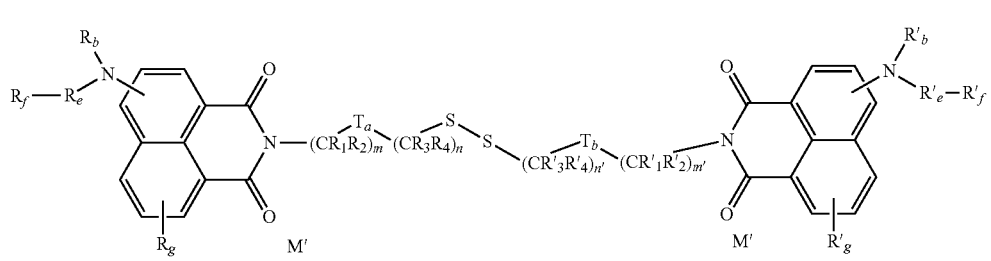
(XIII)

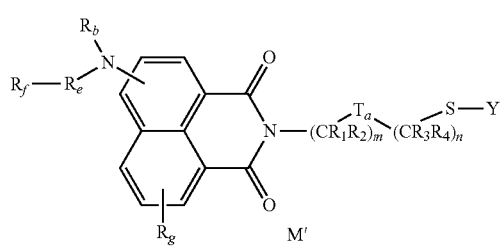
(XIII')

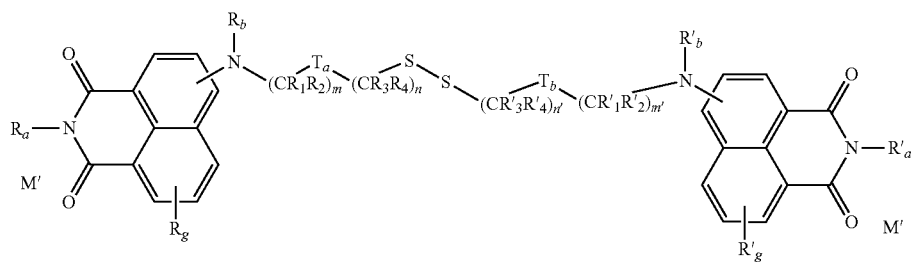
(XIV)

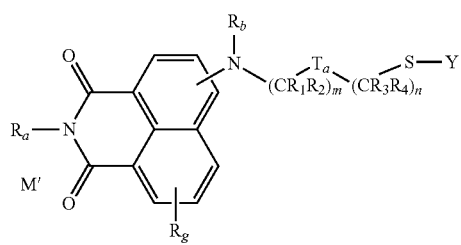
(XIV')

wherein:

G and G', which may be identical or different, are chosen from —$NR_cR_d$, —$NR'_cR'_d$, and $C_1$-$C_6$ alkoxy groups which are optionally substituted;

$R_c$, $R'_c$, $R_d$ and $R'_d$, which may be identical or different, are chosen from hydrogen, aryl($C_1$-$C_4$)alkyl and $C_1$-$C_6$ alkoxy groups and $C_1$-$C_6$ alkyl groups which are optionally substituted;

or alternatively two adjacent radicals $R_c$ and $R_d$, $R'_c$ and $R'_d$ borne by the same nitrogen atom, together form a heterocyclic or heteroaryl group;

$R_g$, $R'_g$, $R''_g$, $R'''_g$, $R_h$, $R'_h$, $R''_h$ and $R'''_h$, which may be identical or different, are chosen from hydrogen, halogen atoms, amino, $C_1$-$C_4$ alkylamino, $C_1$-$C_4$ dialkylamino, cyano, carboxyl, hydroxyl and trifluoromethyl group, acylamino, $C_1$-$C_4$ alkoxy, (poly)hydroxy($C_2$-$C_4$)alkoxy, alkylcarbonyloxy, alkoxycarbonyl and alkylcarbonylamino radicals, acylamino, carbamoyl and alkylsulfonylamino radicals, aminosulfonyl radicals, and $C_1$-$C_{16}$ alkyl radicals optionally substituted with a group chosen from $C_1$-$C_{12}$ alkoxy, hydroxyl, cyano, carboxyl, amino, $C_1$-$C_4$ alkylamino and $C_1$-$C_4$ dialkylamino groups, or alternatively two alkyl radicals borne by the nitrogen atom of the amino group form a 5- to 7-membered heterocycle optionally comprising another nitrogen or non-nitrogen heteroatom;

or alternatively two groups $R_g$ and $R'_g$; $R''_g$ and $R'''_g$; $R_h$, and $R'_h$; $R''_h$ and $R'''_h$ borne by two adjacent carbon atoms together form a benzo or indeno ring, a fused heterocycloalkyl or fused heteroaryl group; wherein the benzo, indeno, heterocycloalkyl and heteroaryl rings are optionally substituted with an entity chosen from halogen atoms, amino, $C_1$-$C_4$ alkylamino, $C_1$-$C_4$ dialkylamino, nitro, cyano, carboxyl, hydroxyl and trifluoromethyl groups, acylamino, $C_1$-$C_4$ alkoxy, (poly)hydroxy($C_2$-$C_4$)alkoxy, alkylcarbonyloxy, alkoxycarbonyl and alkylcarbonylamino radicals, acylamino, carbamoyl and alkylsulfonylamino radicals, aminosulfonyl radicals, and $C_1$-$C_{16}$ alkyl radicals optionally substituted with a group chosen from $C_1$-$C_{12}$ alkoxy, hydroxyl, cyano, carboxyl, amino, $C_1$-$C_4$ alkylamino, and $C_1$-$C_4$ dialkylamino groups, or alternatively two alkyl radicals borne by the nitrogen atom of the amino group form a 5- to 7-membered heterocycle optionally comprising another nitrogen or non-nitrogen heteroatom;

or alternatively two groups $R_i$ and $R_g$; $R'''_i$ and $R'''_g$; $R'_i$ and $R'_h$; and/or $R''_i$ and $R''_h$ together form a fused (hetero)cycloalkyl;

or alternatively when G represents $-NR_cR_d$ and G' represents $-NR'_cR'_d$, two groups $R_c$ and $R'_g$; $R'_c$ and $R''_g$; $R_d$ and $R_g$; $R'_d$ and $R'''_g$ together form a saturated heteroaryl or heterocycle, optionally substituted with at least one ($C_1$-$C_6$)alkyl group, and optionally comprising at least one heteroatom chosen from nitrogen and oxygen;

$R_i$, $R'_i$, $R''_i$, and $R'''_i$, which may be identical or different, are chosen from hydrogen and $C_1$-$C_4$ alkyl groups;

$R_1$, $R_2$, $R_3$, $R_4$, $R'_1$, $R'_2$, $R'_3$ and $R'_4$, which may be identical or different, are chosen from hydrogen and $C_1$-$C_4$ alkyl, $C_1$-$C_{12}$ alkoxy, hydroxyl, cyano, carboxyl, amino, $C_1$-$C_4$ alkylamino and $C_1$-$C_4$ dialkyl amino group, the alkyl radicals possibly forming, with the nitrogen atom that bears them, a 5- to 7-membered heterocycle optionally comprising another nitrogen or non-nitrogen heteroatom;

$T_a$ and $T_b$, which may be identical or different, are chosen from i) a covalent σ bond, ii) at least one radical chosen from $-SO_2-$, $-O-$, $-S-$, $-N(R)-$, $-N^+(R)(R^o)-$, and $-CO-$, wherein R, $R^o$, which may be identical or different, are chosen from hydrogen, $C_1$-$C_4$ alkyl and $C_1$-$C_4$ hydroxyalkyl radicals;

and aryl($C_1$-$C_4$)alkyl radicals, or iii) cationic or non-cationic, heterocycloalkyl or heteroaryl radicals;

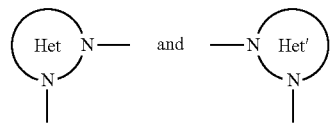

which may be identical or different, are chosen from optionally substituted heterocyclic groups;

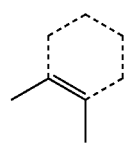

is chosen from aryl and heteroaryl groups fused to the imidazolium or phenyl ring; or alternatively is absent from the imidazolium or phenyl ring;

m, m', n and n', which may be identical or different, are integers ranging from 0 to 6 inclusive, wherein the sums m+n and m'+n' are equal to integers ranging from 1 to 10 inclusive;

Y is chosen from hydrogen and the following protecting groups:

($C_1$-$C_4$)alkylcarbonyl;

arylcarbonyl;

($C_1$-$C_4$)alkoxycarbonyl;

aryloxycarbonyl;

aryl($C_1$-$C_4$)alkoxycarbonyl;

(di)($C_1$-$C_4$)(alkyl)aminocarbonyl;

($C_1$-$C_4$)(alkyl)arylaminocarbonyl;

optionally substituted aryl;

5- or 6-membered monocyclic heteroaryl;

5- or 6-membered cationic monocyclic heteroaryl;

8- to 11-membered cationic bicyclic heteroaryl;

cationic heterocycles having the following formula:

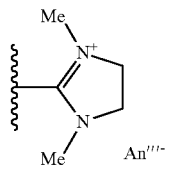 [SMILES: *C1=[N+](C)CCN1C]

$-C(NH_2)=N^+H_2$; $An'''^-$; wherein $An'''^-$ is an anionic counterion;

$-C(NH_2)=NH$;

$SO_3^-M^+$, wherein $M^+$ is a metal ion; and

M' is an anionic counterion.

9. The composition according to claim 1, wherein the at least one direct dye of formula (I) is chosen from:
the dyes of formulae (XV) to (XV') below:

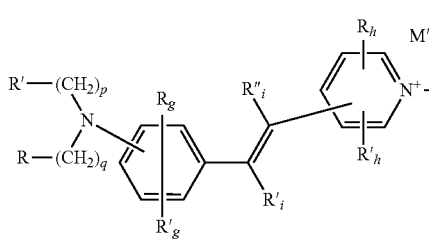

(XV)

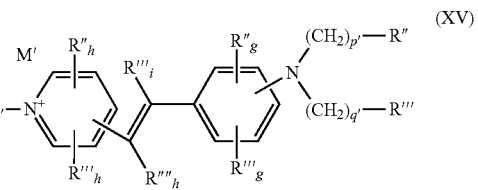

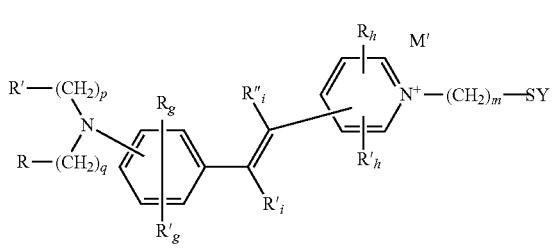

(XV')

wherein in formulae (XV) and (XV'):
R and R''', which may be identical or different, are chosen from hydroxyl, amino ($NR_aR_b$) and ammonium ($N^+R_aR_bR_c$)$An^−$ groups; wherein $R_a$, $R_b$ and $R_c$, which may be identical or different, are chosen from hydrogen atom and ($C_1$-$C_4$)alkyl groups;
or alternatively two alkyl groups $R_a$ and $R_b$ of the amino or ammonium group form a 5- to 7-membered heterocycle optionally comprising another nitrogen or non-nitrogen heteroatom;
R' and R'', which may be identical or different, are chosen from hydrogen and hydroxyl, amino ($NR_aR_b$) and ammonium ($N^+R_aR_bR_e$) $An^−$ groups;
$R_g$, $R'_g$, $R''_g$, $R'''_g$, $R_h$, $R'_h$, $R''_h$ and $R'''_h$, which may be identical or different, are chosen from hydrogen, halogen atoms, amino, (di)($C_1$-$C_4$)alkylamino, cyano, carboxyl, hydroxyl, trifluoromethyl, acylamino, $C_1$-$C_4$ alkoxy, (poly)hydroxy($C_2$-$C_4$)alkoxy, ($C_1$-$C_4$)alkylcarbonyloxy, ($C_1$-$C_4$)alkoxycarbonyl, ($C_1$-$C_4$)alkylcarbonylamino, acylamino, carbamoyl and ($C_1$-$C_4$)alkylsulfonylamino groups, aminosulfonyl radicals and ($C_1$-$C_{16}$)alkyl radicals optionally substituted with a group chosen from ($C_1$-$C_{12}$)alkoxy, hydroxyl, cyano, carboxyl, amino and (di)($C_1$-$C_4$) alkylamino groups, or alternatively the two alkyl radicals borne by the nitrogen atom of the amino group form a 5- to 7-membered heterocycle optionally comprising another nitrogen or non-nitrogen heteroatom;
$R'_i$, $R''_i$, $R'''_i$ and $R''''_i$, which may be identical or different, are chosen from hydrogen and ($C_1$-$C_4$)alkyl groups;
m and m', which may be identical or different, are integers ranging from 1 to 10 inclusive;
p, p', q and q', which may be identical or different, are integers ranging from 1 to 6 inclusive;
M' is an anionic counterion; and Y is chosen from hydrogen and the following protecting groups:
($C_1$-$C_4$)alkylcarbonyl;
arylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl;
($C_1$-$C_4$)(alkyl)arylaminocarbonyl;
optionally substituted aryl;
5- or 6-membered monocyclic heteroaryl;
5- or 6-membered cationic monocyclic heteroaryl;
8- to 11-membered cationic bicyclic heteroaryl;
cationic heterocycles of following formula:

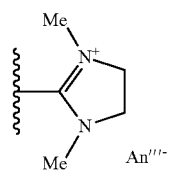

—C($NH_2$)=$N^+H_2$ $An'''^−$; wherein $An'''^−$ is an anionic counterion;
—C($NH_2$)=NH; and
$SO_3^−M^+$, wherein $M^+$ is a metal ion;
it being understood that when the compound of formula (XV) or (XV') contains other cationic parts, it is combined with one or more anionic counterions that afford formula (XV) or (XV') electrical neutrality; and the dyes of formulae (XVI) or (XVI') below:

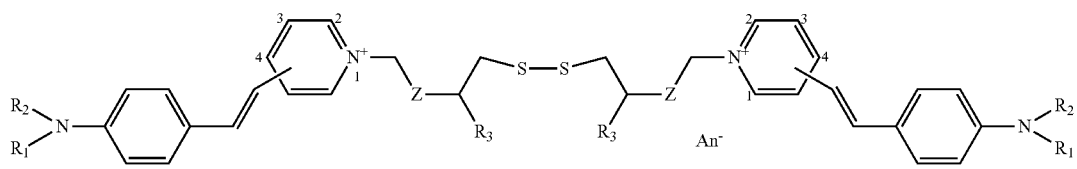

(XVI)

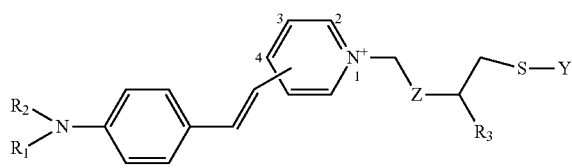

(XVI')

wherein in formulae (XVI) and (XVI'):
$R_1$ is chosen from $C_1$-$C_6$ alkyl groups substituted with at least one group chosen from hydroxyl and —C(O)OR' groups, wherein R' is chosen from hydrogen, and $C_1$-$C_4$ alkyl groups or a group —C(O)—O⁻ and, in the latter case, an anionic counterion An⁻ is absent;
$R_2$ is chosen from $C_1$-$C_6$ alkyl groups optionally substituted with at least one hydroxyl group;
or alternatively the groups $R_1$ and $R_2$ form, together with the nitrogen atom that bears them, a saturated heterocyclic radical substituted with at least one group chosen from hydroxyl, (poly)hydroxy($C_1$-$C_4$)alkyl and/or —C(O)—OR' groups, wherein R' is chosen from hydrogen, and $C_1$-$C_4$ alkyl groups or a group —C(O)—O⁻ and, in the latter case, an anionic counterion An⁻ is absent;
$R_3$ is chosen from hydrogen and —C(O)OR'' groups, wherein R'' is chosen from hydrogen, alkali metals and $C_1$-$C_6$ alkyl groups or alternatively $R_3$ is a —C(O)—O⁻ group and, in the latter case, an anionic counterion An⁻ is absent;
Z is chosen from divalent amido groups —C(O)—N(R)— and —N(R)—C(O)—, and divalent $C_1$-$C_{10}$ alkylene groups interrupted with an amido group chosen from —(CH$_2$)$_{n'}$—C(O)—N(R)—(CH$_2$)$_p$— and —(CH$_2$)$_{n''}$—N(R)—C(O)—(CH$_2$)$_p$—, wherein n' is an integer ranging from 0 to 3 inclusive; p is an integer ranging from 0 to 4 inclusive, n'' is an integer ranging from 0 to 3 inclusive and R is chosen from hydrogen and $C_1$-$C_6$ alkyl groups;
An⁻ is an anionic counterion;
Y is chosen from hydrogen and the following protecting groups:

($C_1$-$C_4$)alkylcarbonyl;
arylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl;
($C_1$-$C_4$)(alkyl)arylaminocarbonyl;
optionally substituted aryl;
5- or 6-membered monocyclic heteroaryl;
5- or 6-membered cationic monocyclic heteroaryl;
8- to 11-membered cationic bicyclic heteroaryl;
cationic heterocycles of following formula:

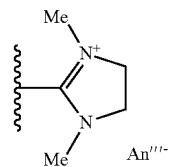

—C(NH$_2$)=N⁺H$_2$ An'''⁻; wherein An'''⁻ is an anionic counterion;
—C(NH$_2$)=NH; and
SO$_3^-$M⁺, wherein M⁺ is a metal ion;
it being understood that when the compound of formula (XVI) or (XVI') contains other cationic parts, it is combined with one or more anionic counterions that afford formula (XVI) or (XVI') electrical neutrality.

10. The composition according to claim 1, wherein the at least one direct dye of formula (I) is chosen from dyes of the following chemical structures:

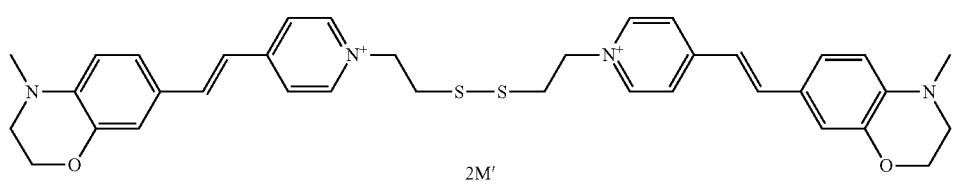

2M'

-continued
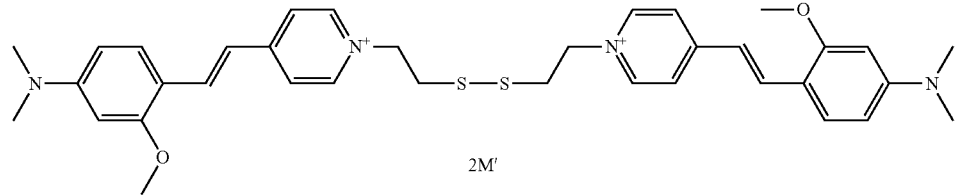
26
2M′
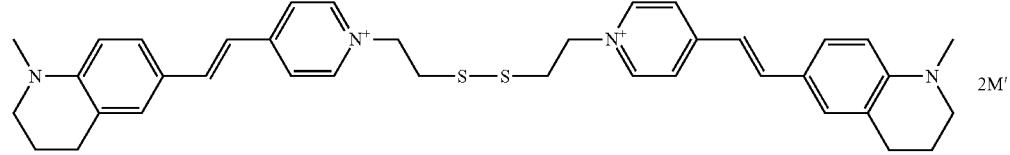
27
2M′
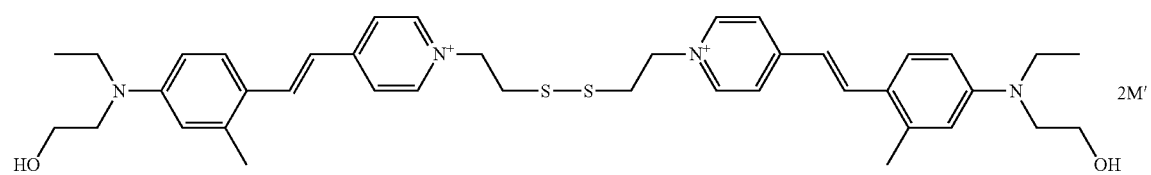
28
2M′
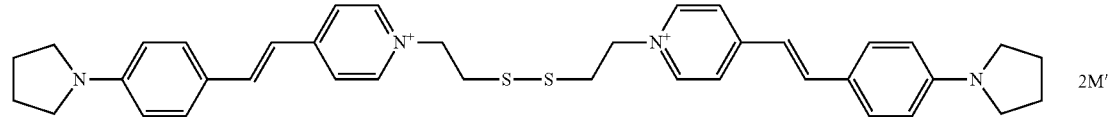
29
2M′
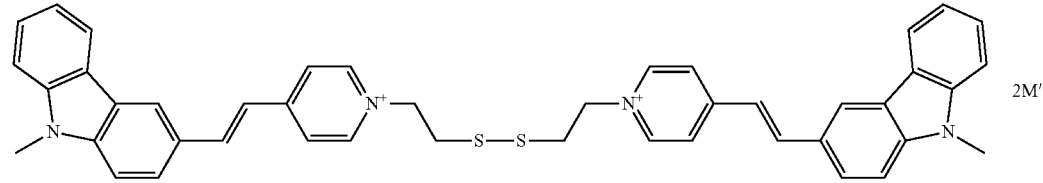
30
2M′
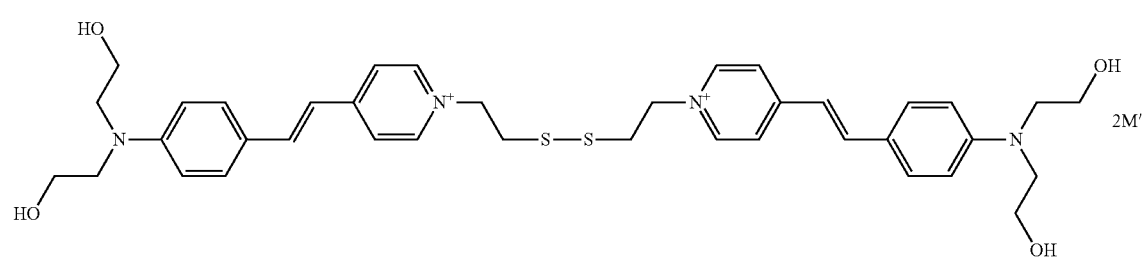
31
2M′
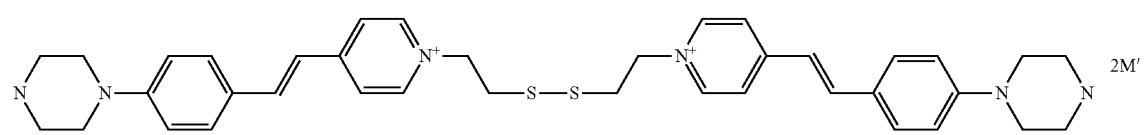
32
2M′
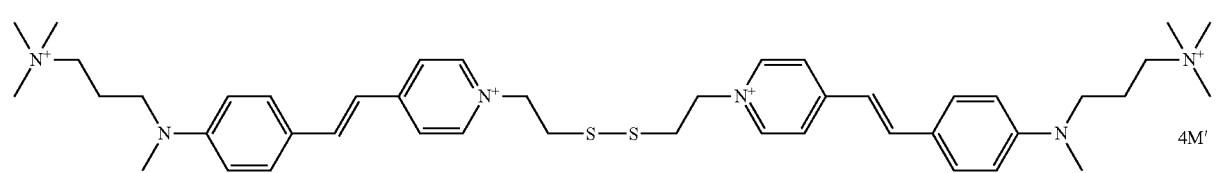
33
4M′

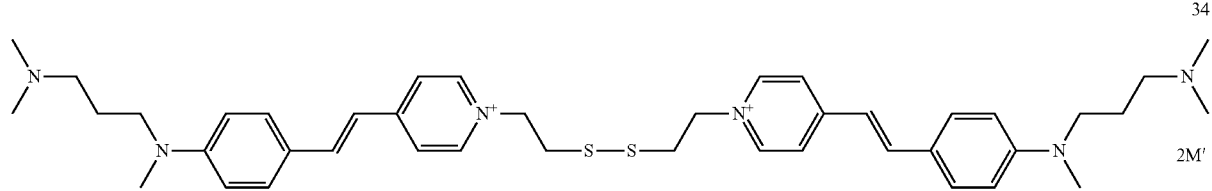
34
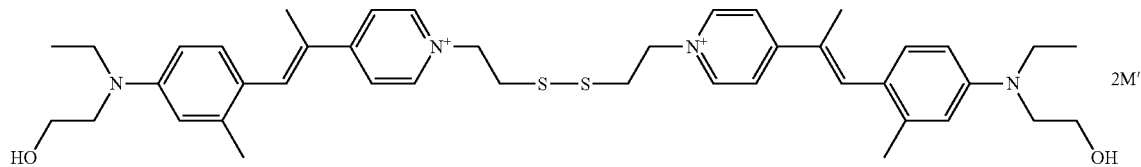
35
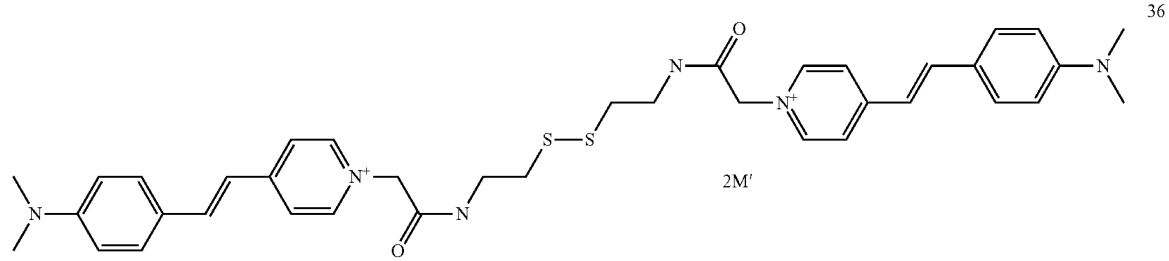
36
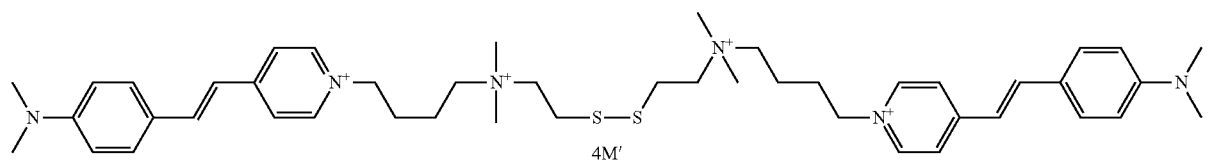
37
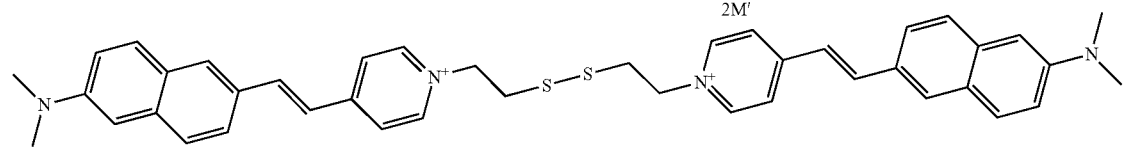
38
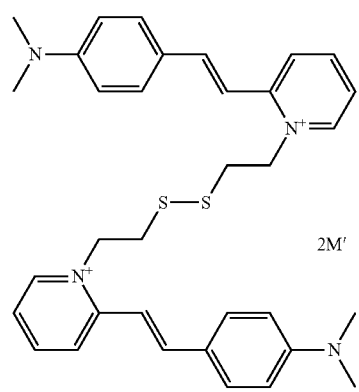
39
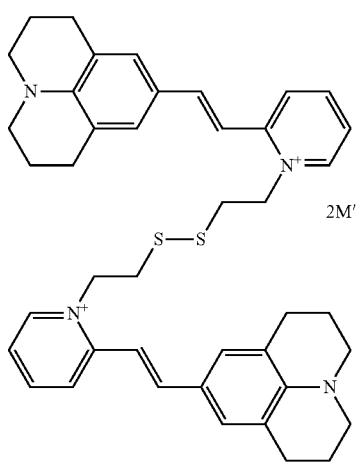
40

127 128
-continued
41
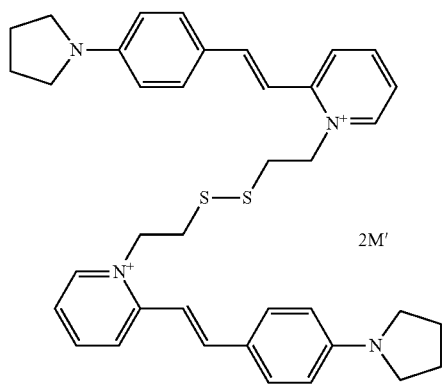
42
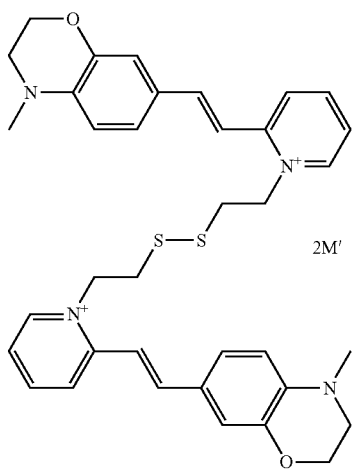
43
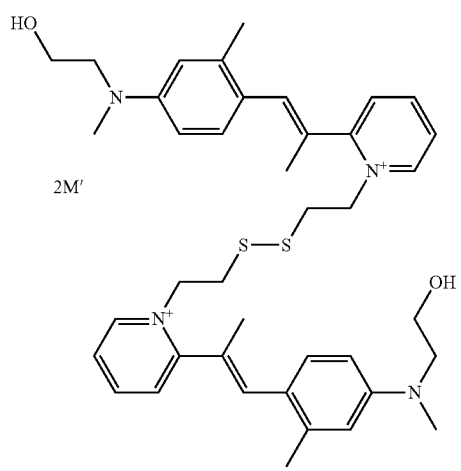
44
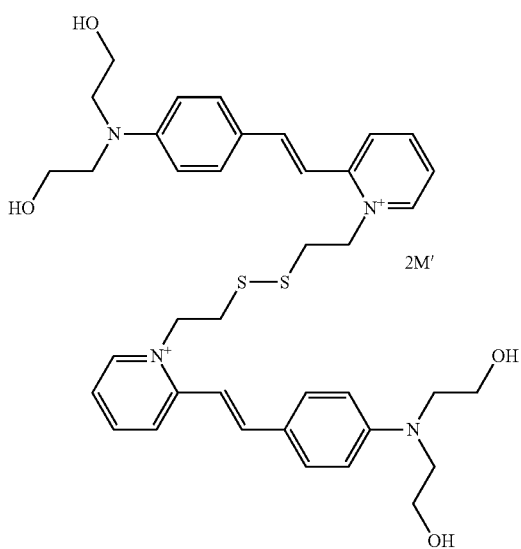
45
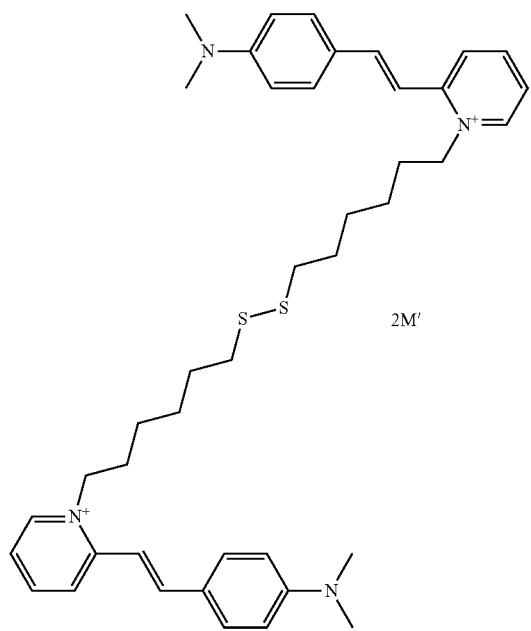

-continued
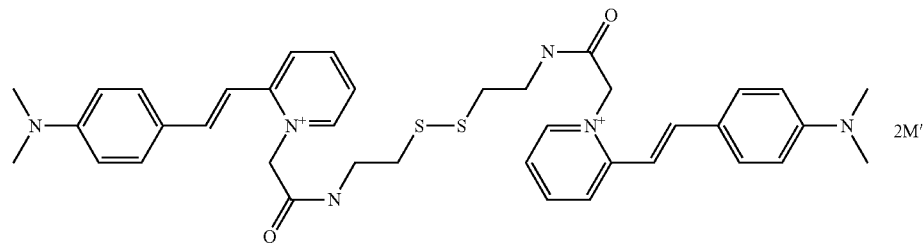
46 2M'
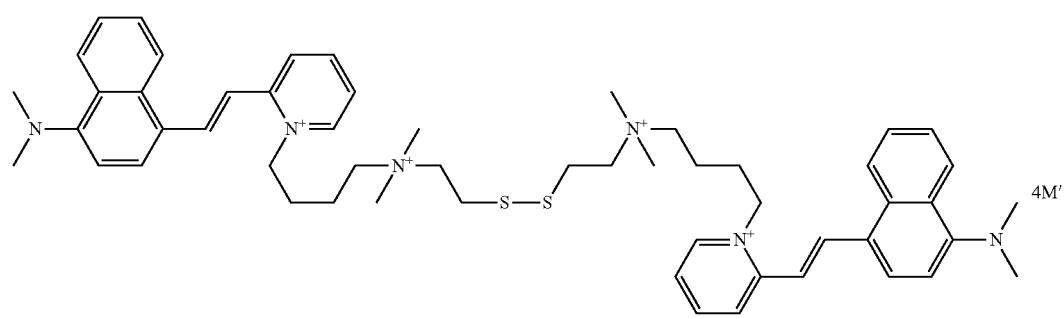
47 4M'
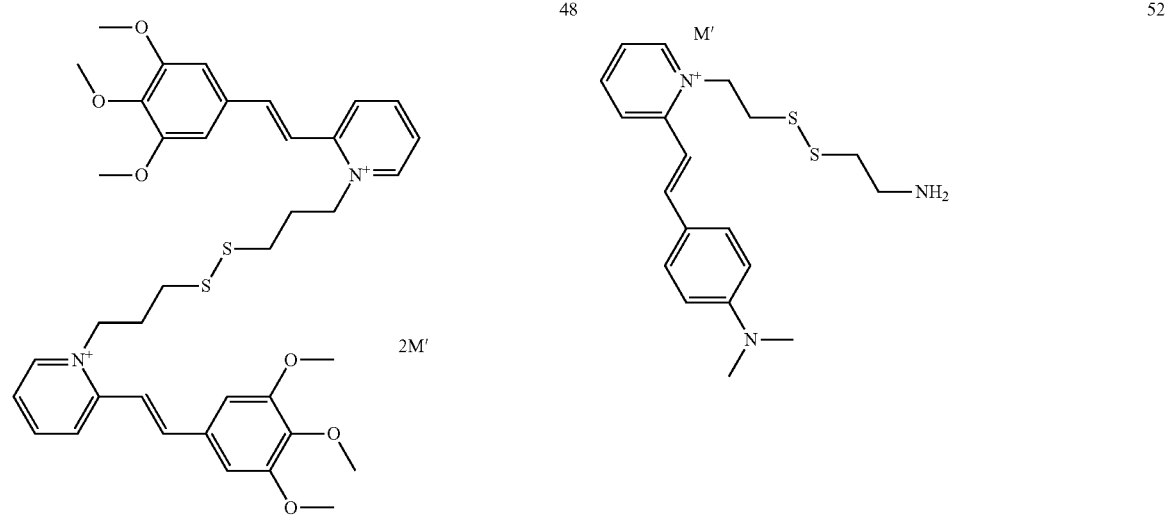
48 2M'
52 M'
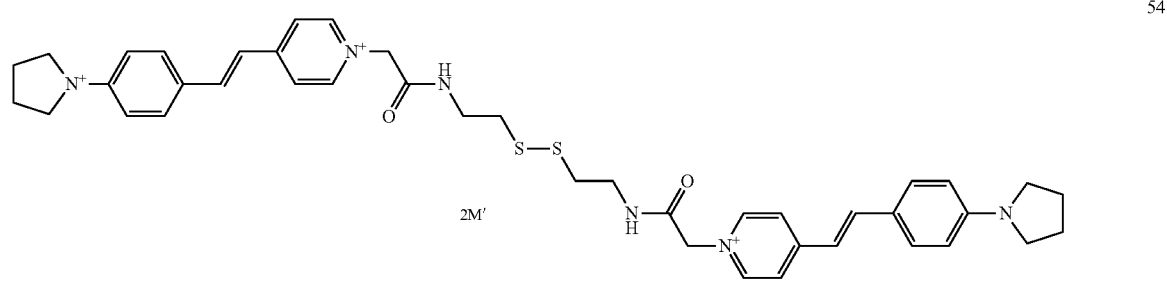
54 2M'
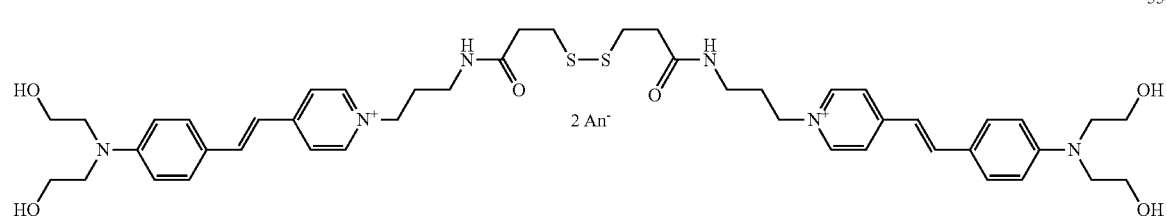
55 2 An⁻

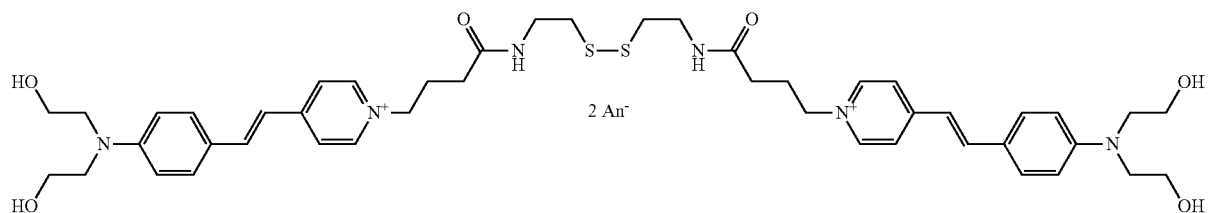
56
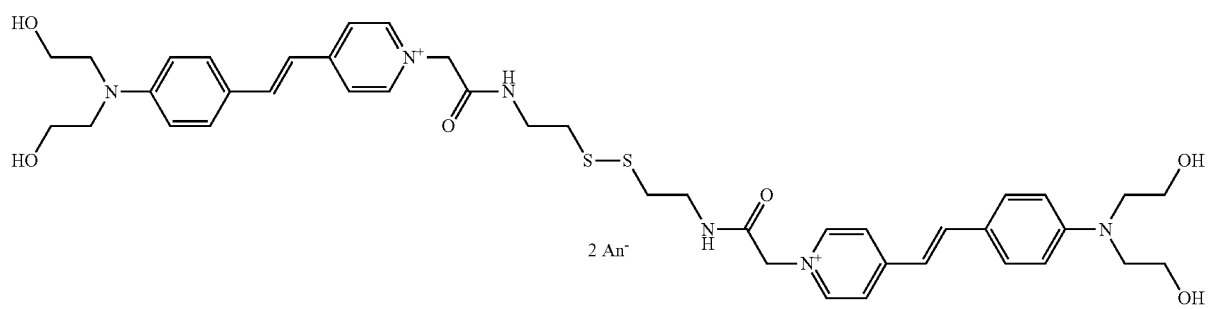
57
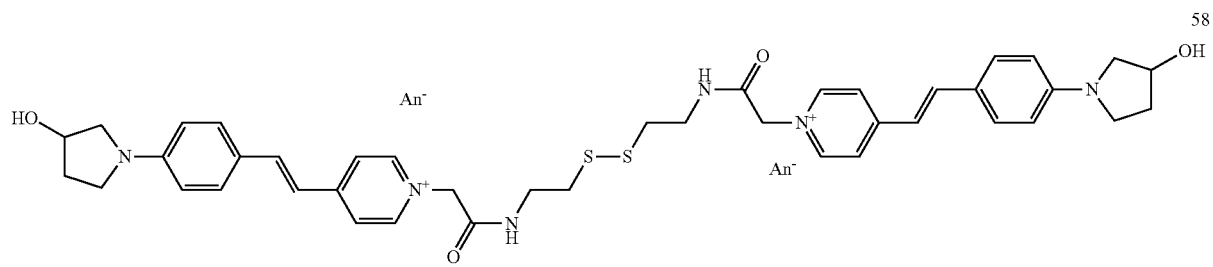
58
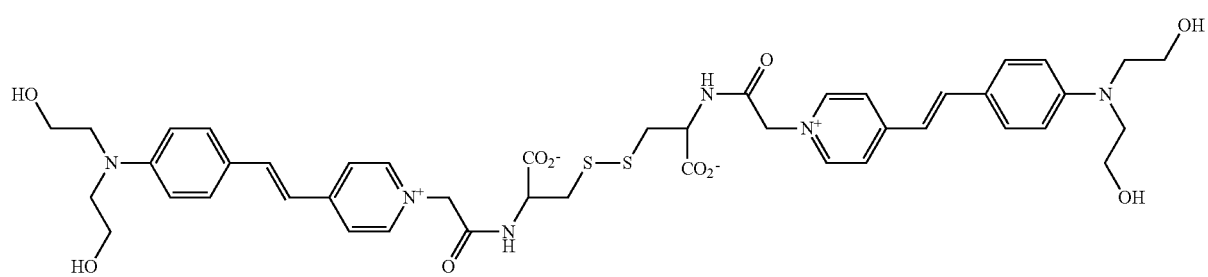
59
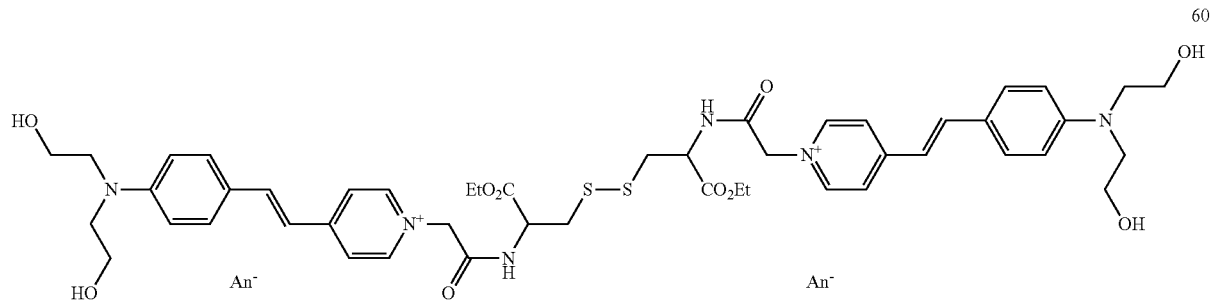
60

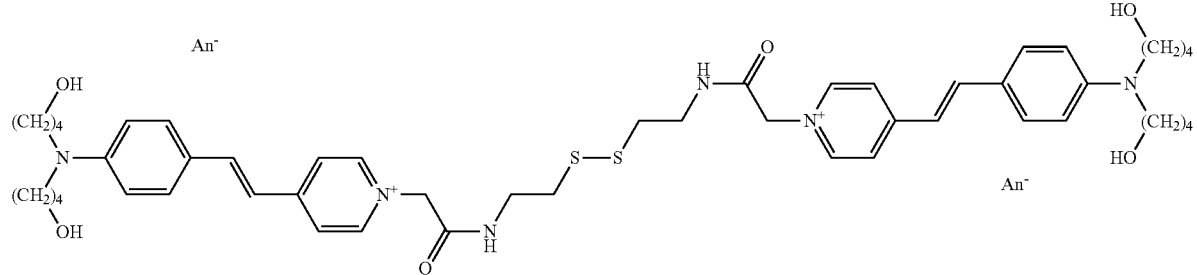
61
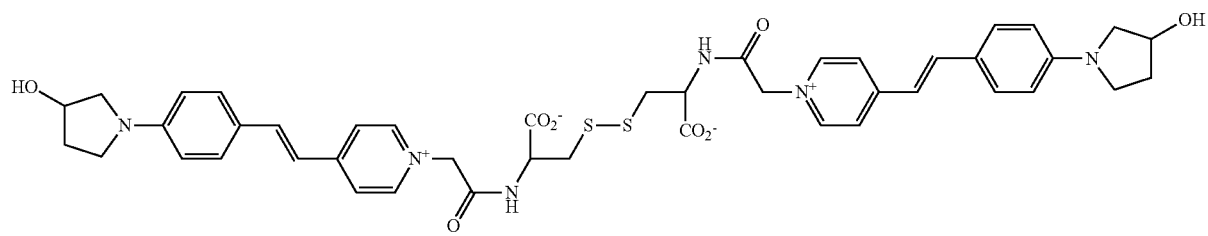
62
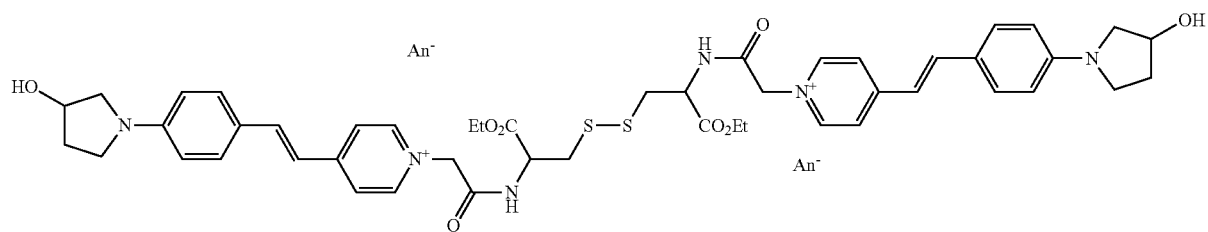
63
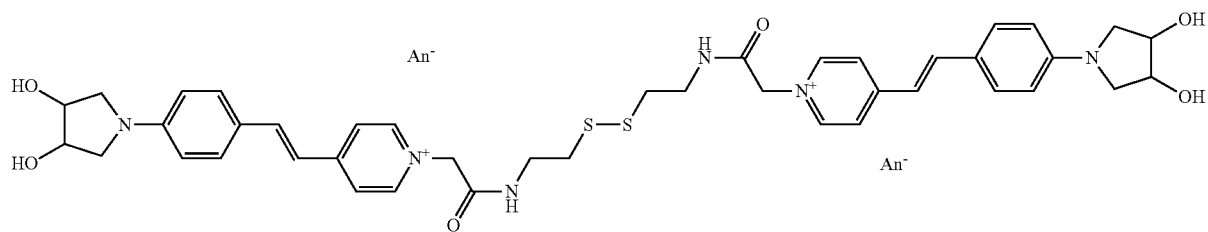
64
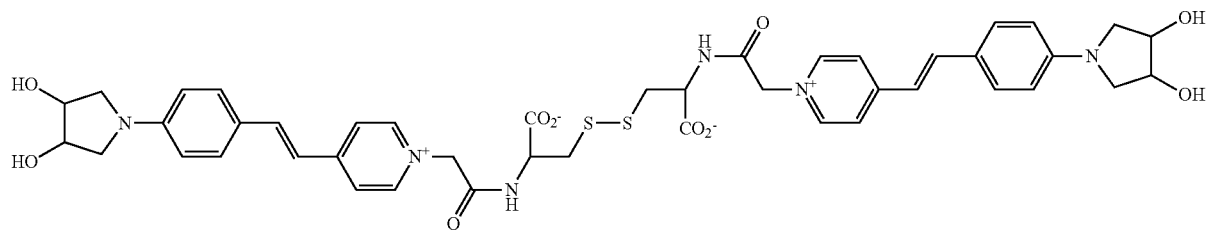
65

-continued
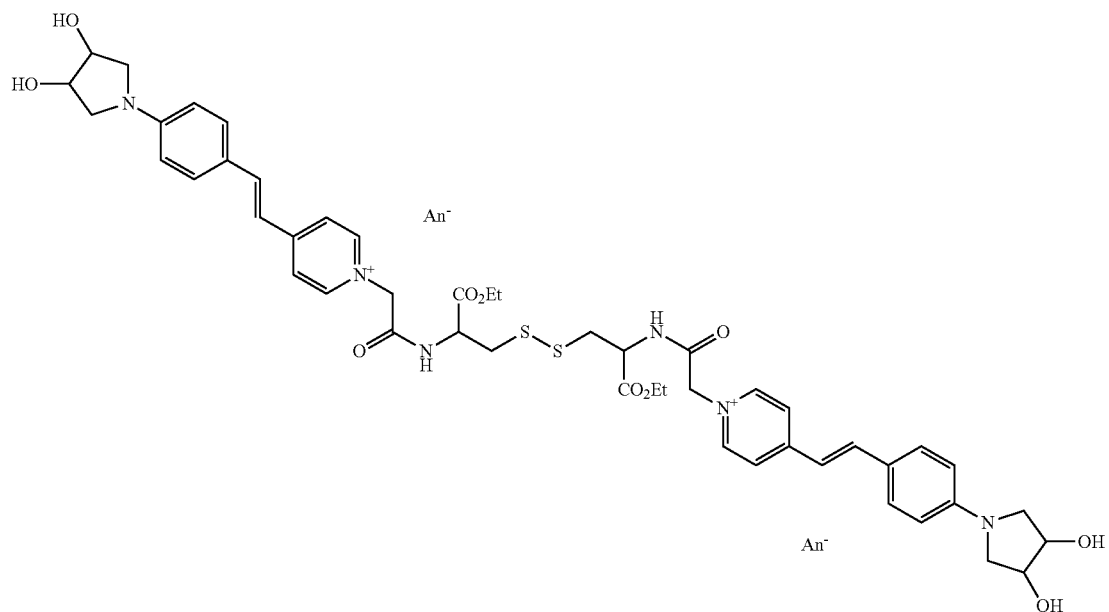
66
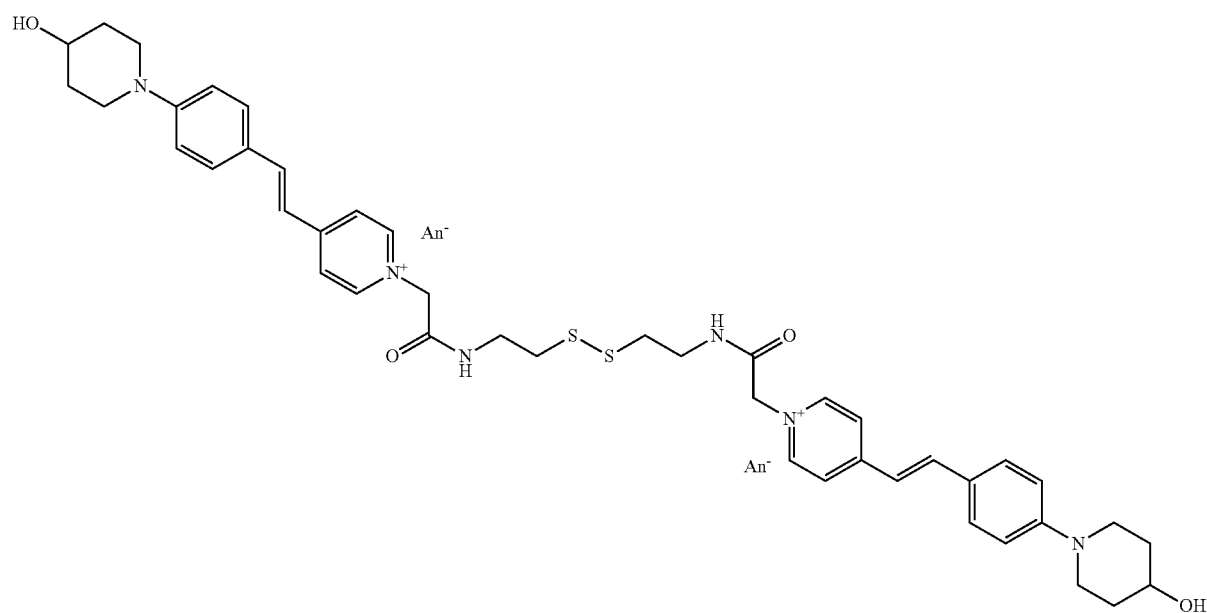
67
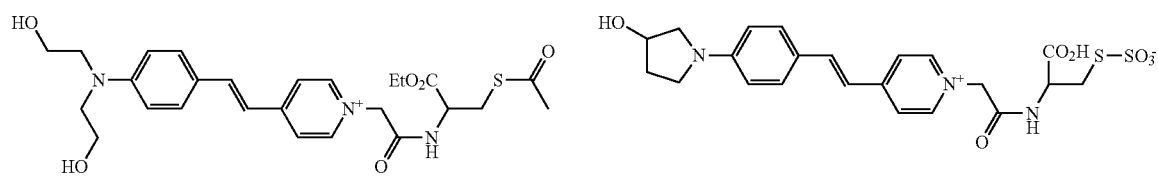
68
69

137 138
-continued
70
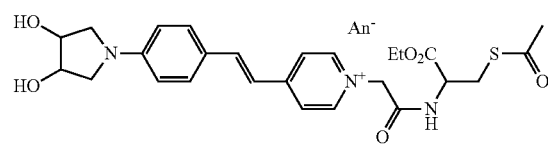
71
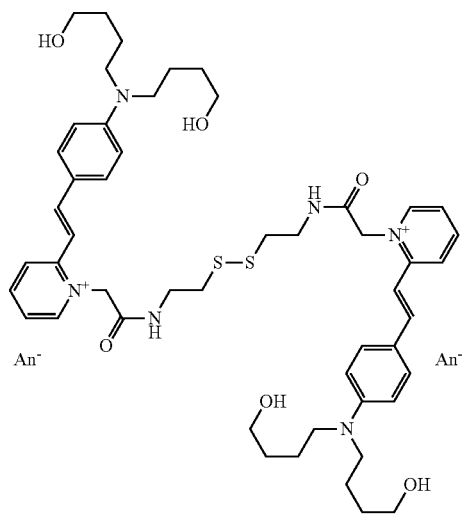
72
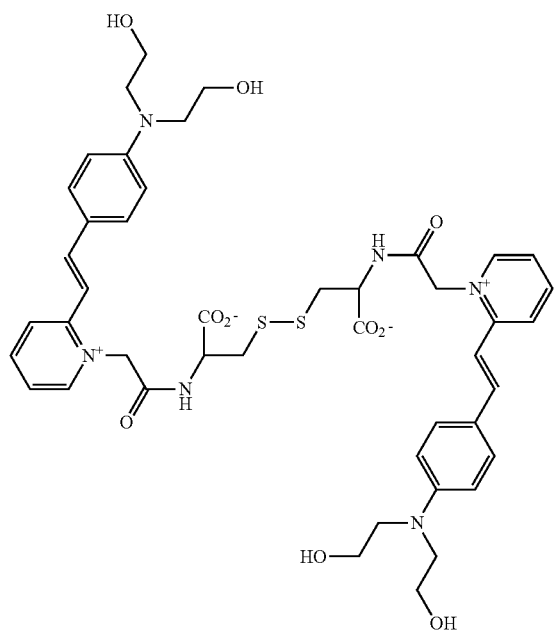
73
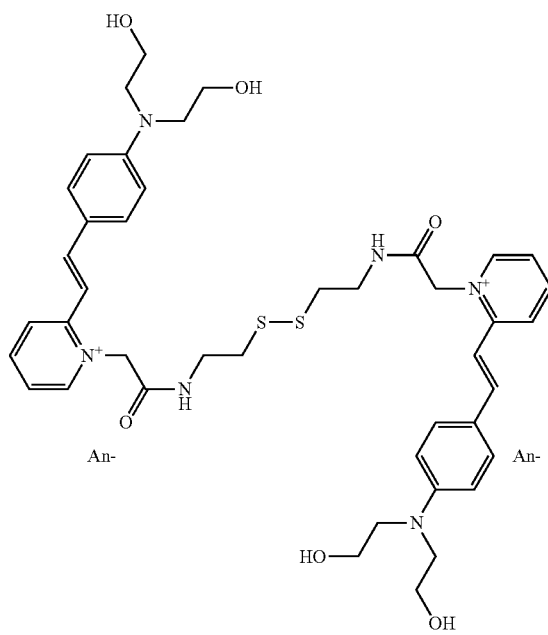

-continued
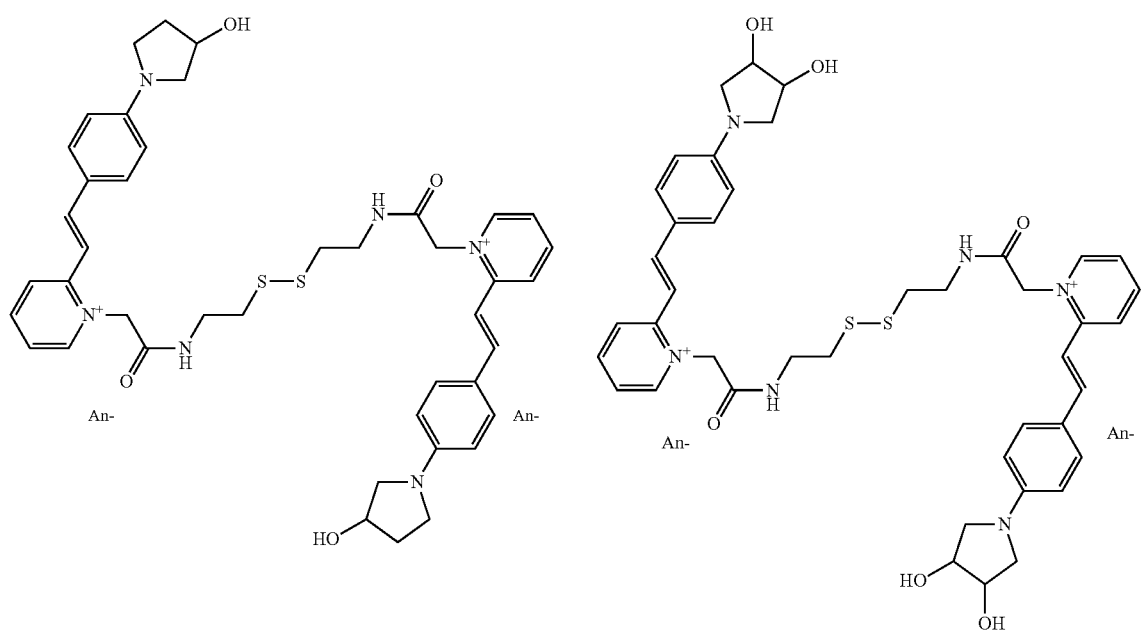
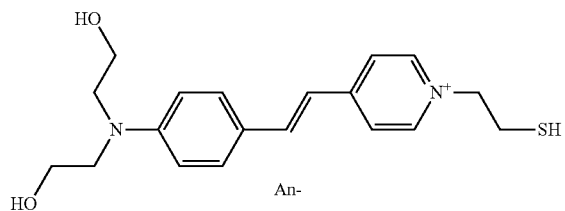
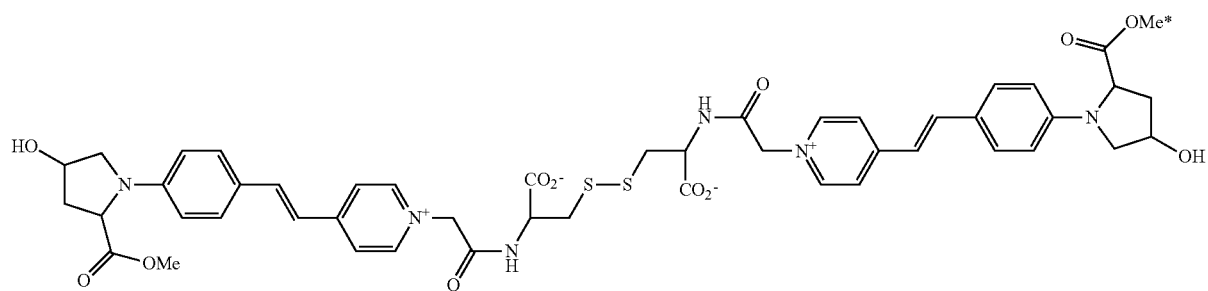
Me⁺ represents an alkali metal or an alkaline-earth metal; or a methyl
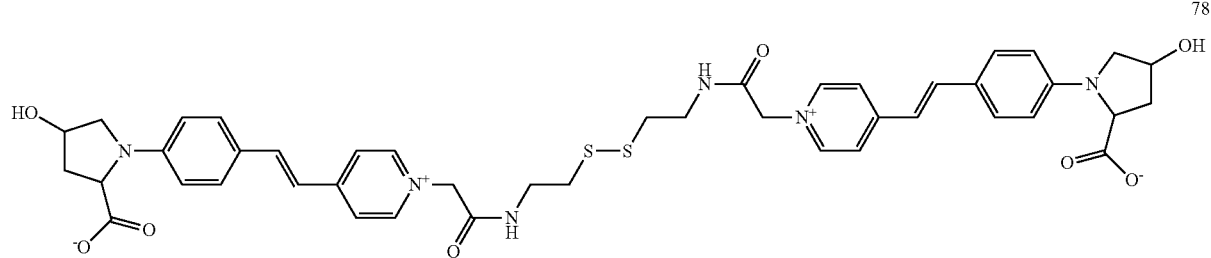

-continued
79
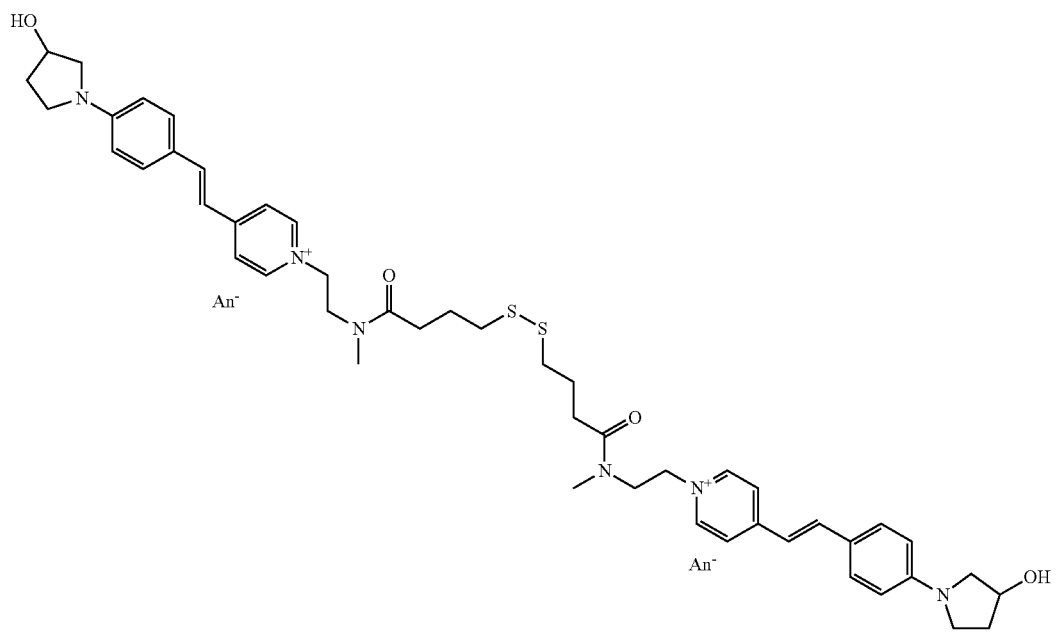
80
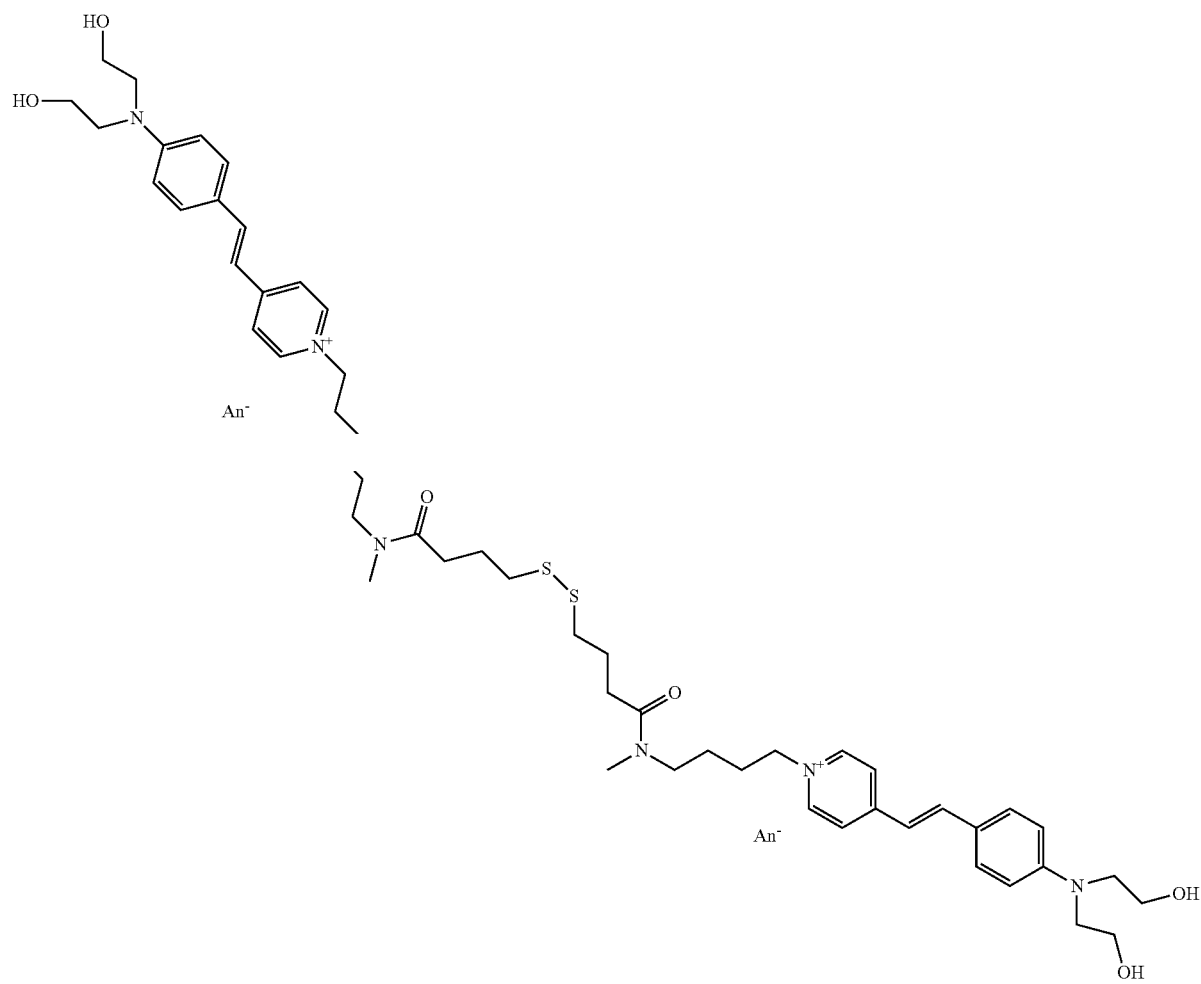

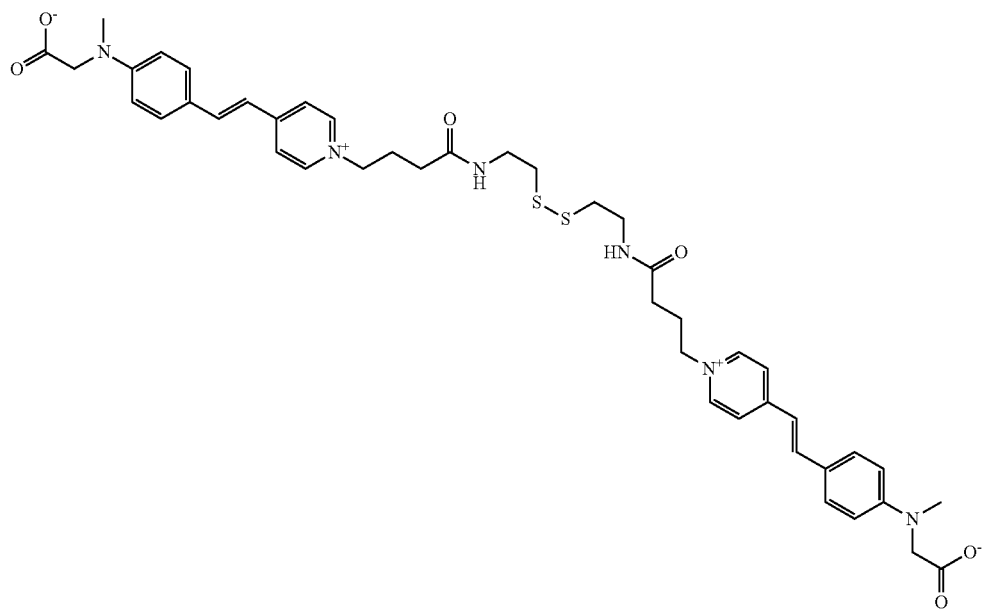
81
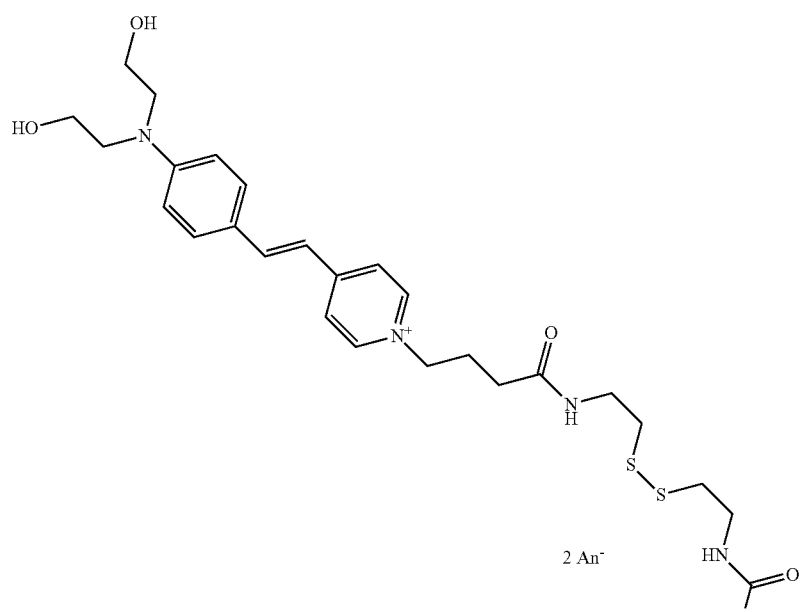
82

145
146
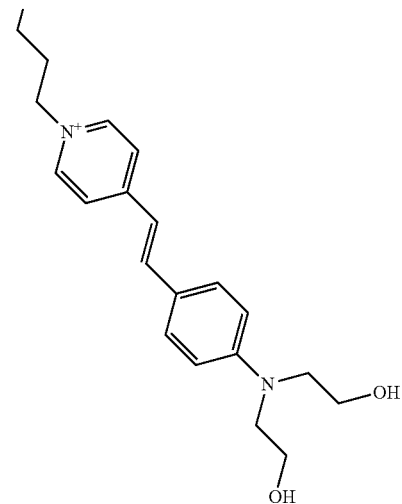
83
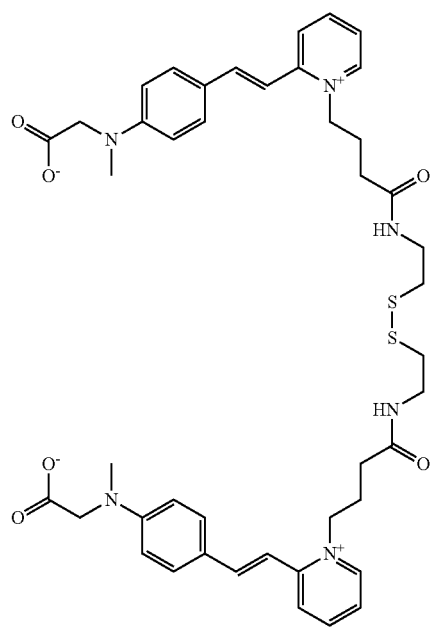
84
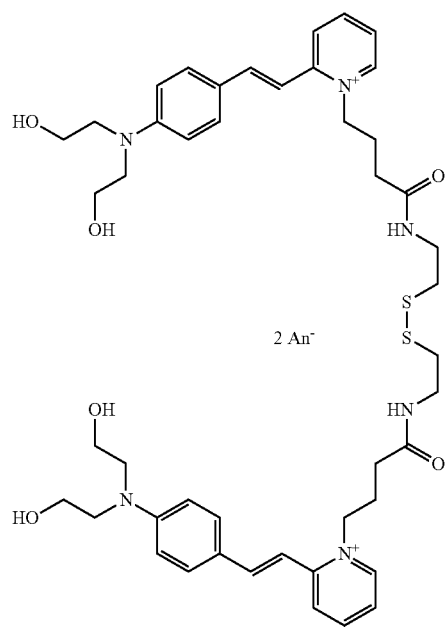
2 An⁻
85
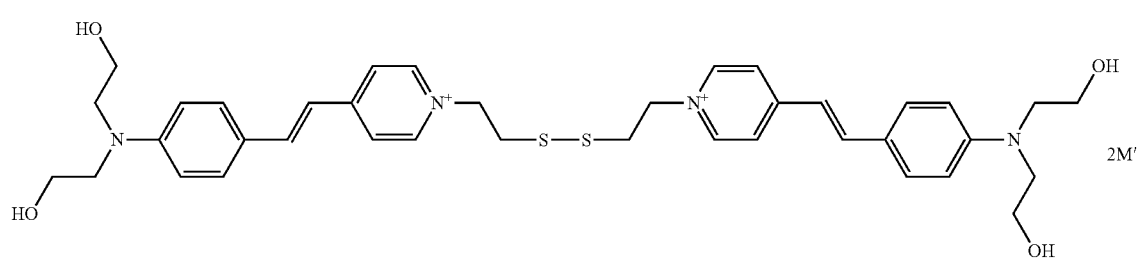
2M'
86
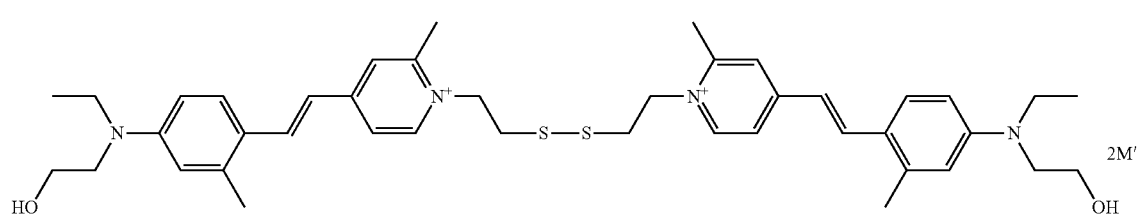
2M'

-continued
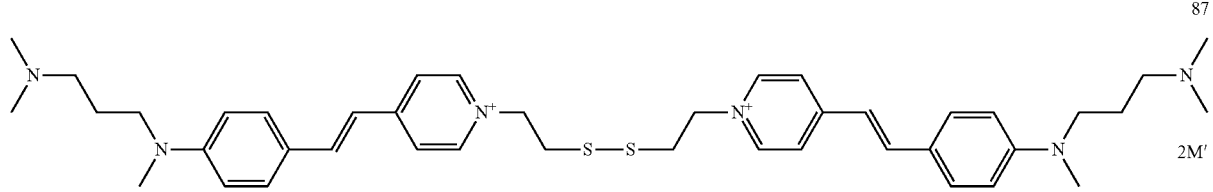
87
2M'
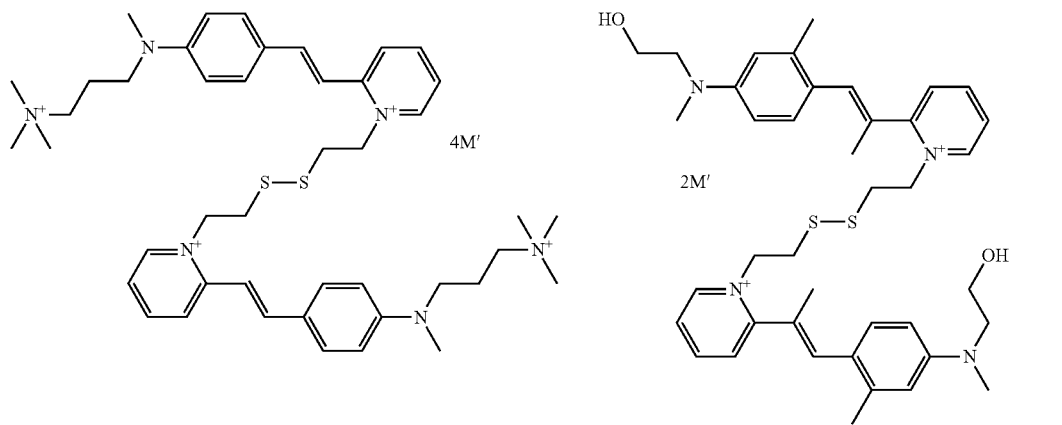
88
4M'
89
2M'
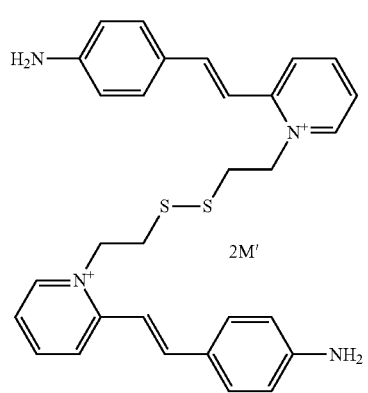
90
2M'
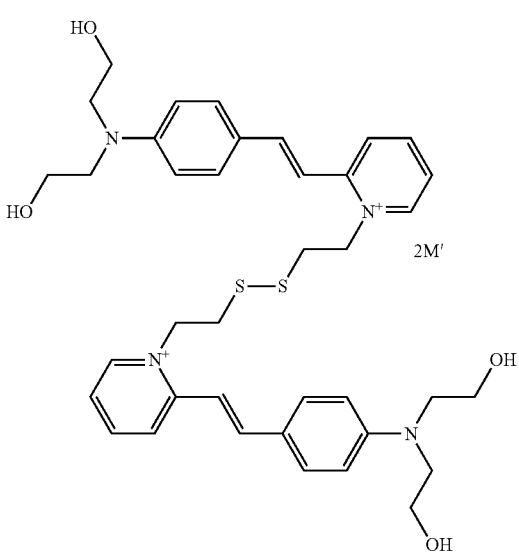
91
2M'
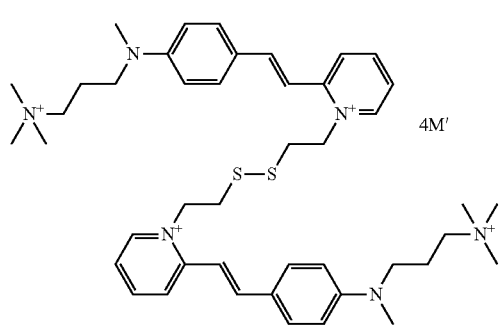
92
4M'
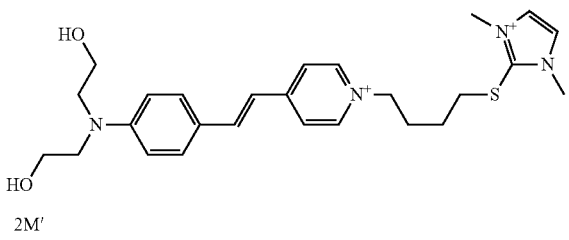
93
2M'

-continued
94
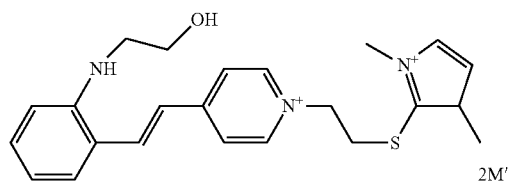
2M'
95
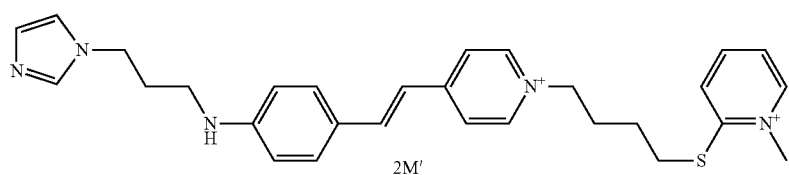
2M'
96
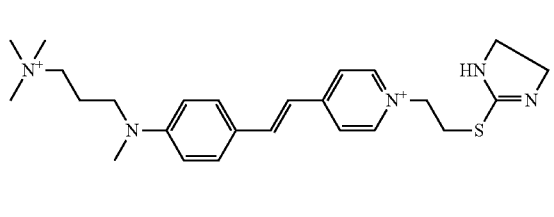
97
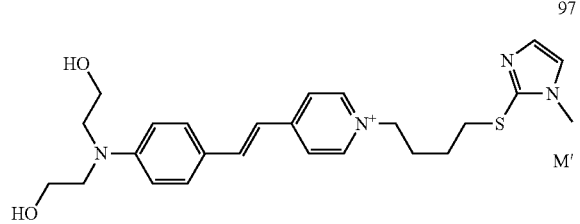
M'
98
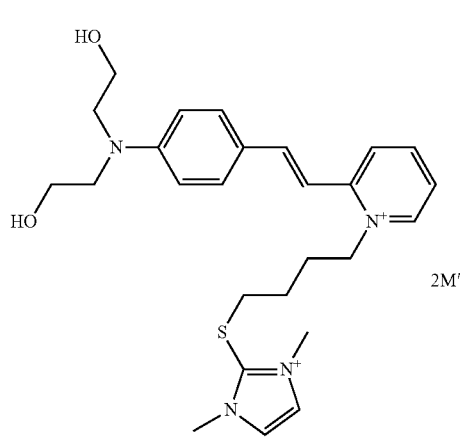
2M'
99
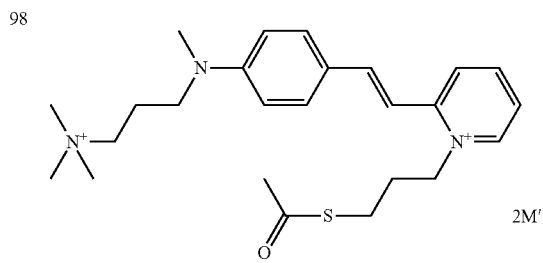
2M'
100
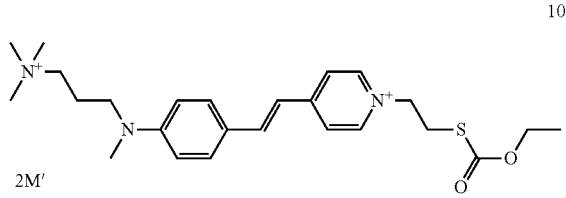
2M'
101
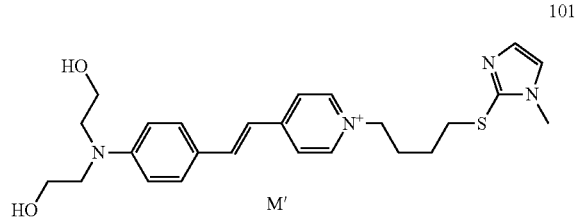
M'
102
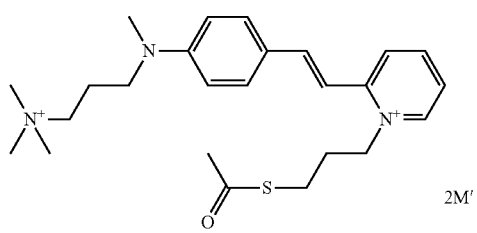
2M'
102
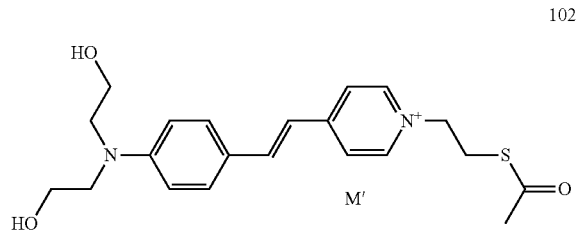
M'

-continued
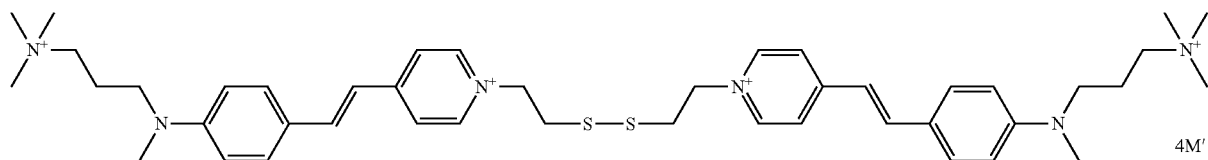
103
4M'
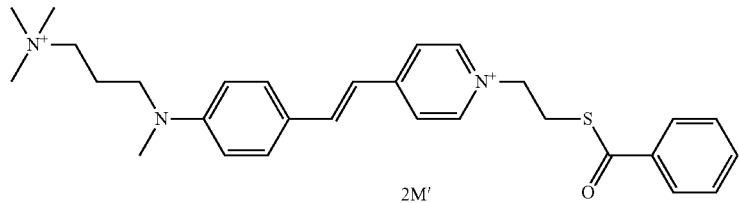
104
2M'
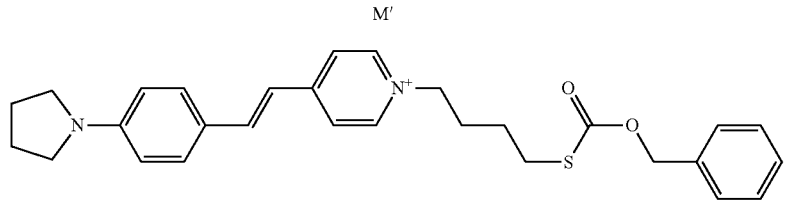
105
M'
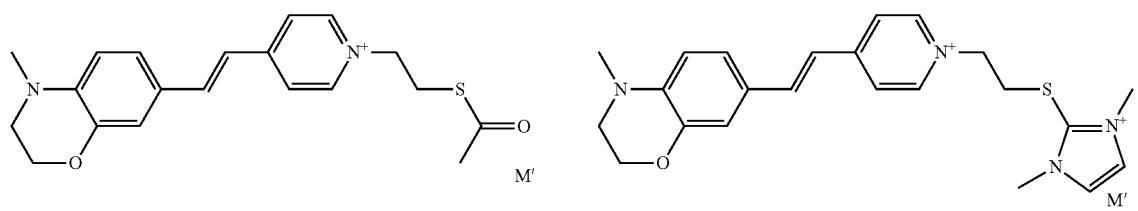
106 107
M' M'
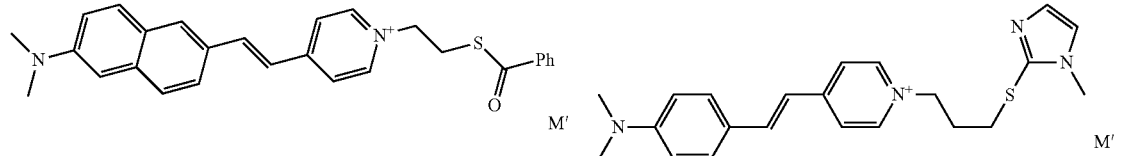
108 109
M' M'
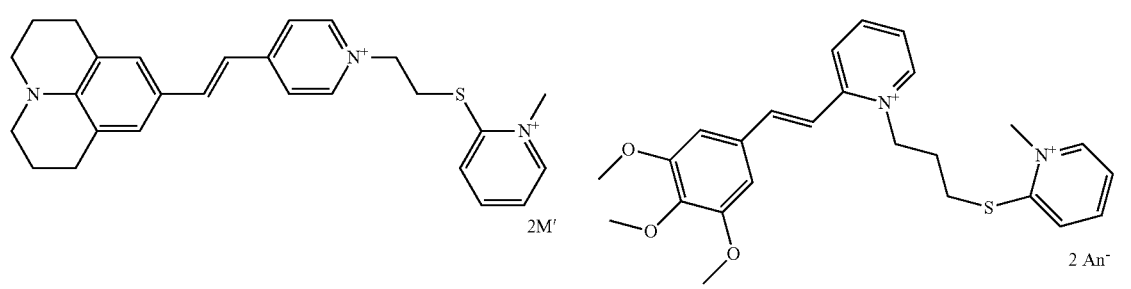
110 111
2M' 2 An⁻

-continued
112
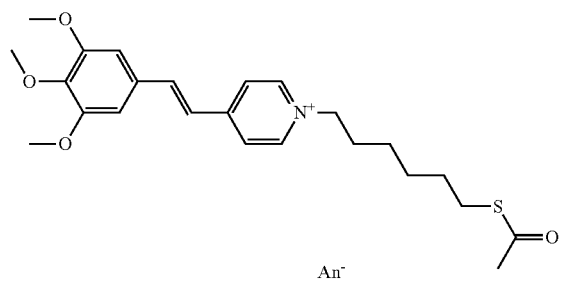
An⁻
113
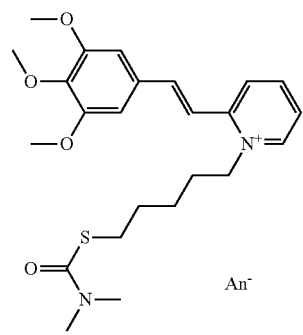
An⁻
114
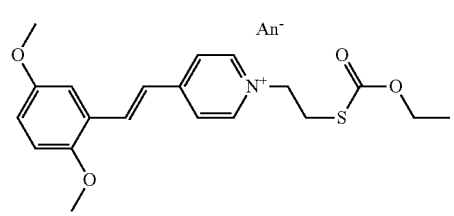
An⁻
115
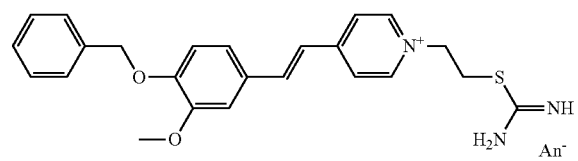
An⁻
116
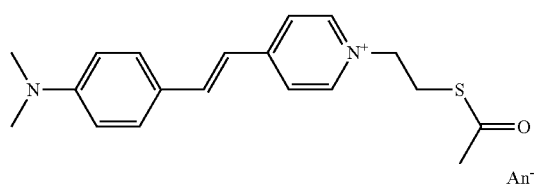
An⁻
117
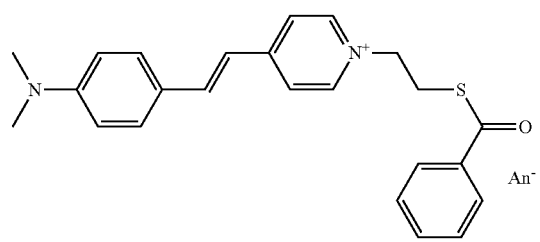
An⁻
118
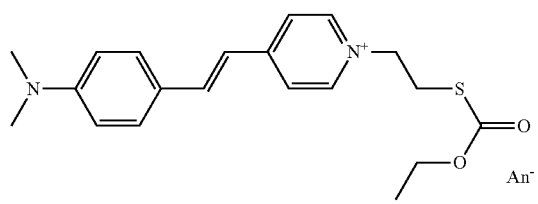
An⁻
119
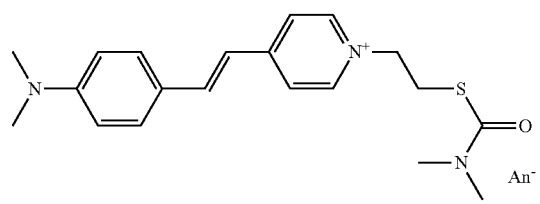
An⁻
120
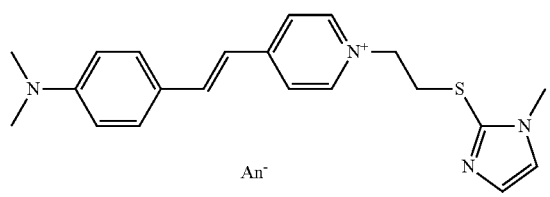
An⁻
121
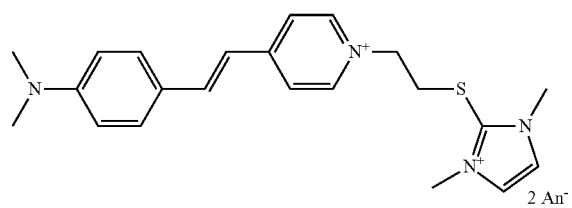
2 An⁻

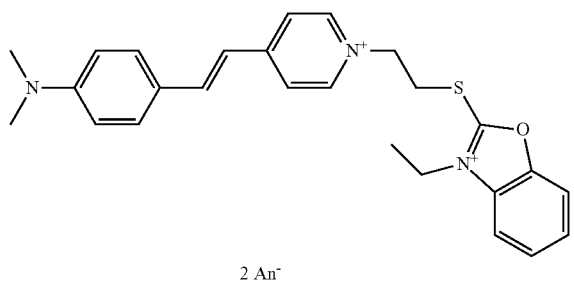

122

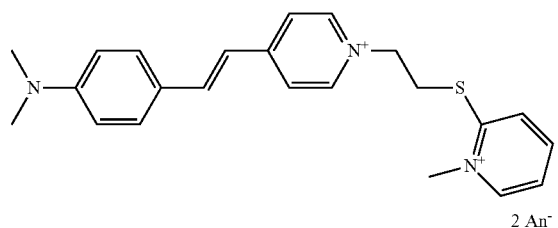

123

2 An⁻

2 An⁻ wherein An⁻ and M', which may be identical or different are anionic counterions.

11. The composition according to claim 10, wherein An⁻ and M' are identical and/or are chosen from halides and alkyl sulphates.

12. The composition according to claim 10, wherein the at least one direct dye of formula (I) is chosen from dyes of formulae 44 and 55.

13. The composition according to claim 1, wherein ii) the at least one fatty alcohol is a non-ethoxylated fatty alcohol of structure R—OH, wherein R is chosen from saturated or unsaturated, linear or branched radicals comprising from 8 to 40 carbon atoms, optionally substituted with at least one hydroxyl group.

14. The composition according to claim 13, wherein ii) the at least one fatty alcohol is a non-ethoxylated fatty alcohol chosen from lauryl alcohol, cetyl alcohol, stearyl alcohol, cetylstearyl alcohol, oleyl alcohol, behenyl alcohol, linoleyl alcohol, undecylenyl alcohol, palmitoleyl alcohol, arachidonyl alcohol, erucyl alcohol, myristyl alcohol, and mixtures thereof.

15. The composition according to claim 1, wherein ii) the at least one fatty alcohol is a sparingly ethoxylated fatty alcohol of the following formula:

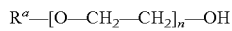

$R^a$—[O—CH$_2$—CH$_2$]$_n$—OH wherein:
  $R^a$ is chosen from linear or branched $C_8$-$C_{40}$ alkyl groups and linear or branched $C_8$-$C_{40}$ alkenyl groups, optionally substituted with at least one hydroxyl group, and
  n is an integer ranging from 1 to 6 inclusive.

16. The composition according to claim 15, wherein ii) the at least one fatty alcohol is chosen from lauryl alcohol containing 2 OE, lauryl alcohol containing 3 OE, decyl alcohol containing 3 OE, decyl alcohol containing 5 OE, stearyl alcohol containing 2 OE, stearyl alcohol containing 3 OE, stearyl alcohol containing 4 OE, stearyl alcohol containing 5 OE, cetyl alcohol containing 2 OE, cetyl alcohol containing 3 OE, cetyl alcohol containing 4 OE and cetyl alcohol containing 5 OE, and mixtures thereof, such as cetearyl alcohol containing 3 OE, cetearyl alcohol containing 4 OE and cetearyl alcohol containing 5 OE.

17. The composition according to claim 1, wherein iii) the at least one cationic surfactant is chosen from:
a) compounds of formula (XVII) below:

(XVII)

wherein in formula (XVII):
  $R_8$, $R_9$, $R_{10}$ and $R_{11}$, which may be identical or different, are chosen from linear or branched aliphatic groups comprising from 1 to 30 carbon atoms, and aromatic groups, wherein at least one of the groups $R_8$, $R_9$, $R_{10}$ and $R_{11}$ comprises from 8 to 30 carbon atoms and the aliphatic groups optionally comprise at least one heteroatom,
  $X^-$ is an anionic counterion;
b) compounds of formula (XVIII) below:

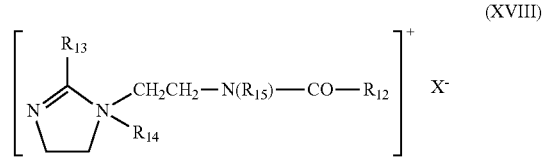

(XVIII)

wherein in formula (XVIII):
  $R_{12}$ is chosen from alkenyl and alkyl groups comprising from 8 to 30 carbon atoms;
  $R_{13}$ is chosen from hydrogen, $C_1$-$C_4$ alkyl groups and alkenyl and alkyl groups comprising from 8 to 30 carbon atoms;
  $R_{14}$ is chosen from $C_1$-$C_4$ alkyl groups;
  $R_{15}$ is chosen from hydrogen and $C_1$-$C_4$ alkyl groups;
  $X^-$ is anionic counterion;
c) compounds of formula (XIX) below:

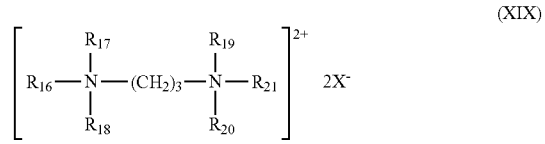

(XIX)

wherein in formula (XIX):
  $R_{16}$ is chosen from alkyl groups comprising from about 16 to 30 carbon atoms, which may be optionally hydroxylated and/or interrupted with at least one oxygen atom;
  $R_{17}$ is chosen from hydrogen, alkyl groups comprising from 1 to 4 carbon atoms and —$(CH_2)_3$—$N^+(R_{16a})(R_{17a})(R_{18a})$, wherein $R_{16a}, R_{17a}, R_{18a}$, which may be identical or different, are chosen from hydrogen and alkyl groups comprising from 1 to 4 carbon atoms;
  $R_{18}, R_{19}, R_{20}$ and $R_{21}$, which may be identical or different, are chosen from hydrogen and alkyl groups comprising from 1 to 4 carbon atoms, and
  $X^-$ is an anionic counterion;
d) compounds of formula (XX) below:

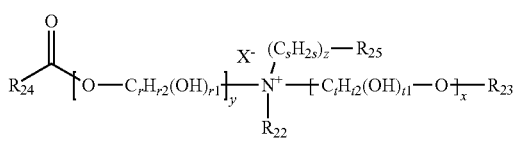

(XX)

wherein in formula (XX):
  $R_{22}$ is chosen from $C_1$-$C_6$ alkyl, $C_1$-$C_6$ hydroxyalkyl and $C_1$-$C_6$ dihydroxyalkyl groups;
  $R_{23}$ is chosen from:
    the group

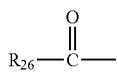

linear or branched, saturated or unsaturated $C_1$-$C_{22}$ hydrocarbon-based groups $R_{27}$,
  hydrogen;
  $R_{25}$ is chosen from:
    the group

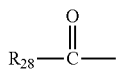

linear or branched, saturated or unsaturated $C_1$-$C_6$ hydrocarbon-based groups $R_{29}$,
  hydrogen;
  $R_{24}, R_{26}$ and $R_{28}$, which may be identical or different, are chosen from linear or branched, saturated or unsaturated $C_7$-$C_{21}$ hydrocarbon-based groups;
  r, s and t, which may be identical or different, are integers ranging from 2 to 6 inclusive;
  r1 and t1 which may be identical or different, are equal to 0 or 1, wherein r2+r1=2r and t1+t2=2t,
  y is an integer ranging from 1 to 10 inclusive;
  x and z, which may be identical or different, are integers ranging from 0 to 10 inclusive;
  $X^-$ is an organic or inorganic anionic counterion;
with the proviso that the sum x+y+z ranges from 1 to 15 inclusive, that when x is 0, then $R_{23}$ denotes $R_{27}$ and that when z is 0, then $R_{25}$ denotes $R_{29}$.

18. The composition according to claim 17, wherein iii) the at least one cationic surfactant is chosen from cetyltrimethylammonium, behenyltrimethylammonium and dipalmitoylethylhydroxyethylmethylammonium salts, and mixtures thereof.

19. The composition according to claim 1, wherein iv) the at least one alkaline agent is chosen from aqueous ammonia, alkali metal carbonates and bicarbonates, alkanolamines, oxyethylenated and/or oxypropylenated ethylenediamines, amino acids and the compounds of formula (XXI) below:

(XXI)

wherein:
  W is chosen from divalent $C_1$-$C_6$ alkylene radicals optionally substituted with a radical chosen from hydroxyl and $C_1$-$C_6$ alkyl radicals, and/or optionally interrupted with at least one heteroatom chosen from oxygen and $NR^u$;
  $R^x, R^y, R^z R^t$ and $R^u$, which may be identical or different, are chosen from hydrogen and $C_1$-$C_6$ alkyl, $C_1$-$C_6$ hydroxyalkyl and $C_1$-$C_6$ aminoalkyl radicals.

20. The composition according to claim 1, wherein v) the at least one reducing agent is chosen from thioglycolic acid, cysteine, and esters and salts thereof.

21. A method for dyeing and/or lightening keratin fibers, comprising applying to the keratin fibers:
  i) at least one dye of formula (I) according to claim 1;
  ii) at least one fatty alcohol;
  iii) at least one cationic surfactant;
  iv) at least one alkaline agent
  v) at least one reducing agent chosen from thioglycolic acid, thiolactic acid, 3-mercaptopropionic acid, thiomalic acid, 2,3-dimercaptosuccinic acid, cysteine, N-glycyl-L-cysteine, L-cysteinylglycine, and esters and salts thereof; thioglycerol; cysteamine and $C_1$-$C_4$ acyl derivatives thereof; N-mesylcysteamine; N-acetylcysteine; N-(mercapto-2-ethyl) gluconamide; pantetheine, N-(mercaptoalkyl)-ω-hydroxyalkylamides; N-mono- or N,N-dialkylmercapto-4-butyramides; aminomercaptoalkyl amides; N-(mercaptoalkyl)succinamic acids and N-(mercaptoalkyl)succinimides; alkylamino mercaptoalkyl amides; the azeotropic mixture of 2-hydroxypropyl thioglycolate and of (2-hydroxy-1-methyl)ethyl thioglycolate; ammonium thioglycolate; mercaptoalkylamino amides; and N-mercaptoalkylalkanediamides;
  vi) optionally at least one chemical oxidizing agent; and
  vii) optionally at least one organic thickening polymer;
wherein the ingredients i) to vii) are applied to the keratin fibers either together or separately.

22. The method according to claim 21, comprising applying to the keratin fibers a reducing composition comprising iv) at least one alkaline agent, v) at least one reducing agent and optionally ii) at least one fatty alcohol, followed by the application of a dye composition comprising i) at least one direct dye of formula (I), ii) at least one fatty alcohol and iii) at least one cationic surfactant.

23. The method according to claim 21, wherein the keratin fibers are dark keratin fibers having a tone depth of less than or equal to 6, and wherein the at least one direct dye of formula (I) is chosen from:
dyes of formulae (XII) and (XII'):

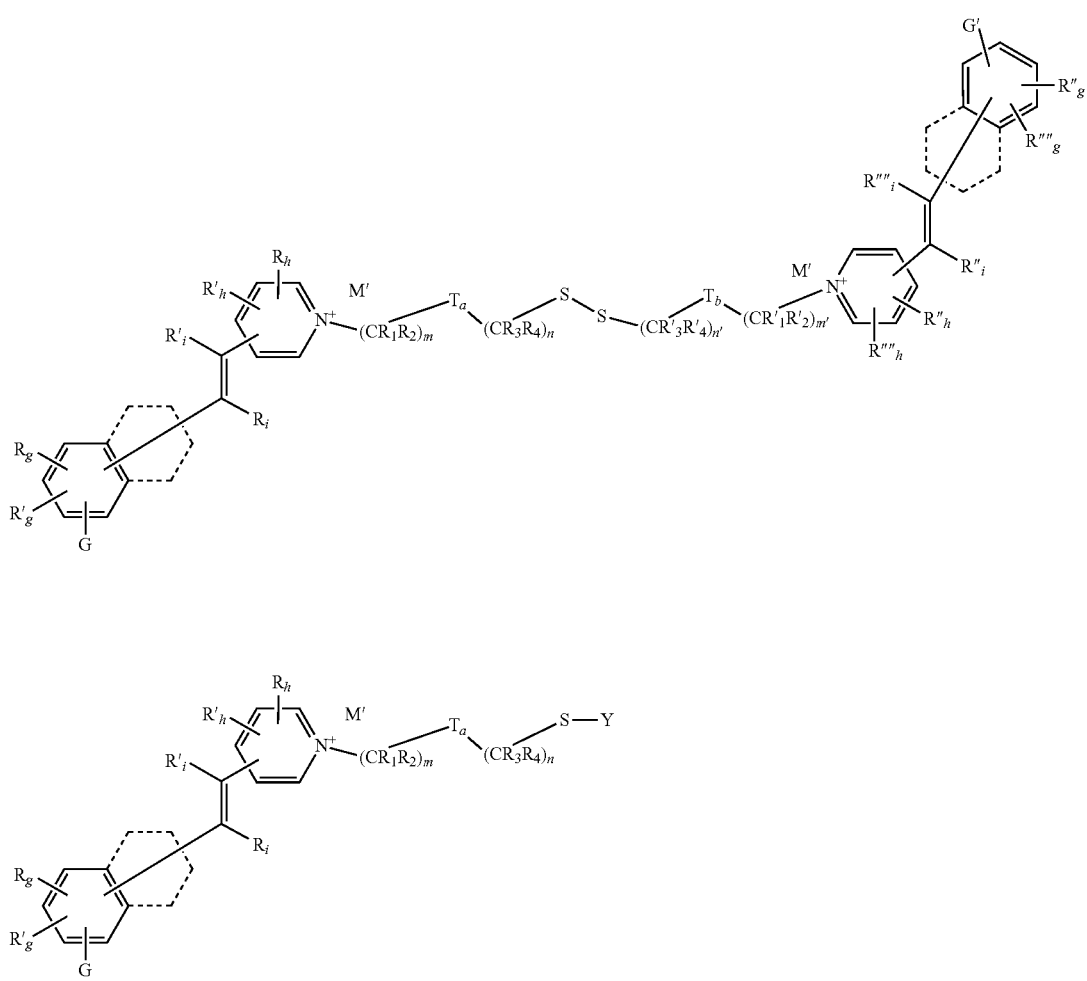

wherein:
G and G', which may be identical or different, are chosen from —NR'$_c$R'$_d$, and $C_1$-$C_6$ alkoxy groups which are optionally substituted;

$R_g$, R'$_g$, R"$_g$, R'''$_g$, $R_h$, R'$_h$, R"$_h$ and R'''$_h$, which may be identical or different, are chosen from hydrogen, halogen atoms, amino, $C_1$-$C_4$ alkylamino, $C_1$-$C_4$ dialkylamino, cyano, carboxyl, hydroxyl and trifluoromethyl group, acylamino, $C_1$-$C_4$ alkoxy, (poly)hydroxy($C_2$-$C_4$)alkoxy, alkylcarbonyloxy, alkoxycarbonyl and alkylcarbonylamino radicals, acylamino, carbamoyl and alkylsulfonylamino radicals, aminosulfonyl radicals, and $C_1$-$C_{16}$ alkyl radicals optionally substituted with a group chosen from $C_1$-$C_{12}$ alkoxy, hydroxyl, cyano, carboxyl, amino, $C_1$-$C_4$ alkylamino and $C_1$-$C_4$ dialkylamino groups, or alternatively two alkyl radicals borne by the nitrogen atom of the amino group form a 5- to 7-membered heterocycle optionally comprising another nitrogen or non-nitrogen heteroatom;

or alternatively two groups $R_g$ and R'$_g$; R"$_g$ and R'''$_g$; $R_h$, and R'$_h$; R"$_h$ and R'''$_h$ borne by two adjacent carbon atoms together form a benzo or indeno ring, a fused heterocycloalkyl or fused heteroaryl group; wherein the benzo, indeno, heterocycloalkyl and heteroaryl rings are optionally substituted with an entity chosen from halogen atoms, amino, $C_1$-$C_4$ alkylamino, $C_1$-$C_4$ dialkylamino, nitro, cyano, carboxyl, hydroxyl and trifluoromethyl groups, acylamino, $C_1$-$C_4$ alkoxy, (poly)hydroxy($C_2$-$C_4$)alkoxy, alkylcarbonyloxy, alkoxycarbonyl and alkylcarbonylamino radicals, acylamino, carbamoyl and alkylsulfonylamino radicals, aminosulfonyl radicals, and $C_1$-$C_{16}$ alkyl radicals optionally substituted with a group chosen from $C_1$-$C_{12}$ alkoxy, hydroxyl, cyano, carboxyl, amino, $C_1$-$C_4$ alkylamino, and $C_1$-$C_4$ dialkylamino groups, or alternatively two alkyl radicals borne by the nitrogen atom of the amino group form a 5- to 7-membered heterocycle optionally comprising another nitrogen or non-nitrogen heteroatom;

or alternatively two groups $R_i$ and $R_g$; R'''$_i$ and R'''$_g$; R'$_i$ and R'$_h$; and/or R"$_i$ and R"$_h$ together form a fused (hetero)cycloalkyl;

or alternatively when G represents —NR$_c$R$_d$ and G' represents —NR'$_c$R'$_d$, two groups $R_c$ and R'$_g$; R'$_c$ and R"$_g$; $R_d$ and $R_g$; R'$_d$ and R'''$_g$ together form a saturated heteroaryl or heterocycle, optionally substituted with at least one $(C_1-C_6)$alkyl group, and optionally comprising at least one heteroatom chosen from nitrogen and oxygen;

$R_i$, $R'_i$, $R''_i$, and $R'''_i$, which may be identical or different, are chosen from hydrogen and $C_1-C_4$ alkyl groups;

$R_1$, $R_2$, $R_3$, $R_4$, $R'_1$, $R'_2$, $R'_3$ and $R'_4$, which may be identical or different, are chosen from hydrogen and $C_1-C_4$ alkyl, $C_1-C_{12}$ alkoxy, hydroxyl, cyano, carboxyl, amino, $C_1-C_4$ alkylamino and $C_1-C_4$ dialkyl amino group, the alkyl radicals possibly forming, with the nitrogen atom that bears them, a 5- to 7-membered heterocycle optionally comprising another nitrogen or non-nitrogen heteroatom;

$T_a$ and $T_b$, which may be identical or different, are chosen from i) a covalent σ bond, ii) at least one radical chosen from —$SO_2$—, —O—, —S—, —N(R)—, —$N^+(R)(R^o)$—, and —CO—, wherein R, $R^o$, which may be identical or different, are chosen from hydrogen, $C_1-C_4$ alkyl and $C_1-C_4$ hydroxyalkyl radicals; and aryl$(C_1-C_4)$alkyl radicals, or iii) cationic or non-cationic, heterocycloalkyl or heteroaryl radicals;

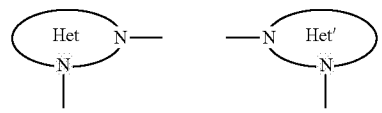

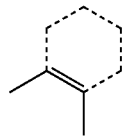

is chosen from aryl and heteroaryl groups fused to the imidazolium or phenyl ring; or alternatively is absent from the imidazolium or phenyl ring;

m, m', n and n', which may be identical or different, are integers ranging from 0 to 6 inclusive, wherein the sums m+n and m'+n' are equal to integers ranging from 1 to 10 inclusive;

Y is chosen from hydrogen and the following protecting groups:
$(C_1-C_4)$alkylcarbonyl;
arylcarbonyl;
$(C_1-C_4)$alkoxycarbonyl;
aryloxycarbonyl;
aryl$(C_1-C_4)$alkoxycarbonyl;
(di)$(C_1-C_4)$(alkyl)aminocarbonyl;
$(C_1-C_4)$(alkyl)arylaminocarbonyl;
optionally substituted aryl;
5- or 6-membered monocyclic heteroaryl;
5- or 6-membered cationic monocyclic heteroaryl;
8- to 11-membered cationic bicyclic heteroaryl;
cationic heterocycles having the following formula:

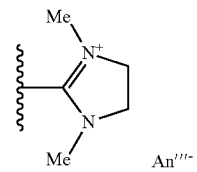

—$C(NH_2)=N^+H_2$; $An''''^-$; wherein $An''''^-$ is an anionic counterion;
—$C(NH_2)=NH$;
$SO_3^-M^+$, wherein $M^+$ is a metal ion; and
M' is an anionic counterion.

24. The method according to claim 23, wherein the at least one direct dye of formula (I) is chosen from dyes of the following chemical structures:

44

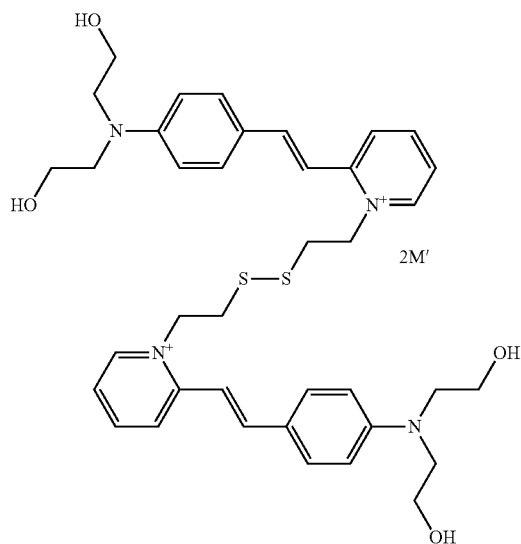

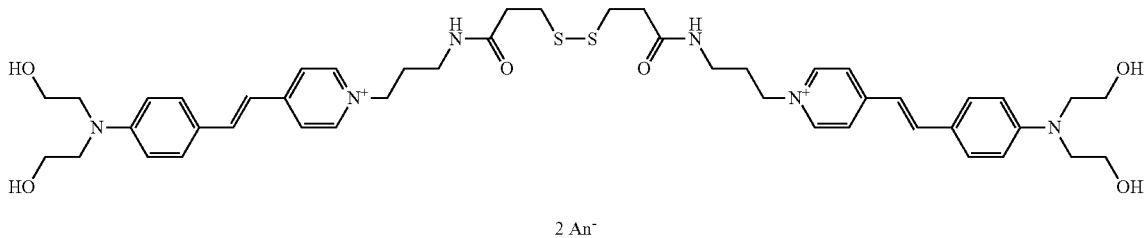

2 An⁻

25. A multi-compartment device or kit for dyeing keratin fibers comprising:

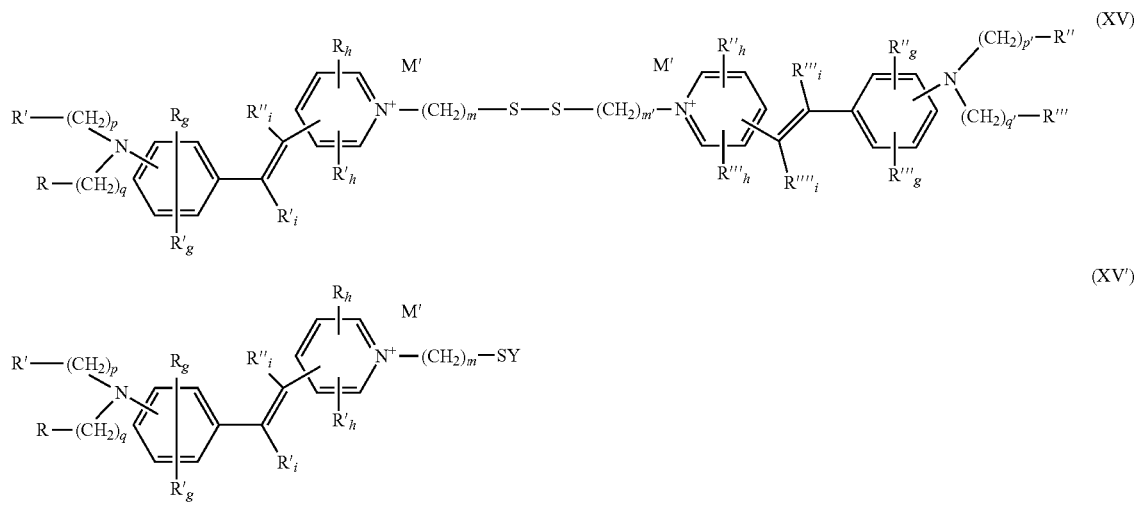

a first compartment comprising a dye composition comprising 0 at least one direct dye of formula (I) according to claim 1;
a second compartment comprising at least one reducing agent v) chosen from thioglycolic acid, thiolactic acid, 3-mercaptopropionic acid, thiomalic acid, 2,3-dimercaptosuccinic acid, cysteine, N-glycyl-L-cysteine, L-cysteinylglycine, and esters and salts thereof; thioglycerol; cysteamine and $C_1$-$C_4$ acyl derivatives thereof; N-mesylcysteamine; N-acetylcysteine; N-(mercapto-2-ethyl) gluconamide; pantetheine, N-(mercaptoalkyl)-ω-hydroxyalkylamides; N-mono- or N, N-dialkylmercapto-4-butyramides; aminomercaptoalkyl amides; N-(mercaptoalkyl)succinamic acids and N-(mercaptoalkyl)succinimides; alkylamino mercaptoalkyl amides; the azeotropic mixture of 2-hydroxypropyl thioglycolate and of (2-hydroxy-1-methyl)ethyl thioglycolate; ammonium thioglycolate; mercaptoalkylamino amides; and N-mercaptoalkylalkanediamides; and
optionally, a third compartment comprising vi) at least one chemical oxidizing agent; wherein the first and/or second compartment further comprises ii) at least one fatty alcohol, iii) at least one cationic surfactant, and/or iv) at least one alkaline agent.

26. The method according to claim 21, wherein the keratin fibers have a tone height of less than or equal to 6, wherein the at least one direct dye of formula (I) is chosen from dyes of formulae (XV), (XV'):

wherein in formulae (XV) and (XV'):
R and R''', which may be identical or different, are chosen from hydroxyl, amino ($NR_aR_b$) and ammonium ($N^+R_aR_bR_c$)An⁻ groups; wherein $R_a$, $R_b$ and $R_c$, which may be identical or different, are chosen from hydrogen atom and ($C_1$-$C_4$)alkyl groups, and An⁻ is an anionic counterion;
or alternatively two alkyl groups $R_a$ and $R_b$ of the amino or ammonium group form a 5- to 7-membered heterocycle optionally comprising another nitrogen or non-nitrogen heteroatom;
R' and R'', which may be identical or different, are chosen from hydrogen and hydroxyl, amino ($NR_aR_b$) and ammonium ($N^+R_aR_bR_c$) An⁻ groups;
$R_g$, $R'_g$, $R''_g$, $R'''_g$, $R_h$, $R'_h$, $R''_h$ and $R'''_h$, which may be identical or different, are chosen from hydrogen, halogen atoms, amino, (di)($C_1$-$C_4$)alkylamino, cyano, carboxyl, hydroxyl, trifluoromethyl, acylamino, $C_1$-$C_4$ alkoxy, (poly)hydroxy($C_2$-$C_4$)alkoxy, ($C_1$-$C_4$)alkylcarbonyloxy, ($C_1$-$C_4$)alkoxycarbonyl, ($C_1$-$C_4$)alkylcarbonylamino, acylamino, carbamoyl and ($C_1$-$C_4$)alkylsulfonylamino groups, aminosulfonyl radicals and ($C_1$-$C_{16}$)alkyl radicals optionally substituted with a group chosen from ($C_1$-$C_{12}$)alkoxy, hydroxyl, cyano, carboxyl, amino and (di)($C_1$-$C_4$) alkylamino, or alternatively the two alkyl radicals borne by the nitrogen atom of the amino group form a 5- to 7-membered heterocycle optionally comprising another nitrogen or non-nitrogen heteroatom;

$R'_i$, $R''_i$, $R'''_i$ and $R''''_i$, which may be identical or different, are chosen from hydrogen and ($C_1$-$C_4$)alkyl groups;

m and m', which may be identical or different, are integers ranging from 1 to 10 inclusive;

p, p', q and q', which may be identical or different, are integers ranging from 1 to 6 inclusive;

M' is an anionic counterion; and

Y is chosen from hydrogen and the following protective groups:
($C_1$-$C_4$)alkylcarbonyl;
arylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl;
($C_1$-$C_4$)(alkyl)arylaminocarbonyl;
optionally substituted aryl;
5- or 6-membered monocyclic heteroaryl;
5- or 6-membered cationic monocyclic heteroaryl;
8- to 11-membered cationic bicyclic heteroaryl;
cationic heterocycles of following formula:

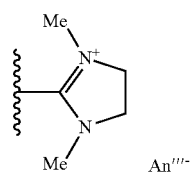 [SMILES: *C1=[N+](C)CCN1C]

—C($NH_2$)=$N^+H_2$ An''''⁻; wherein An''''⁻ is an anionic counterion;
—C($NH_2$)=NH; and
$SO_3^-M^+$, wherein $M^+$ is a metal ion;

it being understood that when the compound of formula (XV) or (XV') contains other cationic parts, it is combined with one or more anionic counterions that afford formula (XV) or (XV') electrical neutrality.

27. The method according to claim 21, wherein the keratin fibers have a tone height of less than or equal to 6, wherein the at least one direct dye of formula (I) is chosen from dyes of formulae (XVI), (XVI'):

wherein in formula (XVI) and (XVI'):

$R_1$ is chosen from $C_1$-$C_6$ alkyl groups substituted with at least one group chosen from hydroxyl groups and —C(O)OR' groups, wherein R' is chosen from hydrogen and $C_1$-$C_4$ alkyl groups or alternatively a group —C(O)—O⁻ and, in the latter case, the anionic counterion An⁻ is absent;

$R_2$ is chosen from $C_1$-$C_6$ alkyl groups optionally substituted with at least one hydroxyl group;

or alternatively the groups $R_1$ and $R_2$ form, together with the nitrogen atom that bears them, a saturated heterocyclic radical substituted with at least one hydroxyl, (poly)hydroxy($C_1$-$C_4$)alkyl and/or —C(O)OR' group wherein R' is chosen from hydrogen and $C_1$-$C_4$ alkyl groups or a group —C(O)—O⁻ and, in the latter case, the anionic counterion An⁻ is absent;

$R_3$ is chosen from hydrogen and —C(O)OR'' groups wherein R'' is chosen from hydrogen, alkali metals and $C_1$-$C_6$ alkyl groups, or alternatively $R_3$ is a group —C(O)—O⁻ and, in the latter case, the anionic counterion An⁻ is absent;

Z is chosen from divalent amido groups —C(O)—N(R)—, —N(R)—C(O)—, and divalent $C_1$-$C_{10}$ alkylene groups interrupted with an amido group chosen from —($CH_2$)$_n$'—C(O)—N(R)—($CH_2$)$_p$—, —($CH_2$)$_{n''}$—N(R)—C(O)—($CH_2$)$_p$—, wherein n' is an integer ranging from 0 to 3 inclusive; p is an integer ranging from 0 to 4 inclusive, n'' is an integer ranging from 0 to 3 inclusive and R is chosen from hydrogen and $C_1$-$C_6$ alkyl groups;

An⁻ is an anionic counterion;

Y is chosen from hydrogen and the following protective groups:
($C_1$-$C_4$)alkylcarbonyl;
arylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl;
($C_1$-$C_4$)(alkyl)arylaminocarbonyl;
optionally substituted aryl;
5- or 6-membered monocyclic heteroaryl;
5- or 6-membered cationic monocyclic heteroaryl;
8- to 11-membered cationic bicyclic heteroaryl;
cationic heterocycles of following formula:

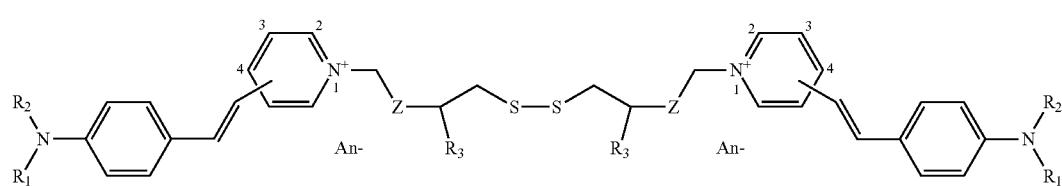

(XVI)

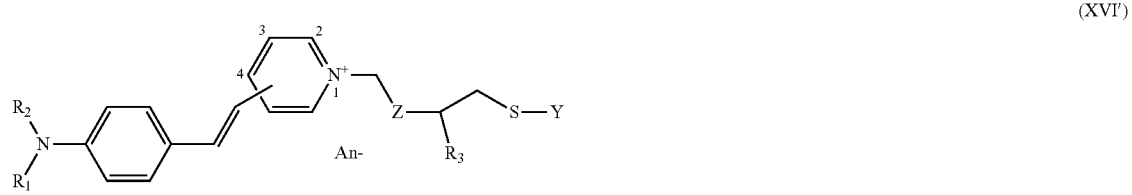

(XVI')

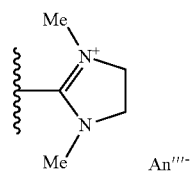 [SMILES: *C1=[N+](C)CCN1C]
—C(NH$_2$)=N$^+$H$_2$ An''''$^-$; wherein An''''$^-$ is an anionic counterion;
—C(NH$_2$)=NH; and
SO$_3$$^-$M$^+$, wherein M$^+$ is a metal ion;
it being understood that when the compound of formula (XVI) or (XVI') contains other cationic parts, it is combined with one or more anionic counterions that afford formula (XVI) or (XVI') electrical neutrality.
* * * * *